(12) United States Patent
Rao et al.

(10) Patent No.: US 9,303,016 B2
(45) Date of Patent: Apr. 5, 2016

(54) DERIVATIVES OF AZA ADAMANTANE AND USES THEREOF

(71) Applicant: CONNEXIOS LIFE SCIENCES PVT. LTD., Bangalore (IN)

(72) Inventors: Jagannath Madanahalli Ranganath Rao, Bangalore (IN); Uppala Venkatesham, Bangalore (IN); Sivanageswara Rao Doppalapudi, Bangalore (IN); Bommegowda Yadaganahalli Kenchegowda, Bangalore (IN); George Fernand, Bangalore (IN); Jenson George, Bangalore (IN); G R Madhavan, Bangalore (IN); Gorle Paidapu Naidu, Bangalore (IN); V. S. Naga Rajesh Kadambari, Bangalore (IN); S Jagannath, Bangalore (IN); R Manivannan, Bangalore (IN); T Senthil Kumar, Bangalore (IN); B Siva Senthil Kumar, Bangalore (IN); Rayi Mallikarjuna, Bangalore (IN)

(73) Assignee: CONNEXIOS LIFE SCIENCES PVT. LTD., Bangalore (IN)

( * ) Notice: Subject to any disclaimer, the term of this patent is extended or adjusted under 35 U.S.C. 154(b) by 0 days.

(21) Appl. No.: 14/367,814

(22) PCT Filed: Dec. 21, 2012

(86) PCT No.: PCT/IN2012/000842
§ 371 (c)(1),
(2) Date: Jun. 20, 2014

(87) PCT Pub. No.: WO2013/111150
PCT Pub. Date: Aug. 1, 2013

(65) Prior Publication Data
US 2015/0141650 A1    May 21, 2015

(30) Foreign Application Priority Data
Dec. 22, 2011 (IN) .......................... 4526/CHE/2011

(51) Int. Cl.
| | | |
|---|---|---|
| C07D 401/06 | (2006.01) |
| C07D 405/14 | (2006.01) |
| C07D 401/14 | (2006.01) |
| C07D 409/14 | (2006.01) |
| C07D 417/06 | (2006.01) |
| C07D 471/04 | (2006.01) |
| C07D 471/08 | (2006.01) |

(52) U.S. Cl.
CPC ............ *C07D 401/06* (2013.01); *C07D 401/14* (2013.01); *C07D 405/14* (2013.01); *C07D 409/14* (2013.01); *C07D 417/06* (2013.01); *C07D 471/04* (2013.01); *C07D 471/08* (2013.01)

(58) Field of Classification Search
CPC ... C07D 471/08; A61K 31/439; A61K 31/404
See application file for complete search history.

(56) References Cited

U.S. PATENT DOCUMENTS 8,329,909 B2 * 12/2012 Kozawa et al. ............... 546/131
2006/0149070 A1   7/2006 Rohde et al.

FOREIGN PATENT DOCUMENTS

| EP | 1125922 A1 | 8/2001 |
|---|---|---|
| WO | 2008/134221 A2 | 11/2008 |
| WO | 2009/106817 A2 | 9/2009 |
| WO | 2009/114173 A1 | 9/2009 |
| WO | 2009/138386 A2 | 11/2009 |
| WO | 2010/046445 A2 | 4/2010 |
| WO | 2010/123115 A1 | 10/2010 |
| WO | 2011/030349 A1 | 3/2011 |

OTHER PUBLICATIONS

International Search Report for PCT/IN2012/000842 published on WIPO website on Aug. 1, 2013.

* cited by examiner

*Primary Examiner* — Rita Desai
(74) *Attorney, Agent, or Firm* — Hauptman Ham, LLP

(57) ABSTRACT

The present invention relates to certain amide derivatives that have the ability to inhibit 11-β-hydroxysteroid dehydrogenase type 1 (11β-HSD-1) and which are therefore useful in the treatment of certain disorders that can be prevented or treated by inhibition of this enzyme. In addition the invention relates to the compounds, methods for their preparation, pharmaceutical compositions containing the compounds and the uses of these compounds in the treatment of certain disorders. It is expected that the compounds of the invention will find application in the treatment of conditions such as non-insulin dependent type 2 diabetes mellitus (NIDDM), insulin resistance, obesity, impaired fasting glucose, impaired glucose tolerance, lipid disorders such as dyslipidemia, hypertension and as well as other diseases and conditions.

16 Claims, No Drawings

DERIVATIVES OF AZA ADAMANTANE AND USES THEREOF

FIELD OF THE INVENTION

The present invention relates to aza adamantane derivatives that have the ability to inhibit 11-β-hydroxysteroid dehydrogenase type 1 (11β-HSD-1) and which are therefore useful in the treatment of certain disorders that can be prevented or treated by inhibition of this enzyme. In addition the invention relates to the compounds, methods for their preparation, pharmaceutical compositions containing the compounds and the uses of these compounds in the treatment of certain disorders. It is expected that the compounds of the invention will find application in the treatment of conditions such as non-insulin dependent type 2 diabetes mellitus (NIDDM), insulin resistance, obesity, impaired fasting glucose, impaired glucose tolerance, lipid disorders such as dyslipidemia, hypertension and as well as other diseases and conditions.

BACKGROUND OF THE INVENTION

Glucocorticoids are stress hormones with regulatory effects on carbohydrate, protein and lipid metabolism. Cortisol (or hydrocortisone in rodent) is the most important human glucocorticoid. 11-beta hydroxyl steroid dehydrogenase or 11 beta-HSD1 (11β-HSD-1) is a member of the short chain dehydrogenase super-family of enzymes which converts functionally inert cortisone to active cortisol locally, in a pre-receptor manner. Given that the enzyme is abundantly expressed in metabolically important tissues, such as adipose, muscle, and liver, that become resistant to insulin action in Type 2 Diabetes, inhibition of 11β-HSD-1 offers the potential to restore the glucose lowering action of insulin in these tissues without impacting the central HPA. Another important 11-beta hydroxyl steroid dehydrogenase, namely Type 2 11-beta-HSD (11β-HSD-2), which converts cortisol into cortisone, is a unidirectional dehydrogenase mainly located in kidney and protects minerallocorticoid receptors from illicit activation by glucocorticoids.

Multiple lines of evidence indicate that 11β-HSD-1-mediated intracellular cortisol production may have a pathogenic role in Obesity, Type 2 Diabetes and its co-morbidities.

In humans, treatment with non-specific inhibitor carbenoxolone improves insulin sensitivity in lean healthy volunteers and people with type2 diabetes (Walker B R et al (1995)). Likewise, 11β-HSD-1 activity was decreased in liver and increased in the adipose tissue of obese individuate. Similarly 11β-HSD-1 mRNA was found to be increased in both visceral and subcutaneous adipose tissue of obese patients (Desbriere R et al (2006)) and was positively related to BMI and central obesity in Pima Indians, Caucasians and Chinese youth (Lindsay R S et al (2003), Lee Z S et al (1999)). Adipose tissue 11β-HSD-1 and Hexose-6-Phosphate Dehydrogenase gene expressions have also been shown to increase in patients with type 2 diabetes mellitus (Uçkaya G et al (2008)). In human skeletal muscle 11β-HSD-1 expression was found to be positively associated with insulin resistance (Whorwood C B et al (2002)). Increased 11β-HSD-1 expression was also seen in diabetic myotubes (Abdallah B M et al (2005)).

Various studies have been conducted in rodent models to substantiate the role of 11β-HSD-1 in diabetes and obesity. For example, over-expression of 11β-HSD-1 specifically in adipose tissue causes development of metabolic syndrome (glucose intolerance, obesity, dyslipidemia and hypertension) in mice (Masuzaki H et al (2001)). Conversely, when 11β-HSD-1 gene was knocked out, the resulting mice showed resistance to diet induced obesity and improvement of the accompanying dysregulation of glucose and lipid metabolism (Kotelevtsev Y et al (1997), Morton N M et al (2001), Morton N M et al (2004)). In addition, treatment of diabetic mouse models with specific inhibitors of 11β-HSD-1 caused a decrease in glucose output from the liver and overall increase in insulin sensitivity (Alberts P et al (2003)).

The results of the preclinical and early clinical studies suggest that the treatment with a selective and potent inhibitor of 11β-HSD-1 will be an efficacious therapy for type 2 diabetes, obesity and metabolic syndrome.

The role of 11β-HSD-1 as an important regulator of liver glucocorticoid level and thus of hepatic glucose production is well substantiated. Hepatic insulin sensitivity was improved in healthy human volunteers treated with the non-specific 11β-HSD-1 inhibitor carbenoxolone (Walker B R (1995)). Many in vitro and in vivo (animal model) studies showed that the mRNA levels and activities of two key enzymes (PEPCK and G6PC) in gluconeogenesis and glycogenolysis were reduced by reducing 11β-HSD-1 activity. Data from these models also confirm that inhibition of 11β-HSD-1 will not cause hypoglycemia, as predicted since the basal levels of PEPCK and G6Pase are regulated independently of glucocorticoids (Kotelevtsev Y (1997)).

In the pancreas cortisol is shown to inhibit glucose induced insulin secretion as well as increase stress induced beta cell apoptosis. Inhibition of 11β-HSD-1 by carbenoxolone in isolated murine pancreatic beta-cells improves glucose-stimulated insulin secretion (Davani B et al (2000)). Recently, it was shown that 11β-HSD-1 within alpha cells regulates glucagon secretion and in addition may act in a paracrine manner to limit insulin secretion from beta cells (Swali A et al (2008)). Levels of 11β-HSD-1 in islets from ob/ob mice were shown to be positively regulated by glucocorticoids and were lowered by a selective 11β-HSD-1 inhibitor and a glucocorticoid receptor antagonist. Increased levels of 11β-HSD-1 were associated with impaired GSIS (Ortsater H et al (2005)). In Zuker diabetic rats, troglitazone treatment improved metabolic abnormalities with a 40% decline in expression of 11β-HSD-1 in the islets (Duplomb L et al (2004)). Cortisol inhibition may lead to an increase in the insulin gene transcription and a normalization of first phase insulin secretion (Shinozuka Y et al (2001)).

In human skeletal muscle 11β-HSD-1 expression is positively associated insulin resistance and increased expression of 11β-HSD-1 was also reported in type 2 diabetic myotubes (Abdallah B M et al (2005)). Recently the contribution of cortisol in muscle pathology is being considered for modulating its action. Very recently it has been demonstrated that targeted reduction or pharmacological inhibition of 11β-HSD-1 in primary human skeletal muscle prevents the effect of cortisone on glucose metabolism and palmitate oxidation (Salehzadeh F et al (2009)). Over activity of cortisol in muscle leads to muscle atrophy, fibre type switch and poor utilization of glucose due to insulin resistance. Cortisol might have a direct role in reducing muscle glucose uptake.

Obesity is an important factor in Metabolic syndrome as well as in the majority (>80%) of type 2 diabetics, and omental (visceral) fat appears to be of central importance. 11β-HSD-1 activity is increased in the both visceral and subcutaneous adipose tissue of obese individual (Lindsay R S et al (2003)). Cortisol activity in adipose is known to increase the adipogenic program. Inhibition of 11β-HSD-1 activity in pre-adipocytes has been shown to decrease the rate of differentiation into adipocytes (Bader T et al (2002)). This is predicted to result in diminished expansion (possibly reduction)

of the omental fat depot, i.e., reduced central obesity (Bujalska I J et al (1997) and (2006)). Intra-adipose cortisol levels have been associated with adipose hypertrophy, independent of obesity (Michailidou Z et al (2006)).

Cortisol in coordination with adrenergic signalling is also known to increase lipolysis which leads to increase in plasma free fatty acid concentrations which, in turn, is the primary cause of many deleterious effects of obesity (TomLinson J W et al (2007)).

Adrenalectomy attenuates the effect of fasting to increase both food intake and hypothalamic neuropeptide Y expression. This supports the role of glucocorticoids in promoting food intake and suggests that inhibition of 11β-HSD-1 in the brain might increase satiety and therefore reduce food intake (Woods S C (1998)). Inhibition of 11β-HSD-1 by a small molecule inhibitor also decreased food intake and weight gain in diet induced obese mice (Wang S J Y et al (2006)).

The effects discussed above therefore suggest that an effective 11β-HSD-1 inhibitor would have activity as an anti-obesity agent.

Cortisol in excess can also trigger triglyceride formation and VLDL secretion in liver, which can contribute to hyperlipidemia and associated dyslipidemia. It has been shown that 11β-HSD-1−/− transgenic mice have markedly lower plasma triglyceride levels and increased HDL cholesterol levels indicating a potential atheroprotective phenotype (Morton N M et al (2001)). In a diet-induced obese mouse model, a non-selective inhibitor of 11β-HSD-1 reduced plasma free fatty acid as well as triacylglycerol (Wang S J et al (2006)). Overexpression of 11β-HSD-1 in liver increased liver triglyceride and serum free fatty acids with the up regulation of hepatic lipogenic genes (Paterson J M et al (2004). It has been illustrated that inhibition of 11β-HSD-1 improves triglyceridemia by reducing hepatic VLDL-TG secretion, with a shift in the pattern of TG-derived fatty acid uptake toward oxidative tissues, in which lipid accumulation is prevented by increased lipid oxidation (Berthiaume M et al (2007)).

Atherosclerotic mouse model (APOE −/−) which are susceptible to atheroma when fed high fat diet, are protected against development of atherosclerosis when treated with 11β-HSD-1 inhibitors (Hermanowski-Vostaka A et al, (2005)).

Inhibition of 11β-HSD-1 in mature adipocytes is expected to attenuate secretion of the plasminogen activator inhibitor 1 (PAI-1)—an independent cardiovascular risk factor (Halleux C M et al (1999)). Furthermore, there is a clear correlation between glucocorticoid activity and cardiovascular risk factor suggesting that a reduction of the glucocorticoid effects would be beneficial (Walker B R et al (1998), Fraser R et al (1999)).

The association between hypertension and insulin resistance might be explained by increased activity of cortisol. Recent data show that the intensity of dermal vasoconstriction after topical application of glucocorticoids is increased in patients with essential hypertension (Walker B R et al (1998)). Glucocorticoid was shown to increase the expression of angiotensin receptor in vascular cell and thus potentiating the renin-angiotensin pathway (Ullian M E et al (1996)), (Sato A et al (1994)). Role of cortisol in NO signalling and hence vasoconstriction has been proved recently (Liu Y et al (2009)). These findings render 11β-HSD-1 a potential target for controlling hypertension and improving blood-flow in target tissues.

In the past decade, concern on glucocorticoid-induced osteoporosis has increased with the widespread use of exogenous glucocorticoids (GC). GC-induced osteoporosis is the most common and serious side-effect for patients receiving GC. Loss of bone mineral density (BMD) is greatest in the first few months of GC use. Mature bone-forming cells (osteoblasts) are considered to be the principal site of action of GC in the skeleton. The whole differentiation of mesenchymal stem cell toward the osteoblast lineage has been proven to be sensitive to GC as well as collagen synthesis (Kim C H et al (1999)). The effects of GC on this process are different according to the stage of differentiation of bone cell precursors. The presence of intact GC signalling is crucial for normal bone development and physiology, as opposed to the detrimental effect of high dose exposure (Pierotti S et al (2008), Cooper M S et al (2000)). Other data suggest a role of 11β-HSD-1 in providing sufficiently high levels of active glucocorticoid in osteoclasts, and thus in augmenting bone resorption (Cooper M S et al (2000)). The negative effect on bone nodule formation could be blocked by the non-specific inhibitor carbenoxolone suggesting an important role of 11β-HSD-1 in the glucocorticoid effect (Bellows C G et al (1998)).

Stress and glucocorticoids influence cognitive function (de Quervain D J et al (1998)). The enzyme 11β-HSD-1 controls the level of glucocorticoid action in the brain also known to contributes to neurotoxicity (Rajan V et al (1996)). It has been also suggested that inhibiting 11β-HSD-1 in the brain may result in reduced anxiety (Tronche F et al (1999)). Thus, taken together, the hypothesis is that inhibition of 11β-HSD-1 in the human brain would prevent reactivation of cortisone into cortisol and protect against deleterious glucocorticoid-mediated effects on neuronal survival and other aspects of neuronal function, including cognitive impairment, depression, and increased appetite.

Recent data suggest that the levels of the glucocorticoid target receptors and the 11β-HSD-1 enzymes determine the susceptibility to glaucoma (Stokes, J. et al. (2000)). Ingestion of carbenoxolone, a non-specific inhibitor of 11β-HSD-1, was shown to reduce the intraocular pressure by 20% in normal subjects. There are evidences that 11β-HSD-1 isozyme may modulate steroid-regulated sodium transport across the NPE, thereby influencing intra ocular pressure (IOP). 11β-HSD-1 is suggested to have a role in aqueous production, rather than drainage, but it is presently unknown if this is by interfering with activation of the glucocorticoid or the mineralocorticoid receptor, or both (Rauz S et al (2001; 2003)).

The multitude of glucocorticoid action is exemplified in patients with prolonged increase in plasma glucocorticoids, so called "Cushing's syndrome". These patients have prolonged increase in plasma glucocorticoids and exhibit impaired glucose tolerance, type 2 diabetes, central obesity, and osteoporosis. These patients also have impaired wound healing and brittle skin. Administration of glucocorticoid receptor agonist (RU38486) in Cushing's syndrome patients reverses the features of metabolic syndrome (Neiman L K et al (1985)).

Glucocorticoids have been shown to increase risk of infection and delay healing of open wounds. Patients treated with glucocorticoids have 2-5-fold increased risk of complications when undergoing surgery. Glucocorticoids influence wound healing by interfering with production or action of cytokines and growth factors like IGF, TGF-beta, EGF, KGF and PDGF (Beer H D et al (2000)). TGF-beta reverses the glucocorticoid-induced wound-healing deficit in rats by PDGF regulation in macrophages (Pierce G F et al (1989)). It has also been shown that glucocorticoids decrease collagen synthesis in rat and mouse skin in vivo and in rat and human fibroblasts (Oishi Y et al, 2002).

Glucocorticoids have also been implicated in conditions as diverse aspolycystic Ovaries Syndrome, infertility, memory dydsfunction, sleep disorders, myopathy (Endocrinology. 2011 January; 152(1):93-102. Epub 2010 Nov. 24. PMID: 21106871) and muscular dystrophy. As such the ability to target enzymes that have an impact on glucocorticoid levels is expected to provide promise for the treatment of these conditions.

Based on patent literature and company press releases, there are many compound tested for 11β-HSD-1 inhibition in the different stages of drug discovery pipeline.

Incyte Corporation's INCB13739 has proceeded furthest to phase IIb stage of clinical trial. The results of phase IIa trial for type 2 diabetes (28-days, placebo-controlled, two-step hyperinsulinemic clamp studies) showed that it was safe and well tolerated without any serious side effects and hypoglycemia.

Though this molecule significantly improved hepatic insulin sensitivity there was no appreciable improvement in plasma glucose levels. The molecule appeared to be having positive effects on risk factors for cardiovascular disease including reduction of LDL, total cholesterol and triglycerides as well as more modest increases in HDL. INCB13739 is currently being studied in a dose ranging phase IIb trials in T2D patients whose glucose levels are not controlled by metformin monotherapy.

In the pre-clinical stage, Incyte's lead inhibitor INCB13739 was tested in rhesus monkey and was shown to inhibit adipose 11β-HSD-1 (INCB013739, a selective inhibitor of 11β-Hydroxysteroid Dehydrogenase Type 1 (11βHSD1) improves insulin sensitivity and lowers plasma cholesterol over 28 days in patients with type 2 diabetes mellitus.

The evidence therefore strongly suggests that compounds that are inhibitors of 11β-Hydroxysteroid Dehydrogenase would be useful in the treatment of a number of clinical conditions associated with the expression of this enzyme. In addition it would be desirable if the inhibitors were selective inhibitors so as not to interfere with the functioning of closely related enzymes such as 11β-HSD-2 which is known to provide a protective effect in the body.

OBJECTS OF INVENTION

The principal object of the invention is to provide compounds that are inhibitors of 11β-Hydroxysteroid Dehydrogenase. These compounds would be expected to be useful in the treatment of 11β-Hydroxysteroid Dehydrogenase related conditions as discussed above.

A further object is to provide a pharmaceutical composition containing a compound that is an inhibitor of 11β-Hydroxysteroid Dehydrogenase and a pharmaceutically acceptable excipient, diluent or carrier.

A further object is to provide a method of prevention or treatment of a condition associated with 11β-Hydroxysteroid Dehydrogenase activity in a mammal.

STATEMENT OF INVENTION

The present invention provides compounds of Formula (I):

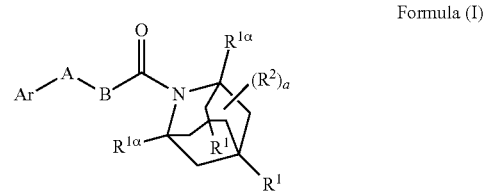

Formula (I)

wherein:
each $R^1$, $R^{1\alpha}$ and $R^2$ is independently selected from the group consisting of H, halogen, OH, $NO_2$, CN, SH, $NH_2$, $CF_3$, $OCF_3$, $OCH_3$, $CH_2OH$, $CH_2CO_2H$, $CH_2CH_2CO_2H$, $CH_2NH_2$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^3$, $SO_3H$, $SO_2NR^3R^4$, $SO_2R^3$, $SONR^3R^4$, $SOR^3$, $COR^3$, $COOH$, $COOR^3$, $CONR^3R^4$, $NR^3COR^4$, $NR^3COOR^4$, $NR^3SO_2R^4$, $NR^3CONR^3R^4$, and $NR^3R^4$;

Ar is an optionally substituted $C_1$-$C_{18}$heteroaryl group or an optionally substituted $C_2$-$C_{12}$heterocycloalkyl group;

A is selected from the group consisting of S, SO, $SO_2$, O, and —$CR^aR^b$—;

B is a group of the formula —$(CR^cR^d)_n$—;

wherein each $R^a$, $R^b$, $R^c$ and $R^d$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, optionally substituted $C_1$-$C_{18}$heteroaryl, $SR^3$, $SO_3H$, $SO_2NR^3R^4$, $SO_2R^3$, $SONR^3R^4$, $SOR^3$, $COR^3$, $COOH$, $COOR^3$, $CONR^3R^4$, $NR^3COR4^3$, $NR^3COOR^4$, $NR^3SO_2R^4$, $NR^3CONR^3R^4$, $NR^3R^4$;

or any two $R^a$, $R^b$, $R^c$ and $R^d$ on the same carbon atom when taken together may form a substituent of the formula:

wherein each $R^3$ and $R^4$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;

$R^5$ is selected from the group consisting of O, S, and $NR^6$;

$R^6$ is selected from the group consisting of H, $OR^7$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl;

$R^7$ is selected from the group consisting of H, optionally substituted $C_1$-$C_{12}$alkyl, optionally substituted $C_2$-$C_{10}$heteroalkyl, optionally substituted $C_3$-$C_{12}$cycloalkyl, optionally substituted $C_6$-$C_{18}$aryl, and optionally substituted $C_1$-$C_{18}$heteroaryl;

or any two or more $R^a$, $R^b$, $R^c$ and $R^d$ may join together to form a multiple bond between adjacent carbon atoms such as a double or triple bond, or a cyclic moiety connecting the carbon atoms to which they are attached;

n is an integer selected from the group consisting of 0, 1, 2, 3, and 4;

a is an integer selected from the group consisting of 0, 1, 2, 3, 4, 5, 6, 7, 8, 9, and 10;

or a pharmaceutically acceptable salt, N-oxide, or prodrug thereof.

As with any group of structurally related compounds which possess a particular utility, certain embodiments of variables of the compounds of the Formula (I), are particularly useful in their end use application.

In some embodiments A is S. In some embodiments A is SO. In some embodiments A is $SO_2$. In some embodiments A is O. In some embodiments A is $CR^aR^b$.

In some embodiments where A is $CR^aR^b$, $R^a$ and $R^b$ are each independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$. In some embodiments $R^a$ is H. In some embodiments $R^b$ is H. In some embodiments $R^a$ and $R^b$ are different such that the carbon is a chiral carbon. In some embodiments one of $R^a$ and $R^b$ is H and the other is an optionally substituted alkyl.

In some embodiments $R^b$ is H and $R^a$ is optionally substituted alkyl. In some embodiments $R^b$ is H and $R^a$ is selected from the group consisting of methyl, ethyl, propyl, isopropyl and butyl.

B is a group of the formula —$(CR^cR^d)_n$—. In some embodiments n is 0. In some embodiments n is 1. In some embodiments n is 2.

In some embodiments $R^c$ and $R^d$ are each independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$. In some embodiments both $R^c$ and $R^d$ are H such that B is $CH_2$.

In some embodiments any two or more $R^a$, $R^b$, $R^c$ and $R^d$ may join together to form a multiple bond between adjacent carbon atoms such as a double or triple bond, or a cyclic moiety connecting the carbon atoms to which they are attached.

In some embodiments two of $R^a$, $R^b$, $R^c$ and $R^d$ on adjacent carbon atoms are joined to form a double bond. In some embodiments four of $R^a$, $R^b$, $R^c$ and $R^d$ on adjacent carbon atoms are joined to form a triple bond.

In some embodiments one of $R^a$ and $R^b$ and one or $R^c$ and $R^d$ when taken together with the carbon atoms to which they are attached form a cyclic moiety. Examples of cyclic moieties that may be formed include cyclopropyl, cyclobutyl, cyclopentyl and cyclohexyl.

In some embodiments n=2 and one of $R^a$ and $R^b$ and one or $R^c$ and $R^d$ on the carbon atom two carbons removed (on the beta carbon) when taken together with the carbon atoms to which they are attached and the alpha carbon atom form a cyclic moiety. Examples of cyclic moieties that may be formed include cyclobutyl, cyclopentyl and cyclohexyl.

In some embodiments A is $CR^aR^b$ and B is $CH_2$, this provides compounds of formula (II):

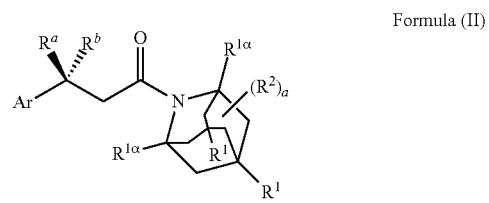

Formula (II)

wherein $R^1$, $R^{1\alpha}$, $R^a$, $R^b$, $R^2$ and Ar, are as defined above.

The group Ar may be any optionally substituted $C_1$-$C_{18}$ heteroaryl moiety. Suitable heteroaryl groups include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, pyridyl, quinolyl, isoquinolinyl, indolyl, and thienyl. In each instance where there is the possibility of multiple sites of substitution on the heteroaryl ring all possible attachment points are contemplated. Merely by way of example if the heteroaryl is a pyridyl moiety it may be a 2-pyridyly, a 3-pyridyl or a 4-pyridyl.

In some embodiments Ar is a group of the formula 3:

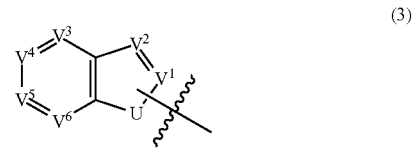

(3)

wherein each $V^1$, $V^2$, $V^3$, $V^4$, $V^5$ and $V^6$ is independently selected from the group consisting of N and $CR^8$;

U is selected from the group consisting of $NR^9$, O, S and $CR^9_2$, wherein each $R^8$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_2$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_1$heteroaryloxy, optionally substituted $C_1$-$C_{12}$alkylamino, $SR^{10}$, $SO_3H$, $SO_2NR^{10}R^{11}$, $SO_2R^{10}$, $OSO_2R^{10}$, $SONR^{10}R^{11}$, $SOR^{10}$, $COR^{10}$, $COOH$, $COOR^{10}$, $CONR^{10}R^{11}$, $NR^{10}COR^{11}$, $NR^{10}COOR^{11}$, $NR^{10}SO_2R^{11}$, $NR^{10}CONR^{10}R^{11}$, and $NR^{10}R^{11}$;

wherein $R^9$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, optionally substituted $C_1$-$C_{18}$heteroaryl, $SO_3H$, $SO_2NR^{10}R^{11}$, $SO_2R^{10}$, $SONR^{10}R^{11}$, $SOR^{10}$, $COR^{10}$, $COOH$, $COOR^{10}$, and $CONR^{10}R^{11}$;

wherein each $R^{10}$ and $R^{11}$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl.

In some embodiments Ar is selected from the group consisting of:

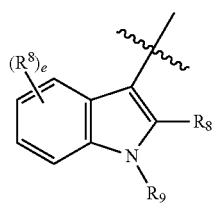
(3a)

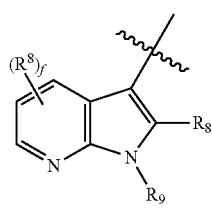
(3b)

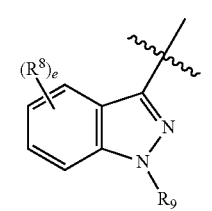
(3c)

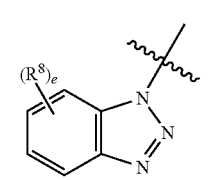
(3d)

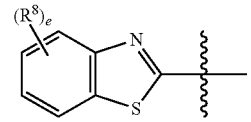
(3e)

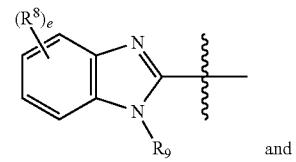
(3f)
and

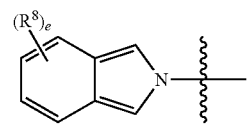
(3g)

wherein $R^8$ and $R^9$ is as defined above;

e is an integer selected from the group consisting of 0, 1, 2, 3 and 4;

f is an integer selected the group consisting of 0, 1, 2, and 3.

In some embodiments A is $CR^aR^b$, B is $CH_2$ and Ar is a group of formula (3a), this provides compounds of formula (IVa):

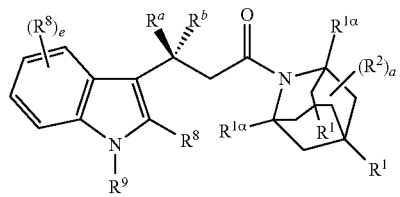
Formula (IVa)

wherein $R^1$, $R^{1\alpha}$, $R^a$, $R^b$, $R^2$, $R^8$, $R^9$ and e, are as defined above.

In some embodiments A is $CR^aR^b$, B is $CH_2$ and Ar is a group of formula (3b), this provides compounds of formula (IVb):

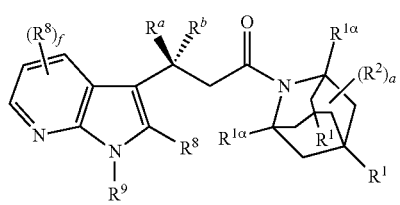
Formula (IVb)

wherein $R^1$, $R^{1\alpha}$, $R^a$, $R^b$, $R^2$, $R^8$, $R^9$ and f, are as defined above.

In some embodiments A is $CR^aR^b$, B is $CH_2$ and Ar is a group of formula (3c), this provides compounds of formula (IVc):

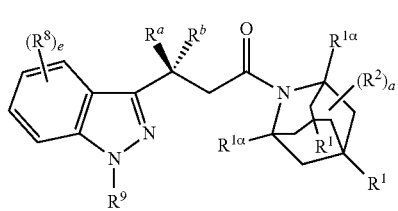

Formula (IVc)

wherein $R^1$, $R^{1\alpha}$, $R^a$, $R^b$, $R^2$, $R^8$, $R^9$ and e, are as defined above.

In some embodiments A is $CR^aR^b$, B is $CH_2$ and Ar is a group of formula (3d), this provides compounds of formula (IVd):

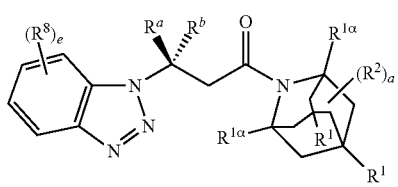

Formula (IVd)

wherein $R^1$, $R^{1\alpha}$, $R^a$, $R^b$, $R^2$, $R^8$ and e, are as defined above.

In some embodiments A is $CR^aR^b$, B is $CH_2$ and Ar is a group of formula (3e), this provides compounds of formula (IVe):

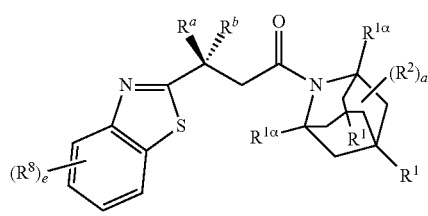

Formula (IVe)

wherein $R^1$, $R^{1\alpha}$, $R^a$, $R^b$, $R^2$, $R^8$ and e, are as defined above.

In some embodiments A is $CR^aR^b$, B is $CH_2$ and Ar is a group of formula (3f), this provides compounds of formula (IVf):

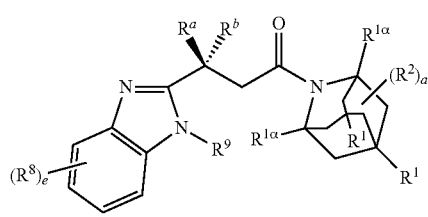

Formula (IVf)

wherein $R^1$, $R^{1\alpha}$, $R^a$, $R^b$, $R^2$, $R^8$, $R^9$ and e, are as defined above.

In some embodiments A is $CR^aR^b$, B is $CH_2$ and Ar is a group of formula (3 g), this provides compounds of formula (IVg):

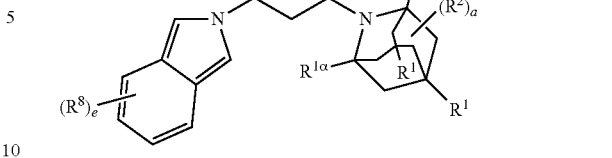

Formula (IVg)

wherein $R^1$, $R^{1\alpha}$, $R^a$, $R^b$, $R^2$, $R^8$, and e, are as defined above.

In some embodiments e is 1. In some embodiments e is 2. In some embodiments e is 3. In some embodiments e is 4. In circumstances where e is 1 the $R^8$ group may be located at either the 4, 5, 6, or 7 position on the six membered ring. In some embodiments where e is 1 the $R^8$ substituent is located at the 4 position on the ring. In some embodiments where e is 1 the $R^8$ substituent is located at the 5 position on the ring. In some embodiments where e is 1 the $R^8$ substituent is located at the 6 position on the ring. In some embodiments where e is 1 the $R^8$ substituent is located at the 7 position on the ring.

In some embodiments f is 1. In some embodiments f is 2. In some embodiments f is 3. In some embodiments where f is 1 the $R^8$ substituent is located at the 4 position on the ring. In some embodiments where f is 1 the $R^8$ substituent is located at the 5 position on the ring. In some embodiments where f is 1 the $R^8$ substituent is located at the 6 position on the ring. In some embodiments where f is 1 the $R^8$ substituent is located at the 7 position on the ring.

In some embodiments of the compounds described above each $R^1$ is independently selected from the group consisting of H, OH, F, Cl, Br, $CH_3$, $CH_2CO_2H$, $CH_2CH_2CO_2H$, $CO_2H$, $CONH_2$, $CH_2OH$, $CH_2NH_2$, CN, $OCH_3$, Ocyclopropyl, and $OCHF_2$. In some embodiments one $R^1$ is H and the other $R^1$ is OH. In some embodiments both $R^1$ are H.

In some embodiments of the compounds described above each $R^{1\alpha}$ is independently selected from the group consisting of H, OH, F, Cl, Br, $CO_2H$, $CONH_2$, $CH_2OH$, CN, $OCH_3$, and $OCHF_2$. In some embodiments one $R^{1\alpha}$ is H and the other $R^{1\alpha}$ is OH. In some embodiments both $R^{1\alpha}$ are H.

In some embodiments each $R^2$ is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_3$, $CF_3$, and $OCF_3$ In some embodiments a is 0. In some embodiments a is 1. In some embodiments a is 2. In some embodiments a is 3. In some embodiments a is 4. In some embodiments a is 5. In some embodiments a is 6. In some embodiments a is 7. In some embodiments a is 8. In some embodiments a is 9. In some embodiments a is 10.

In some embodiments of the compounds of the invention containing an $R^3$ group, the $R^3$ group is selected from H and $C_1$-$C_{12}$alkyl. In some embodiments $R^3$ is H. in some embodiments $R^3$ is methyl.

In some embodiments of the compounds of the invention containing an $R^4$ group, the $R^4$ group is selected from H and $C_1$-$C_{12}$alkyl. In some embodiments $R^4$ is H. in some embodiments $R^4$ is methyl.

In some embodiments of the compounds of the invention containing an $R^5$ group, the $R^5$ group is selected from O and S. In some embodiments $R^5$ is O. in some embodiments $R^5$ is S.

In some embodiments of the compounds of the invention containing an $R^6$ group, the $R^6$ group is selected from H and $C_1$-$C_{12}$alkyl. In some embodiments $R^6$ is H. in some embodiments $R^6$ is methyl.

In some embodiments of the compounds of the invention containing an $R^7$ group, the $R^7$ group is selected from H and $C_1$-$C_{12}$alkyl. In some embodiments $R^7$ is H. in some embodiments $R^7$ is methyl.

$R^8$ may be selected from a wide range of possible substituents as discussed above. In some embodiments each $R^8$ is independently selected from the group consisting of H, halogen, OH, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl. Exemplary $R^8$ substituents include H, $CH_3$, $CH_2CH_3$, $CH_2CH_2CH_3$, $CH(CH_3)_2$, $(CH_2)_3CH_3$, cyclopropyl, I, Br, F, I, OH, $NO_2$, $NH_2$, CN, $SO_3H$, $OCH_3$, $OCH(CH_3)_2$, $OCH_2CH_2CH_3$, $OSO_2CF_3$, $CF_3$, and $OCF_3$.

$R^9$ may be selected from a wide range of possible substituents as discussed above. In some embodiments each $R^9$ is independently selected from the group consisting of H, halogen, OH, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl. Exemplary $R^9$ substituents include $CH_3$, $CH_2CH_3$, $CH_2CH_2CH_3$, $CH(CH_3)_2$, $(CH_2)_3CH_3$, I, Br, F, I, OH, $NO_2$, $NH_2$, CN, $SO_3H$, $OCH_3$, $OCH_2CH_2CH_3$, $CF_3$, and $OCF_3$.

Many if not all of the variables discussed above may be optionally substituted. If the variable is optionally substituted then in some embodiments each optional substituent is independently selected from the group consisting of halogen, $=O$, $=S$, $-CN$, $-NO_2$, $-CF_3$, $-OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, $-C(=O)OH$, $-C(=O)R^e$, $-C(=O)OR^e$, $C(=O)NR^eR^f$, $C(=NOH)R^e$, $C(=NR^e)NR^fR^g$, $NR^eR^f$, $NR^eC(=O)R^f$, $NR^eC(=O)OR^f$, $NR^eC(=O)NR^fR^g$, $NR^eC(=NR^f)NR^gR^h$, $NR^eSO_2R^f$, $-SR^e$, $SO_2NR^eR^f$, $-OR^e$, $OC(=O)NR^eR^f$, $OC(=O)R^e$ and acyl, wherein $R^e$, $R^f$, $R^g$ and $R^h$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_1$-$C_{10}$heteroalkyl, $C_3$-$C_{12}$cycloalkyl, $C_3$-$C_{12}$cycloalkenyl, $C_1$-$C_{12}$heterocycloalkyl, $C_1$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: F, Cl, Br, $=O$, $=S$, $-CN$, $-NO_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, $-C(O)OR^a$, COOH, SH, and acyl.

In some embodiments each optional substituent is independently selected from the group consisting of: F, Br, Cl, $=O$, $=S$, $-CN$ methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, $-NO_2$, phenoxy, hydroxy, methoxy, trifluoro-methoxy, ethoxy, and methylenedioxy.

Alternatively, two optional substituents on the same moiety when taken together may be joined to form a fused cyclic substituent attached to the moiety that is optionally substituted. Accordingly the term optionally substituted includes a fused ring such as a cycloalkyl ring, a heterocycloalkyl ring, an aryl ring or a heteroaryl ring.

In addition to compounds of formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention and a pharmaceutically acceptable carrier, diluent or excipient.

In a further aspect the present invention provides a method of prevention or treatment of a condition in a mammal, the method comprising administering an effective amount of a compound of the invention. In one embodiment the condition is a condition that can be treated by inhibition of 11β-HSD1.

In yet an even further aspect the invention provides the use of a compound of the invention in the preparation of a medicament for the treatment of a condition in a mammal. In one embodiment the condition is a condition that can be treated by inhibition of 11β-HSD1.

In yet an even further aspect the invention provides the use of a compound of the invention in the treatment of a condition in a mammal. In one embodiment the condition is a condition that can be treated by inhibition of 11β-HSD1.

In some embodiments the condition is selected from the group consisting of is selected from the group consisting of diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy and other ocular disorders, nephropathy, neuropathy, myopathy, osteoporosis, osteoarthritis, dementia, depression, neurodegenerative disease, psychiatric disorders, Polycystic ovaries syndrome, infertility, Cushing's Disease, Cushing's syndrome, viral diseases, and inflammatory diseases.

In some embodiments the condition is diabetes. In some embodiments the condition is type II diabetes.

In some embodiments the compound is administered in combination with an adjuvant. In some embodiments the adjuvant is selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha.-glucosidase inhibitors; (f) GLP-1, GLP-1 analogs, and GLP-1 receptor agonists; and combinations thereof.

In one other embodiment the compound is administered as a substitute for monotherapy or combination therapy, in an event of failure of treatment by an agent selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha.-glucosidase inhibitors; (f) GLP-1, GLP-1 analogs, and GLP-1 receptor agonists; and combinations thereof.

In one embodiment the insulin sensitizing agent is selected from the group consisting of (i) PPAR-gamma-agonists, (ii)

PPAR-alpha-agonists, (iii) PPAR-alpha/gamma-dual agonists, (iv) biguanides, and combinations thereof.

These and other teachings of the invention are set forth herein.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^e$, —C(=O)OR$^e$, C(=O)NR$^e$R$^f$, C(=NOH)R$^e$, C(=NR$^e$)NR$^f$R$^g$, NR$^e$R$^f$, NR$^e$C(=O)R$^f$, NR$^e$C(=O)OR$^f$, NR$^e$C(=O)NR$^f$R$^g$, NR$^e$C(=NR$^f$)NR$^g$R$^h$, NR$^e$SO$_2$R$^f$, —SR$^e$, SO$_2$NR$^e$R$^f$, —OR$^e$, OC(=O)NR$^e$R$^f$, OC(=O)R$^e$ and acyl, wherein R$^e$, R$^f$, R$^g$ and R$^h$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_1$-C$_{10}$heteroalkyl, C$_3$-C$_{12}$cycloalkyl, C$_3$-C$_{12}$cycloalkenyl, C$_1$-C$_{12}$heterocycloalkyl, C$_1$-C$_{12}$heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. The alkenyl group is preferably a 1-alkenyl group. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{12}$alkyl, more preferably a C$_1$-C$_{10}$alkyl, most preferably C$_1$-C$_6$ unless otherwise noted. Examples of suitable straight and branched C$_1$-C$_6$alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a (alkyl)$_2$N— group, in which each alkyl may be the same or different and are each as defined herein for alkyl. The alkyl group is preferably a C$_1$-C$_6$alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a C$_1$-C$_6$alkyloxy. Examples include, but are not limited to, methoxy and ethoxy. The group may be a terminal group or a bridging group.

"Alkyloxyalkyl" refers to an alkyloxy-alkyl- group in which the alkyloxy and alkyl moieties are as defined herein.

The group may be a terminal group or a bridging group. If the group is a terminal group it is bonded to the remainder of the molecule through the alkyl group.

"Alkyloxyaryl" refers to an alkyloxy-aryl- group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl- group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aminoalkyl" means an $NH_2$-alkyl- group in which the alkyl group is as defined herein. The group may be a terminal group or a bridging group. If the group is a terminal group it is bonded to the remainder of the molecule through the alkyl group.

"Aminosulfonyl" means an $NH_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. Di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group, may be a terminal group or a bridging group. If the group is a terminal group it is bonded to the remainder of the molecule through the alkenyl group.

"Cycloalkylheteroalkyl" means a cycloalkyl-heteroalkyl- group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

Failure of treatment can be defined as condition in which a non-fasting blood glucose level of less than 200 mg/dl and a blood glucose level during fasting (deprived of food for at least 8 hr) of less than 126 mg/dl are retained after administration of the agent in its recommended dose.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl- group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$heterocycloalkyl group. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl)methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Specific compounds of the invention include the following:

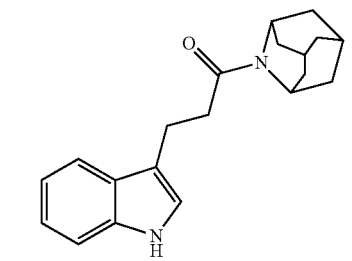

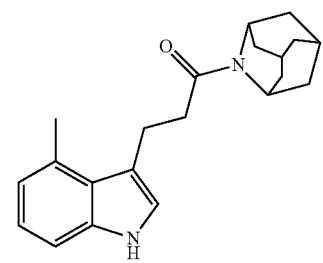

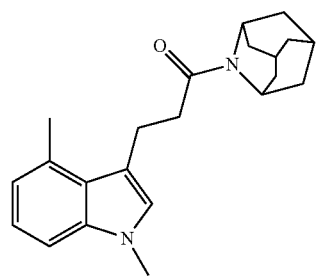

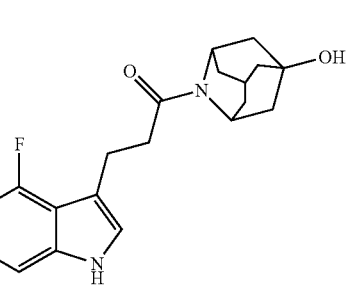

-continued

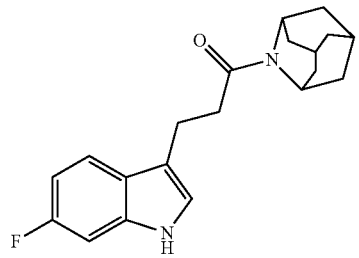

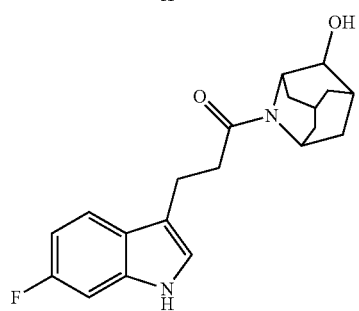

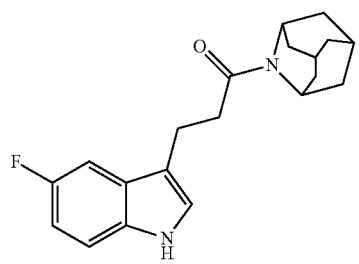

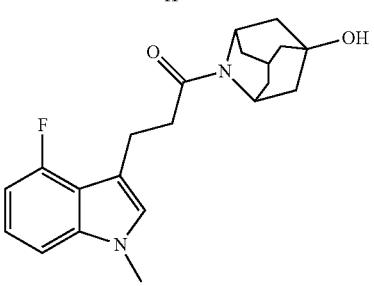

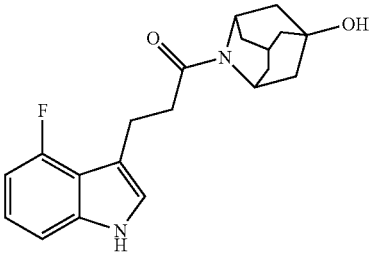

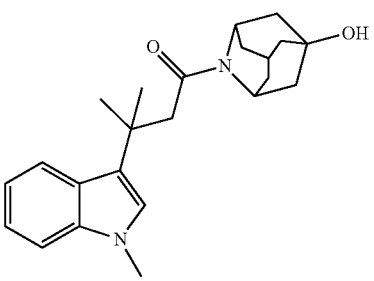

25
-continued
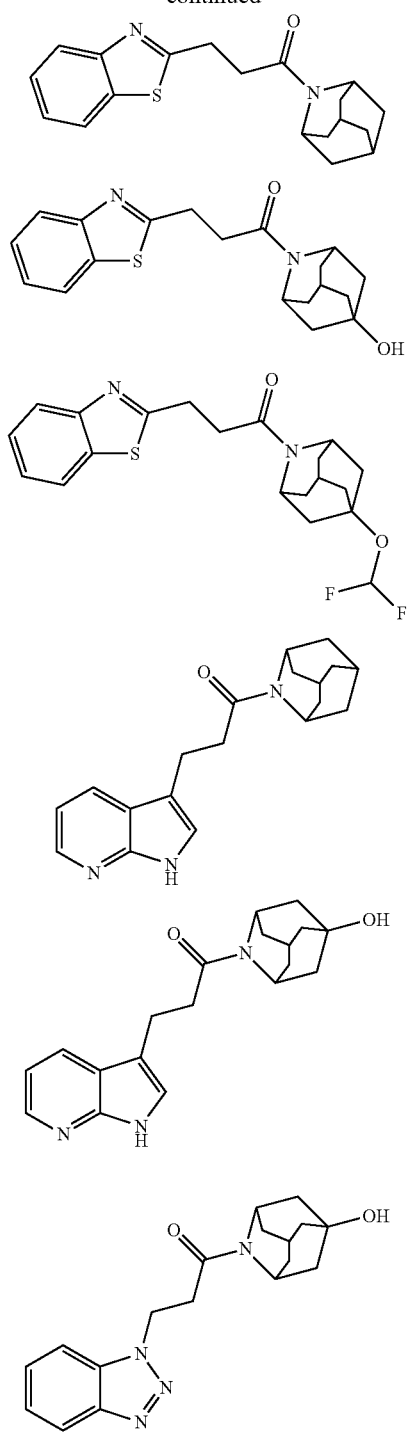
26
-continued
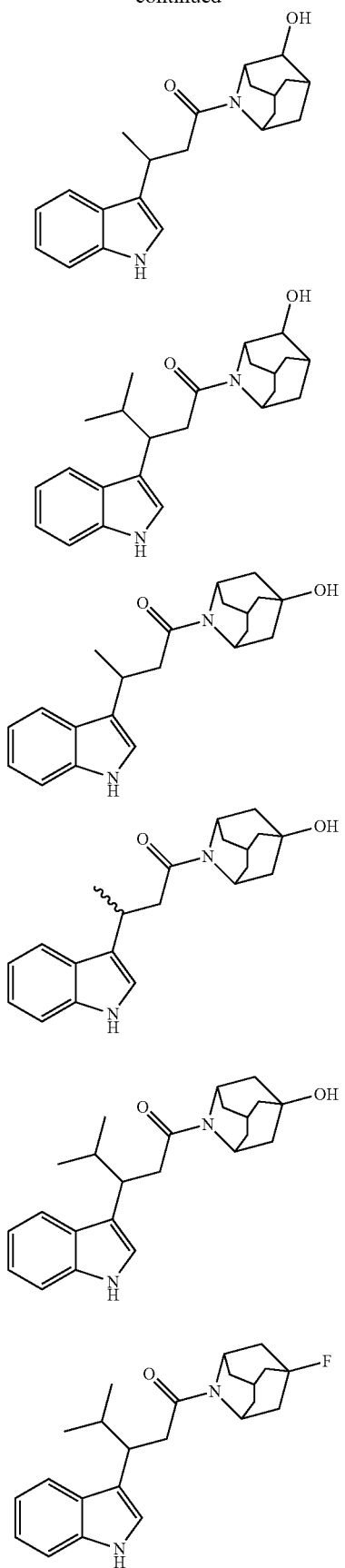

-continued
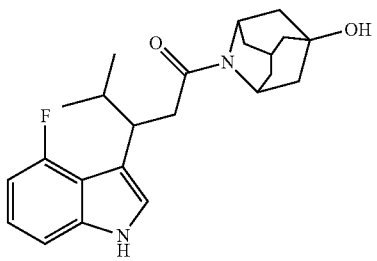
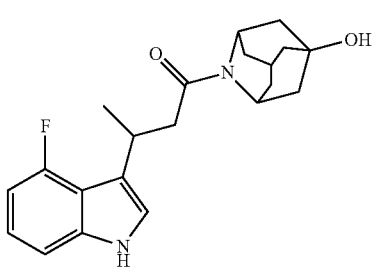
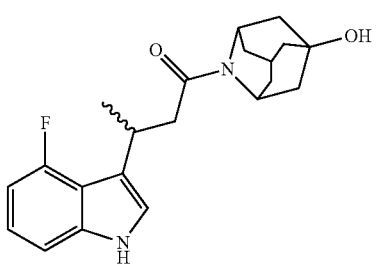
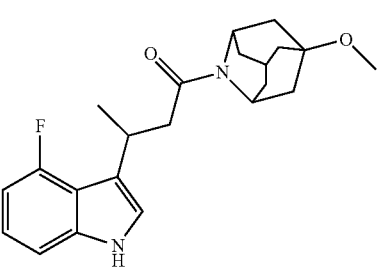
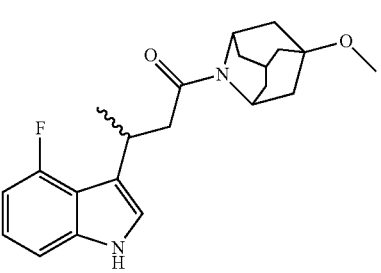
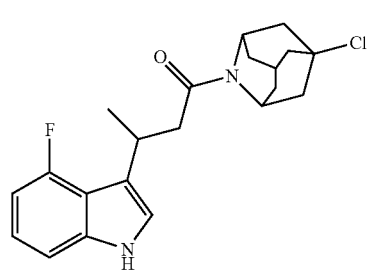
-continued
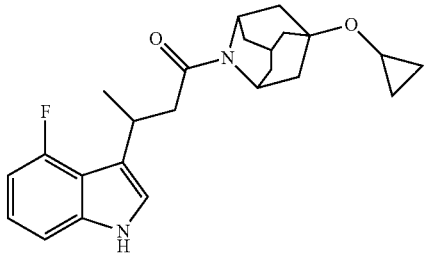
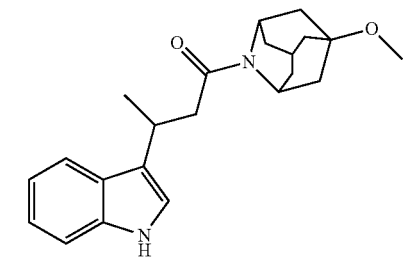
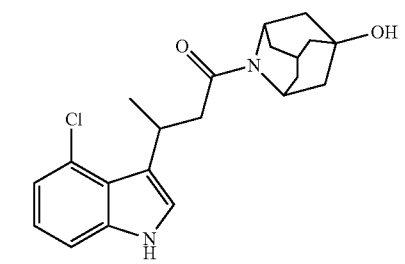
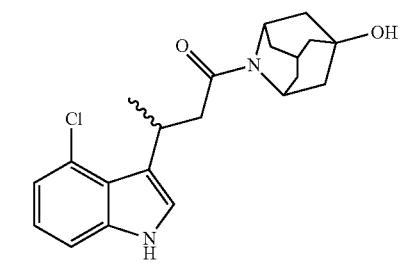
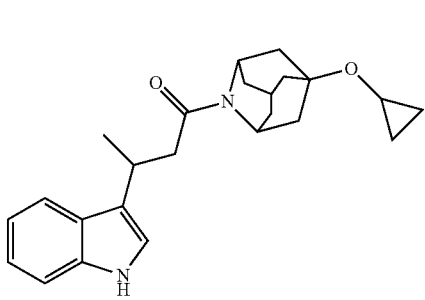
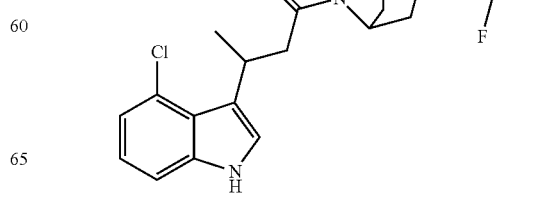

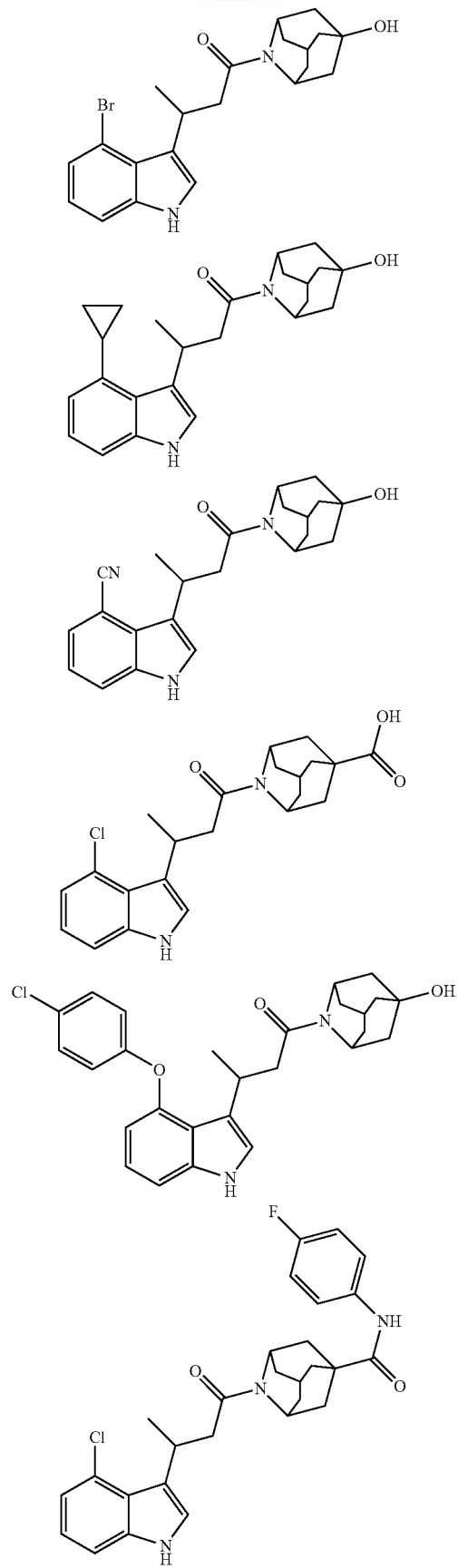
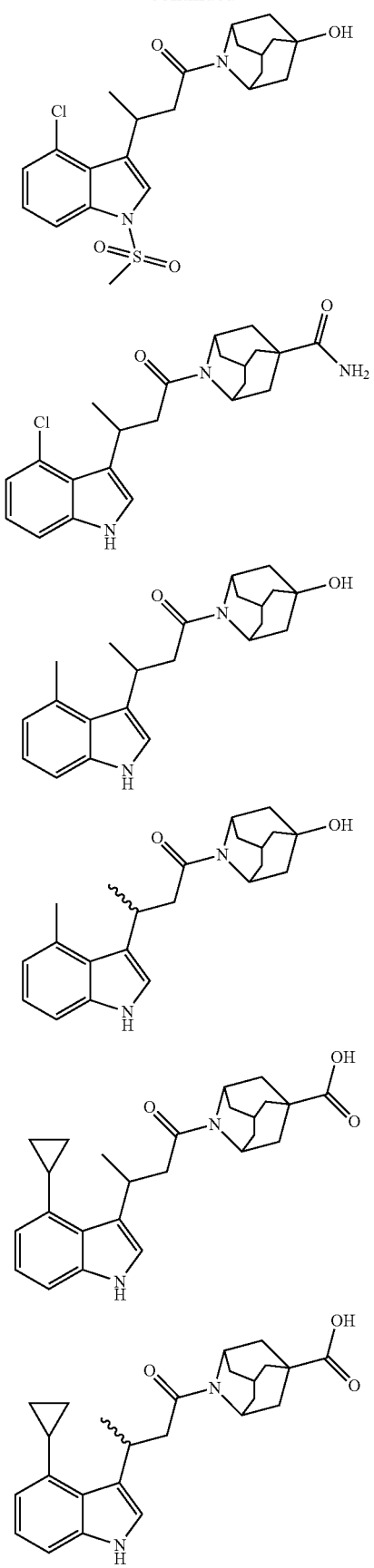

-continued
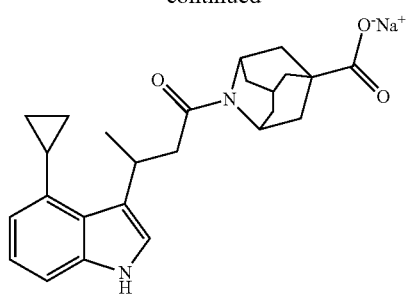
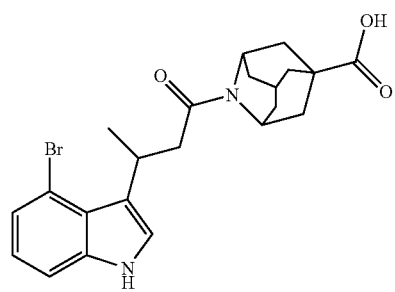
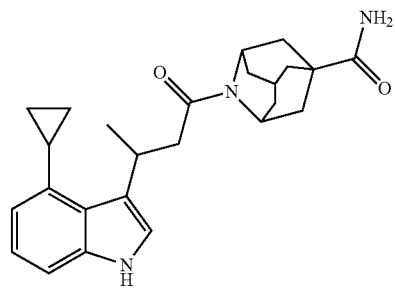
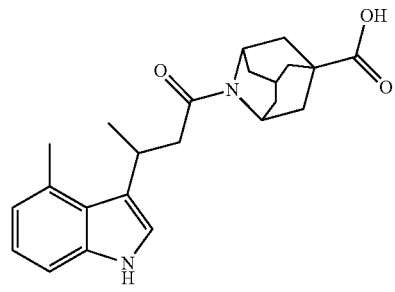
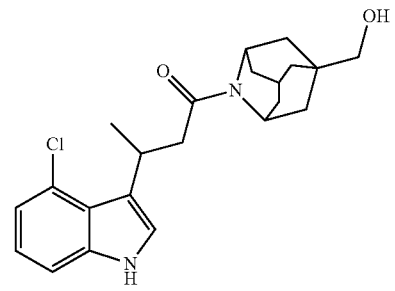
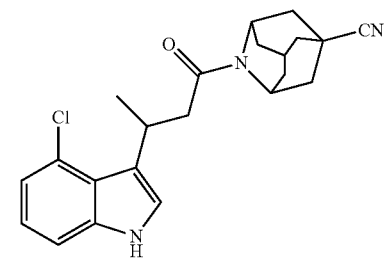
-continued
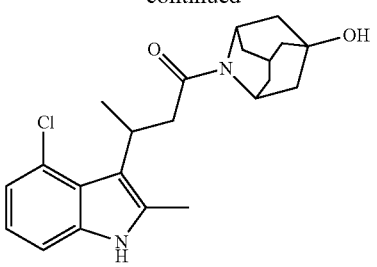
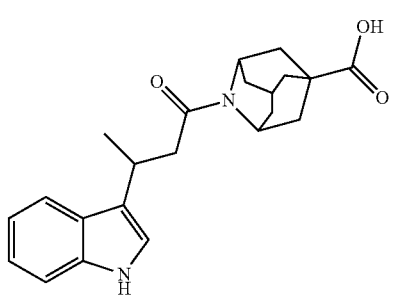
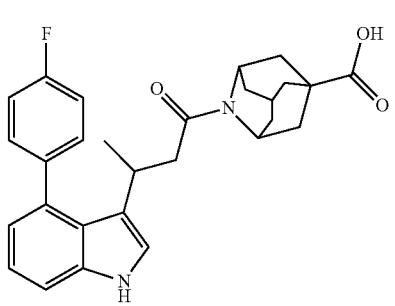
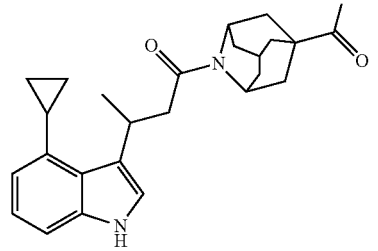
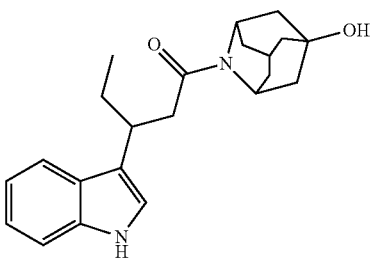

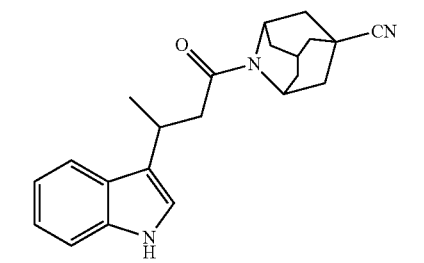
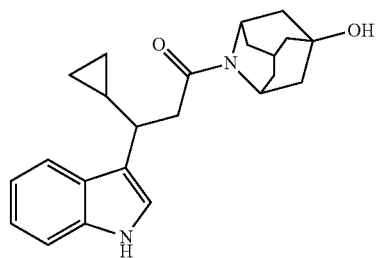
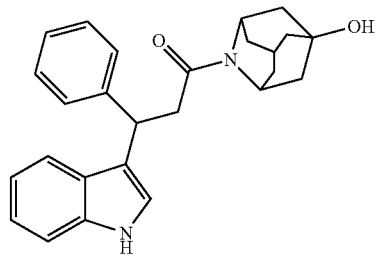
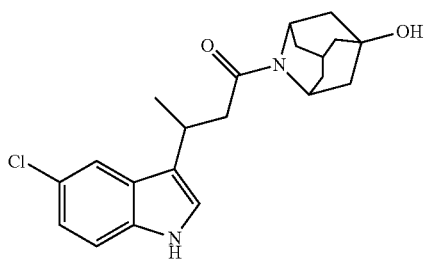
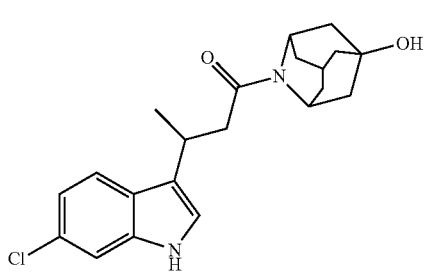
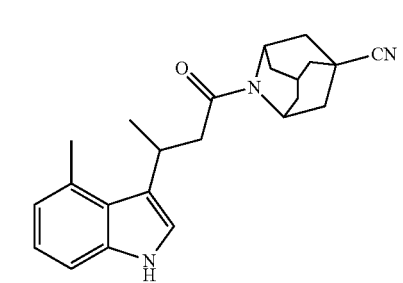
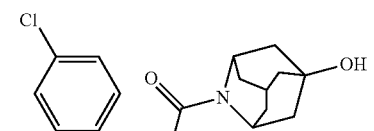
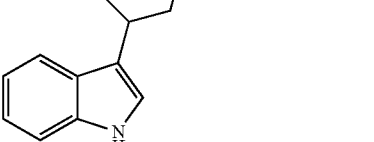
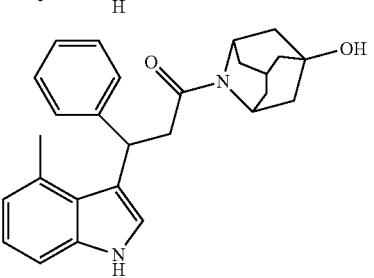
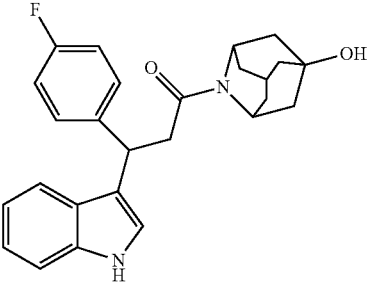
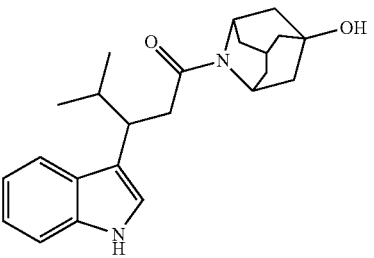
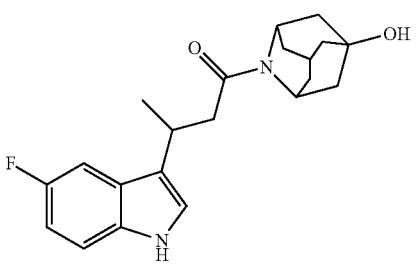
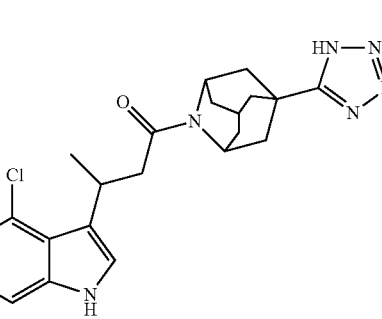

35
-continued
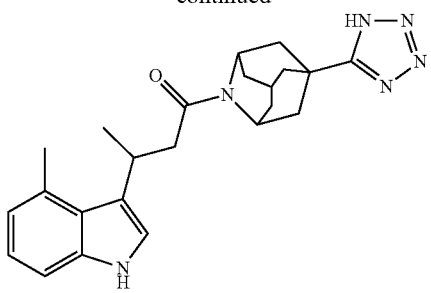
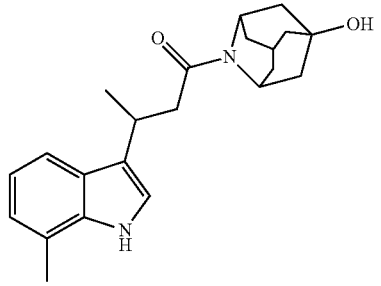
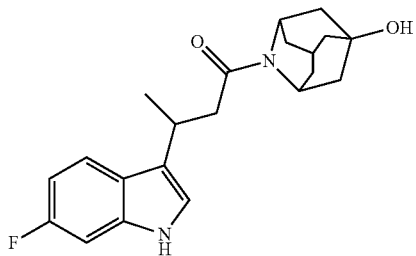
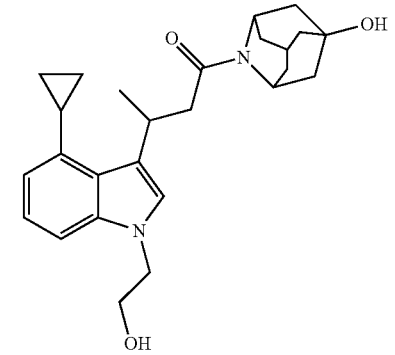
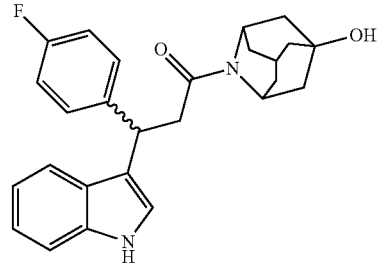
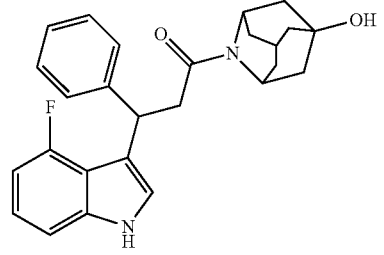
36
-continued
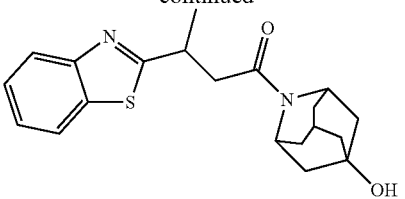
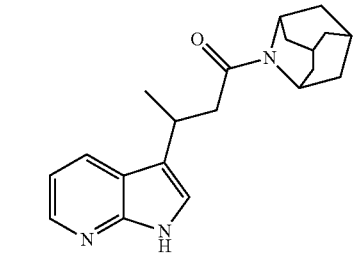
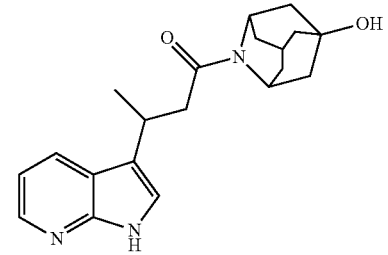
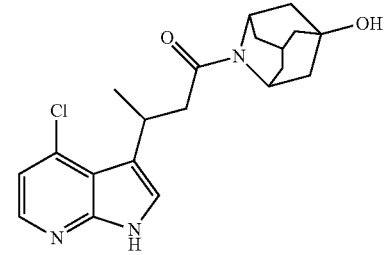
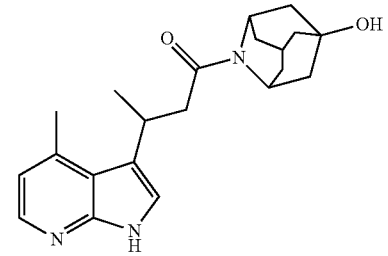
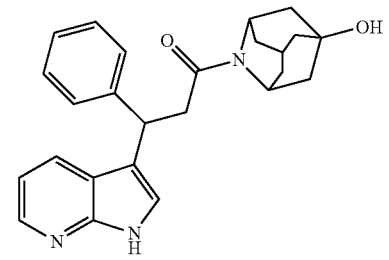
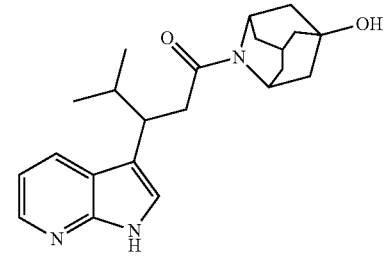

37
-continued
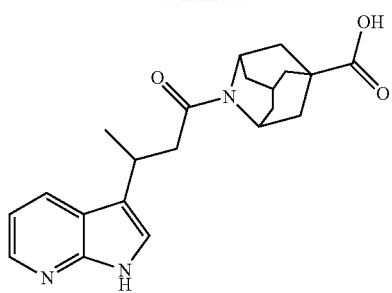
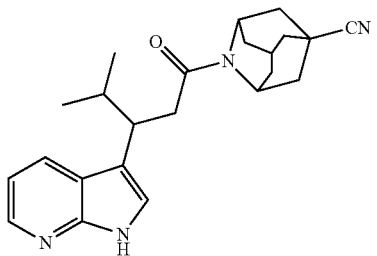
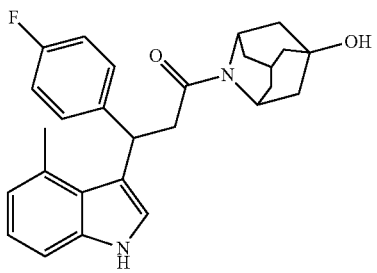
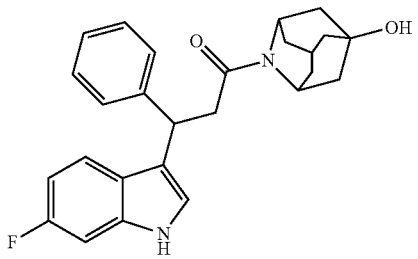
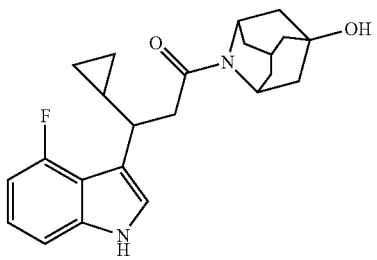
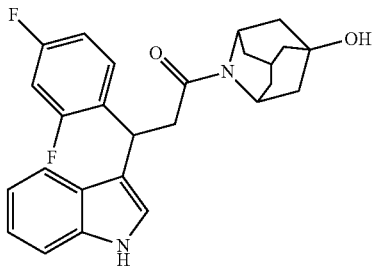
38
-continued
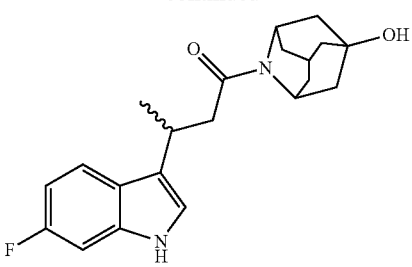
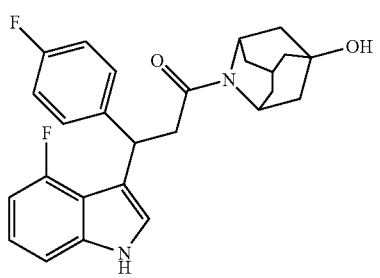
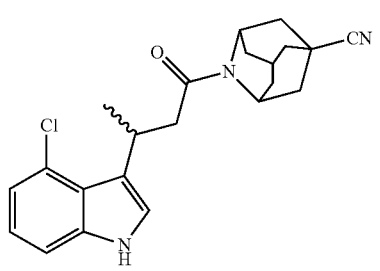
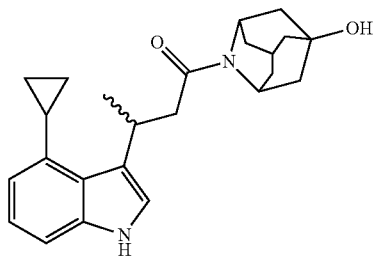
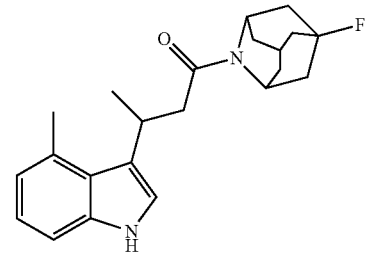
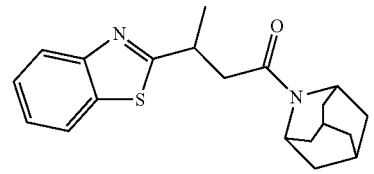
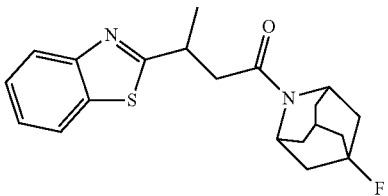

-continued
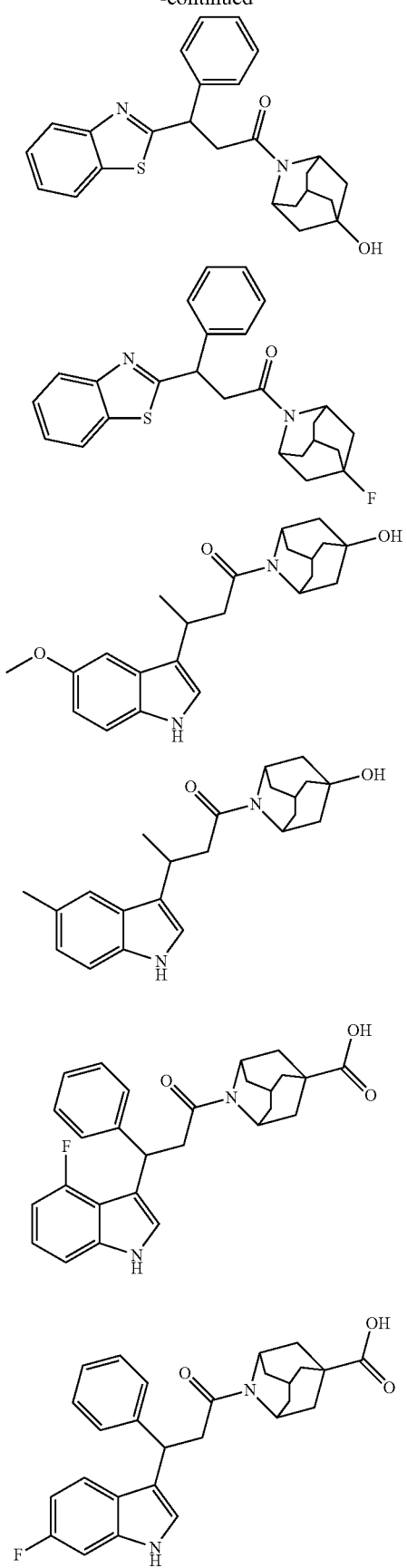
-continued
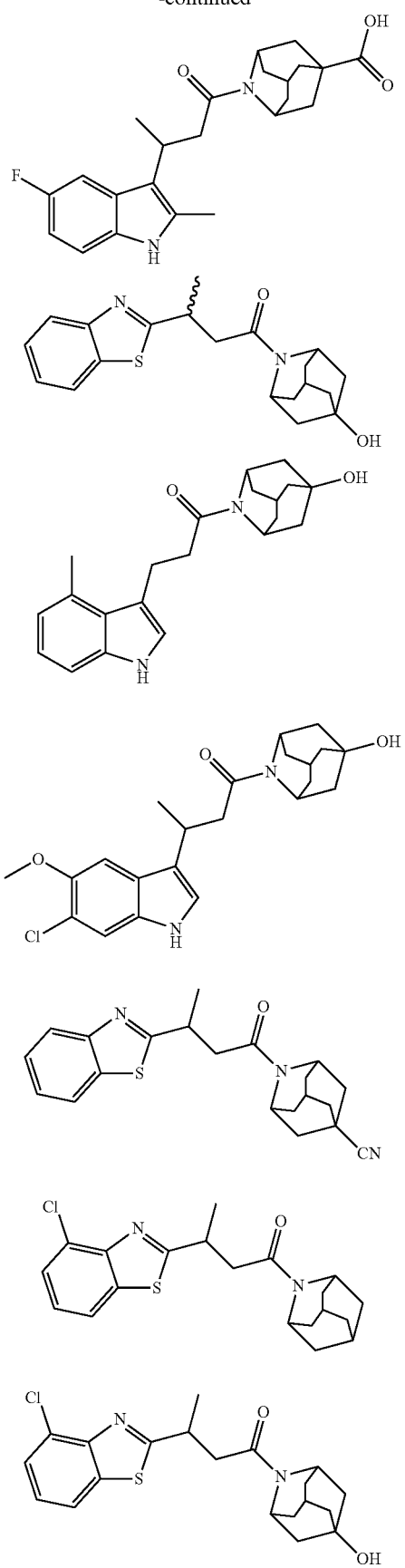

-continued
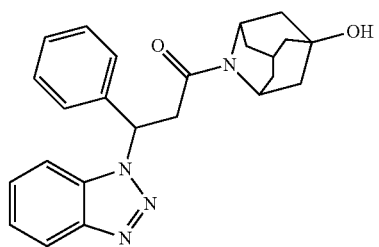
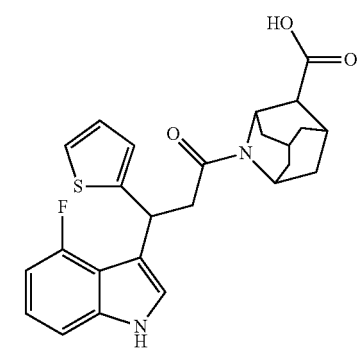
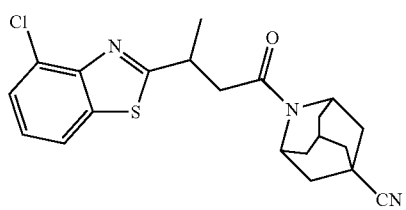
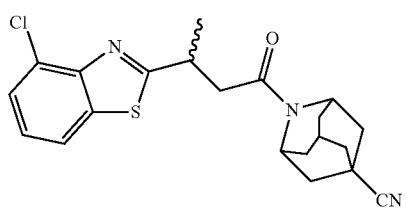
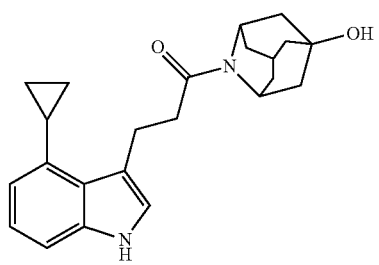
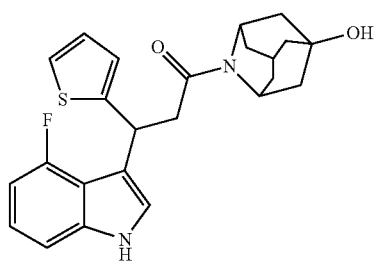
-continued
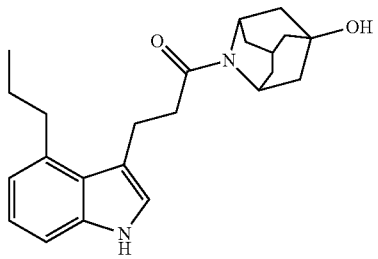
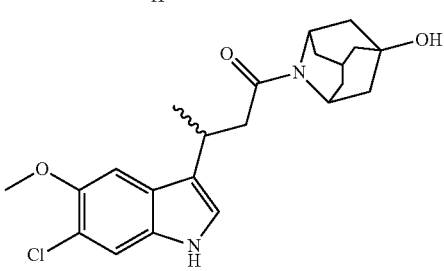
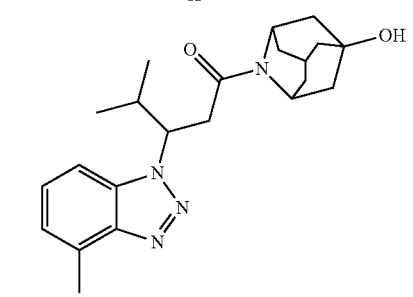
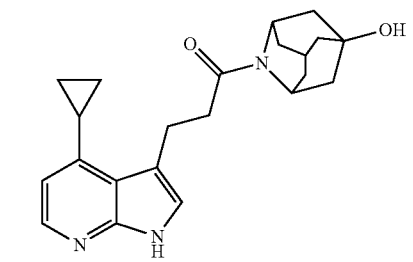
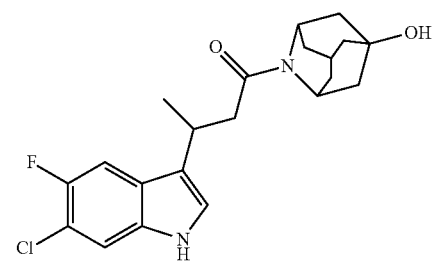
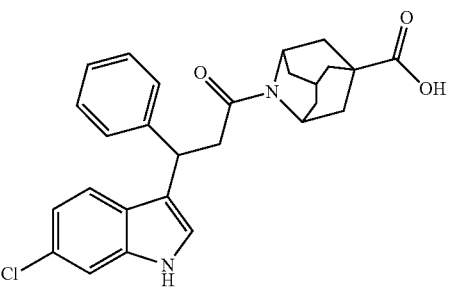

43
-continued
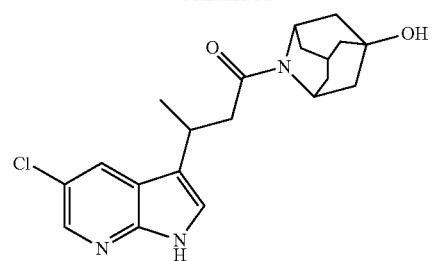
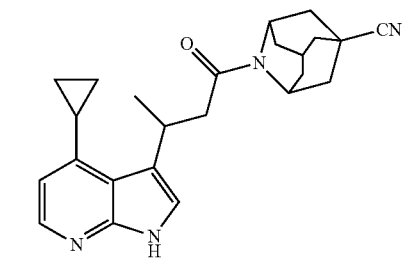
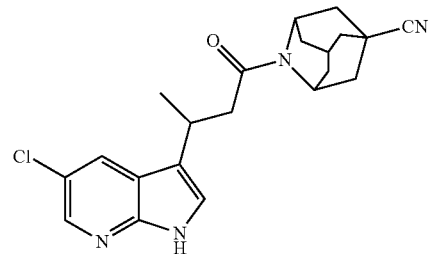
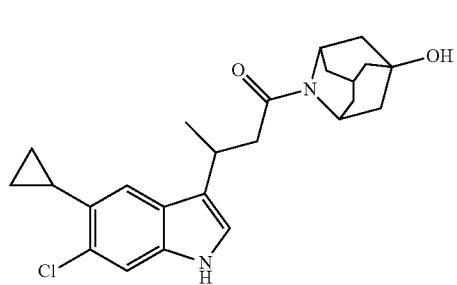
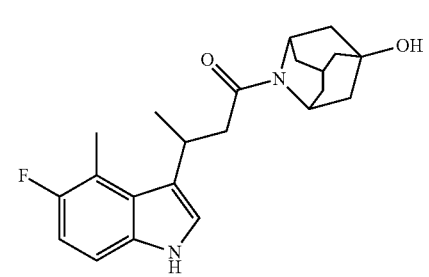
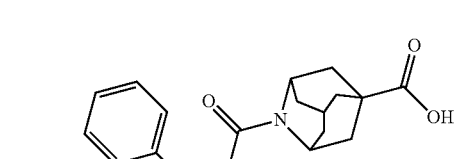
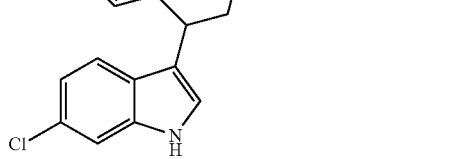
44
-continued
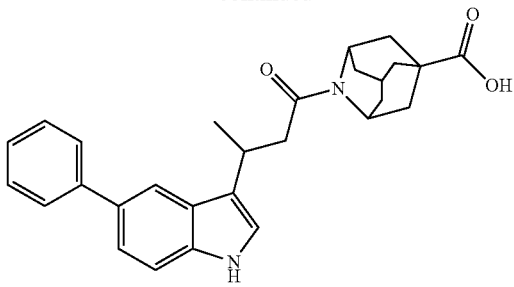
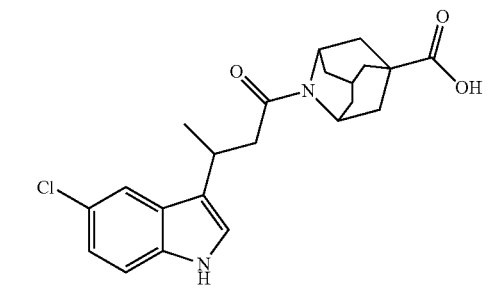
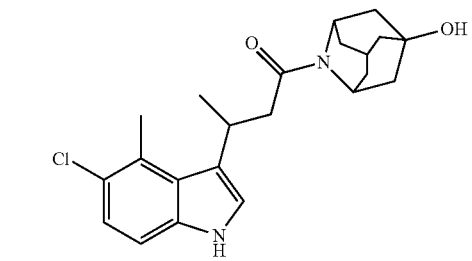
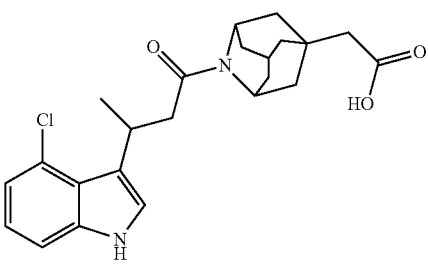
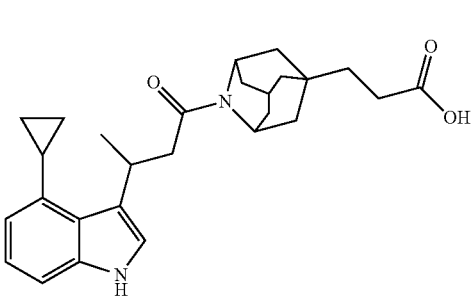
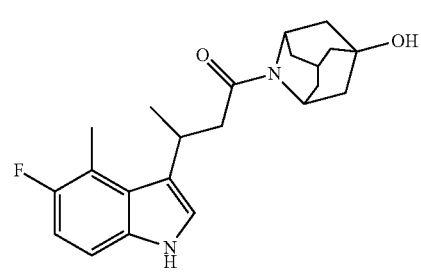

45
-continued
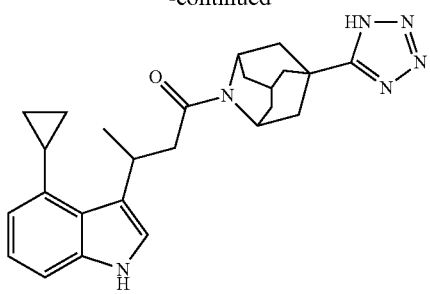
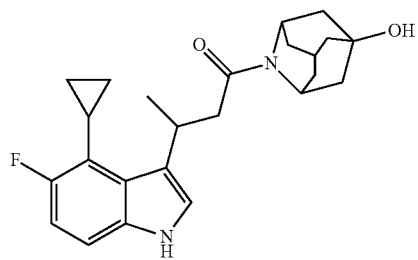
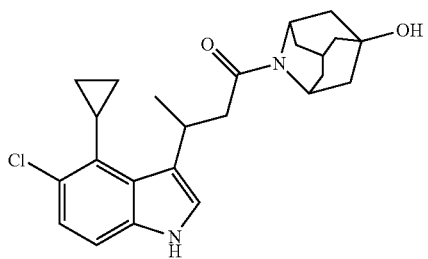
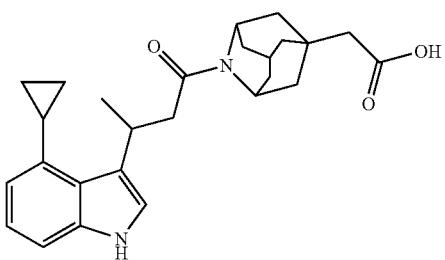
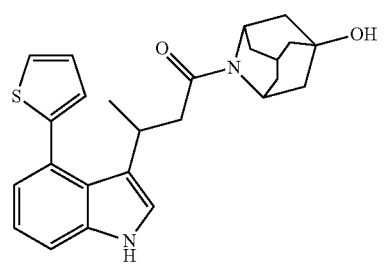
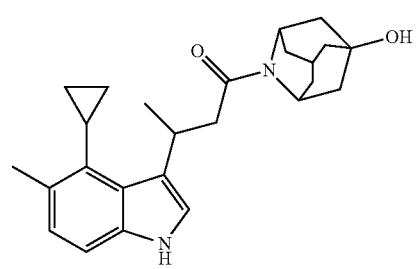
46
-continued
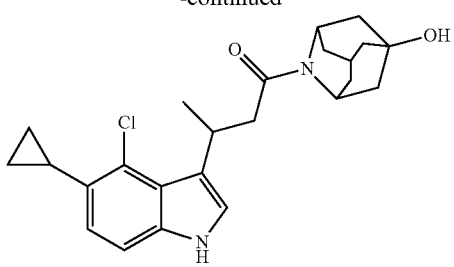
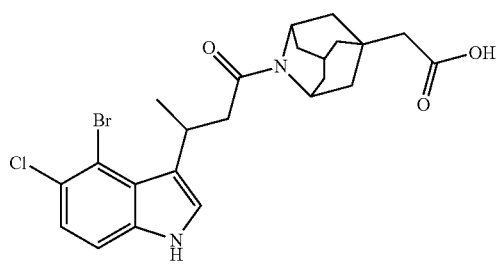
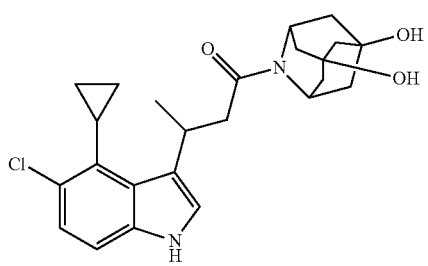
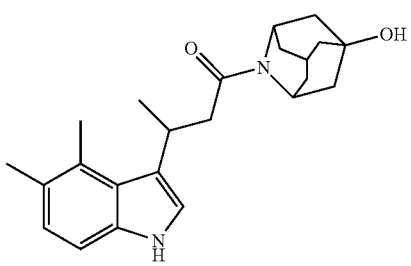
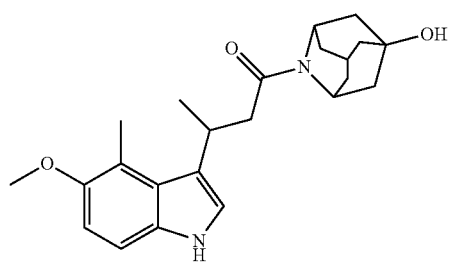
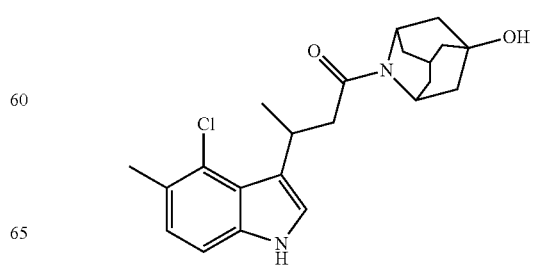

47
-continued
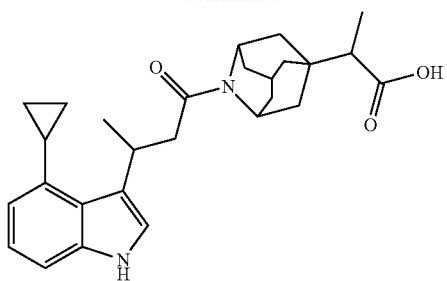
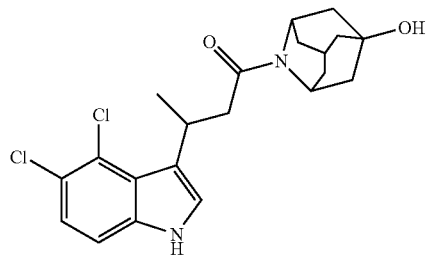
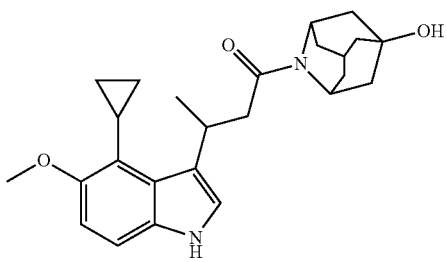
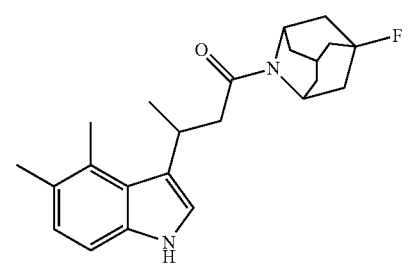
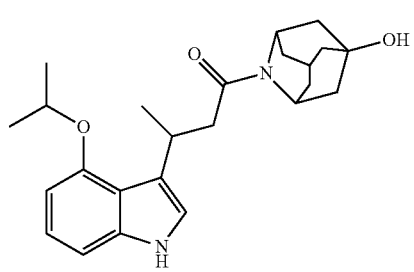
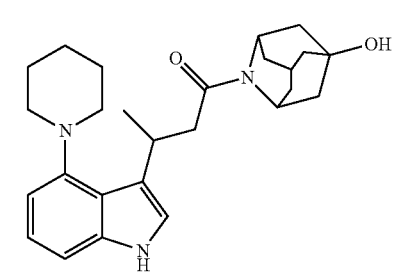
48
-continued
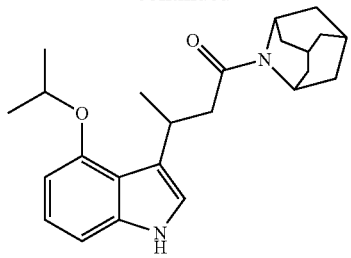
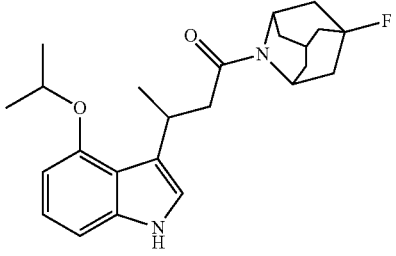
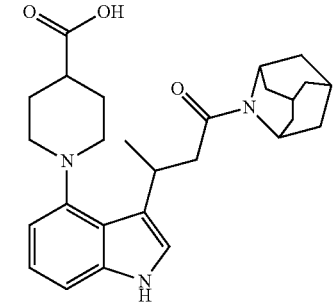
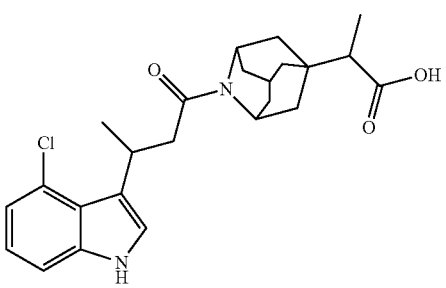
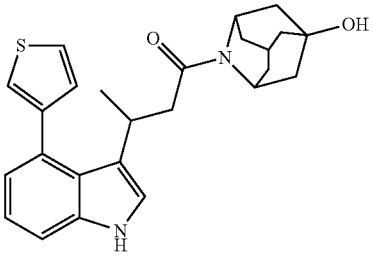
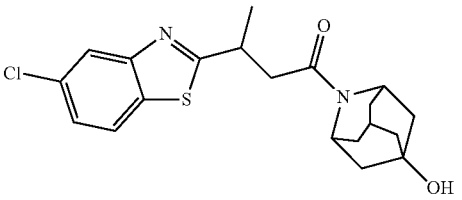

49
-continued
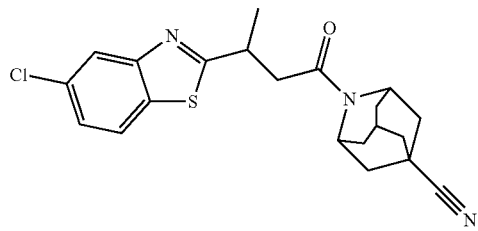
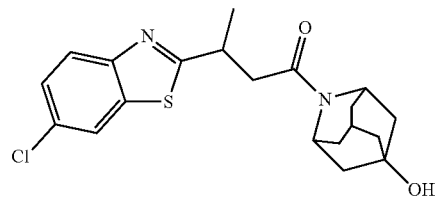
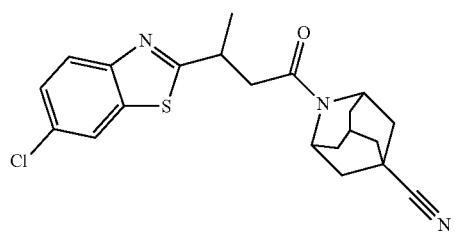
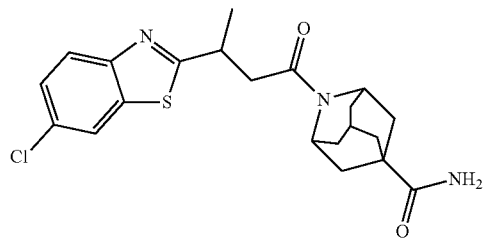
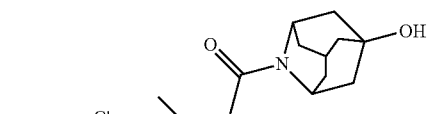
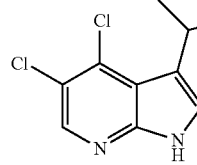
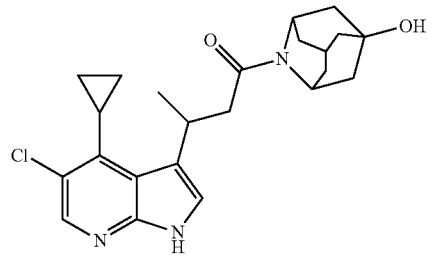
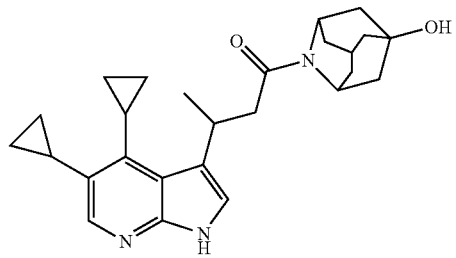
50
-continued
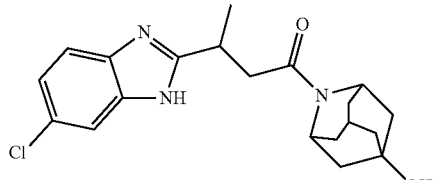
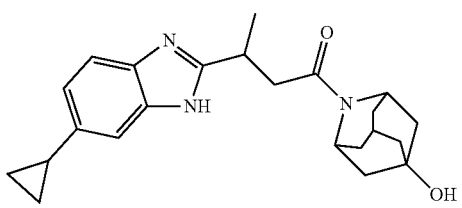
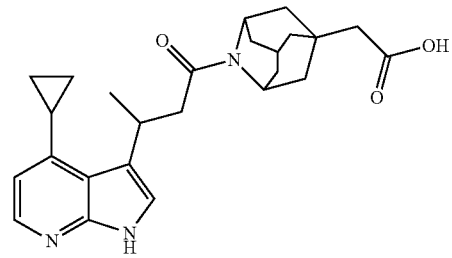
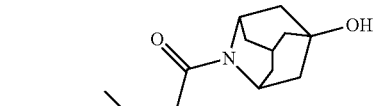
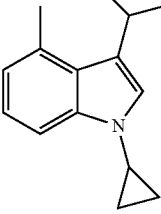
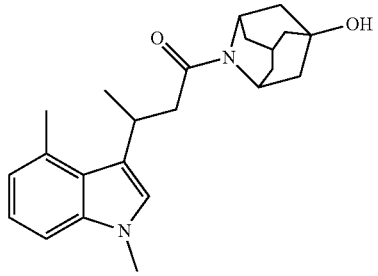
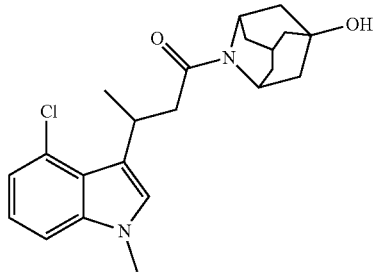

51
-continued
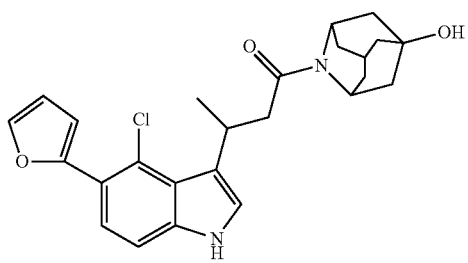
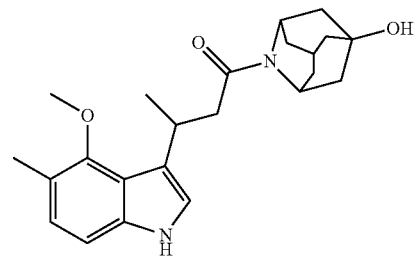
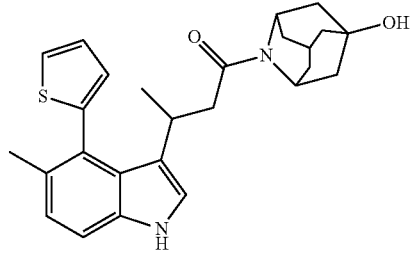
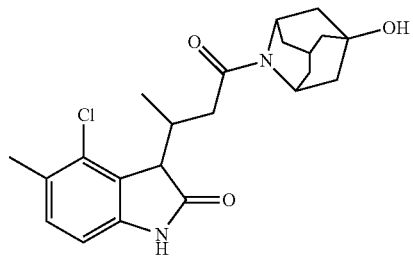
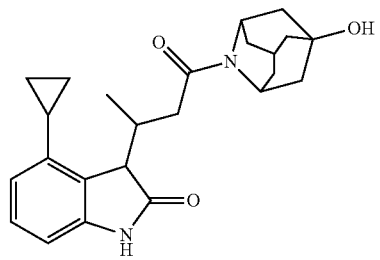
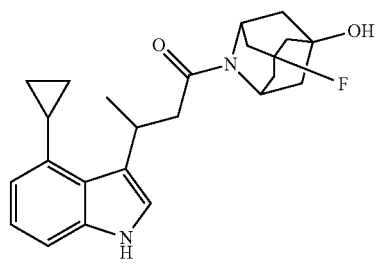
52
-continued
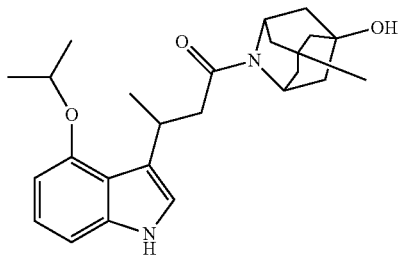
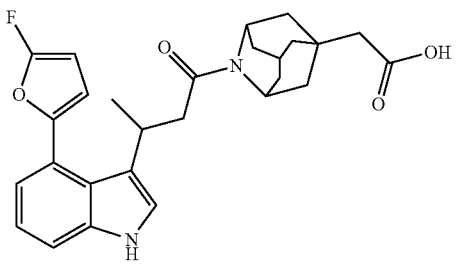
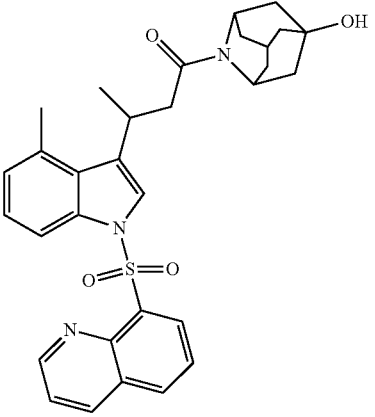
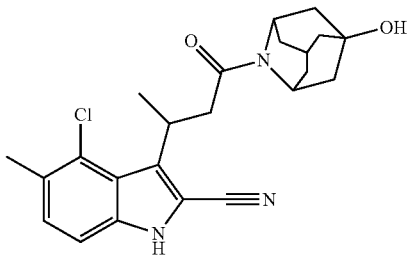
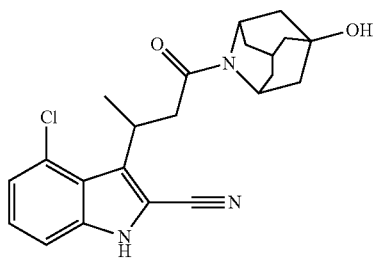
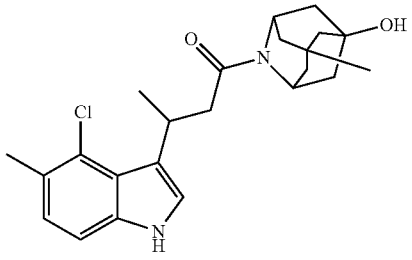

53
-continued
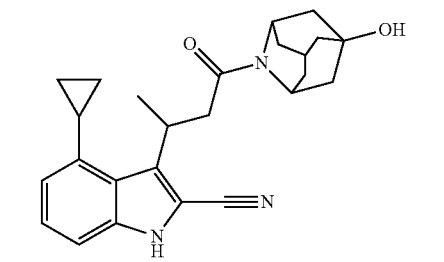
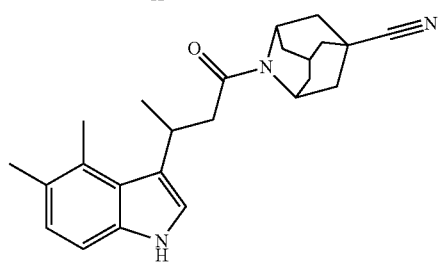
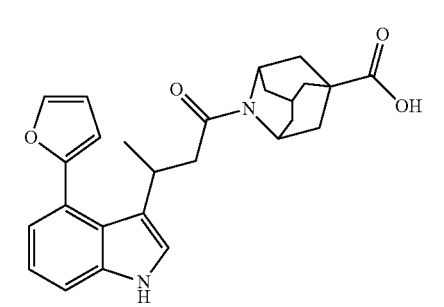
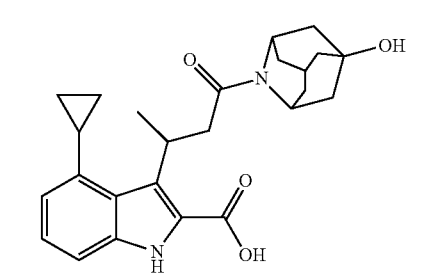
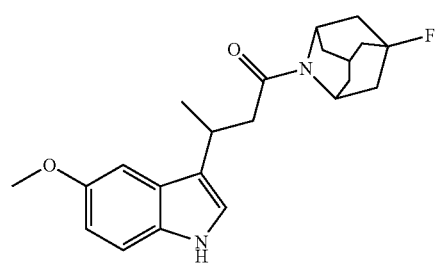
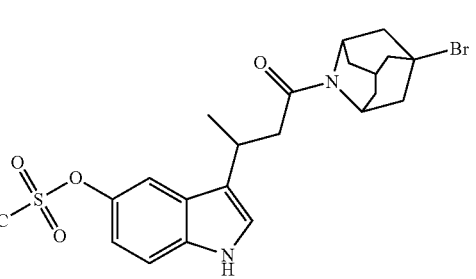
54
-continued
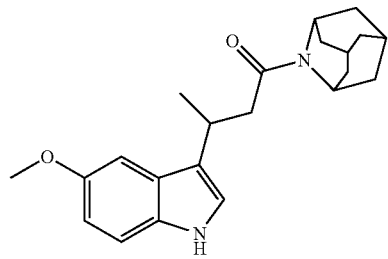
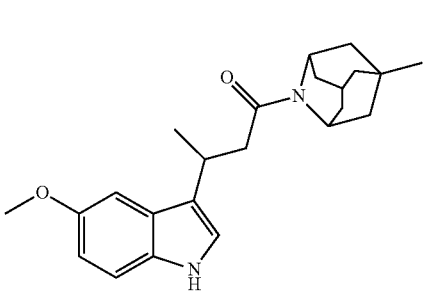
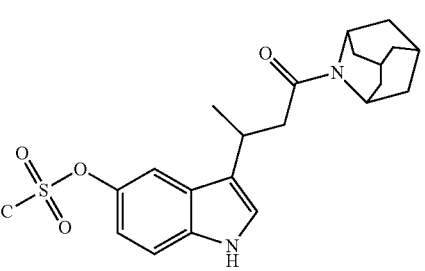
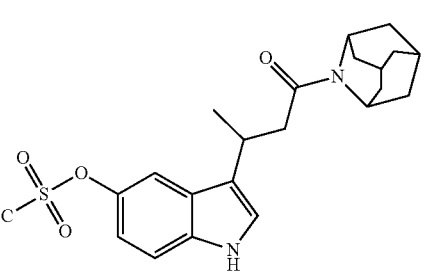
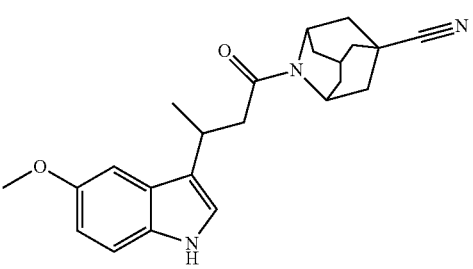
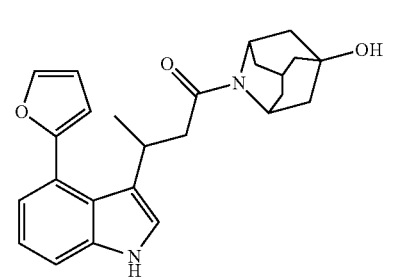

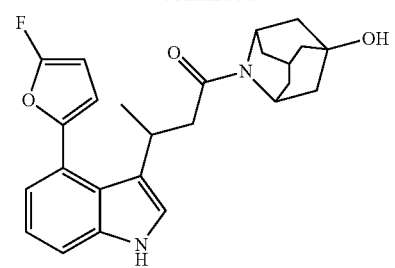
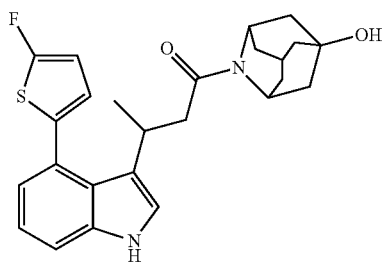
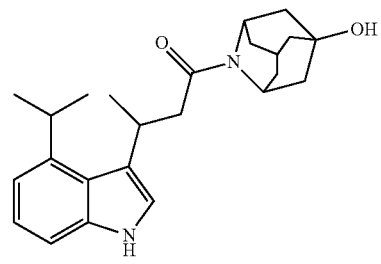
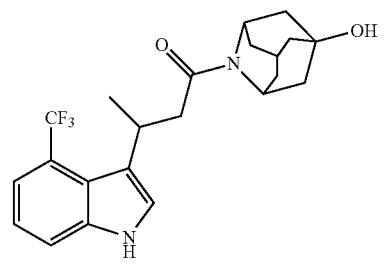
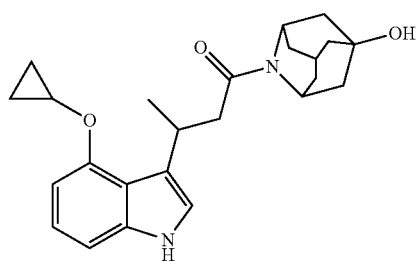
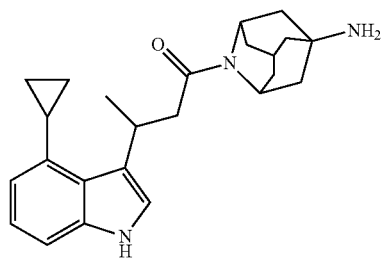
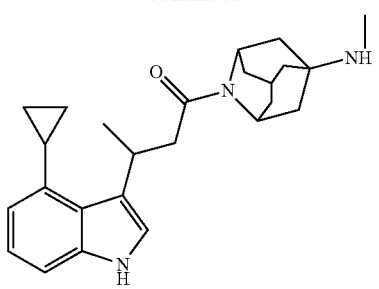
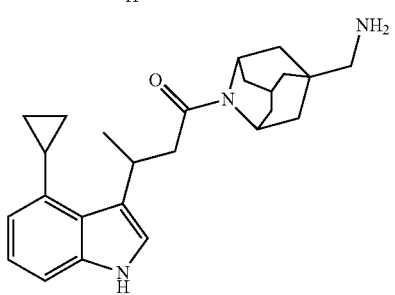
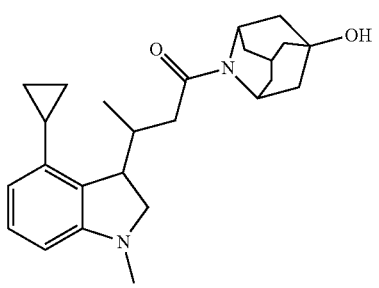
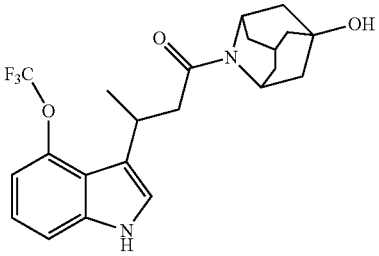
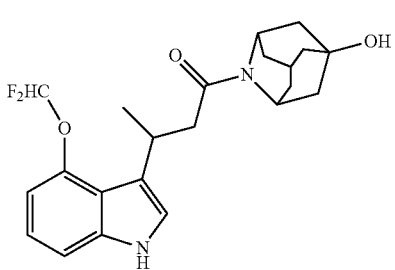
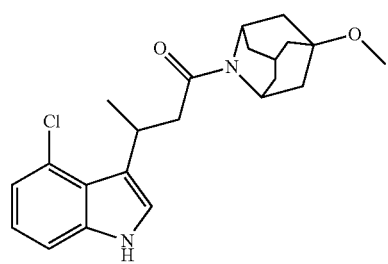

57
-continued
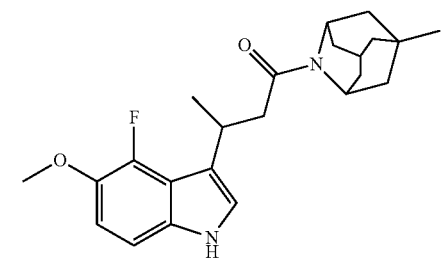
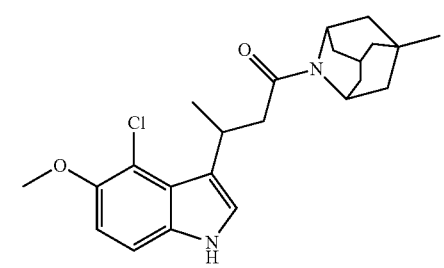
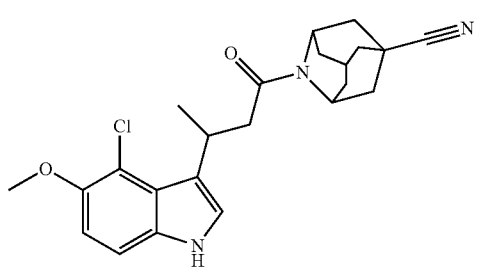
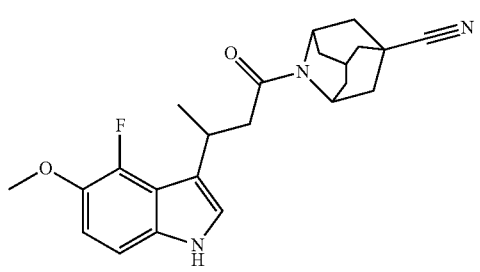
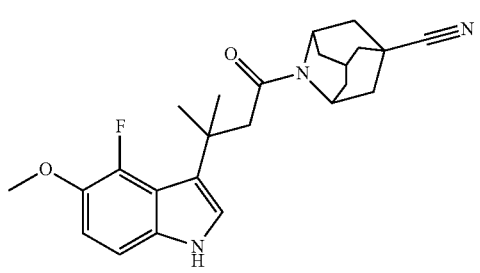
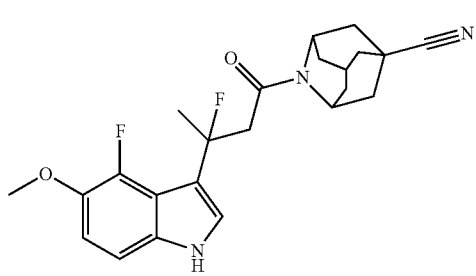
58
-continued
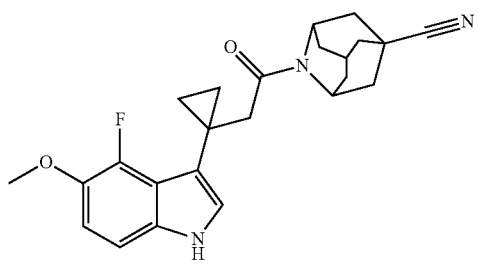
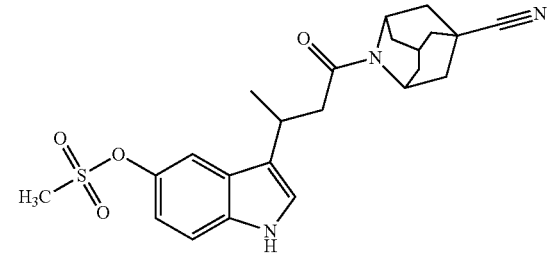
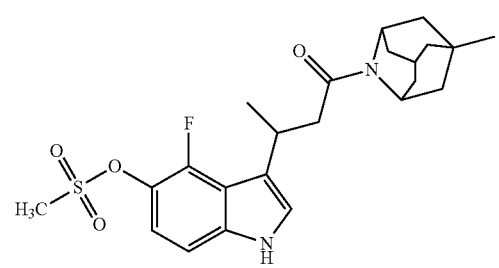
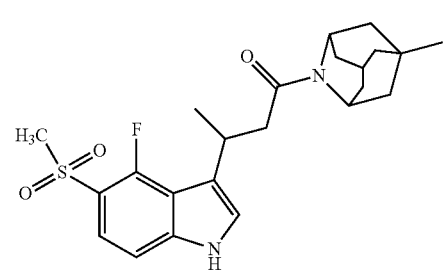
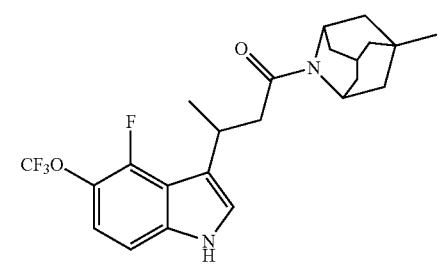
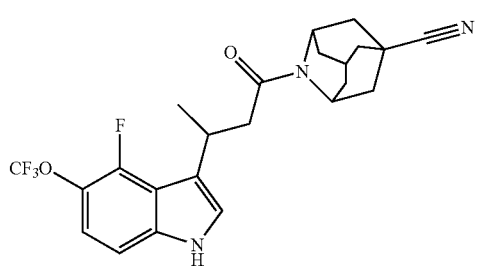

59
-continued
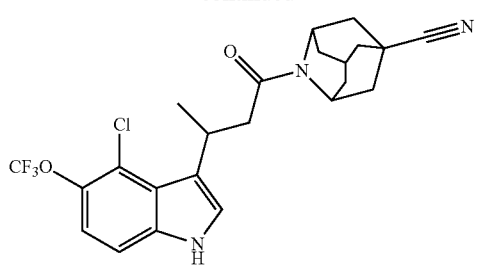
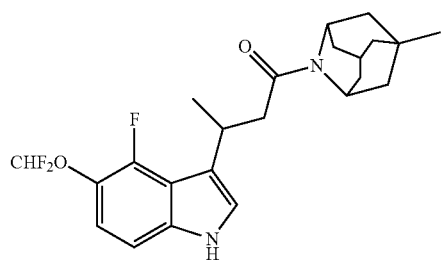
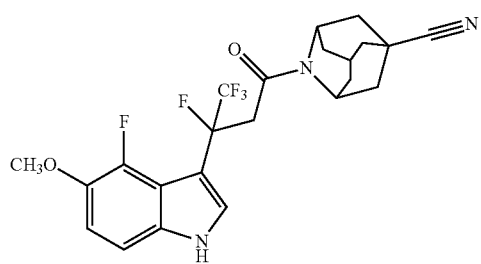
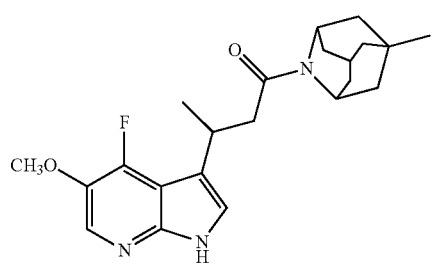
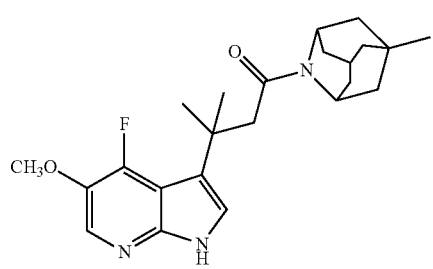
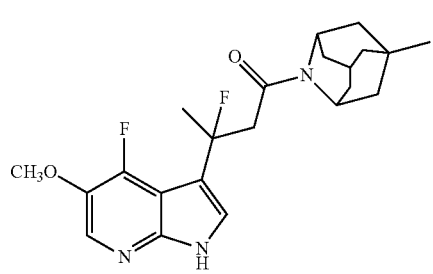
60
-continued
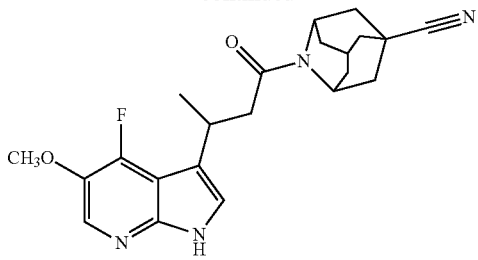
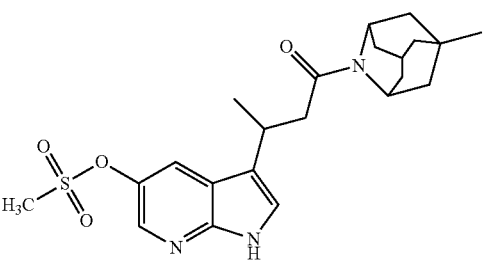
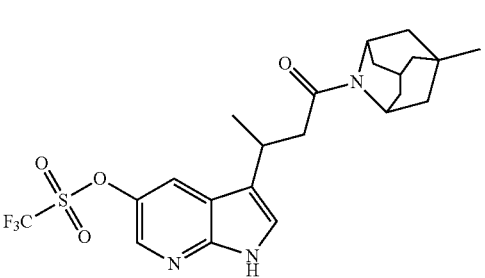
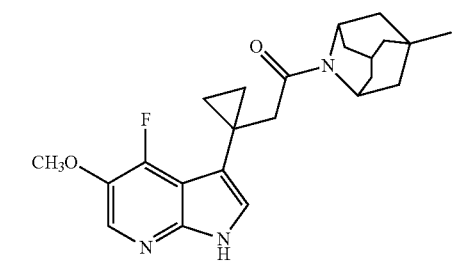
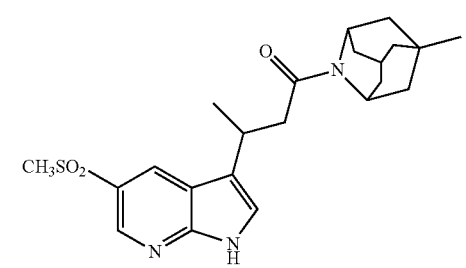
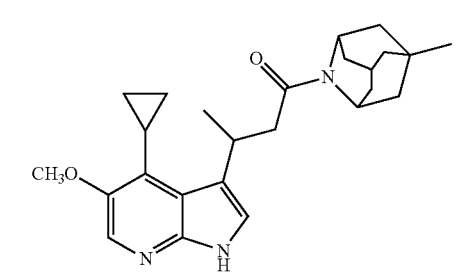

61
-continued
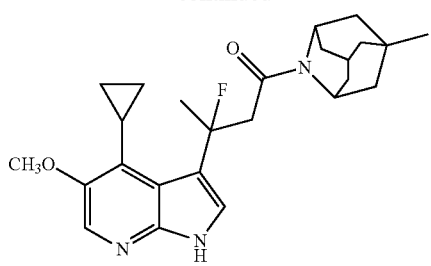
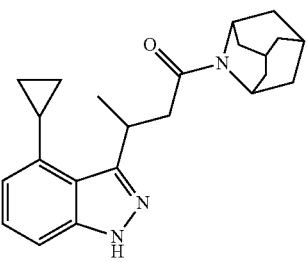
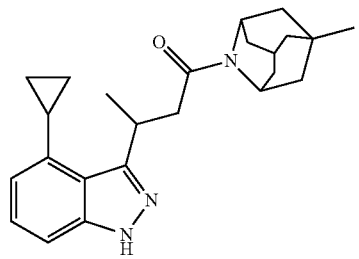
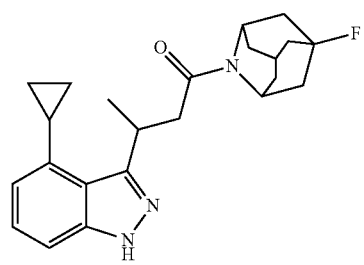
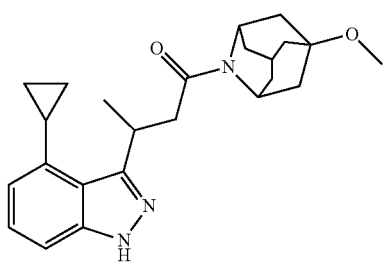
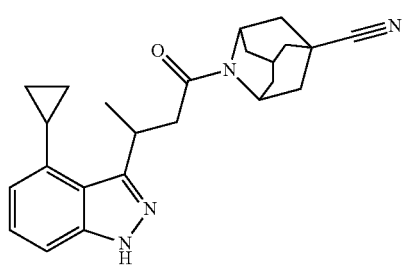
62
-continued
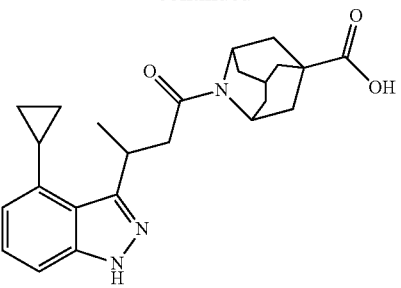
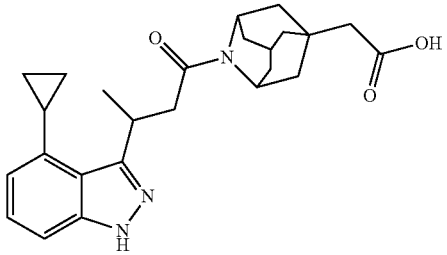
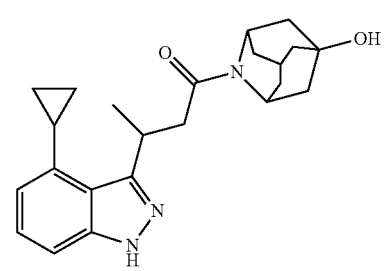
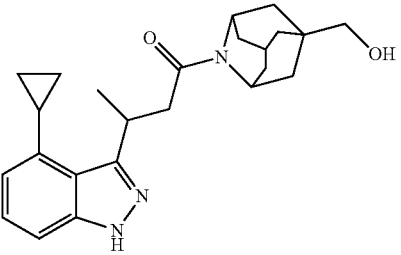
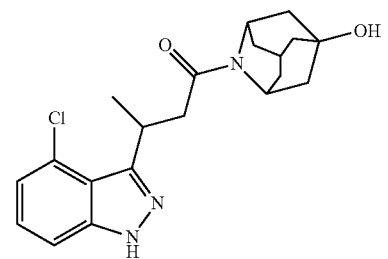
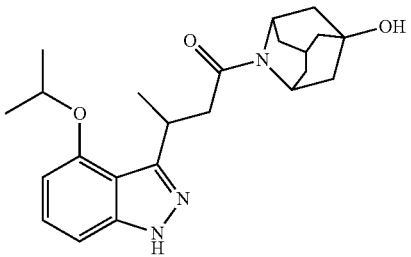

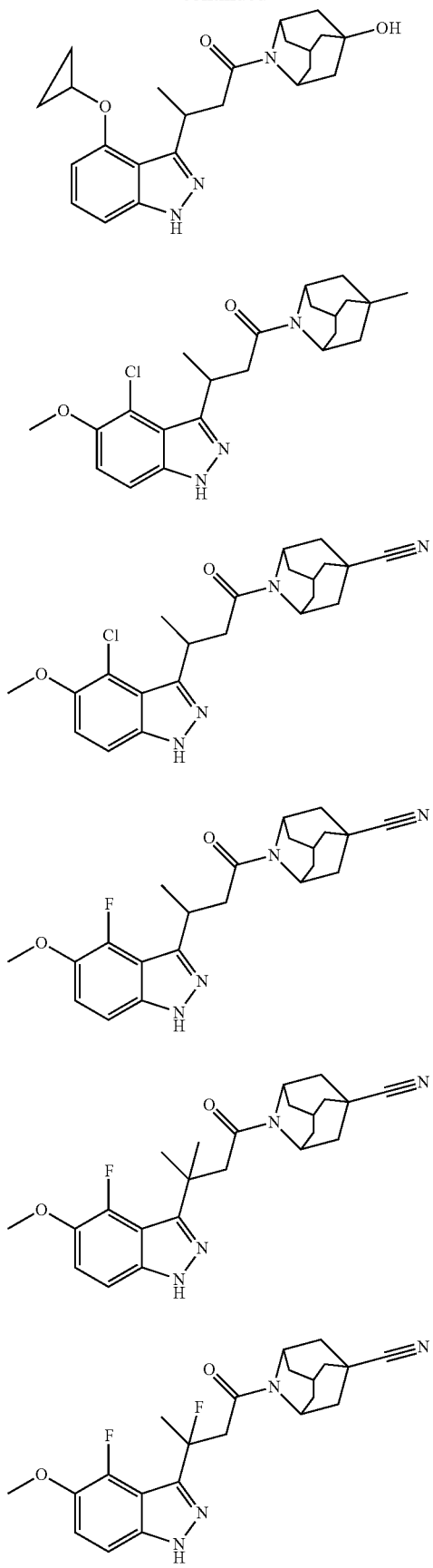
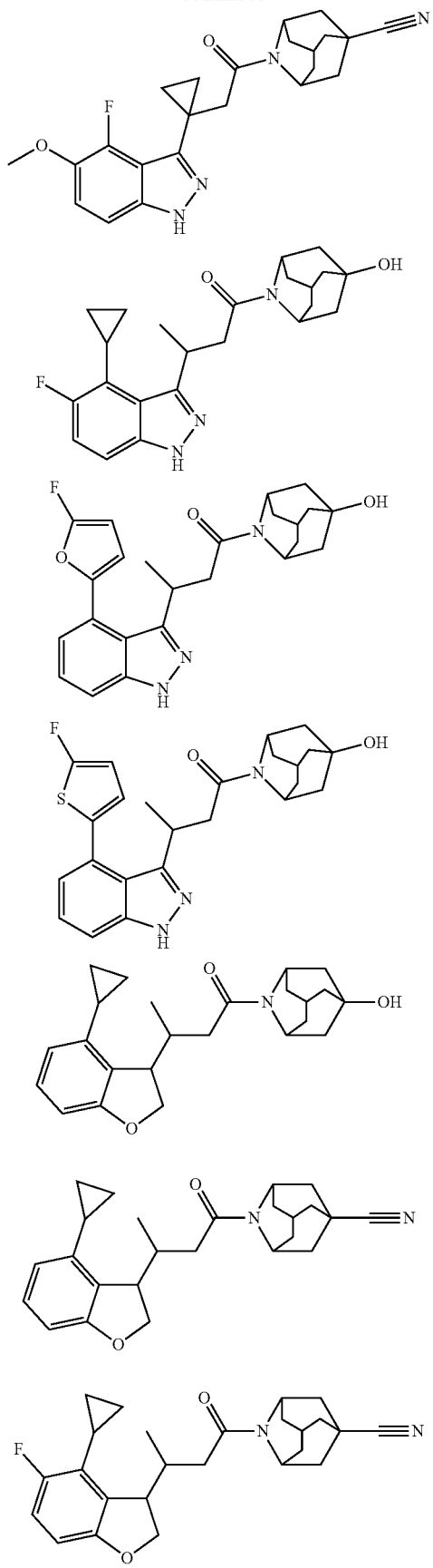

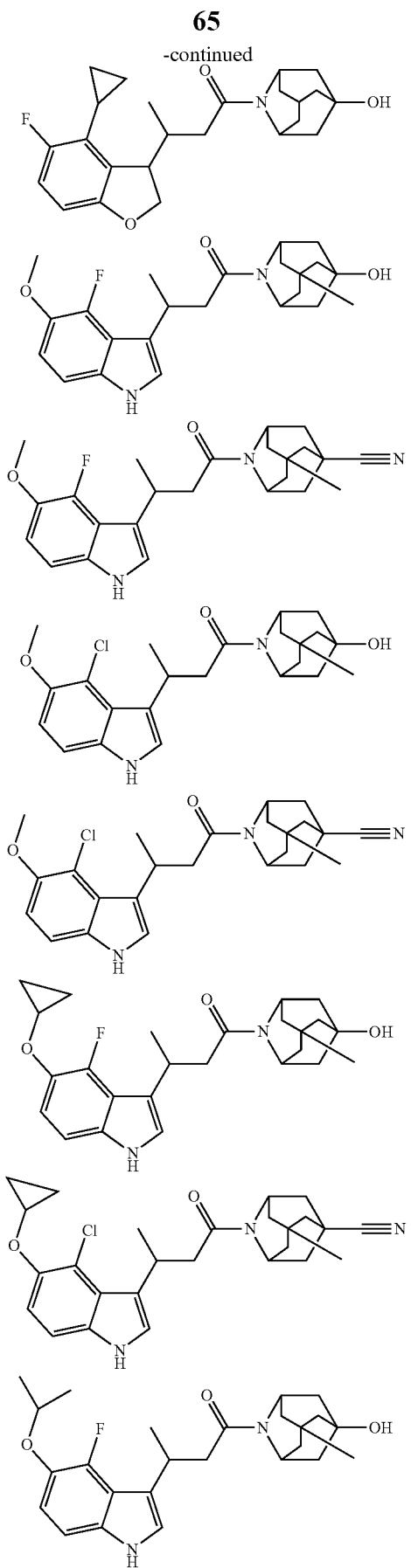
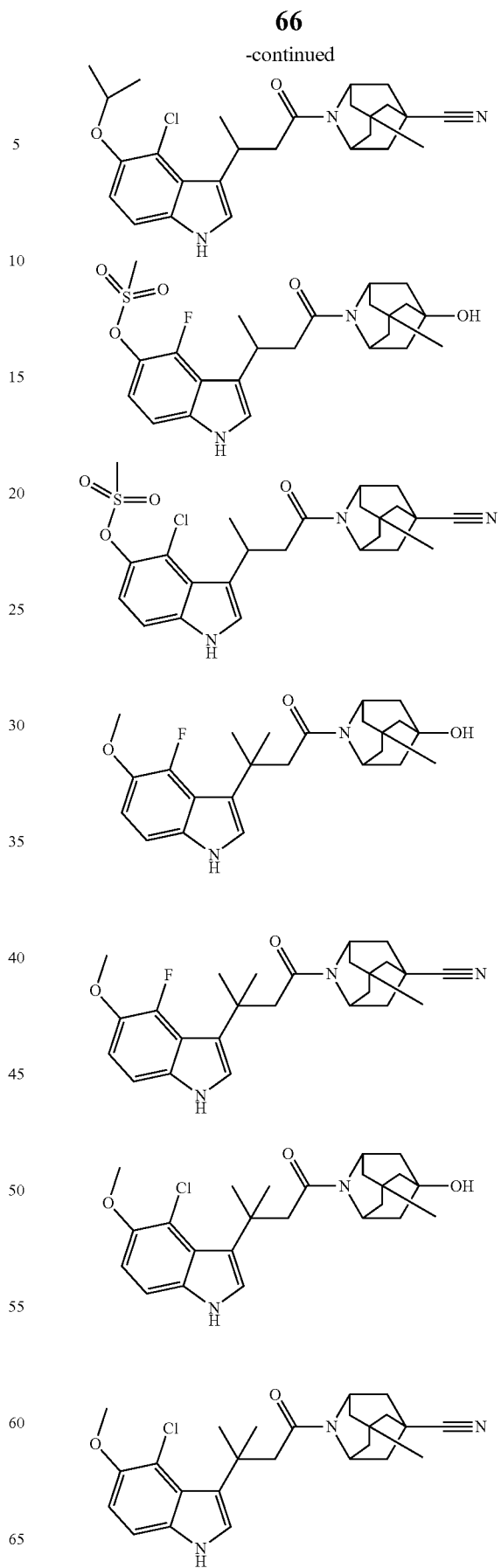

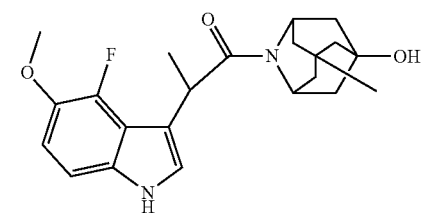
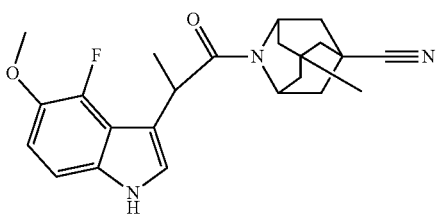
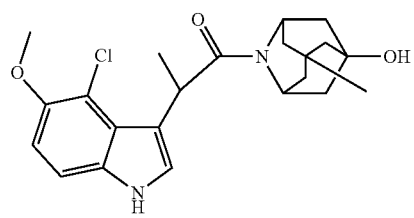
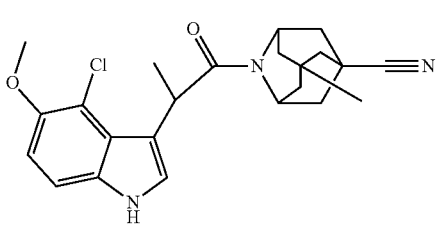
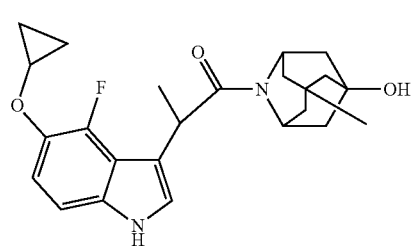
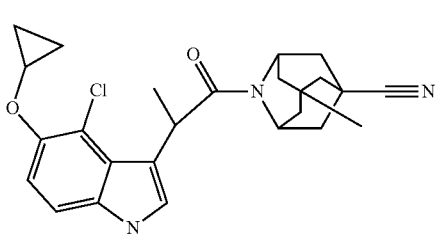
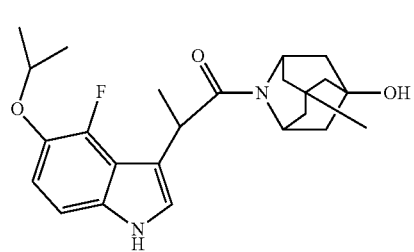
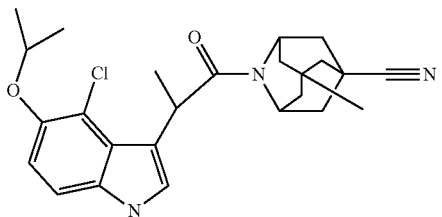
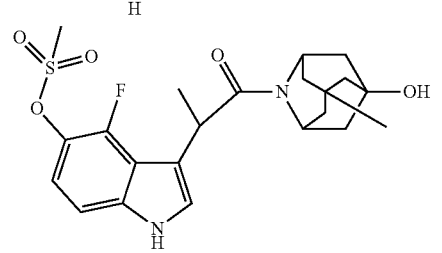
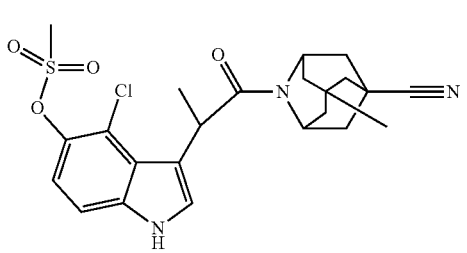
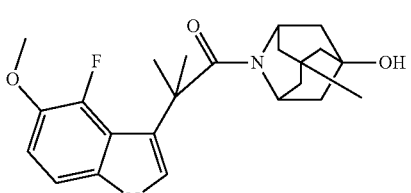
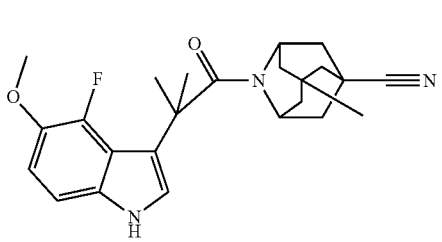
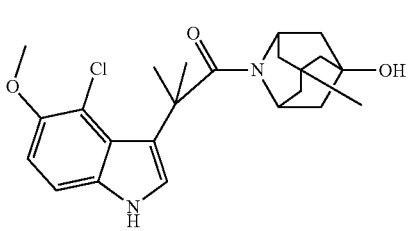
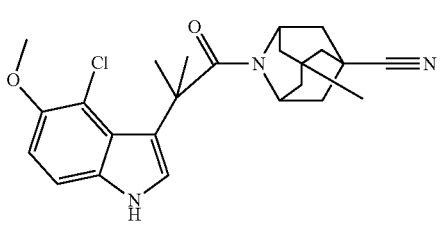

-continued
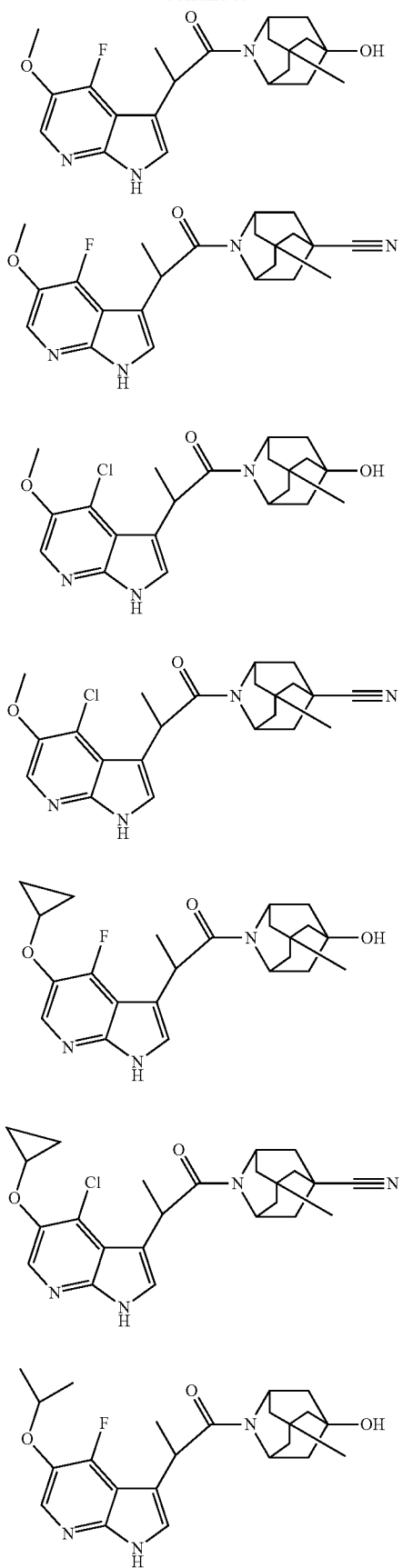
-continued
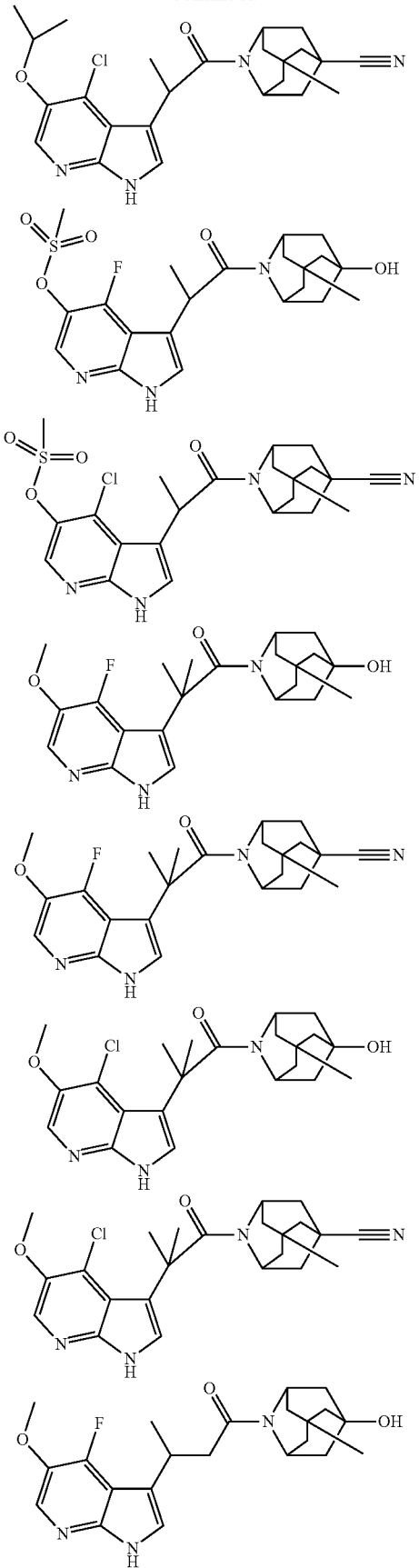

-continued
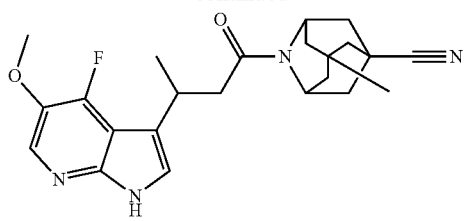
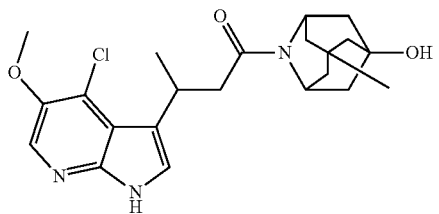
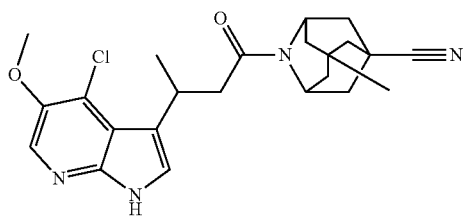
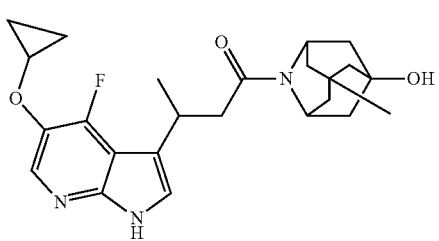
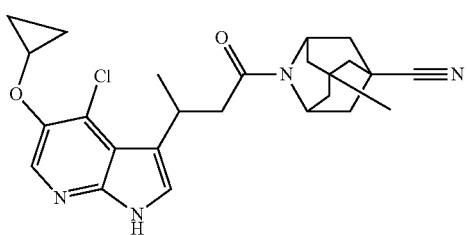
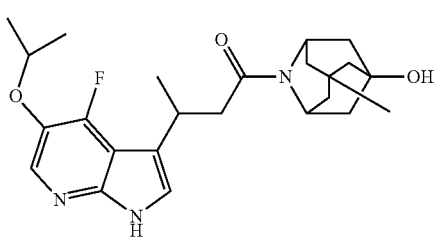
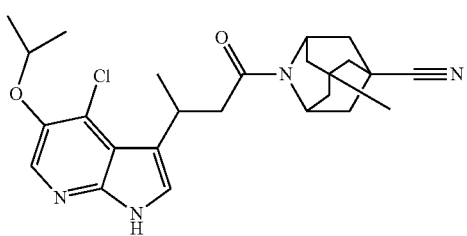
-continued
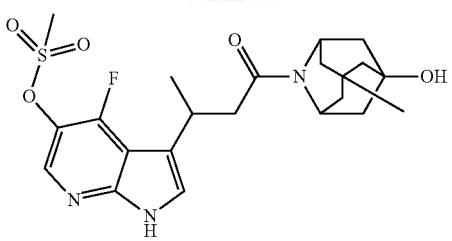
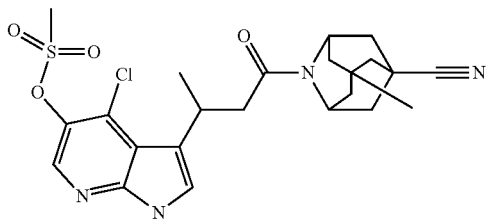
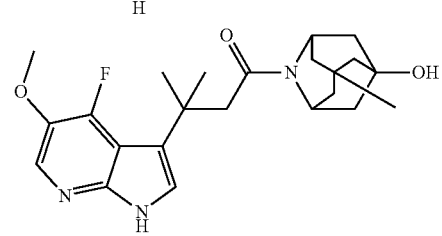
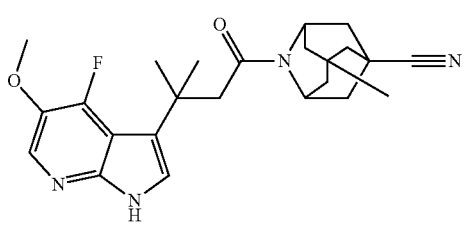
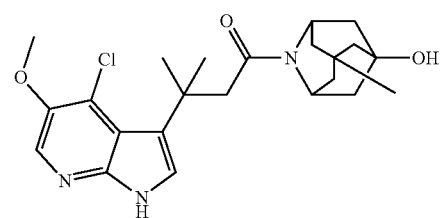
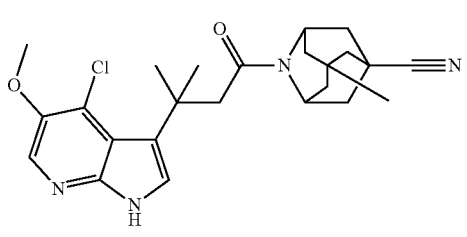
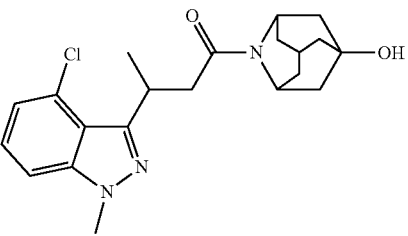

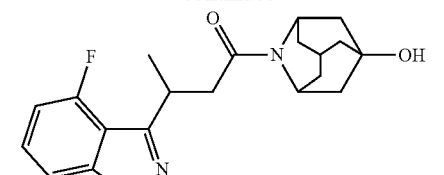
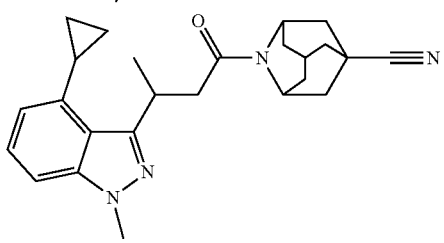
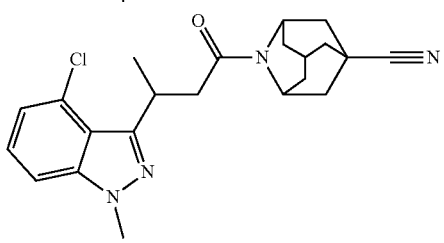
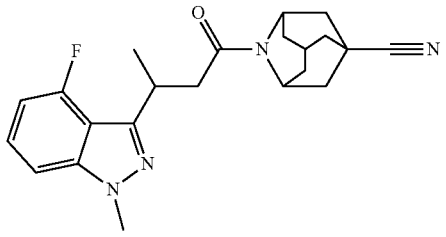
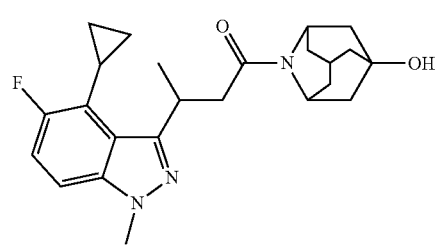
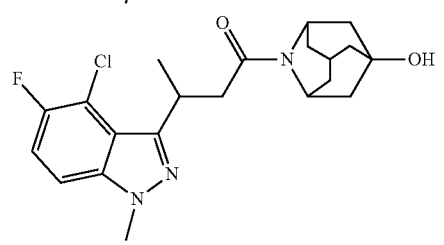
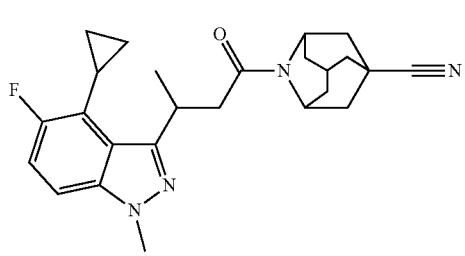
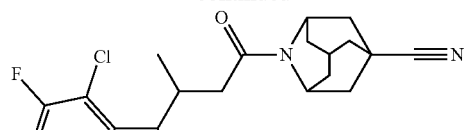
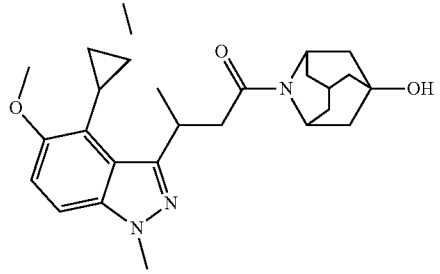
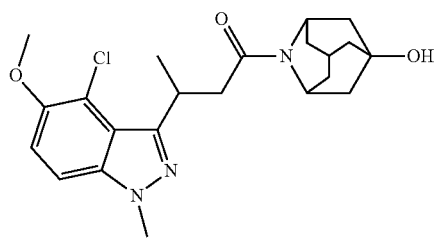
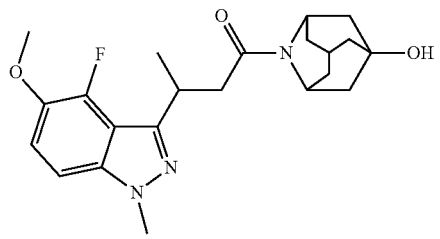
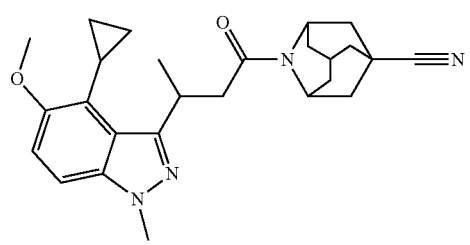
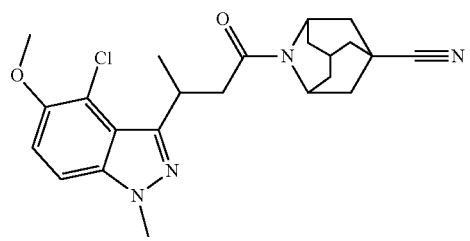
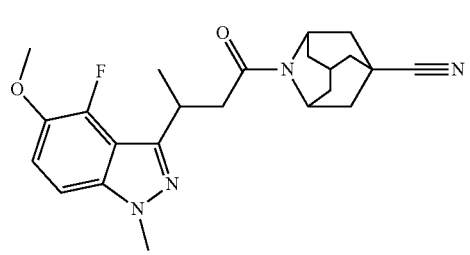

-continued
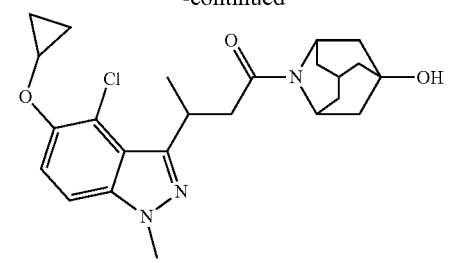
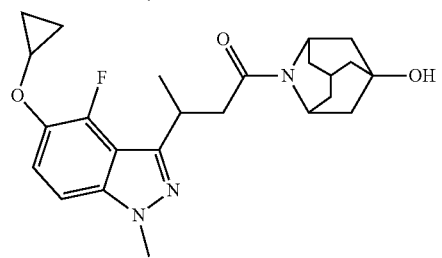
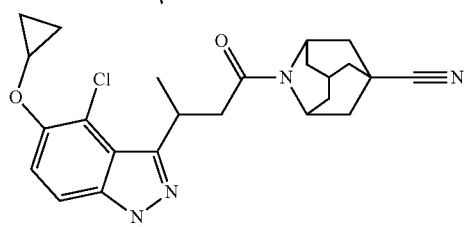
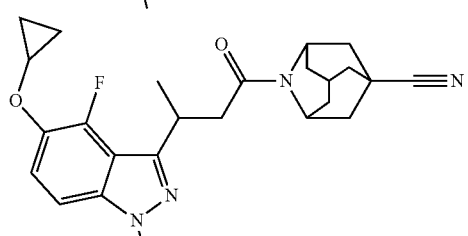
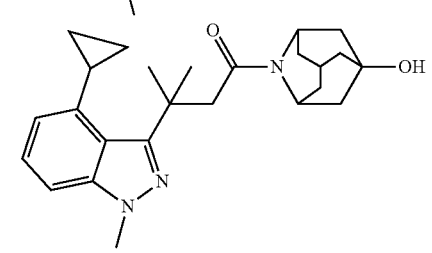
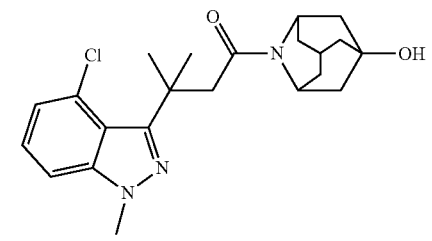
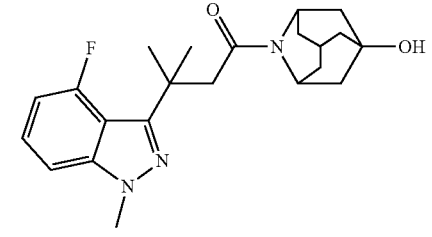
-continued
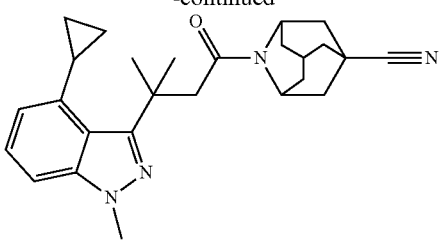
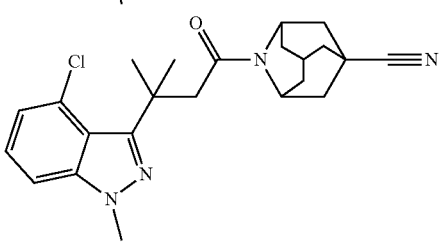
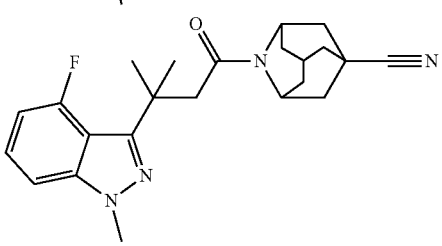
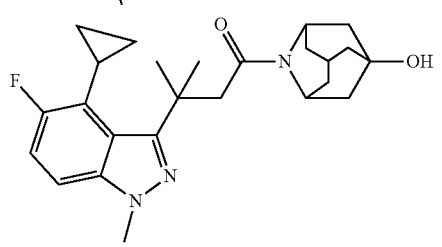
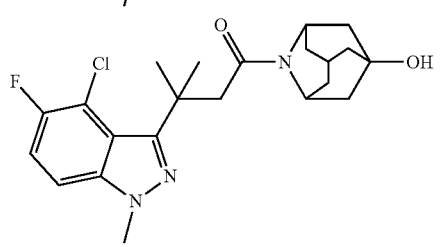
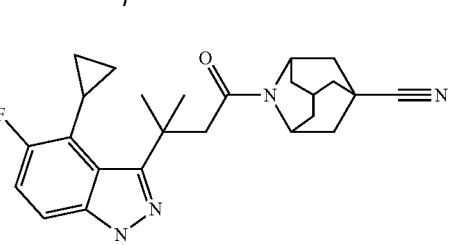
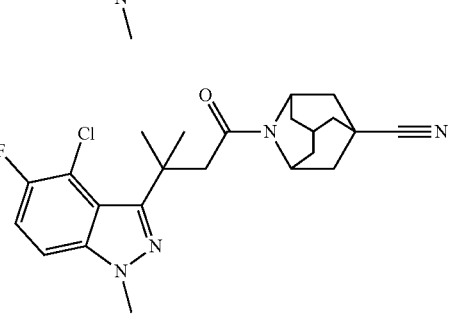

77
-continued
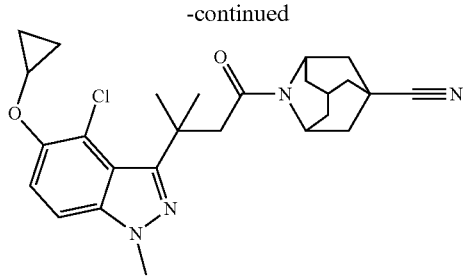
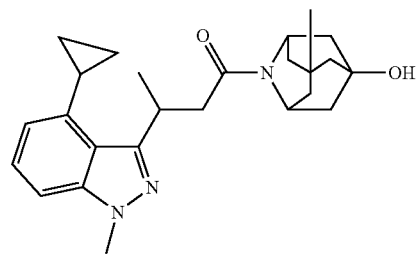
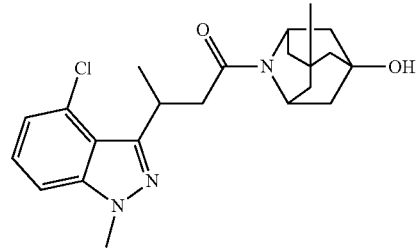
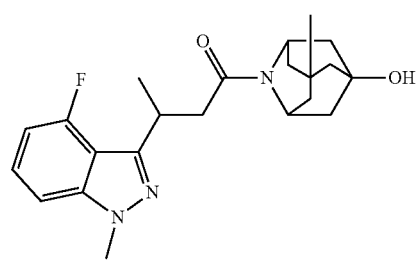
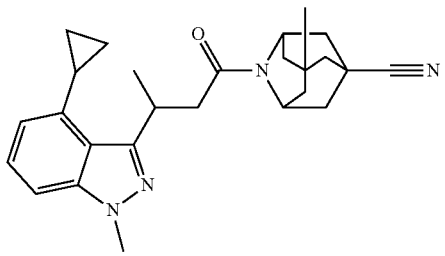
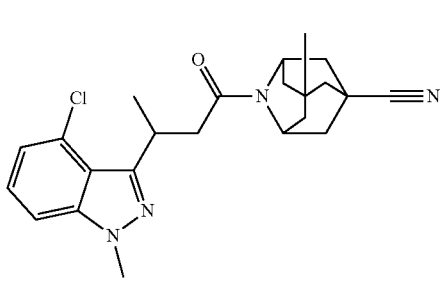
78
-continued
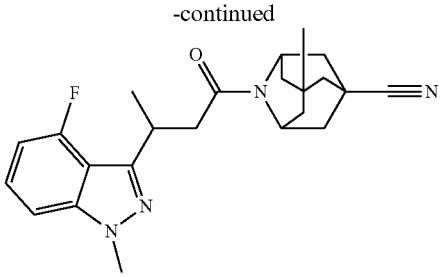
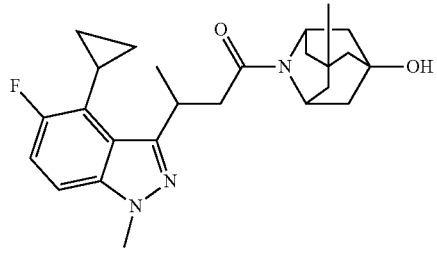
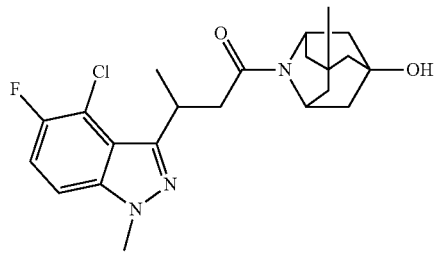
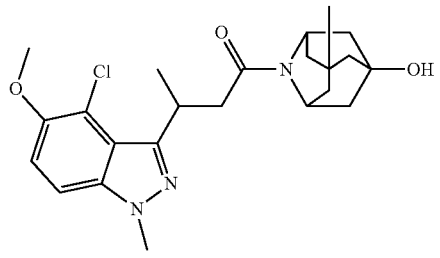
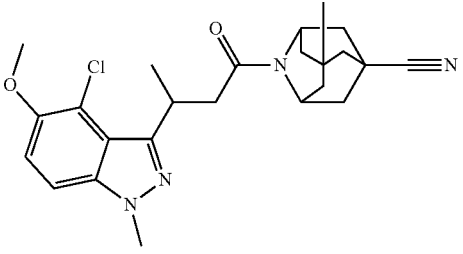
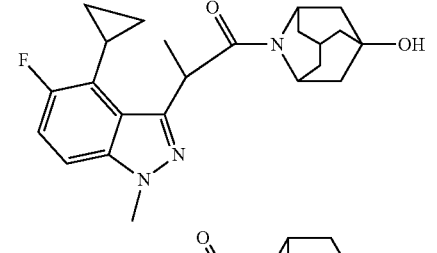
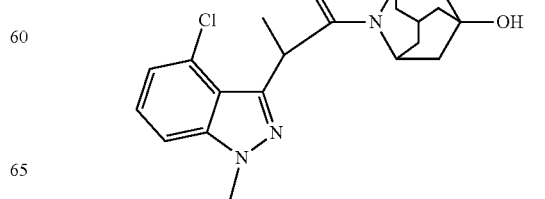

-continued
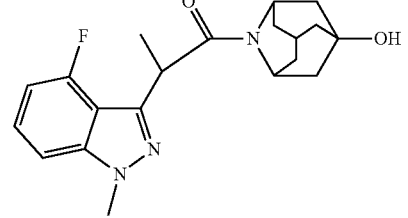
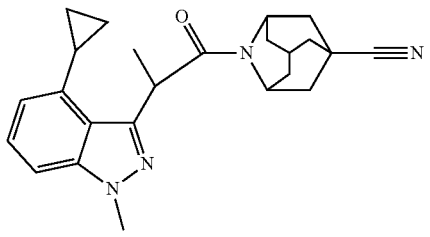
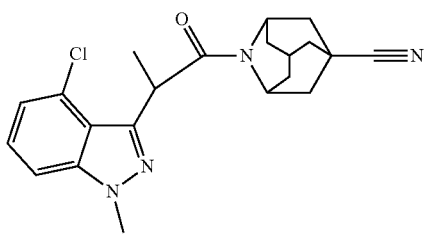
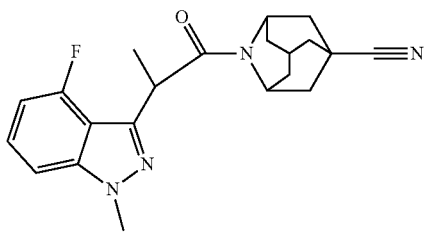
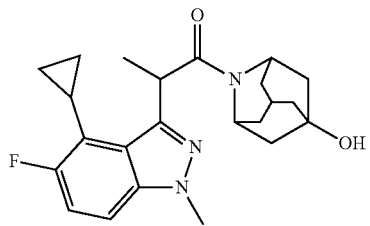
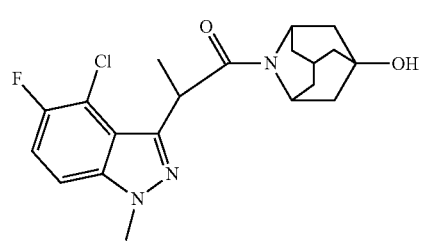
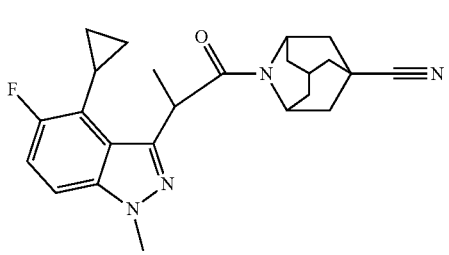
-continued
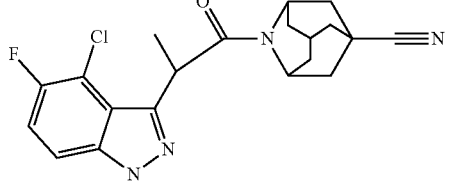
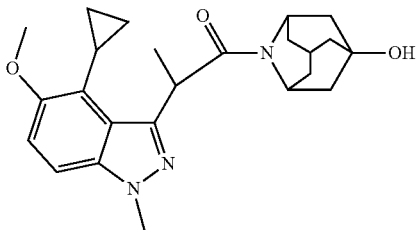
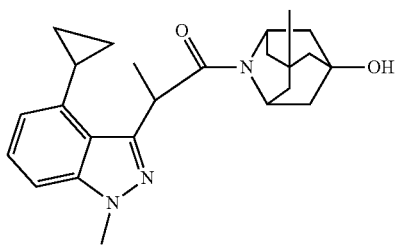
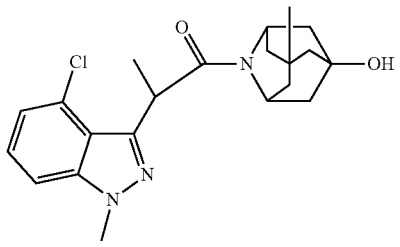
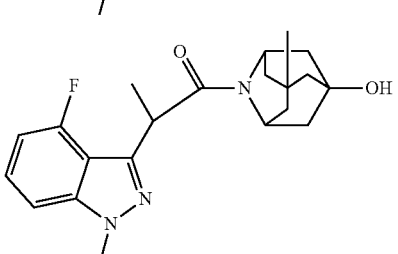
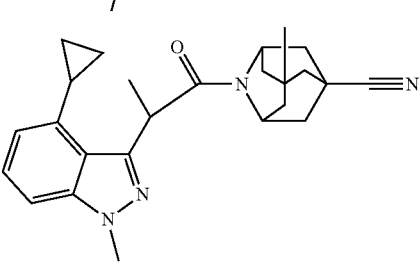
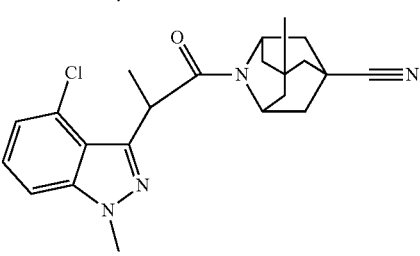

-continued
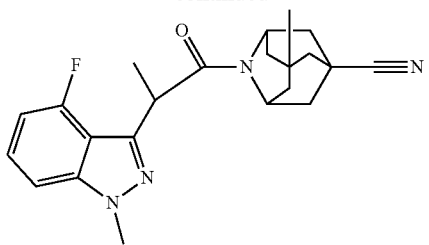
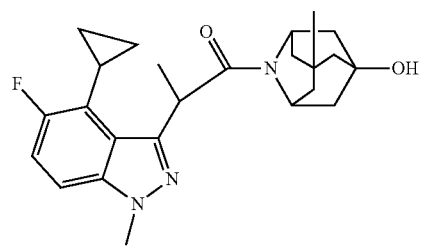
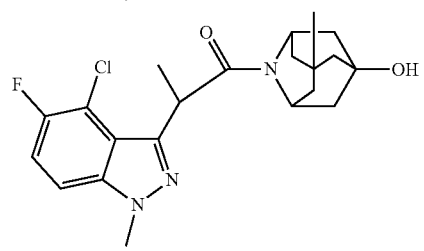
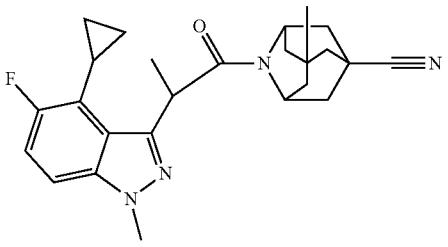
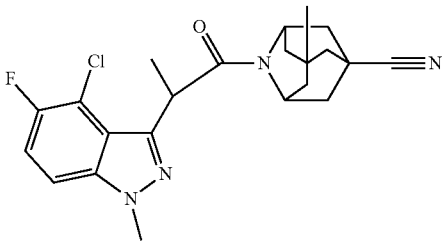
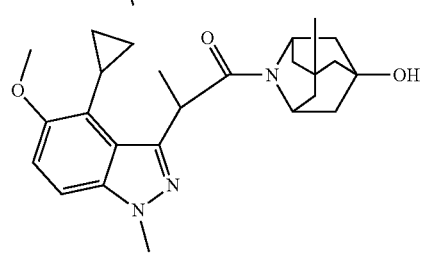
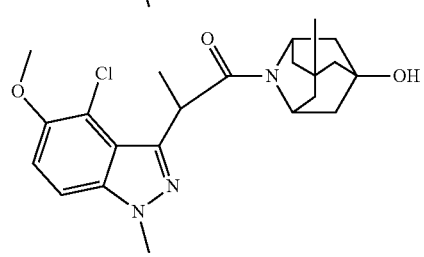
-continued
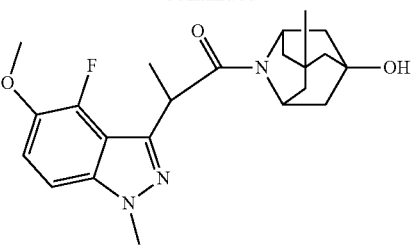
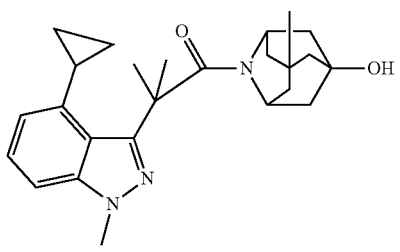
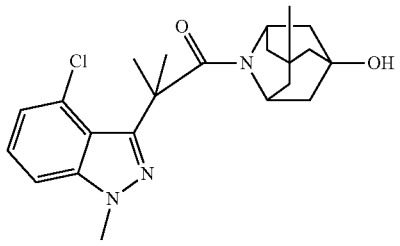
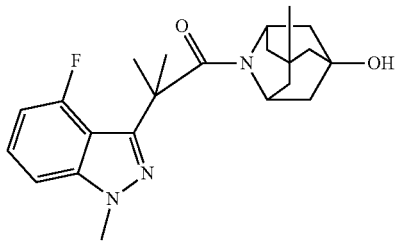
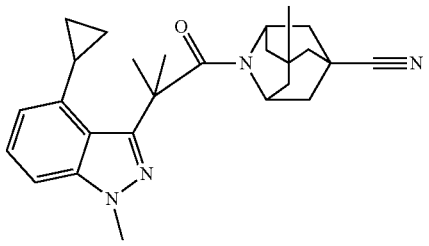
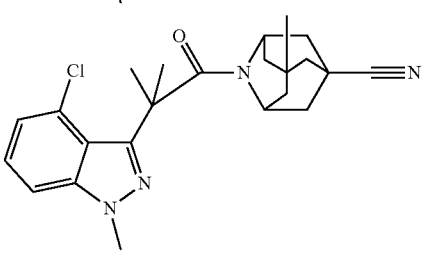

-continued
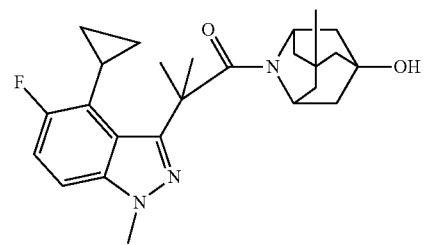
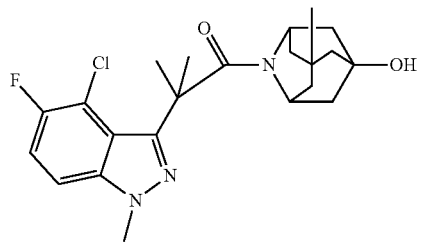
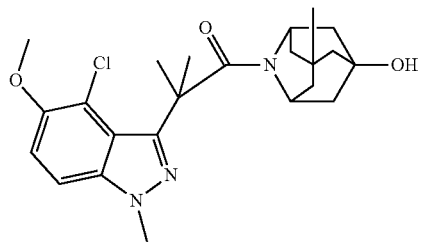
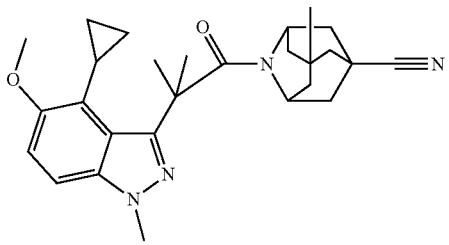
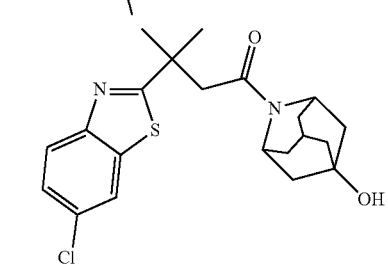
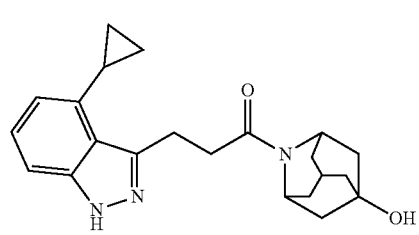
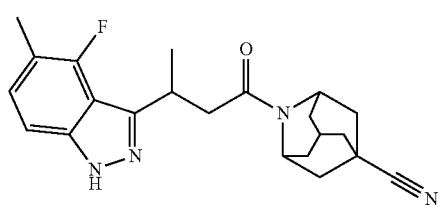
-continued
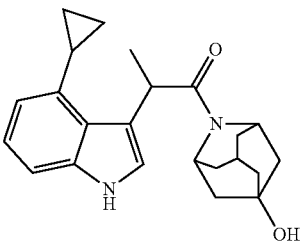
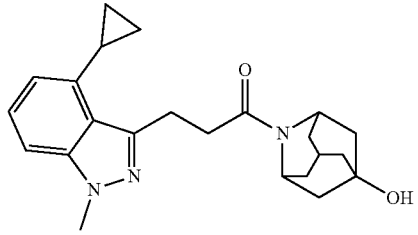
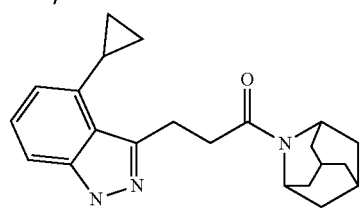
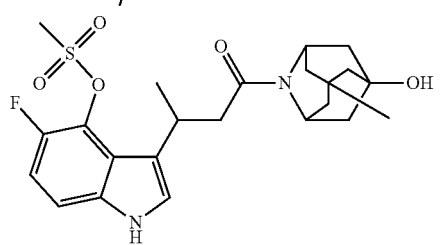
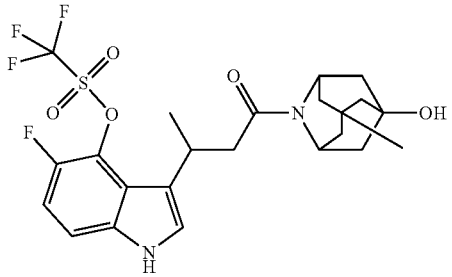
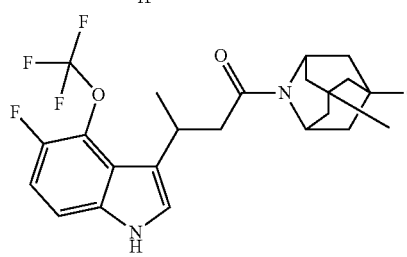
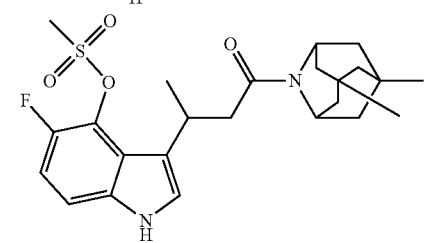

85
-continued
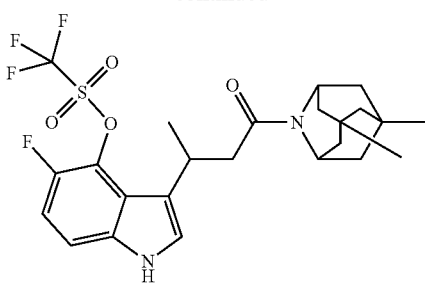
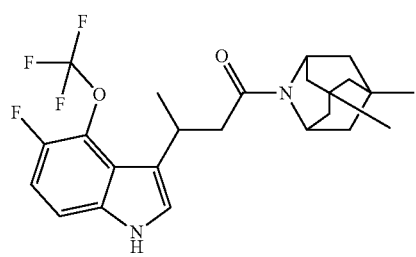
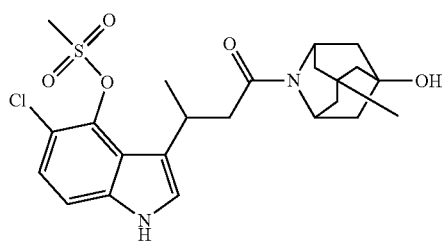
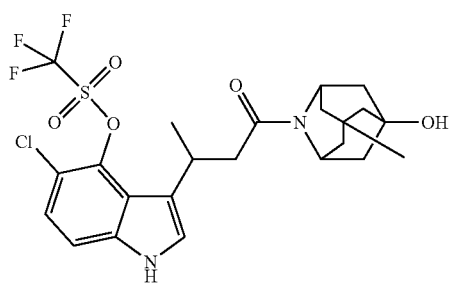
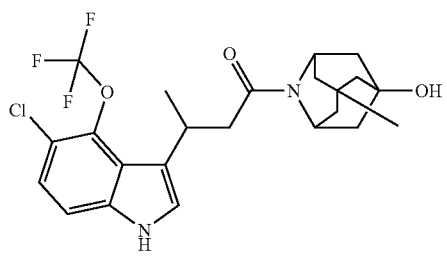
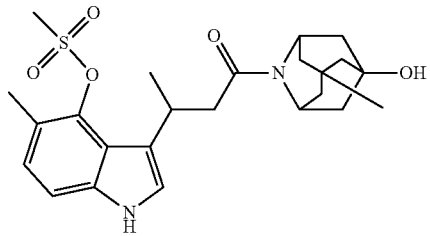
86
-continued
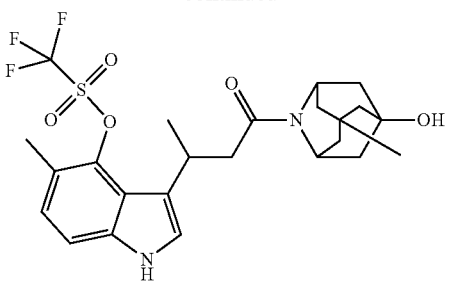
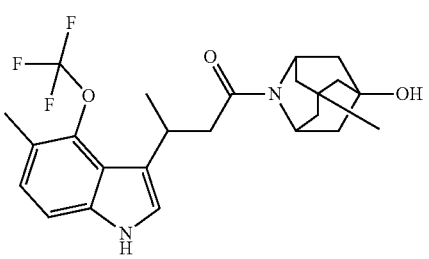
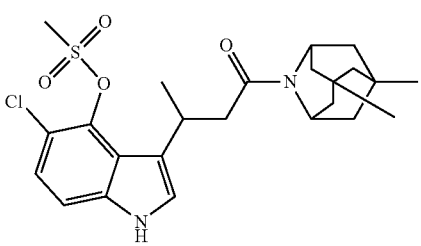
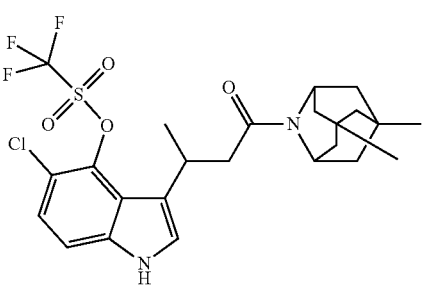
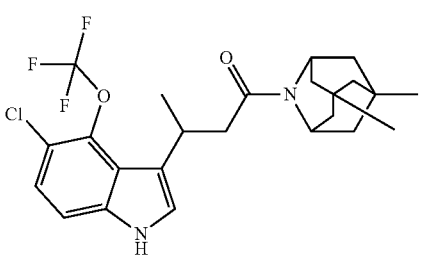
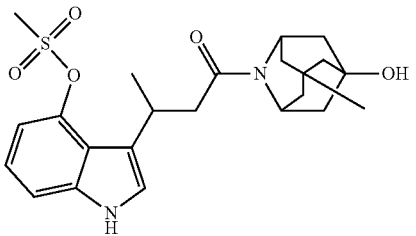

87
-continued
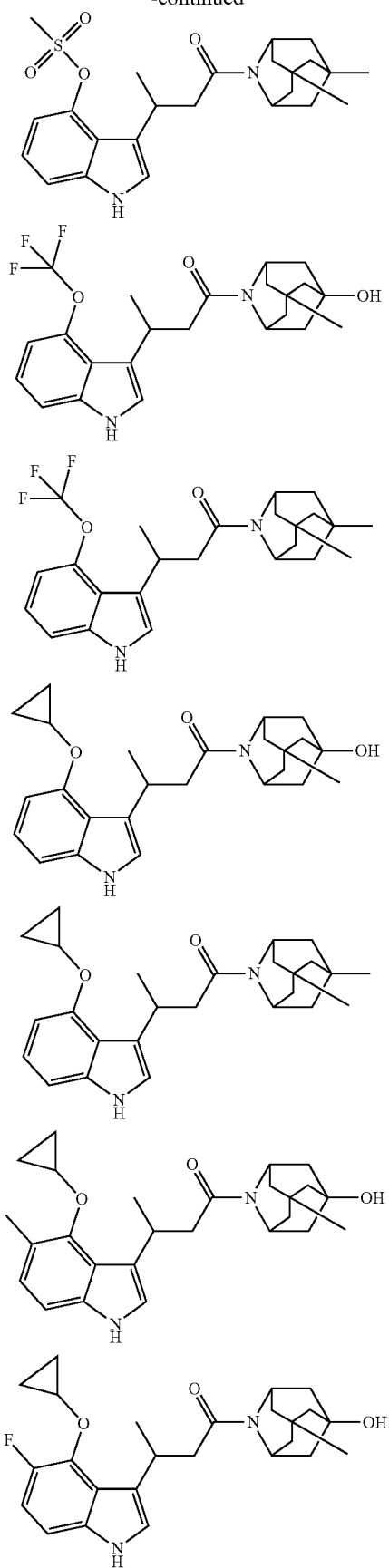
88
-continued
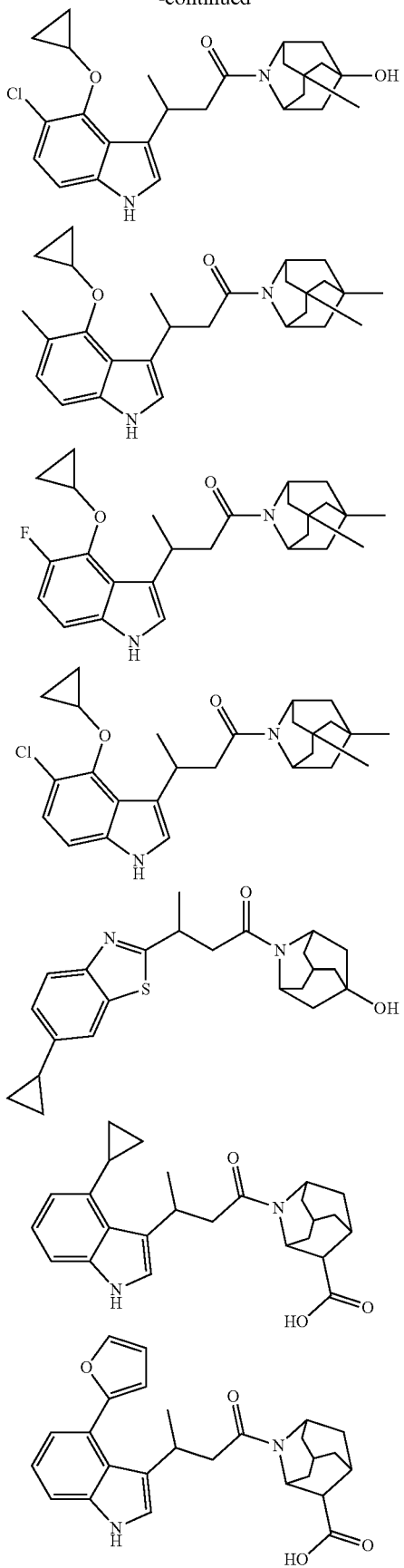

-continued

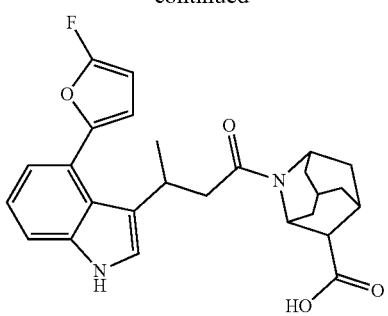

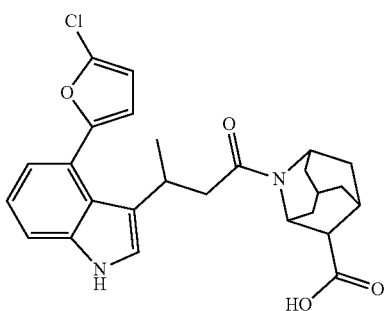

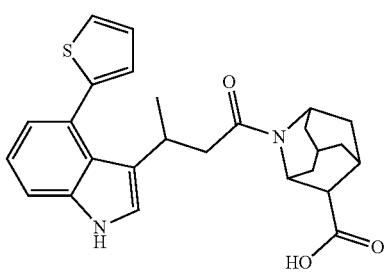

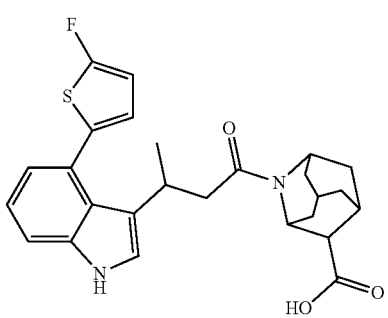

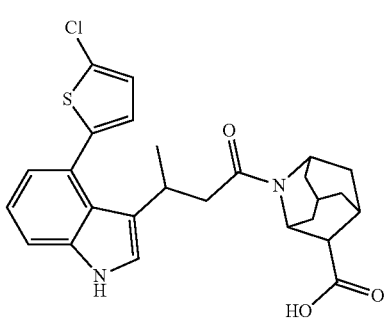

-continued

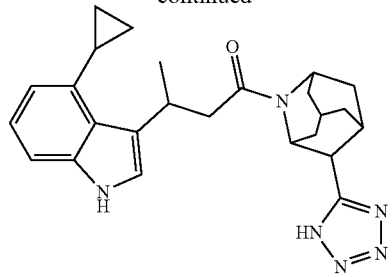

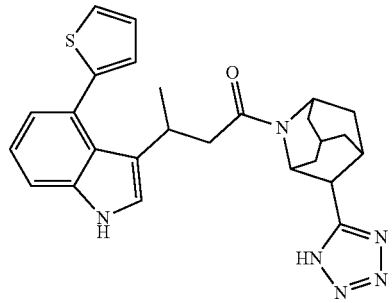

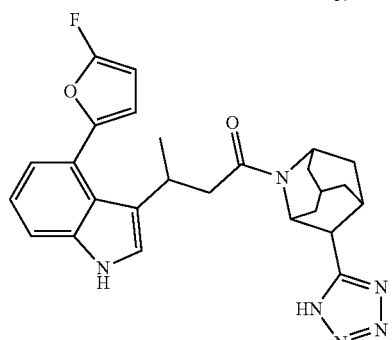

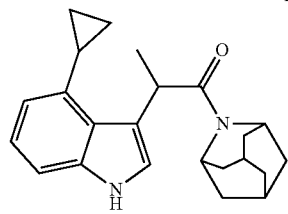

or pharmaceutically acceptable salt, isomer or prodrug thereof.

The compounds have the ability to inhibit 11β-HSD1. The ability to inhibit 11β-HSD1 may be a result of the compounds acting directly and solely on the 11β-HSD1 to modulate/potentiate biological activity. However, it is understood that the compounds may also act at least partially on other factors associated with 11β-HSD1 activity.

The inhibition of 11β-HSD1 may be carried out in any of a number of ways known in the art. For example if inhibition of 11β-HSD1 in vitro is desired an appropriate amount of the compound may be added to a solution containing the 11β-HSD1. In circumstances where it is desired to inhibit 11β-HSD1 in a mammal, the inhibition of the 11β-HSD1 typically involves administering the compound to a mammal containing the 11β-HSD1.

Accordingly the compounds may find a multiple number of applications in which their ability to inhibit 11β-HSD1 enzyme of the type mentioned above can be utilised.

Accordingly compounds of the invention would be expected to have useful therapeutic properties especially in relation to diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy, nephropathy, neuropathy, osteoporosis, osteoarthritis, dementia, depression, neurodegenerative disease, psychiatric disorders, Cushing's Disease, Cushing's syndrome, virus diseases, and inflammatory diseases.

Administration of compounds within Formula (I) to humans can be by any of the accepted modes for enteral administration such, as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the activator compound may be selectively toxic or more toxic to rapidly proliferating cells, e.g. cancerous tumours, than to normal cells.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

The compound of the invention may also be administered in combination with (or simultaneously or sequentially with) an adjuvant to increase compound performance. Suitable adjuvants may include (a) dipeptidyl peptidase-IV (DP-IV) inhibitors; (b) insulin sensitizing agents; (iv) biguanides; (c) insulin and insulin mimetics; (d) sulfonylureas and other insulin secretagogues; (e) alpha-glucosidase inhibitors; and (f) GLP-1, GLP-1 analogs, and GLP-1 receptor agonists. The adjuvants may be part of the same composition, or the adjuvants may be administered separately (either simultaneously or sequentially). The order of the administration of the composition and the adjuvant will generally known to the medical practitioner involved and may be varied.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

The symbols, abbreviations and conventions in the processes, schemes, and examples are consistent with those used in the contemporary scientific literature. Specifically but not meant as limiting, the following abbreviations may be used in the examples and throughout the specification.

g (grams)
L (liters)
Hz (Hertz)
mol (moles)
RT (room temperature)
min (minutes)
MeOH (methanol)
$CHCl_3$ (chloroform)
DCM (dichloromethane)
DMSO (dimethylsulfoxide)
EtOAc (ethyl acetate)
mg (milligrams)
mL (milliliters)
psi (pounds per square inch)
mM (millimolar)
MHz (megahertz)
h (hours)
TLC (thin layer chromatography)
EtOH (ethanol)
$CDCl_3$ (deuterated chloroform)
HCl (hydrochloric acid)

DMF (N,N-dimethylformamide)
THF (tetrahydrofuran)
K₂CO₃ (potassium carbonate)
Na₂SO₄ (sodium sulfate)
RM (Reaction Mixture)

Unless otherwise indicated, all temperatures are expressed in ° C. (degree centigrade). All reactions conducted at room temperature unless otherwise mentioned.

All the solvents and reagents used are commercially available and purchased from Sigma Aldrich, Fluka, Acros, Spectrochem, Alfa Aesar, Avra, Qualigens, Merck, Rankem and Leonid Chemicals.

¹H NMR spectra were recorded on a Bruker AV 300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on single quadruple 6120 LCMS from Agilent technologies, using either atmospheric chemical ionization (APCI) or Electrospray ionization (ESI) or in the combination of these two sources.

All samples were run on SHIMADZU system with an LC-20 AD pump, SPD-M20A diode array detector, SIL-20A auto sampler.

SYNTHETIC SCHEME 1

One scheme for making certain compounds of the invention is shown in scheme 1 below.

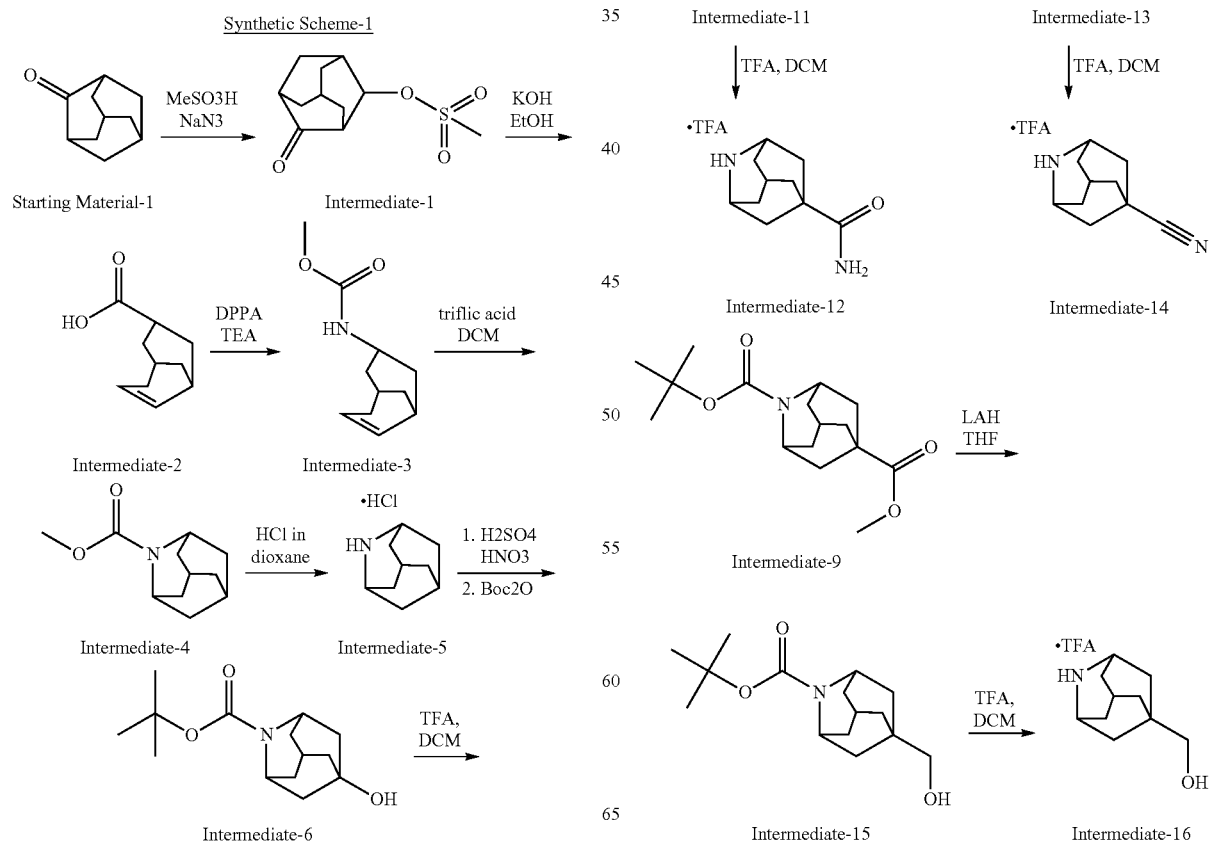

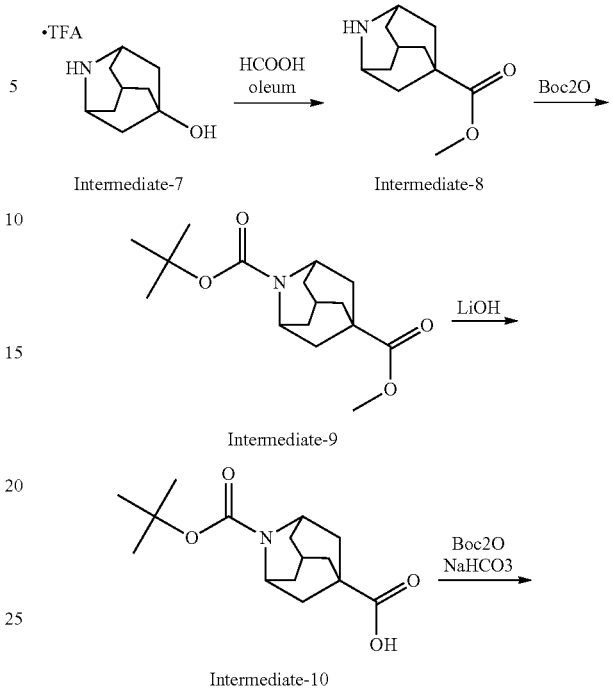

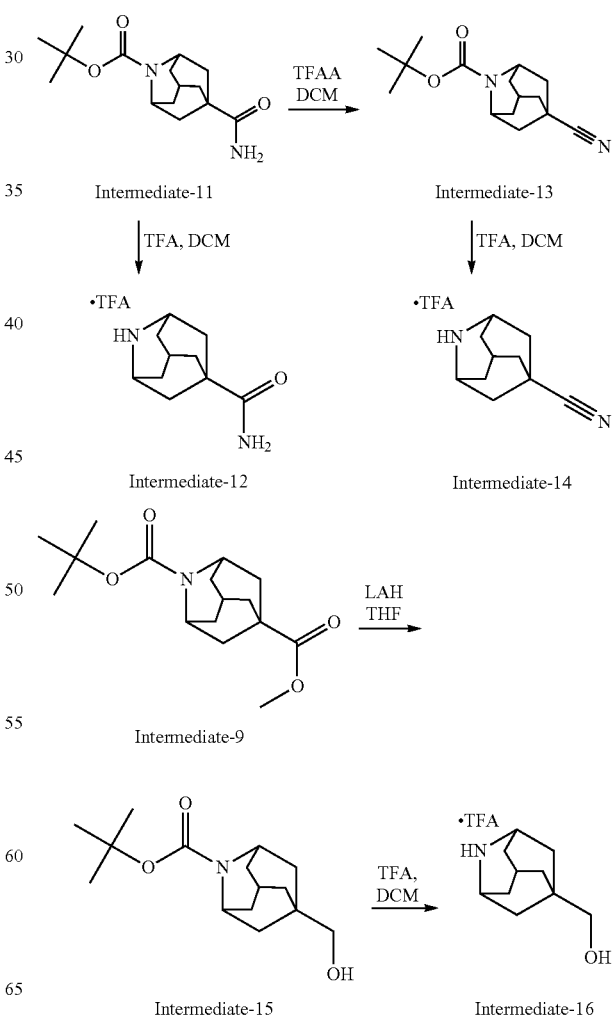

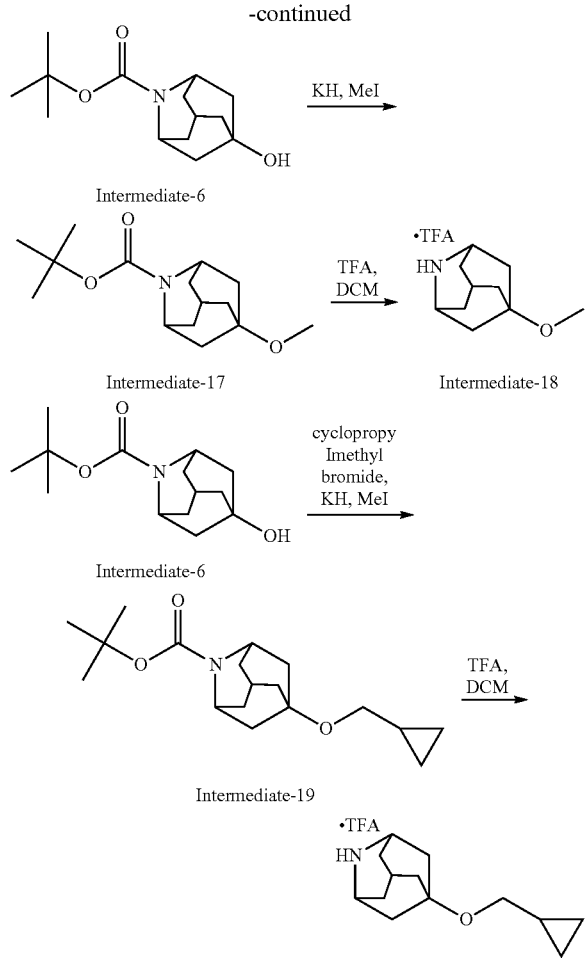

Synthesis of 4-oxotricyclo[3.3.1.1$^{3,7}$]dec-2-yl methanesulfonate (Intermediate-1)

A 1000 mL RB flask fitted with magnetic stirrer was charged with methanesulfonic acid (416.0 g, 4328.8 mmol) and Starting Material-1 (50.0 g, 333 mmol). To this sodium azide (23.0 g, 351 mmol) was added portion wise for 2 hours. Then reaction mixture was stirred at 20-25° C. for 3 days. Upon completion of the reaction (reaction monitored by TLC), reaction mixture was quenched with ice-water (3000 mL) and extracted with ethyl acetate (1000×3 mL). The organic layer was washed with brine solution, dried over anhydrous sodium sulfate and concentrated to give title Intermediate-1 (54.0 g, yield=66%).

Synthesis of bicyclo[3.3.1]non-6-ene-3-carboxylic acid (Intermediate-2)

A 2000 mL RB flask fitted with magnetic stirrer was charged with 1200 mL of ethanol and Intermediate-1 (54.0 g, 221.3 mmol). Potassium hydroxide (84.0 g, 150 mmol) was further added to this reaction mixture followed by addition of 950 mL of water. The reaction mixture was stirred at 110° C. for 12 hours. After completion of the reaction (reaction was monitored by TLC), reaction mixture was concentrated under vacuum. The resulted crude material was acidified with 1N HCl (pH=2) and extracted with ethyl acetate (250×3 mL). The organic layer was washed with brine solution, dried over anhydrous sodium sulfate and concentrated to give Intermediate-2 (32.0 g, yield=88%).

Synthesis of methyl bicyclo[3.3.1]non-6-en-3-ylcarbamate (Intermediate-3)

A 500 mL RB flask fitted with magnetic stirrer under nitrogen atmosphere charged with toluene (100 mL), Intermediate-2 (16.0 g, 96 mmol) and DPPA (28.8 g, 105 mmol). Reaction mixture was cooled to 0° C., and then triethylamine (15.4 g, 143.9 mmol) was added. The reaction mixture was stirred at room temperature for 1 hour. Then reaction mixture was heated at 80° C. for 8 h and 12 h at room temperature. To this 100 mL of methanol was added and refluxed for 12 hours. After the reaction, it was concentrated under vacuum. Obtained Crude was extracted with ethyl acetate. The organic layer was washed with 1N HCl, Saturated NaHCO$_3$ solution, brine solution and was then dried over anhydrous sodium sulfate and concentrated. Crude material was purified by silica gel column chromatography eluting with 6% of EtOAc in to give Intermediate-3 (8.0 g, yield=42%).

Synthesis of methyl 2-azatricyclo[3.3.1.1$^{3,7}$]decane-2-carboxylate (Intermediate-4)

A 100 mL RB flask fitted with magnetic stirrer was charged with 50 mL of dichloromethane and Intermediate-4 (5.0 g, 25.6 mmol). To this reaction mixture, triflouromethane sulfonic acid (19.2 g, 125.2 mmol) was added at 0° C. The reaction mixture was then stirred at room temperature for 12 hours. After completion of reaction, the reaction mixture was quenched with water and extracted with dichloromethane. The organic layer was washed with saturated sodium bicarbonate solution, brine solution and the reaction mass was dried over anhydrous sodium sulfate and was concentrated to give Intermediate-4 (4.3 g, yield=86%).

Synthesis of 2-azatricyclo[3.3.1.1$^{3,7}$]decane (Intermediate-5)

A 50 mL pressurized seal tube fitted with magnetic stirrer was charged with Intermediate-4 (3.0 g, 15 mmol) in HCl containing 1,4-Dioxane (20 mL). Then the reaction mixture was stirred at 90° C. for 8 hours. After completion of the reaction (reaction was monitored by LCMS) it was concentrated followed by trituration with mixture of hexane:ether (1:1) to give Intermediate-5 (3.0 g, yield=100%).

Synthesis of tert-butyl 5-hydroxy-2-azatricyclo [3.3.1.1$^{3,7}$]decane-2-carboxylate (Intermediate-6)

A 250 mL RB fitted with magnetic stirrer was charged with Intermediate 5 (3.0 g, 21.6 mmol), concentrated nitric acid (30 mL), and H$_2$SO$_4$ (5 mL). The reaction mixture was stirred at 80° C. for 12 hours. Upon completion of the reaction (reaction was monitored by LC-MS) reaction mixture was quenched with water and basified with sodium carbonate. The aqueous layer was washed with DCM (100 mL) and resulting aqueous layer was diluted with THF (200 mL) and cooled to 0° C. The pH of the mixture was adjusted to basic using Triethyl amine (5 mL). To this reaction mixture Boc-anhydride (6.0 g, 27.52 mmol) was added. The resulting mixture was stirred at room temperature for 12 hours. Upon completion of the reaction (reaction was monitored by LC-MS)

reaction mixture was extracted with Ethyl acetate (100 mL×3). Combined organic layer was washed with water and brine and the reaction mass was dried over sodium sulfate. Organic layer was concentrated to obtain a crude intermediate which was then purified by silica gel column chromatography eluting with 40% of EtOAc to give Intermediate-6 (2.5 g, yield=50%).

Synthesis of 2-azatricyclo[3.3.1.1$^{3,7}$]decan-5-ol (Intermediate-7)

A 100 mL RB flask fitted with magnetic stirrer was charged with Intermediate-6 (5.5 g, 21.5 mmol) in DCM (30 mL). The reaction mixture thus formed was cooled to 0° C. to which trifluoroacetic acid (7.4 g, 65.2 mmol) was added and stirred for 4 hours. After completion of the reaction (reaction was monitored by LCMS) the reaction mixture was concentrated followed by trituration with mixture of hexane:ether (1:1) to give Intermediate-7 (3.4 g, yield=100%).

Synthesis of methyl 2-azatricyclo[3.3.1.1$^{3,7}$]decane-5-carboxylate, intermediate-8

To 2-azatricyclo[3.3.1.1$^{3,7}$]decan-5-ol (Intermediate-7) (1.5 g, 5.9 mmol, 1 eq), 98% formic acid (9 ml) was added drop wise with vigorous gas evolution for over 30 minutes to a rapidly stirred 30% oleum (36 ml) heated to 60° C. Upon completion of this addition, 99% formic acid (9 ml) was slowly added for the next 30 minutes. The reaction mixture was stirred for another 1 hr at 60° C. (monitored by LCMS). The reaction mixture thus formed was then slowly poured into vigorously stirred methanol (75 ml) cooled to 00° C. The mixture was allowed to slowly warm to room temperature while stirring the reaction mixture for 4-5 hrs. The mixture was then concentrated under vacuum. The residue was poured into ice (30 g) and basified with saturated $Na_2CO_3$ solution. The aqueous layer was extracted with 5% methanol in DCM (3×100 ml). Combined organic layer was washed with brine and dried over $Na_2SO_4$. The organic layer was finally concentrated to get intermediate-8, (550 mg, 50% yield) as an oily mass.

Synthesis of 2-tert-butyl 5-methyl 2-azatricyclo [3.3.1.1$^{3,7}$]decane-2,5-dicarboxylate, intermediate-9

Methyl 2-azatricyclo[3.3.1.1$^{3,7}$]decane-5-carboxylate, Intermediate-8 (0.32 g, 1.6 mmol) was added into THF (5 mL) and cooled to 0° C. Triethyl amine (1.3 mL) was added to the reaction mixture followed by addition of Boc-anhydride (0.5 g, 1.96 mmol). The resulting mixture was stirred at room temperature for 6 hours. Upon completion of the reaction (reaction was monitored by LC-MS) reaction mixture was extracted with Ethyl acetate (100 mL×3). Combined organic layer was washed with water and brine and was dried over sodium sulfate. Organic layer was concentrated to give crude intermediate-9, which was purified by silica gel column chromatography eluting with 15% of EtOAc to give Intermediate-9 (0.32 g, yield=66%).

Synthesis of 2-(tert-butoxycarbonyl)-2-azatricyclo [3.3.1.1$^{3,7}$]decane-5-carboxylic acid, Intermediate-10

To a 0° C. cooled stirred solution of 2-tert-butyl 5-methyl 2-azatricyclo[3.3.1.1$^{3,7}$]decane-2,5-dicarboxylate, intermediate-9 (0.16 g, 0.5 mmol) dissolved in methanol (3 ml), THF (1 ml) and water (1 ml), LiOH (50 mg, 2 mmol) was added and the resulting reaction mass was stirred at room temperature for 6 hrs. Upon completion of the reaction (reaction monitored by TLC), the solvent present in the reaction mixture was completely removed under vacuum and the crude residue was acidified with saturated citric acid solution and extracted with ethyl acetate (3×15 ml). The organic layer was then washed with brine solution and dried over sodium sulfate and was finally concentrated under vacuum to get intermediate-10 as an oily mass, 0.16 g (95%).

Synthesis of tert-butyl 5-carbamoyl-2-azatricyclo [3.3.1.1$^{3,7}$]decane-2-carboxylate, Intermediate-11

A 50 mL RB flask fitted with magnetic stirrer was charged with 5 mL of acetonitrile and 2-(tert-butoxycarbonyl)-2-azatricyclo[3.3.1.1$^{3,7}$]decane-5-carboxylic acid, Intermediate-10 (0.16 g, 0.56 mmol). Under $N_2$ atm, pyridine (60 mg, 0.6 mmol) and Boc-anhydride (0.148 g, 0.6 mmol) was added to the reaction mixture and was stirred for 1 hr. After 1 hr, ammonium bicarbonate solid (75 mg, 0.9 mmol) was added and the reaction mixture was stirred at room temperature for 12 hours. After completion of the reaction (reaction was monitored by TLC), reaction mixture was concentrated under vacuum. The resulted crude material was extracted with ethyl acetate (25 ml×3). The organic layer was washed with ammonium chloride solution and saturated sodium bi carbonate solution. It was then dried over anhydrous sodium sulfate and concentrated to give Intermediate-11, as an oily mass (0.14 g, yield=87%).

Synthesis of 2-azatricyclo[3.3.1.1$^{3,7}$]decane-5-carboxamide, Intermediate-12

To a 100 mL RB flask fitted with magnetic stirrer was charged tert-butyl 5-carbamoyl-2-azatricyclo[3.3.1.1$^{3,7}$]decane-2-carboxylate, Intermediate-11 (0.1 g, 0.0357 mmol) in DCM (5 mL). The reaction mixture was cooled to 0° C. and trifluoroacetic acetic anhydride (0.21 g, 0.17 mmol) was added and stirred for 4 hours. After completion of the reaction (reaction was monitored by LCMS) reaction mixture was concentrated followed by trituration with mixture of hexane: ether (1:1) to give Intermediate-12 (0.09 g, yield=90%).

Synthesis of tert-butyl 5-cyano-2-azatricyclo [3.3.1.1$^{3,7}$]decane-2-carboxylate, Intermediate-13

A 50 mL RB flask fitted with magnetic stirrer was charged with 5 mL of DCM and tert-butyl 5-carbamoyl-2-azatricyclo [3.3.1.1$^{3,7}$]decane-2-carboxylate, Intermediate-11 (0.8 g, 2.8 mmol). Under $N_2$ atm, triethyl amine (1.15 g, 11.4 mmol) and trifluoroacetic anhydride (2.4 g, 11.4 mmol) was added and stirred for 6 hr. After completion of the reaction (reaction was monitored by TLC), reaction mixture was quenched with KHSO4 solution and extracted with DCM (50 ml×3). The organic layer was washed with saturated sodium bi carbonate solution followed by brine solution. Finally the reaction mixture was dried over anhydrous sodium sulfate and concentrated to give crude Intermediate-13, which was subjected to column chromatogram (10% EtOAc in PE) as a off-white solid (0.5 g, yield=70%).

Synthesis of 2-azatricyclo[3.3.1.1$^{3,7}$]decane-5-carbonitrile, Intermediate-14

A 50 mL RB flask fitted with magnetic stirrer was charged with tert-butyl 5-cyano-2-azatricyclo[3.3.1.1$^{3,7}$]decane-2-carboxylate, Intermediate-13 (0.5 g, 1.98 mmol) in DCM (5 mL). Then reaction mixture was cooled to 0° C. and trifluoroacetic acid (1.1 g, 9.54 mmol) was added and stirred for 4 hours. After completion of the reaction (reaction was monitored by LCMS) the reaction mixture was concentrated followed by the process of trituration with mixture of hexane:ether (1:1) to give Intermediate-14 (0.5 g, yield=97%).

Synthesis of tert-butyl 5-(hydroxymethyl)-2-azatricyclo[3.3.1.1$^{3,7}$]decane-2-carboxylate, Intermediate-15

A 50 mL RB flask fitted with magnetic stirrer was charged with 5 mL of THF, 2-tert-butyl 5-methyl 2-azatricyclo[3.3.1.1$^{3,7}$]decane-2,5-dicarboxylate, Intermediate-9 (0.15 g, 0.5 mmol) and cooled to 0° C. Under $N_2$ atm, LAH was added portion wise (30 mg, 0.8 mmol) and stirred for 2 hr. After completion of the reaction (reaction was monitored by TLC), reaction mixture was quenched with ethyl acetate and washed with water followed by 1N HCl solution. The organic layer was washed with brine solution. Finally the organic layer was dried over anhydrous sodium sulfate and concentrated to give crude Intermediate-15, as an oily mass (0.12 g, yield=88%).

Synthesis of 2-azatricyclo[3.3.1.1$^{3,7}$]dec-5-ylmethanol, Intermediate-16

To a 50 mL RB flask fitted with magnetic stirrer tert-butyl 5-(hydroxymethyl)-2-azatricyclo[3.3.1.1$^{3,7}$]decane-2-carboxylate, Intermediate-15 (0.12 g, 0.45 mmol) in DCM (5 mL) was added. The reaction mixture was cooled to 00° C. followed by addition of trifluoroacetic acid (0.26 g, 2.2 mmol). This mixture was stirred for 4 hours. After completion of the reaction (reaction was monitored by LCMS) reaction mixture was concentrated followed by trituration with mixture of hexane:ether (1:1) to give Intermediate-16 (0.12 g, yield=97%) as an oily mass.

Synthesis of tert-butyl 5-methoxy-2-azatricyclo[3.3.1.1$^{3,7}$]decane-2-carboxylate, Intermediate-17

A 15 mL seal tube fitted with magnetic stirrer was charged with 5 mL of THF, tert-butyl 5-hydroxy-2-azatricyclo[3.3.1.1$^{3,7}$]decane-2-carboxylate, Intermediate-6 (0.15 g, 0.5 mmol). Potassium hydride (47 mg, 1.1 mmol) was added to this mixture at 0° C., under $N_2$ atm. The reaction mixture was then stirred at room temperature for 30 minutes. Methyl iodide was slowly added (0.12 g, 0.8 mmol) at 0° C. and the resulting reaction mass was refluxed at 60° C. under sealed condition for 12 hrs. After completion of the reaction (reaction was monitored by TLC), reaction mixture was quenched with cold water and extracted with ethyl acetate (25 ml×3). The organic layer was washed with sodium chloride solution, was dried over anhydrous sodium sulfate and was concentrated to give crude Intermediate-17, which was subjected to column chromatogram (22% EtOAc in PE) to obtain an oily mass (0.1 g, yield=70%).

Synthesis of 5-methoxy-2-azatricyclo[3.3.1.1$^{3,7}$]decane, Intermediate-18

To a 50 mL RB flask fitted with magnetic stirrer was charged tert-butyl 5-methoxy-2-azatricyclo[3.3.1.1$^{3,7}$]decane-2-carboxylate, Intermediate-17 (0.1 g, 0.037 mmol) in DCM (5 mL). Then reaction mixture was cooled to 0° C. and trifluoroacetic acid (0.22 g, 1.8 mmol) was added and stirred for 4 hours. After completion of the reaction (reaction was monitored by LCMS) reaction mixture was concentrated followed by trituration with mixture of hexane:ether (1:1) to give Intermediate-18 (0.09 g, yield=95%) as an oily mass.

Synthesis of tert-butyl 5-(cyclopropylmethoxy)-2-azatricyclo[3.3.1.1$^{3,7}$]decane-2-carboxylate, Intermediate-19

A 15 mL seal tube fitted with magnetic stirrer was charged with 5 mL of THF, tert-butyl 5-hydroxy-2-azatricyclo[3.3.1.1$^{3,7}$]decane-2-carboxylate, Intermediate-6 (50 mg, 0.2 mmol). To the tube, potassium hydride (20 mg, 0.5 mmol) was added at 0° C., under $N_2$ atm. The reaction mass was stirred at room temperature for 30 minutes. To this mixture, cyclopropyl methyl bromide (40 mg, 0.3 mmol) was slowly added at 0° C. and the resulting reaction mass was refluxed at 60° C. under sealed condition for 12 hrs. After completion of the reaction (reaction was monitored by TLC), reaction mixture was quenched with cold water and extracted with ethyl acetate (25 ml×3). The organic layer was washed with sodium chloride solution, dried over anhydrous sodium sulfate and concentrated to give crude Intermediate-17, which was subjected to column chromatogram (18% EtOAc in PE) to obtain an oily mass (50 mg, yield=80%).

Synthesis of 5-(cyclopropylmethoxy)-2-azatricyclo[3.3.1.1$^{3,7}$]decane, Intermediate-20

To a 50 mL RB flask fitted with magnetic stirrer was charged tert-butyl 5-(cyclopropylmethoxy)-2-azatricyclo[3.3.1.1$^{3,7}$]decane-2-carboxylate, Intermediate-19 (50 mg, 0.016 mmol) in DCM (5 mL). Then reaction mixture was cooled to 0° C. and trifluoroacetic acid (0.099 g, 0.084 mmol) was added and stirred for 4 hours. After completion of the reaction (reaction was monitored by LCMS) the reaction mixture was concentrated followed by trituration with mixture of hexane:ether (1:1) to give Intermediate-20 (50 mg, yield=95%) as an oily mass.

Example 1

1-(2-azatricyclo[3.3.1.1$^{3,7}$]dec-2-yl)-3-(1H-indol-3-yl) propan-1-one (1)

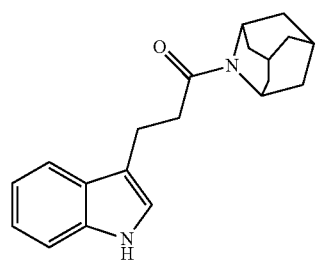

(1)

SYNTHETIC SCHEME 2

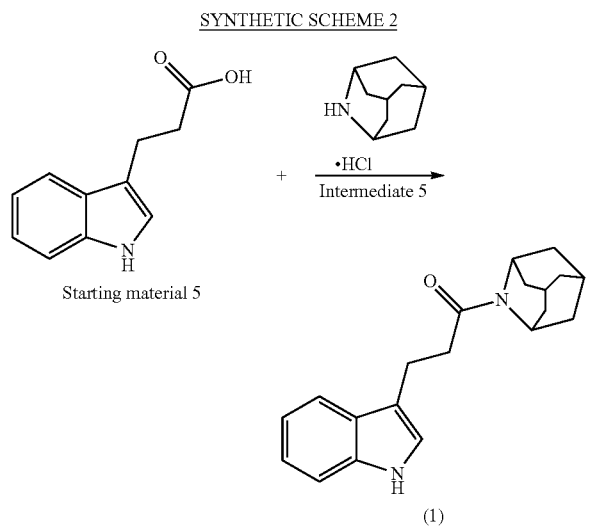

Example 1

1-(2-azatricyclo[3.3.1.1$^{3,7}$]dec-2-yl)-3-(1H-indol-3-yl)propan-1-one (1)

Starting Material-2 (0.2 mmol) was added to Intermediate-5 (0.2 mmol) in dichloromethane (DCM), followed by the addition of 1-ethyl-3-(3-dimethylaminopropyl) carbodiimide hydrochloride (EDCl) (0.26 mmol) and 1-Hydroxybenztriazole (HOBt) (0.23 mmol). The reaction mixture was cooled to 0° C. and was maintained at the same temperature for 30 minutes. Further, Triethylamine (0.93 mmol) was added to the reaction mixture, and the resulting solution was stirred at room temperature for 15 hours. The reaction mass was then diluted with equal ratio of DCM and water, and was washed with 1N HCl solution followed by NaHCO$_3$ and brine solution. The organic layer was separated and dried over anhydrous sodium sulfate. The crude product was obtained by evaporating the organic layer under reduced pressure and was purified by silica gel column using Petroleum ether:Ethyl acetate (1:4) as eluent to obtain Compound (1) (9.5 mg, gummy material). $^1$H NMR (300 MHz, CDCl3): δ 7.91 (brs, 1H), 7.54 (d, 1H), 7.28 (d, 1H), 7.12 (t, 1H), 7.02 (t, 1H), 6.98 (s, 1H), 4.82 (s, 1H), 3.92 (s, 1H), 3.06 (t, 2H), 2.61 (t, 2H), 1.97-1.98 (m, 2H), 1.60-1.75 (m, 10H). LC-MS (M+H)$^+$=309.2; HPLC purity=92.94%.

Example 2

1-(2-azatricyclo[3.3.1.1$^{3,7}$]dec-2-yl)-3-(4-methyl-1H-indol-3-yl)propan-1-one (2)

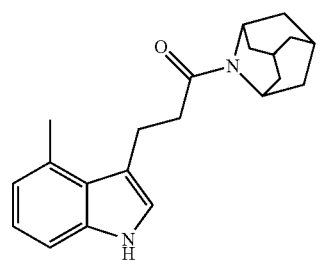

SYNTHETIC SCHEME 3

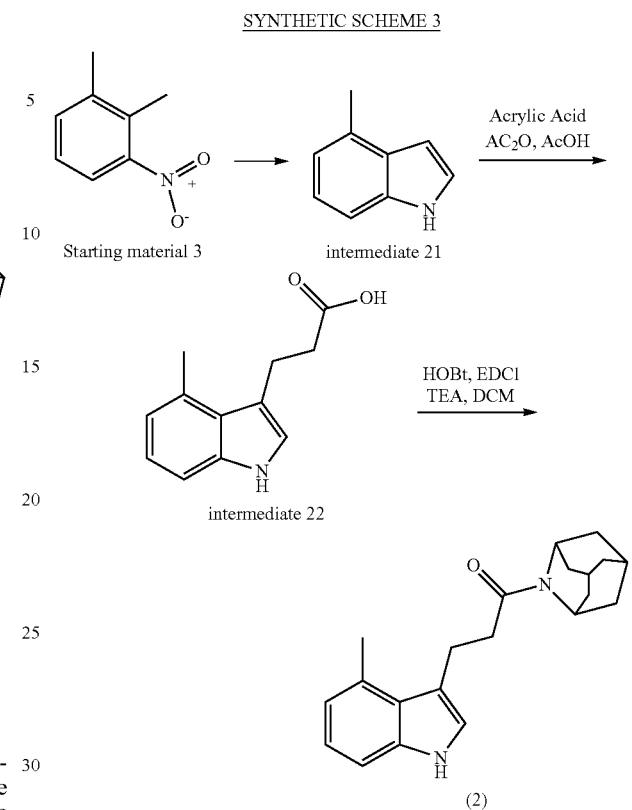

Synthesis of 4-methyl-1H-indole (Intermediate-21)

A 100 mL RB flask fitted with magnetic stirrer and reflux condenser was charged with 60 mL of DMF. To the stirred solvent Starting Material-3 (5 g, 33 mmol) was added followed by Dimethyl formamide dimethyl acetal (13.1 mL, 99.2 mmol). To this Pyrrolidie (3.2 mL, 39.6 mmol) was added and the reaction mixture was heated at 120° C. under Nitrogen atmosphere for 21 hours. After completion of the reaction the mixture was cooled to room temperature and the solvent was removed under reduced pressure. The resulting crude mass was taken in ether (250 mL) and was washed with water (50 mL×3), saturated brine solution (50 mL) and the organic layer was dried over anhydrous sodium sulphate and concentrated. Resulted crude material was taken in Ethyl acetate (50 mL). To this 10% Pd/C (1.0 g, 10% w/w) was added and hydrogenated in a parr shaker for 2 hours. After completion of the reaction (reaction monitored by TLC), the mixture was filtered through celite bed. Filtrate was concentrated to give crude product, which was purified by column chromatography on silica gel (120 meshe) using Petroleum ether (60-80) and ethyl acetate as eluent to give Intermediate-21 (1.2 g).

Synthesis of 3-(4-methyl-1H-indol-3-yl)propanoic acid (Intermediate-22)

A 100 mL RB flask fitted with magnetic stirrer was charged with 2.5 mL of acetic acid. To the stirred solvent acetic anhydride 2.0 mL was added followed by addition of acrylic acid (1.8 mL, 27.4 mmol). To this stirred mixture Intermediate-21 (1.2 g, 9.15 mmol) was added and the reaction mixture was stirred at room temperature for 1 week. After completion of the reaction (reaction was monitored by TLC), reaction mass was basified using 5N NaOH (5 mL) and washed with Ethyl acetate (100 mL×2). The aqueous layer was acidified with concentrated HCl (3 ML) and was extracted using Ethyl acetate (100 mL×3). The combined ethyl acetate layer was washed with brine solution and was concentrated to give Intermediate-22 (350 mg).

Synthesis of Compound (2)

Compound (2) was synthesized by following the procedure used to make Compound (1) (Scheme 2). The crude product was obtained by evaporating the organic layer under reduced pressure and was purified by silica gel column using Petroleum ether:Ethyl acetate as eluent to obtain Compound (2). $^1$H NMR (300 MHz, CDCl3): δ 7.94 (brs, 1H), 7.12 (d, 1H), 6.99 (t, 1H), 6.92 (s, 1H), 6.76 (d, 1H), 4.82 (s, 1H), 3.94 (s, 1H), 3.21 (t, 2H), 2.64 (s, 3H), 2.58 (t, 2H), 2.12-2.17 (m, 1H), 1.64-1.76 (m, 11H). LC-MS (M+H)$^+$=323.2; HPLC purity: 71.84%.

Example 3

1-(2-azatricyclo[3.3.1.1$^{3,7}$]dec-2-yl)-3-(1,4-dimethyl-1H-indol-3-yl)propan-1-one (3)

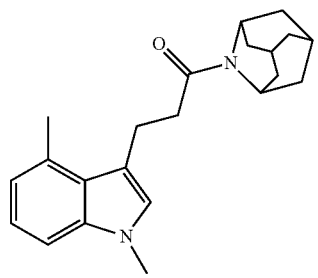

(3)

Synthesis of Compound (3)

Compound (3) was synthesized by following the procedure used to make Compound (1) (Scheme 2). The crude product was obtained by evaporating the organic layer under reduced pressure and was purified by silica gel column using Petroleum ether:Ethyl acetate as eluent to obtain Compound (3). $^1$H NMR (300 MHz, CDCl3): δ 6.98-7.05 (m, 2H), 6.75-6.78 (m, 2H), 4.82 (s, 1H), 3.93 (s, 1H), 3.63 (s, 3H), 3.16-3.22 (m, 2H), 2.64 (s, 3H), 2.55-2.61 (m, 2H), 1.97-2.01 (m, 2H), 1.75-1.79 (m, 2H), 1.70-1.72 (m, 3H), 1.59-1.65 (m, 5H). LC-MS (M+H)$^+$=337.2; HPLC purity: 79.30%.

Example 4

3-(4-fluoro-1H-indol-3-yl)-1-(5-hydroxy-2-azatricyclo[3.3.1.1$^{3,7}$]dec-2-yl)propan-1-one (4)

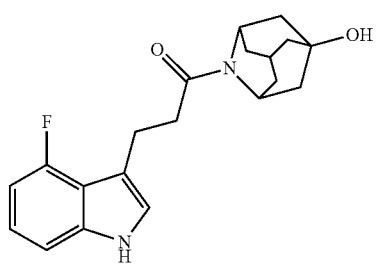

(4)

SYNTHETIC SCHEME 4

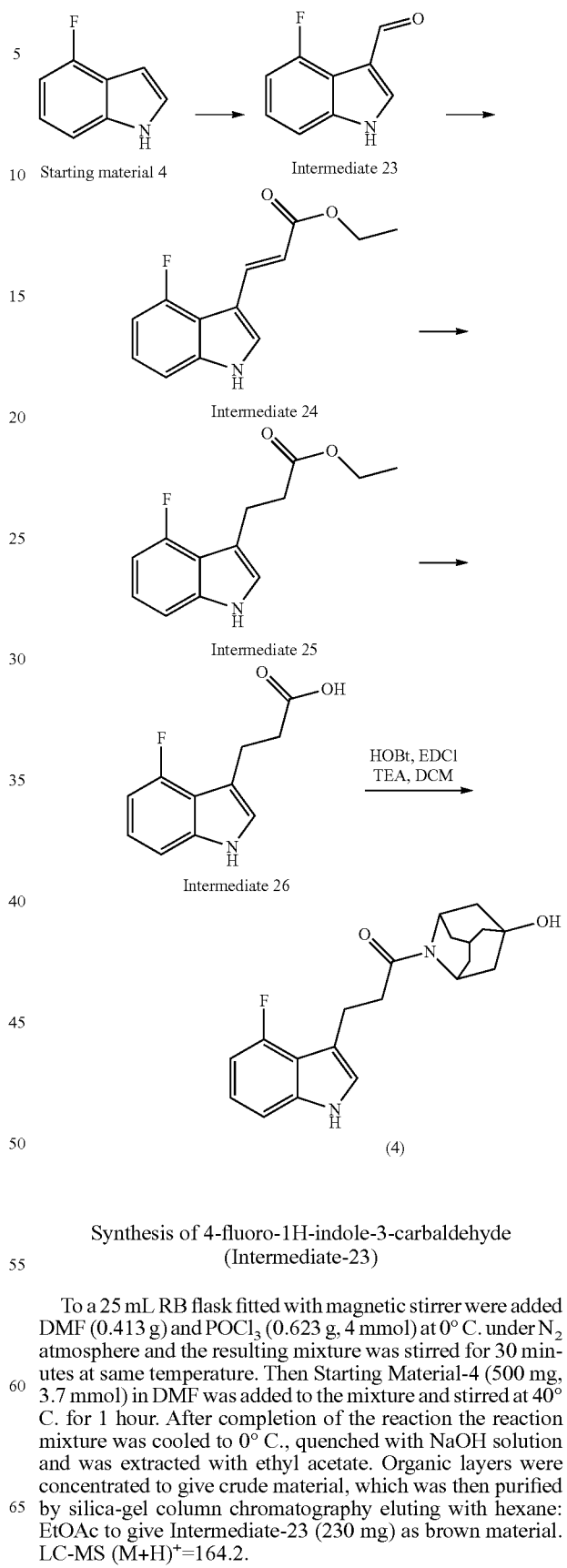

Synthesis of 4-fluoro-1H-indole-3-carbaldehyde (Intermediate-23)

To a 25 mL RB flask fitted with magnetic stirrer were added DMF (0.413 g) and POCl$_3$ (0.623 g, 4 mmol) at 0° C. under N$_2$ atmosphere and the resulting mixture was stirred for 30 minutes at same temperature. Then Starting Material-4 (500 mg, 3.7 mmol) in DMF was added to the mixture and stirred at 40° C. for 1 hour. After completion of the reaction the reaction mixture was cooled to 0° C., quenched with NaOH solution and was extracted with ethyl acetate. Organic layers were concentrated to give crude material, which was then purified by silica-gel column chromatography eluting with hexane: EtOAc to give Intermediate-23 (230 mg) as brown material. LC-MS (M+H)$^+$=164.2.

Synthesis of ethyl (2E)-3-(4-fluoro-1H-indol-3-yl)prop-2-enoate (Intermediate-24)

To a 100 mL RB flask fitted with magnetic stirrer was charged with Intermediate-23 (0.23 g, 1.4 mmol), Ethyl Malonate (0.204 g, 1.5 mmol) and Piperdine (0.011 g, 0.13 mmol) in Pyridine (10 mL). Resulted reaction mixture was heated at 110° C. for 14 hours. After completion of the reaction, the reaction mixture was concentrated to obtain a crude material which was then dissolved in ethyl acetate and washed with water and brine. Organic layer was then concentrated to give crude material, which was purified by silica-gel column chromatography eluting with hexane:EtOAc to give Intermediate-24 (250 mg).

Synthesis of ethyl 3-(4-fluoro-1H-indol-3-yl)propanoate (Intermediate-25)
Intermediate-24 (0.24 g, 1.0 mmol) was taken in EtOAc (10 mL) to which 10% Pd/C (50 mg) was added. The resulting reaction mass was stirred under $H_2$ atmosphere (30 psi) for 4 hours. The reaction mass was filtered through celite bed and concentrated to give Intermediate-25 (240 mg).

Synthesis of 3-(4-fluoro-1H-indol-3-yl)propanoic acid (Intermediate-26)
Intermediate-25 (100 mg, 0.4 mmol) was taken in EtOH:THF:$H_2O$ (5 mL:5 mL:1 mL). To this NaOH (51 mg, 1.2 mmol) was added. Resulting reaction mixture was refluxed for 4 hours. After completion of reaction (reaction monitored by TLC), the reaction mixture was concentrated which was diluted with water, acidified (pH=1 to 2) with 1N HCl, extracted with EtOAc and concentrated to give Intermediate-26 (90 mg).

Synthesis of Compound (4)

Compound (4) was synthesized by following the procedure used to make Compound (1) (Scheme 2). The crude product was obtained by evaporating the organic layer under reduced pressure and was purified by silica gel column using DCM:MeOH as eluent to obtain Compound (4). $^1$H NMR (300 MHz, CDCl3): δ 8.04 (s, 1H), 6.97-7.07 (m, 2H), 6.94 (s, 1H), 6.65-6.71 (m, 1H), 5.01 (s, 1H), 4.21 (s, 1H), 3.08-3.13 (t, 2H), 2.62-2.67 (t, 2H), 2.24 (s, 1H), 1.53-1.74 (m, 10H)$^+$. LC-MS (M+H)$^+$=343.12; HPLC purity: 95.20%.

Example 5

1-(2-azatricyclo[3.3.1.1$^{3,7}$]dec-2-yl)-3-(6-fluoro-1H-indol-3-yl)propan-1-one (5)

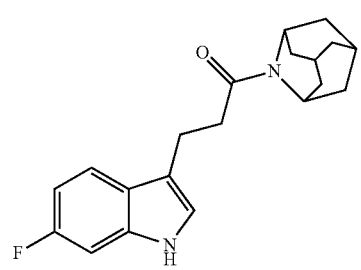

(5)

Synthesis of Compound (5)

Compound (5) was synthesized by following the procedure used to make Compound (1) (Scheme 2). The crude product was obtained by evaporating the organic layer under reduced pressure and was purified by silica gel column using Petroleum ether:Ethyl acetate as eluent to obtain Compound (5). $^1$H NMR (300 MHz, CDCl3): δ 8.02 (brs, 1H), 7.41-7.46 (dd, 1H), 6.95-6.99 (m, 2H), 6.78-6.85 (m, 1H), 4.81 (s, 1H), 3.90 (s, 1H), 3.03-3.08 (t, 2H), 2.63-2.68 (t, 2H), 1.96-2.02 (m, 2H), 1.56-1.76 (m, 10H)$^+$. LC-MS (M+H)$^+$=327.3; HPLC purity: 95.25%.

Example 6

3-(5-fluoro-1H-indol-3-yl)-1-(4-hydroxy-2-azatricyclo[3.3.1.1$^{3,7}$]dec-2-yl)propan-1-one (6)

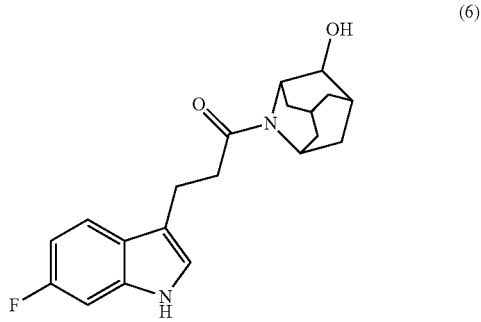 [SMILES: O=C(CCc1c[nH]c2cc(F)ccc12)N1C2CC3CC(C2)C(O)C1C3]

(6)

SYNTHETIC SCHEME 5

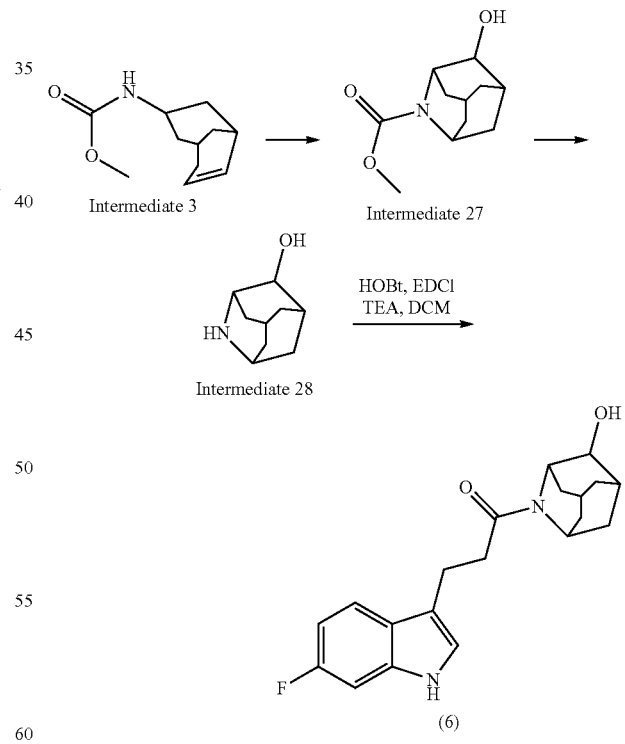

Synthesis of methyl 4-hydroxy-2-azatricyclo[3.3.1.1$^{3,7}$]decane-2-carboxylate (Intermediate-27)

To a 100 mL RB flask fitted with magnetic stirrer was charged 25 mL of Dichloromethane. To this Intermediate-3

(0.5 g, 2.5 mmol), followed by m-CPBA (0.69 g, 4.0 mmol) were added at 0° C. Then reaction mixture was stirred at room temperature for 16 hours. After completion of the reaction, the reaction mixture was quenched using aqueous NaHCO$_3$ solution and was extracted with dichloromethane. Organic layer was concentrated to give Intermediate-27 (0.5 g).

Synthesis of 2-azatricyclo[3.3.1.1$^{3,7}$]decan-4-ol hydrogen chloride salt (Intermediate-28)

A 50 mL pressurized seal tube fitted with magnetic stirrer was charged with Intermediate-27 (0.2 g, 0.9 mmol) in HCl containing 1,4-Dioxane (20 mL). Then reaction mixture was stirred at 90° C. for 8 hours. After completion of the reaction (reaction was monitored by LCMS), it was concentrated followed by trituration with mixture of hexane:ether (1:1) to give Intermediate-28 (0.2 g).

Synthesis of Compound (6)

Compound (6) was synthesized by following the procedure used to make Compound (1) (Scheme 2). The crude product was obtained by evaporating the organic layer under reduced pressure and was purified by silica gel column using DCM: MeOH as eluent to obtain Compound (6). $^1$H NMR (300 MHz, CDCl3): δ 7.97 (brs, 1H), 7.17-7.23 (d, 1H), 7.14-7.15 (d, 1H), 7.02 (s, 1H), 6.84-6.90 (m, 1H), 4.67-4.73 (d, 1H), 3.83 (brs, 0.5H), 3.68 (s, 1H), 3.35 (brs, 1H), 2.98-3.03 (t, 2H), 2.56-2.64 (m, 2H), 2.07-2.11 (m, 1H), 1.97 (m, 1H), 1.61-1.69 (m, 7H). LC-MS (M+H)$^+$=343.1; HPLC purity: 95.88%.

Example 7

1-(2-azatricyclo[3.3.1.1$^{3,7}$]dec-2-yl)-3-(5-fluoro-1H-indol-3-yl)propan-1-one (7)

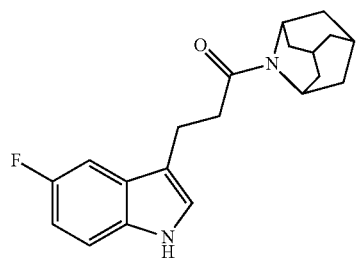

(7)

Synthesis of Compound (7)

Compound (7) was synthesized by following the procedure used to make Compound (1) (Scheme 2). The crude product was obtained by evaporating the organic layer under reduced pressure and was purified by silica gel column using Petroleum ether:Ethyl acetate as eluent to obtain Compound (7). $^1$H NMR (300 MHz, CDCl3): δ 7.94 (s, 1H), 722 (d, 1H), 7.16 (s, 1H), 7.03 (s, 1H), 6.86-6.87 (t, 1H), 4.81 (s, 1H), 3.91 (s, 1H), 2.99-3.04 (t, 2H), 2.57-2.62 (t, 2H), 1.92-1.98 (m, 2H), 1.58-1.75 (m, 10H). LC-MS (M+H)$^+$=327.2; HPLC purity: 96.53%.

Example 8

3-(4-fluoro-1-methyl-1H-indol-3-yl)-1-(5-hydroxy-2-azatricyclo[3.3.1.1$^{3,7}$]dec-2-yl)propan-1-one (8)

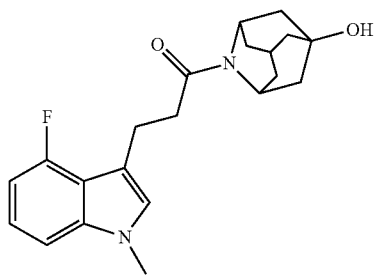

(8)

Synthesis of Compound (8)

Compound (8) was synthesized by following the procedure used to make Compound (1) (Scheme 2). The crude product was obtained by evaporating the organic layer under reduced pressure and was purified by silica gel column using DCM: MeOH as eluent to obtain Compound (8). $^1$H NMR (300 MHz, CDCl3): δ 6.96-7.07 (m, 2H), 6.78 (s, 1H), 6.63-6.69 (m, 1H), 5.01 (s, 1H), 4.21 (s, 1H), 3.64 (s, 3H), 3.05-3.10 (t, 2H), 2.59-2.64 (t, 2H), 2.24 (s, 1H), 1.53-1.74 (m, 10H). LC-MS (M+H)$^+$=357.1; HPLC purity: 89.95%.

Example 9

3-(5-fluoro-1H-indol-3-yl)-1-(5-hydroxy-2-azatricyclo[3.3.1.1$^{3,7}$]dec-2-yl)propan-1-one (9)

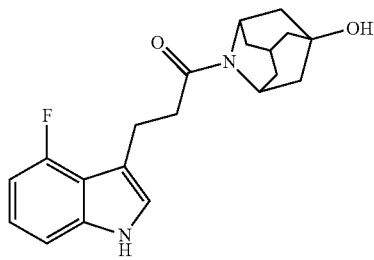

(9)

Synthesis of Compound (9)

Compound (9) was synthesized by following the procedure used to make Compound (1) (Scheme 2). The crude product was obtained by evaporating the organic layer under reduced pressure and was purified by silica gel column using DCM: MeOH as eluent to obtain Compound (9). $^1$H NMR. (300 MHz, CDCl3): δ 7.94 (brs, 1H), 7.19-7.22 (d, 1H), 7.15-7.16 (d, 1H), 7.02 (s, 1H), 6.83-6.90 (m, 1H), 5.02 (s, 1H), 4.01 (s, 1H), 2.99-3.04 (t, 2H), 2.57-2.62 (t, 2H), 2.26 (s, 1H), 1.61-1.97 (m, 10H). LC-MS (M+H)$^+$=343.1; HPLC purity: 93.42%.

Example 10

1-(5-hydroxy-2-azatricyclo[3.3.1.1$^{3,7}$]dec-2-yl)-3-methyl-3-(1-methyl-1H-indol-3-yl)butan-1-one (10)

(10)

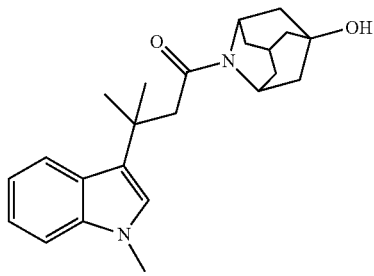

SYNTHETIC SCHEME 6

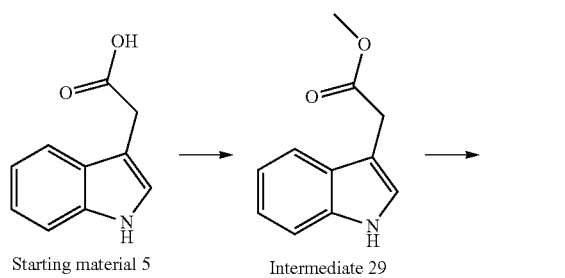

Starting material 5    Intermediate 29

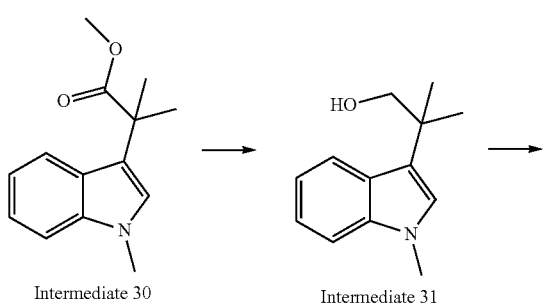

Intermediate 30    Intermediate 31

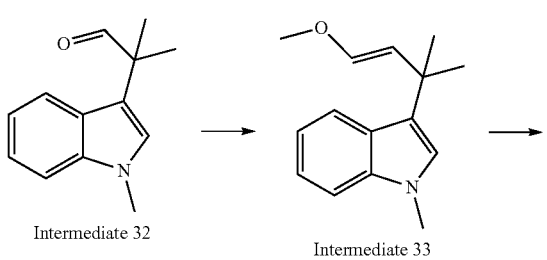

Intermediate 32    Intermediate 33

-continued

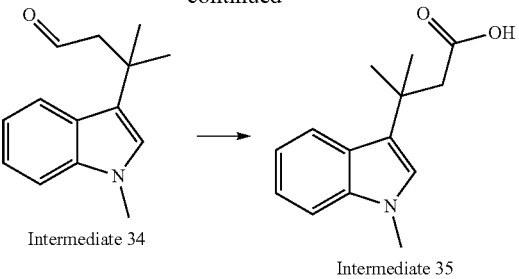

Intermediate 34    Intermediate 35

Synthesis of methyl 1H-indol-3-ylacetate (Intermediate-29)

A 100 mL RB flask fitted with magnetic stirrer was charged with 15 mL of Methanol. To the stirred solvent Starting Material-5 (2.0 g, 11.41 mmol) was added. The resulting mixture was cooled to 0° C. and concentrated H$_2$SO$_4$ (0.5 mL) was added. The reaction mixture was then stirred at room temperature for 1 hour. After completion of the reaction (reaction monitored by TLC), solvent from the reaction mass was removed under reduced pressure. The resulting crude mass was taken in Ethyl acetate (100 mL) and was washed with water (50 mL), Sodium bicarbonate solution (100 mL×2) and saturated brine solution (50 mL). The organic layer was then dried over anhydrous sodium sulphate. Then the solvent was removed under reduced pressure. The product Intermediate-29 was obtained as brown syrup. (2.1 g). LC-MS (M+H)$^+$=190.2.

Synthesis of methyl 2-methyl-2-(1-methyl-1H-indol-3-yl)propanoate (Intermediate-30)

A 100 mL 3 neck RB flask fitted with magnetic stirrer was charged with 10 mL of dry THF. To the stirred solvent diisopropyl amine (401.12 mg, 3.964 mmol) was added and the resulting solution was cooled to −78° C. n-BuLi (2.5 mL, 3.964 mmol) was added and stirred for 1 hour at 0° C. The reaction mixture was again cooled to −78° C. to which Intermediate-29 (150 mg, 0.7928 mmol) was added. The reaction mixture was then stirred for 1 hour. This was followed by addition of Methyl Iodide. The resulting mass was then stirred at room temperature for 15 hours. After completion of the reaction (reaction monitored by TLC), the reaction mass was quenched with saturated ammonium chloride and was extracted using EtOAc (100 mL×3). The combined organic layers were washed with brine and dried after which the solvent was removed under reduced pressure. The resulting crude compound was purified by column chromatography on silica gel (120 meshes) using Petroleum ether (60-80) and ethyl acetate as eluent. The product Intermediate-30 was obtained as a brown syrup. (150 mg). LC-MS (M+H)$^+$=232.2.

Synthesis of 2-methyl-2-(1-methyl-1H-indol-3-yl)propan-1-ol (Intermediate-31)

A 250 mL RB flask fitted with magnetic stirrer was charged with Lithium aluminum hydride (0.983 g, 25.951 mmol) and THF (20 mL) was added to it at 0° C. To this resulting suspension Intermediate-30 (2.0 g, 8.65 mmol) in THF (20 mL) was added and the resulting mixture was stirred at room temperature for 2 hours. After completion of the reaction, reaction mixture was diluted with EtOAc (50 mL) and then quenched with Na$_2$SO$_4$ (5 g). The resulting slurry was stirred at room temperature for 1 hour, filtered through celite and washed with ethyl acetate. The resulting filtrate was concentrated to give Intermediate-31 (0.9 g). $^1$H NMR (300 MHz, DMSO-d6): δ 7.65-7.68 (d, 1H), 7.34-7.36 (d, 1H), 7.07-7.12 (t, 1H), 7.03 (s, 1H), 6.94-6.99 (t, 1H), 4.53-4.57 (t, 1H), 3.71 (s, 3H), 3.54-3.56 (d, 2H), 1.31 (s, 6H).

Synthesis of 2-methyl-2-(1-methyl-1H-indol-3-yl) propanal (Intermediate-32)

A 100 mL RB flask fitted with magnetic stirrer was charged with 30 mL DCM to which Pyridinium chloro chromate (2.466 g, 11.4419 mmol) was added followed by the addition of Intermediate-31 (1.55 g, 7.627 mmol) in 10 mL of DCM. The resulting mixture was stirred at room temperature for 2 hours. After completion of the reaction, the solvent from the reaction mass was removed under reduced pressure to yield the crude compound. Crude mass was purified by column chromatography using 60-120 silica gel and 9:1 Pet ether/ethyl acetate as eluent to give Intermediate-32 (0.79 g). $^1$H NMR (300 MHz, DMSO-d6): δ 9.39 (s, 1H), 7.40-7.44 (t, 1H), 7.32 (s, 1H), 7.13-7.18 (t, 1H), 6.98-7.03 (t, 1H), 3.77 (s, 3H), 1.46 (s, H).

Synthesis of 3-[(3E)-4-methoxy-2-methylbut-3-en-2-yl]-1-methyl-1H-indole (Intermediate-33)

A 100 mL RB flask fitted with magnetic stirrer was charged with 20 mL of dry THF and Methoxy methyl triphenyl phosphonium chloride (2.566 g, 7.487 mmol) followed by Potassium tert butoxide (2.295 g, 20.451 mmol). The resulting mass was stirred at room temperature for 2 hours and then cooled to 0° C. Intermediate-32 (1.37 g, 6.807 mmol) in 10 mL of THF was added to the above reaction mass and was stirred at room temperature for 2 hours. After completion of the reaction the reaction mass was diluted with 10 mL of water and was extracted with ethyl acetate (100 mL×3). The combined organic layers were washed with brine solution and was dried over anhydrous sodium sulfate and concentrated to obtain the crude product. Crude product was purified by column chromatography using 60-120 silica gel and 6% of ethyl acetate in Pet ether as eluent to give Intermediate-33. Yield: 1.12 g (71.8%).

$^1$H NMR (300 MHz, CDCl3): δ 7.73-7.80 (m 1H), 7.33 (s, 1H), 7.16-7.21 (t, 1H), 7.03-7.08 (t, 1H), 6.81 (s, 1H), 5.79-6.34 (m, 1H), 4.58-5.15 (m, 1H), 3.73-3.74 (d, 3H), 3.49-3.53 (d, 3H), 1.55 (s, 6H).

Synthesis of 3-methyl-3-(1-methyl-1H-indol-3-yl) butanal (Intermediate-34)

A 100 mL RB flask fitted with magnetic stirrer was charged with 50.4 mL of 1,4 dioxane and 12.76 mL of water. To this Intermediate-33 (1.12 g, 4.884 mmol) was added followed by addition of p-toluene sulphonic acid (0.0424 g, 0.2232 mmol). The resulting mass was heated at 60° C. for 16 hours. After completion of the reaction, the reaction mixture was quenched with 10 mL of water and extracted with ethyl acetate (100 mL×3) and the combine organic layer was washed with saturated sodium bicarbonate solution followed by brine solution and was dried over anhydrous sodium sulfate and was concentrated to obtain the crude product. The crude product was purified by column chromatography using 60-120 silica gel and 8% of ethyl acetate in Pet ether as eluent to give Intermediate-34. $^1$H NMR (300 MHz, DMSO-d6): δ 9.47-9.49 (t, 1H), 7.73-7.76 (d, 1H), 7.37-7.40 (d, 1H), 7.11-7.16 (t, 1H), 7.10 (s, 1H), 6.99-7.04 (t, 1H) 3.72 (s, 3H), 2.78 (s, 2H), 1.49 (s, 6H).

Synthesis of 3-methyl-3-(1-methyl-1H-indol-3-yl) butanoic acid (Intermediate-35)

A 50 mL RB flask fitted with magnetic stirrer was charged with 10 mL of THF and was cooled to −78° C. to which 2-methyl-2-butene (3 mL) was added and stirred for 15 minutes. Another 100 mL RB flask fitted with magnetic stirrer was charged with Intermediate-34 (557 mg, 2.59 mmol) and tert butanol (15 mL) and was stirred at room temperature and the above prepared THF solution was added to it. Then the resulting mass was cooled to 0° C. to which NaH$_2$PO$_4$ (1.42 g) in water was added followed by addition of NaClO$_2$ (0.35 g) in water. The resulting mixture was stirred at 0° C. for 20 minutes and quenched with water. The pH of the reaction mixture was adjusted to 1-2 using 1N HCl and the product was extracted with ethyl acetate and concentrated to give Intermediate-35 (480 mg). $^1$H NMR (300 MHz, DMSO-d6): δ 11.82 (s, 1H), 7.69-7.71 (d, 1H), 7.35-7.38 (d, 1H), 7.09-7.14 (t, 1H), 7.05 (s, 1H), 6.96-7.01 (t, 1H), 3.71 (s, 3H), 2.66 (s, 2H), 1.48 (s, 6H)

Synthesis of Compound (10)

Compound (10) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (10). $^1$H NMR (300 MHz, DMSO-d6): δ 7.70-7.73 (d, 1H), 7.34-7.37 (d, 1H), 7.10 (t, 1H), 7.04 (s, 1H), 6.98-7.04 (t, 1H), 4.75 (brs, 1H), 4.54 (s, 1H), 3.99 (brs, 1H), 3.70 (s, 3H), 2.60-2.65 (dd, 2H), 2.02 (s, 1H), 1.28-1.62 (m, 16H) LC-MS (M+H)$^+$=367.3; HPLC purity: 88.74%.

Example 11

1-(2-azatricyclo[3.3.1.1$^{3,7}$]dec-2-yl)-3-(1,3-benzothiazol-2-yl)propan-1-one (11)

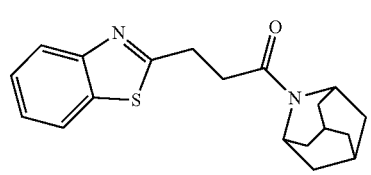

(11)

SYNTHETIC SCHEME 7

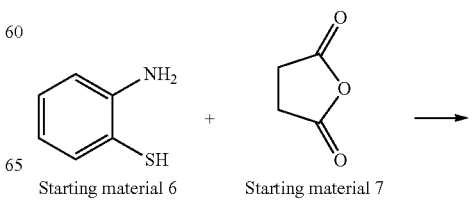

Starting material 6     Starting material 7

-continued

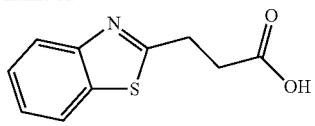

Intermediate 36

Synthesis of 3-(1,3-benzothiazol-2-yl)propanoic acid (Intermediate-36)

Starting material-7 (3.97 mmol) in benzene was added drop wise to the solution of Starting Material-6 (3.97 mmol) in benzene. The resulting solution was heated to reflux for 2 hours. After 2 hours the reaction mass was cooled to room temperature and was extracted with 10% sodium hydroxide solution. The aqueous layer was acidified using Conc.HCl (3 ml) at 0° C. The resulting solids were filtered and dried at room temperature to get Intermediate-36 (660 mg).

Synthesis of Compound (11)

Compound (11) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (11). 1H NMR (300 MHz, CDCl3): δ 7.89-7.91 (d, 1H), 7.76-7.78 (d, 1H), 7.36-7.41 (t, 1H), 7.26-7.31 (t, 1H), 4.79 (s, 1H), 4.01 (s, 1H), 3.40-3.46 (t, 2H), 2.82-2.88 (t, 2H), 1.98-2.02 (m, 2H), 1.66-1.81 (m, 10H). LC-MS: (M+H)+ =327.3; HPLC purity=94.43%.

Example 12

3-(1,3-benzothiazol-2-yl)-1-(5-hydroxy-2-azatricyclo[3.3.1.1$^{3,7}$]dec-2-yl)propan-1-one (12)

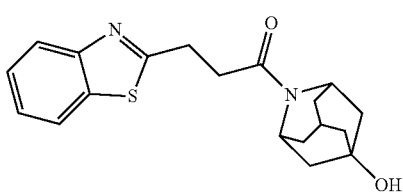

(12)

Synthesis of Compound (12)

Compound (12) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (12). 1H NMR (300 MHz, CDCl3): δ 7.91-7.93 (d, 1H), 7.76-7.79 (d, 1H), 7.37-7.43 (t, 1H), 7.28-7.33 (t, 1H), 4.99 (s, 1H), 4.28 (s, 1H), 3.42-3.47 (t, 2H), 2.88-2.93 (t, 2H), 2.28 (brs, 1H), 1.51-1.79 (m, 10H). LC-MS: (M+H)+=343.1; HPLC purity=99.27%.

Example 13

3-(1,3-benzothiazol-2-yl)-1-[5-(difluoromethoxy)-2-azatricyclo[3.3.1.1$^{3,7}$]dec-2-yl]propan-1-one (13)

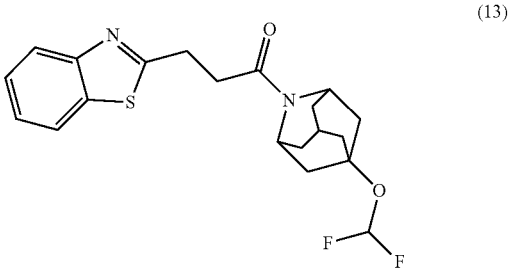 [SMILES: O=C(CCc1nc2ccccc2s1)N1C2CC3CC1CC(OC(F)F)(C3)C2]

(13)

SYNTHETIC SCHEME 8

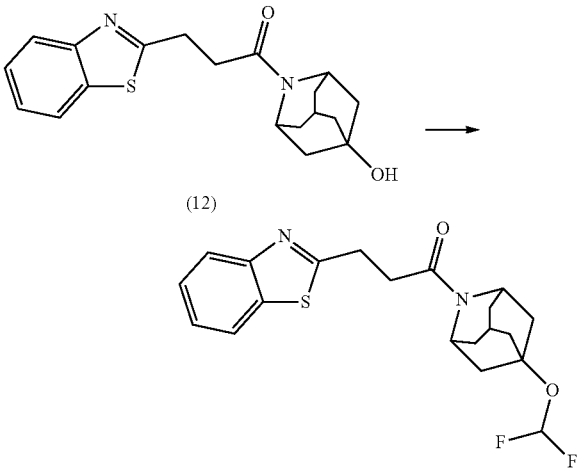

Synthesis of Compound (13)

To a stirred solution of (80 mg, 0.28 mmol) in MeCN (3 mL) was added CuI (88 mg, 0.046 mmol) and heated to 45° C. To this difluoro(fluorosulfonyl)acetic acid (23 mg, 0.46 mmol) was added. The resultant mixture is allowed to stir at the same temperature for 30 minutes. After completion of the reaction, the reaction mixture is quenched with water, extracted with EtOAc and concentrated. Resulted crude material was purified by silica gel column chromatography eluting with hexane:EtOAc to give Compound (13) (40 mg) as dark yellow gummy material. 1H NMR (300 MHz, CDCl3): δ 7.87-7.89 (d, 1H), 7.76-7.78 (d, 1H), 7.35-7.40 (t, 1H), 7.26-7.31 (t, 1H), 5.97-6.48 (t, 1H), 5.03 (brs, 1H), 4.33 (brs, 1H), 3.39-3.44 (t, 2H), 2.85-2.89 (t, 2H), 2.33 (brs, 1H), 1.87-1.98 (m, 4H), 1.57-1.70 (m, 6H). LC-MS: (M+H)+=393.2; HPLC purity=89.63%.

Example 14

1-(2-azatricyclo[3.3.1.1$^{3,7}$]dec-2-yl)-3-(1H-pyrrolo[2,3-b]pyridin-3-yl)propan-1-one (14)

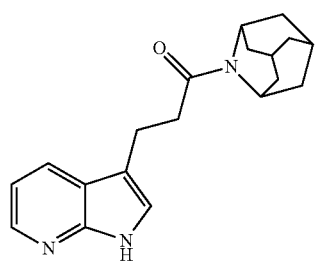

(14)

SYNTHETIC SCHEME 9

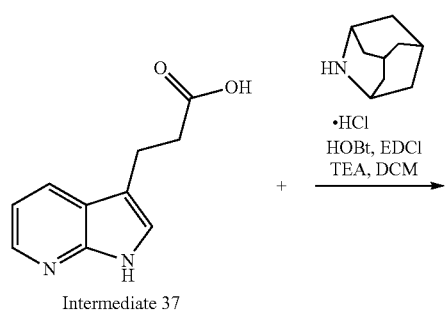

Intermediate 37

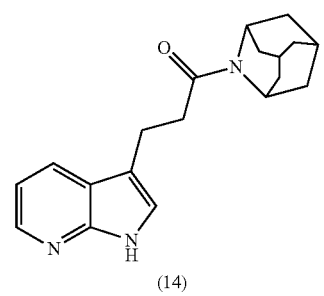

(14)

Synthesis of 3-(1H-pyrrolo[2,3-b]pyridin-3-yl)propanoic acid (Intermediate-37)

Intermediate-37 was synthesized by following the procedure used to make Intermediate-26 (Scheme 4).

Synthesis of Compound (14)

Compound (14) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (14). 1H NMR (300 MHz, CDCl3): δ 8.99 (brs, 1H), 8.22-8.21 (d, 1H), 7.9-7.88 (d, 1H), 7.07 (s, 1H), 7.03-6.99 (t, 1H), 4.81 (s, 1H), 3.92 (s, 1H), 3.07-3.02 (t, 2H), 2.62-2.57 (t, 2H), 1.97-1.98 (m, 3H), 1.76-1.56 (m, 11H). LC-MS: (M+H)+=310.2; HPLC purity=98.28%.

Example 15

1-(5-hydroxy-2-azatricyclo[3.3.1.1$^{3,7}$]dec-2-yl)-3-(1H-pyrrolo[2,3-b]pyridin-3-yl)propan-1-one (15)

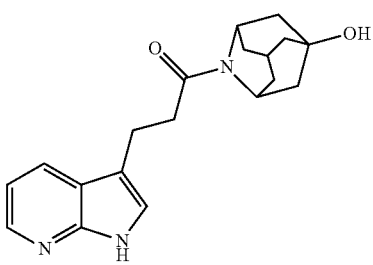

(15)

Synthesis of Compound (15)

Compound (15) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (15). 1H NMR (300 MHz, CDCl3): δ 9.02 (brs, 1H), 8.20-8.22 (d, 1H), 7.86-7.88 (d, 1H), 7.07 (brs, 1H), 6.99-7.03 (dd, 1H), 5.00 (bs, 1H), 4.10 (brs, 1H), 3.02-3.07 (t, 2H), 2.57-2.62 (t, 2H), 2.22 (brs, 1H), 1.45-1.73 (m, 10H). LC-MS: (M+H)+=326.1; HPLC purity=98.04%.

Example 16

3-(1H-benzotriazol-1-yl)-1-(5-hydroxy-2-azatricyclo[3.3.1.1$^{3,7}$]dec-2-yl)propan-1-one (16)

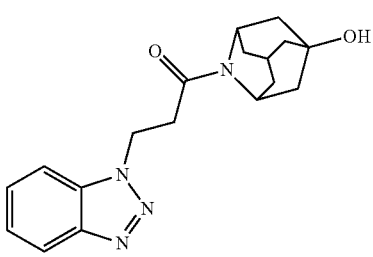

(16)

SYNTHETIC SCHEME 10

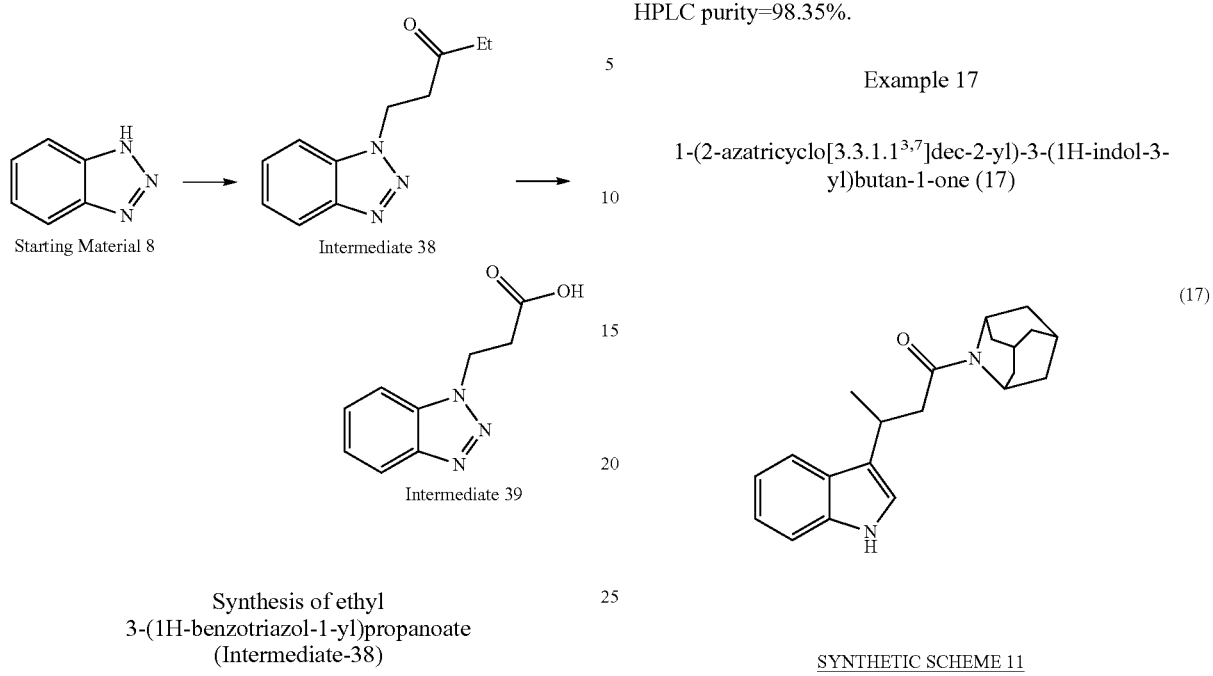

Synthesis of ethyl 3-(1H-benzotriazol-1-yl)propanoate (Intermediate-38)

The starting material-8 (4.1 mmol) in dry THF (5 ml) was cooled to 0° C., followed by the addition of NaH (6.0 mmol). The reaction mixture was gradually warmed to room temperature and allowed to react for 20 minutes. The reaction mixture was again cooled to 0° C., followed by the drop wise addition of ethyl 3-bromopropanoate (4.6 mmol) in THF (2.5 ml). The reaction was allowed for 12 hours at room temperature. After 12 hours the reaction mixture was quenched with ice cooled water and extracted with ethyl acetate. The organic layer was dried over anhydrous $MgSO_4$, and concentrated to obtain Intermediate-38 (70 mg). 1H NMR (300 MHz, CDCl3): δ 7.98-8.01 (1H, d), 7.55-7.58 (d, 1H), 7.41-7.46 (t, 1H), 7.28-7.33 (t, 1H), 4.82-4.87 (t, 2H), 4.00-4.07 (t, 2H), 3.00-3.05 (t, 2H), 1.08-1.1 (t, 3H).

Synthesis of 3-(1H-benzotriazol-1-yl)propanoic acid (Intermediate-39)

At 0° C., LiOH (1.5 mmol) in water (1 ml) was added to Intermediate-38 in the solvent THF:MeOH (1:1, 3 ml each). The reaction was allowed for 12 hours at room temperature. After 12 hours the reaction mixture was concentrated, further acidified with 1N HCl (pH=2). The reaction mixture was extracted with ethyl acetate. The organic layer was dried over anhydrous $MgSO_4$, and evaporated under reduced pressure to obtain Intermediate-39 (60 mg). 1H NMR (300 MHz, CDCl3): δ 7.29-8.00 (4H, m), 4.82-4.87 (t, 2H), 3.09-3.14 (t, 2H).

Synthesis of Compound (16)

Compound (16) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (16). 1H NMR (300 MHz, CDCl3): δ 7.23-7.97 (m, 4H), 4.81-4.92 (m, 3H), 4.10 (brs, 1H), 3.01-3.05 (t, 2H), 2.21 (brs, 1H), 1.40-1.78 (m, 10H). LC-MS: (M+H)+=327.2; HPLC purity=98.35%.

Example 17

1-(2-azatricyclo[3.3.1.1$^{3,7}$]dec-2-yl)-3-(1H-indol-3-yl)butan-1-one (17)

(17)

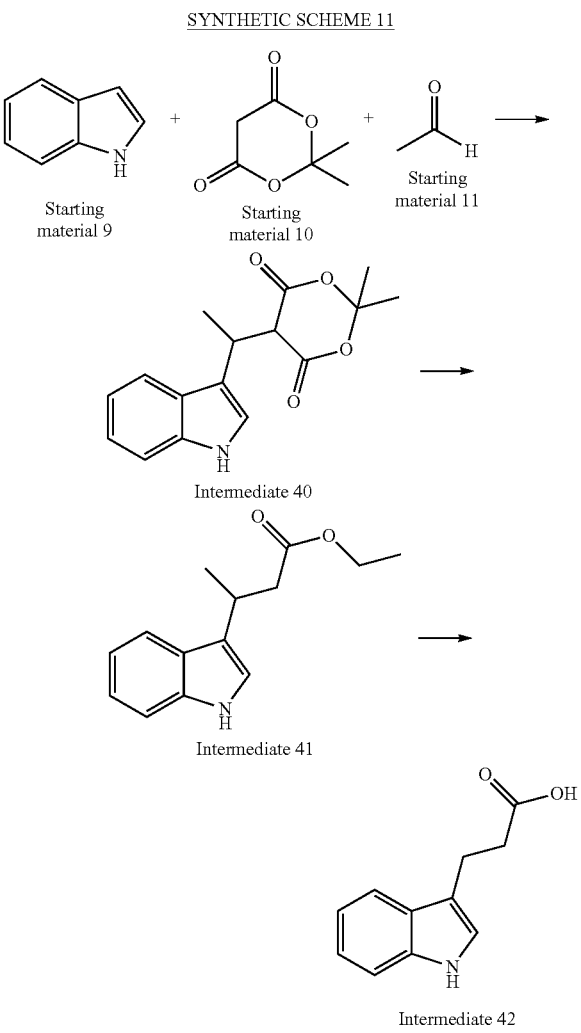

SYNTHETIC SCHEME 11

Synthesis of 5-[1-(1H-indol-3-yl)ethyl]-2,2-dimethyl-1,3-dioxane-4,6-dione (Intermediate-40)

A 100 mL RB flask fitted with magnetic stirrer was charged with Starting Material-9 (4.0 g, 34 mmol), Starting Material-10 (4.92, 34 mmol) and Starting Material-11 (3 g, 68 mmol) in 75 mL of acetonitrile. The resulting solution was stirred at room temperature overnight. After completion of the reaction (reaction monitored by TLC), the solvent was removed under reduced pressure, and the resulting crude compound was purified by column chromatography on silica gel (230-400 mesh) using Petroleum ether (60-80) and ethyl acetate as eluent. The product (intermediate-40) was obtained as a brown liquid (2.51 g). LC-MS (M−H)$^+$=286.

Synthesis of ethyl 3-(1H-indol-3-yl)butanoate (Intermediate-41)

A 100 mL RB flask fitted with magnetic stirrer was charged with intermediate-40 (2.5 g, 8.7 mmol) in 50 mL of pyridine and 8 ml of ethanol. To this mixture copper powder (0.4 g, 5 mol %) was added. Then the resulting reaction mass was refluxed at 110° C. for 3 hours. After completion of the reaction (reaction monitored by TLC), solvent was removed from the reaction mass and the reaction mass was diluted with 100 mL of ethyl acetate. This was followed by washing of the reaction mass with 50 mL 1.5N HCl (2×25 mL) and brine solution. Then the organic layer was dried over 10 g of anhydrous MgSO$_4$. The solvent was removed under reduced pressure, and the resulting crude compound was purified by column chromatography on silica gel (230-400 mesh) using Petroleum ether (60-80) and ethyl acetate as eluent. The product (intermediate-41) was obtained as a brown liquid. (0.380 g). LC-MS (M+H)$^+$=232.

Synthesis of ethyl 3-(1H-indol-3-yl)butanoic acid (Intermediate-42)

A 50 mL RB flask fitted with magnetic stirrer was charged with 6 mL of methanol and 2 mL of water. To the stirred solvent intermediate-41 (0.145 g, 0.62 mmol) and KOH (0.098 g, 2.54 mmol) was added. Then the resulting reaction mass was refluxed at 70° C. for 3 hours. After completion of the reaction (reaction monitored by TLC), solvent was removed from the reaction mass and the reaction mass was diluted with 20 mL of water. The aqueous layer was washed with 20 mL of diethylether and was acidified by 1NHCl to pH 5.5. The product was then extracted with ethyl acetate and the solvent was removed under reduced pressure. The product (intermediate-42) was obtained as a brown liquid (0.115 g). The product obtained above was directly taken for next step without any purification.

Synthesis of Compound (17)

Compound (17) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (17). 1H NMR (300 MHz, CDCl3): δ 7.91 (brs, 1H), 7.60-7.63 (d, 1H), 7.27-7.30 (d, 1H), 7.09-7.13 (t, 1H), 7.01-7.03 (t, 1H), 6.96 (s, 1H), 4.80 (s, 1H), 3.93 (s, 1H), 3.54-3.61 (m, 1H), 2.72-2.79 (m, 1H), 2.45-2.50 (m, 1H), 2.10 (brs, 1H), 1.88-1.97 (m, 1H), 1.66-1.74 (m, 5H), 1.47-1.59 (m, 5H), 1.38-1.41 (d, 3H). LC-MS: (M+H)+=323.3; HPLC purity=90.83%.

Example 18

1-(4-hydroxy-2-azatricyclo[3.3.1.1$^{3,7}$]dec-2-yl)-3-(1H-indol-3-yl)butan-1-one (18)

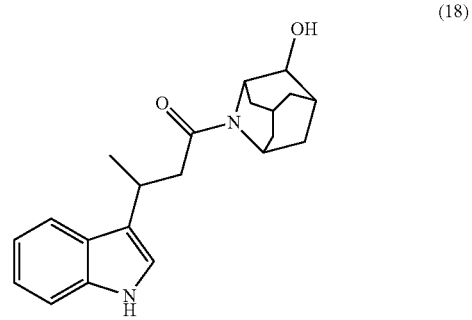 [SMILES: CC(CC(=O)N1C2CC3CC(C2)C(O)C1C3)c1c[nH]c2ccccc12]

(18)

Synthesis of Compound (18)

Compound (18) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (18). 1H NMR (300 MHz, CDCl3): δ 7.92 (brs, 1H), 7.75-7.54 (m, 1H), 7.35-7.27 (m, 1H), 7.14-7.01 (m, 2H), 6.96 (brs, 1H), 4.73-4.64 (d, 1H), 3.89 (s, 1H), 3.67 (s, 1H), 3.37-3.60 (m, 1H), 2.67-2.79 (m, 1H), 2.59-2.46 (m, 1H), 2.08-1.86 (m, 3H), 1.75-1.60 (m, 5H), 1.53-1.44 (m, 2H), 1.38-1.42 (m, 3H). LC-MS: (M+H)+=339.2; HPLC purity=98.80%.

Example 19

1-(4-hydroxy-2-azatricyclo[3.3.1.1$^{3,7}$]dec-2-yl)-3-(1H-indol-3-yl)-4-methylpentan-1-one (19)

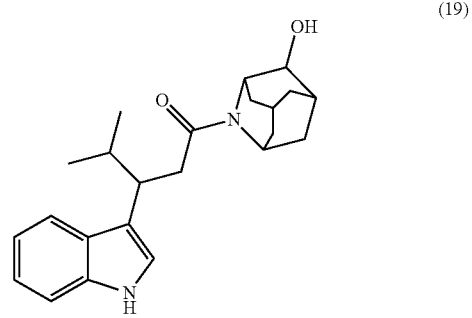 [SMILES: CC(C)C(CC(=O)N1C2CC3CC(C2)C(O)C1C3)c1c[nH]c2ccccc12]

(19)

Synthesis of Compound (19)

Compound (19) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (19). 1H NMR (300 MHz, CDCl3): δ 8.06-7.98 (d, 1H), 7.70-7.56 (d, 1H), 7.36-7.24 (m, 1H), 7.16-7.01 (m, 2H), 6.98-6.91 (d, 1H), 4.57-4.56 (d, 1H), 3.83-3.39 (m, 2H), 3.25-2.90 (m, 2H), 2.80-2.66 (m, 1H), 2.16-2.02 (m, 1H), 1.98-1.66 (m, 4H), 1.54-1.08 (m, 6H), 0.961-0.89 (d, 6H). LC-MS: (M+H)+=367.3; HPLC purity=98.74%.

Example 20

1-(5-hydroxy-2-azatricyclo[3.3.1.1$^{3,7}$]dec-2-yl)-3-(1H-indol-3-yl)butan-1-one (20)

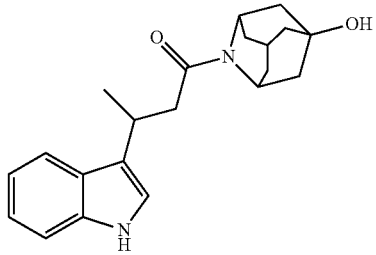

Synthesis of Compound (20)

Compound (20) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (20). 1H NMR (300 MHz, CDCl3): δ 7.99 (brs, 1H), 7.59-7.62 (d, 1H), 7.27-7.29 (d, 1H), 7.08-7.13 (t, 1H), 7.01-7.06 (t, 1H), 6.96 (brs, 1H), 4.98 (brs, 1H), 4.09 (brs, 1H), 3.56-3.61 (q, 1H), 2.73-2.78 (t, 1H), 2.43-2.50 (m, 1H), 1.94-1.97 (m, 1H), 1.42-1.68 (m, 10H), 1.40 (d, 3H). LC-MS: (M+H)+=339.2; HPLC purity=94.22%.

Example 21

1-(5-hydroxy-2-azatricyclo[3.3.1.1$^{3,7}$]dec-2-yl)-3-(1H-indol-3-yl)butan-1-one (21)

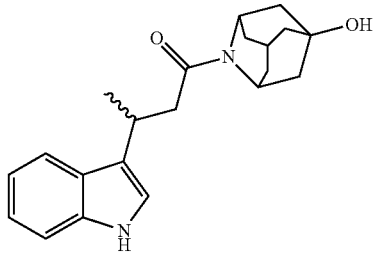

Synthesis of Compound (21) (Peak-1)

Racemate of Compound (20) was separated by using HPLC to give enantiomer Compound (21) (peak-1). 1H NMR (300 MHz, CDCl3): 7.99 (brs, 1H), 7.59-7.62 (d, 1H), 7.27-7.29 (d, 1H), 7.08-7.13 (t, 1H), 7.01-7.06 (t, 1H), 6.96 (brs, 1H), 4.98 (brs, 1H), 4.09 (brs, 1H), 3.56-3.61 (q, 1H), 2.73-2.78 (t, 1H), 2.43-2.50 (m, 1H), 1.94-1.97 (m, 1H), 1.42-1.68 (m, 10H), 1.40 (d, 3H). LC-MS: (M+H)+=339.2; HPLC purity=98.2%, Chiral purity: (RT=19.9 min).

Example 22

1-(5-hydroxy-2-azatricyclo[3.3.1.1$^{3,7}$]dec-2-yl)-3-(1H-indol-3-yl)butan-1-one (22)

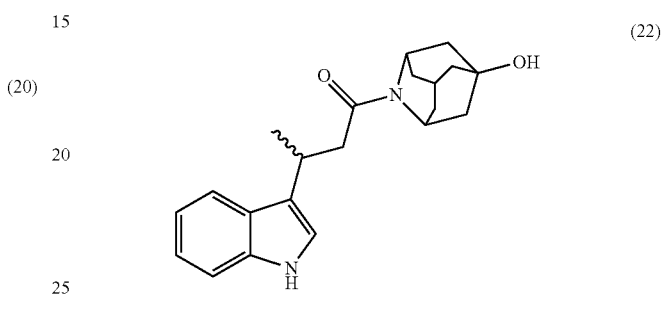

Synthesis of Compound (22) (Peak-1)

Racemate of Compound (20) was separated by using HPLC to give enantiomer Compound (22) (peak-2). 1H NMR (300 MHz, CDCl3): 7.99 (brs, 1H), 7.59-7.62 (d, 1H), 7.27-7.29 (d, 1H), 7.08-7.13 (t, 1H), 7.01-7.06 (t, 1H), 6.96 (brs, 1H), 4.98 (brs, 1H), 4.09 (brs, 1H), 3.56-3.61 (q, 1H), 2.73-2.78 (t, 1H), 2.43-2.50 (m, 1H), 1.94-1.97 (m, 1H), 1.42-1.68 (m, 10H), 1.40 (d, 3H). LC-MS: (M+H)+=339.2; HPLC purity=97.8%; Chiral purity: (RT=22.28 min).

Example 23

1-(5-hydroxy-2-azatricyclo[3.3.1.1$^{3,7}$]dec-2-yl)-3-(1H-indol-3-yl)-4-methylpentan-1-one (23)

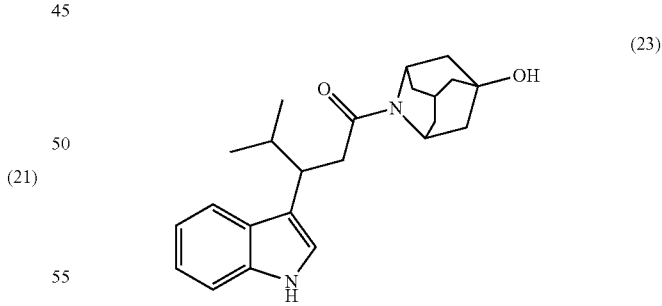

Synthesis of Compound (23)

Compound (23) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain (23). 1H NMR (300 MHz, DMSO-d6): δ 10.77 (s, 1H), 7.50-7.53 (d, 1H), 7.28-7.31 (d, 1H), 7.07 (s, 1H), 6.99-7.04 (t, 1H), 6.90-6.95 (t, 1H), 4.67 (s, 1H), 4.55-4.62 (d, 1H), 4.26-4.29 (d, 1H), 3.22-3.26 (m, 1H), 2.65-2.67 (m, 2H), 1.98 (m, 2H), 1.55-1.62 (d, 5H), 1.36-1.48 (m, 3H), 1.15-1.19 (m, 1H), 1.01-1.06 (m, 1H), 0.77-0.87 (m, 6H). LC-MS: (M+H)+=367.2; HPLC purity=85.41%.

Example 24

1-(5-fluoro-2-azatricyclo[3.3.1.1$^{3,7}$]dec-2-yl)-3-(1H-indol-3-yl)-4-methylpentan-1-one (24)

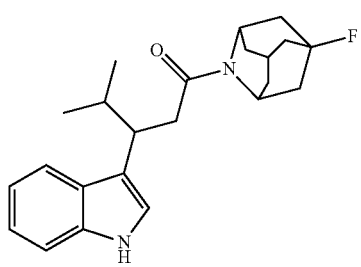

SYNTHETIC SCHEME 12

Synthesis of Compound (24)

Under N$_2$ atmosphere to a stirred solution of Compound (23) (0.035 g, 0.09 mmol), DAST (0.015 g, 0.09 mmol) was added at −78° C. The reaction mixture was stirred for 2 h at same temperature. After completion of the reaction (reaction monitored by TLC), reaction mass was quenched with NaHSO$_3$ Solution and extracted with DCM (3×25 mL). The organic layer was washed with saturated brine solution (15 mL), and concentrated to obtain the crude product. The crude product was loaded on Prep TLC plate (97:3. Chloroform: Methanol) and Compound (24) (12 mg) was collected as pale yellow solid. 1H NMR (300 MHz, CDCl3): δ 7.94 (s, 1H), 7.57-7.59 (d, 1H), 7.25-7.30 (m, 1H), 6.99-7.12 (m, 2H), 6.93 (s, 1H), 4.95 (s, 1H), 4.09 (s, 1H), 3.12-3.21 (m, 1H), 2.72-2.82 (m, 1H) 2.63-2.67 (m, 1H), 2.08-2.25 (m, 3H), 1.72-1.79 (m, 2H), 1.61-1.69 (m, 7H), 0.96-0.98 (d, 3H). 0.71-0.81 (d, 3H). LC-MS: (M+H)+=369.1; HPLC purity=96.16%.

Example 25

3-(4-fluoro-1H-indol-3-yl)-1-(5-hydroxy-2-azatricyclo[3.3.1.1$^{3,7}$]dec-2-yl)-4-methylpentan-1-one (25)

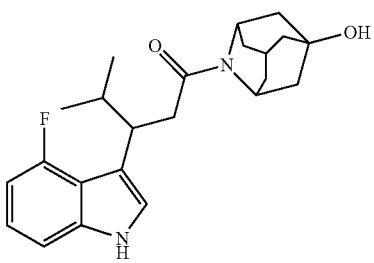

Synthesis of Compound (25)

Compound (25) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (25). 1H NMR (300 MHz, CDCl3): δ 8.29-8.26 (d, 1H), 7.14-7.02 (m, 2H), 6.98 (s, 1H), 6.77-6.71 (t, 1H), 4.93 (s, 1H), 4.21 (s, 1H), 3.25 (m, 1H), 2.91-2.66 (m, 2H), 2.25 (s, 1H), 2.16-2.05 (m, 2H), 1.72-1.34 (m, 9H), 0.79-0.81 (d, 6H). LC-MS: (M+H)+=385.2; HPLC purity=98.37%.

Example 26

3-(4-fluoro-1H-indol-3-yl)-1-(5-hydroxy-2-azatricyclo[3.3.1.1$^{3,7}$]dec-2-yl)butan-1-one (26)

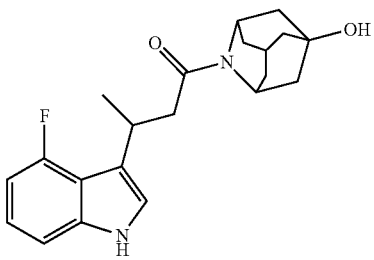

Synthesis of Compound (26)

Compound (26) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (26). 1H NMR (300 MHz, CDCl3): δ 8.15 (brs, 1H), 7.00-7.09 (m, 3H), 6.67-6.73 (t, 1H), 4.99 (s, 1H), 4.25 (s, 1H), 3.59 (m, 1H), 2.90 (s, 1H), 2.63-2.70 (s, 1H), 2.26-2.31 (m, 2H), 1.85 (m, 3H), 1.60-1.72 (m, 6H), 1.35-1.40 (d, 3H). LC-MS: (M+H)+=357.2; HPLC purity=97.11%.

Example 27

3-(4-fluoro-1H-indol-3-yl)-1-(5-hydroxy-2-azatricyclo[3.3.1.1³,⁷]dec-2-yl)butan-1-one (27)

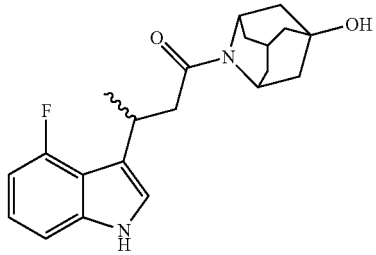

(27)

Synthesis of Compound (27) (Peak-1)

Racemate of Compound (26) was separated by using chiral HPLC to give enantiomer, Compound (27) (peak-1). 1H NMR (300 MHz, CDCl3): δ 8.15 (brs, 1H), 7.00-7.09 (m, 3H), 6.67-6.73 (t, 1H), 4.99 (s, 1H), 4.25 (s, 1H), 3.59 (m, 1H), 2.90 (s, 1H), 2.63-2.70 (s, 1H), 2.26-2.31 (m, 2H), 1.85 (m, 3H), 1.60-1.72 (m, 6H), 1.35-1.40 (d, 3H). LC-MS: (M+H)+=357.2; HPLC purity=99.60%; Column: Chiralpak IA. 4.6 mm×250 mm, mobile phase: Hexanes:EtOH (8:2), chiral purity=92.25% (RT=12.52 min).

Example 28

3-(4-fluoro-1H-indol-3-yl)-1-(5-hydroxy-2-azatricyclo[3.3.1.1³,⁷]dec-2-yl)butan-1-one (28)

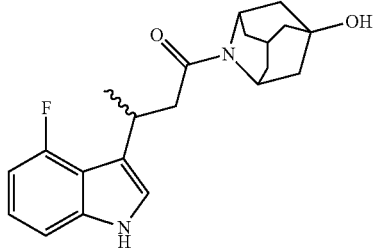

(28)

Synthesis of Compound (28) (Peak-2)

Racemate of Compound (26) was separated by using chiral HPLC to give enantiomer, Compound (28) (peak-2). 1H NMR (300 MHz, CDCl3): δ 8.15 (brs, 1H), 7.00-7.09 (m, 3H), 6.67-6.73 (t, 1H), 4.99 (s, 1H), 4.25 (s, 1H), 3.59 (m, 1H), 2.90 (s, 1H), 2.63-2.70 (s, 1H), 2.26-2.3 (m, 2H), 1.85 (m, 3H), 1.60-1.72 (m, 6H), 1.35-1.40 (d, 3H). LC-MS: (M+H)+=357.2; HPLC purity=94.43%; Column: Chiralpak IA. 4.6 mm×250 mm, mobile phase: Hexanes:EtOH (8:2), Chiral purity=99.69% (RT=11.13 min).

Example 29

3-(4-fluoro-1H-indol-3-yl)-1-(5-methoxy-2-azatricyclo[3.3.1.1³,⁷]dec-2-yl)butan-1-one (29)

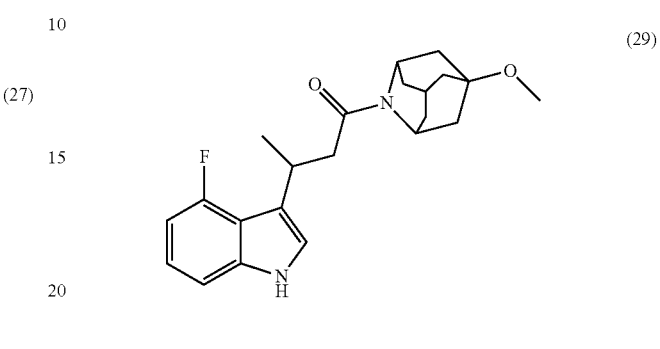

(29)

Synthesis of Compound (29)

Compound (29) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (29). 1H NMR (300 MHz, CDCl3): δ8.06 (brs, 1H), 7.02-7.07 (m, 1H), 6.97-7.01 (m, 1H), 6.94-6.95 (d, 1H), 6.66-6.72 (dd, 1H), 4.26 (brs, 1H), 4.26 (brs, 1H), 3.5-3.6 (m, 1H), 3.05-3.12 (d, 3H), 2.8-2.89 (m, 1H), 2.41-2.48 (m, 1H), 2.17-2.23 (m, 1H), 1.48-1.72 (m, 10H), 1.36-1.38 (d, 3H). LC-MS: (M+H)+=371.2; HPLC purity=97.80%.

Example 30

3-(4-fluoro-1H-indol-3-yl)-1-(5-methoxy-2-azatricyclo[3.3.1.1³,⁷]dec-2-yl)butan-1-one (30)

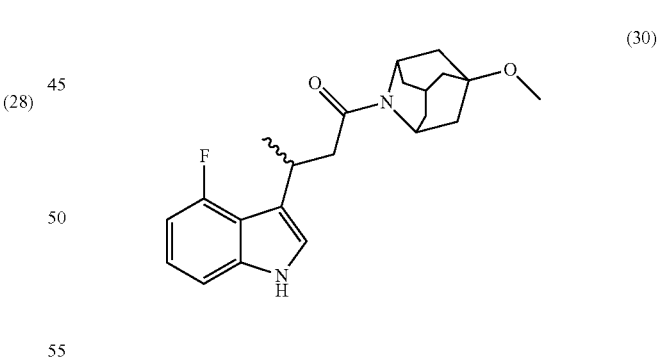

(30)

Synthesis of Compound (30) (Peak-1)

Racemate of Compound (29) was separated by using chiral HPLC to give enantiomer Compound (30) (peak-1). 1H NMR (300 MHz, CDCl3): δ8.06 (brs, 1H), 7.02-7.07 (m, 1H), 6.97-7.01 (m, 1H), 6.94-6.95 (d, 1H), 6.66-6.72 (dd, 1H), 4.26 (brs, 1H), 4.26 (brs, 1H), 3.5-3.6 (m, 1H), 3.05-3.12 (d, 3H), 2.8-2.89 (m, 1H), 2.41-2.48 (m, 1H), 2.17-2.23 (m, 1H), 1.48-1.72 (m, 10H), 1.36-1.38 (d, 3H). LC-MS: (M+H)+=371.2; HPLC purity=99.56%; Chiral purity=99.75% (RT=13.52 min, Column: Chiral pack IA, 4.6 mm×250 mm, mobile phase: MTBE:MeOH (98:02).

Example 31

3-(4-fluoro-1H-indol-3-yl)-1-(5-methoxy-2-azatricyclo[3.3.1.1³,⁷]dec-2-yl)butan-1-one (31)

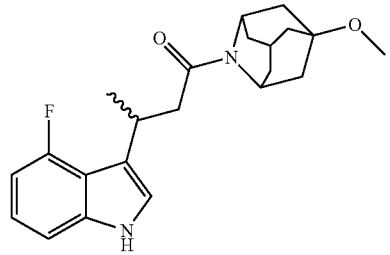

(31)

Synthesis of Compound (31) (Peak-2)

Racemate of Compound (29) was separated by using chiral HPLC to give enantiomer Compound (31). 1H NMR (300 MHz, CDCl3): δ 8.06 (brs, 1H), 7.02-7.07 (m, 1H), 6.97-7.01 (m, 1H), 6.94-6.95 (d, 1H), 6.66-6.72 (dd, 1H), 4.26 (brs, 1H), 4.26 (brs, 1H), 3.5-3.6 (m, 1H), 3.05-3.12 (d, 3H), 2.8-2.89 (m, 1H), 2.41-2.48 (m, 1H), 2.17-2.23 (m, 1H), 1.48-1.72 (m, 10H), 1.36-1.38 (d, 3H). LC-MS: (M+H)+=371.2; HPLC purity=95.79%; Chiral purity=99.88% (RT=16.37 min, Column: Chiral pack IA, 4.6 mm×250 mm, mobile phase: MTBE:MeOH (98:02).

Example 32

1-(5-chloro-2-azatricyclo[3.3.1.1³,⁷]dec-2-yl)-3-(4-fluoro-1H-indol-3-yl)butan-1-one (32)

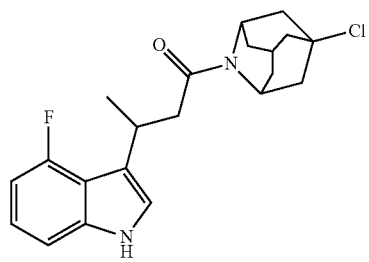

(32)

SYNTHETIC SCHEME 13

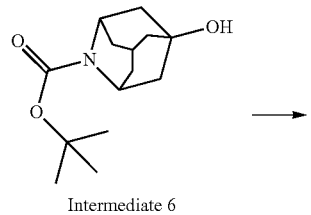

Intermediate 6

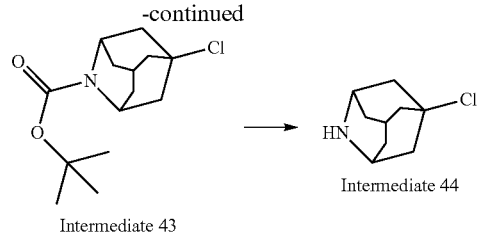

Synthesis of tert-butyl 5-chloro-2-azatricyclo[3.3.1.1³,⁷]decane-2-carboxylate (Intermediate-43)

To a stirred solution of Intermediate-6 (70 mg, 0.19 mmol) in CCl4 (3 mL), SOCl2 (1.5 mL) was added and the reaction mixture was heated at 80° C. for 15 hours. After reaction was completed (reaction was monitored by LC-MS), reaction mass was concentrated to give Intermediate-43 (60 mg).

Synthesis of 5-chloro-2-azatricyclo[3.3.1.1³,⁷]decane, trifluoroacetic acid salt (Intermediate-44)

Intermediate-44 was synthesized by following the procedure used to make Intermediate-20 (Scheme 1).

Synthesis of Compound (32)

Compound (32) was synthesized by following the procedure used to make Compound (1) (Scheme 2). The crude product was obtained by evaporating the organic layer under reduced pressure and was purified by silica gel column using Petroleum ether:Ethyl acetate as eluent to obtain Compound (32). 1H NMR (300 MHz, CDCl3): δ 8.02-8.06 (d, 1H), 7.01-7.09 (m, 2H), 6.94 (s, 1H), 6.67-6.73 (m, 1H), 4.95 (s, 1H), 4.20 (s, 1H), 3.54-3.61 (m, 1H), 2.79-2.88 (m, 1H), 2.40-2.49 (m, 1H), 2.12-2.26 (m, 4H), 1.81-2.02 (m, 3H), 1.5 (m, 4H), 1.36-1.43 (d, 3H). LC-MS: (M+H)+=376.1; HPLC purity=90.30%.

Example 33

1-[5-(cyclopropylmethoxy)-2-azatricyclo[3.3.1.1³,⁷]dec-2-yl]-3-(4-fluoro-1H-indol-3-yl)butan-1-one (33)

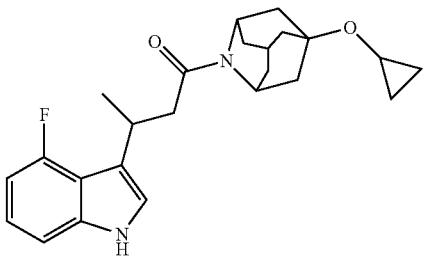

(33)

Synthesis of Compound (33)

Compound (33) was synthesized by using intermediate 20 and following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (33). 1H NMR (300 MHz, CDCl3): δ 8.07 (s, 1H), 6.97-7.07 (m, 2H), 6.95-6.94 (d, 1H), 6.66-6.72 (t, 1H), 4.97 (s, 1H), 4.25 (s, 1H), 3.53-3.60 (m, 1H), 3.00-3.12 (dd, 2H), 2.79-2.89 (m, 1H), 2.40-2.50 (m, 1H), 2.16-2.25 (d, 1H), 2.13-2.26 (d, 1H), 1.54-1.74 (m, 8H), 1.36-1.38 (d, 3H), 0.87-0.89 (m, 1H) 0.41-0.47 (m, 2H), 0.07 (m, 2H). LC-MS: (M+H)+=411.2; HPLC purity=96.10%.

Example 34

3-(1H-indol-3-yl)-1-(5-methoxy-2-azatricyclo[3.3.1.1³,⁷]dec-2-yl)butan-1-one (34)

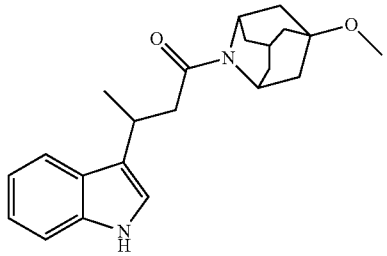

(34)

Synthesis of Compound (34)

Compound (34) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (34). 1H NMR (300 MHz, CDCl3): δ 7.95 (brs, 1H), 7.59-7.62 (d, 1H), 7.26-7.29 (d, 1H) 7.07 (m, 2H), 6.95 (s, 1H), 4.99 (brs, 1H), 4.10 (brs, 1H), 3.50-3.67 (m, 1H), 3.00-3.12 (d, 3H), 2.74-2.82 (m, 1H), 2.42-2.52 (m, 1H), 2.15-2.12 (m, 1H), 1.46-1.72 (m, 6H), 1.36-1.38 (d, 3H), 0.99-1.46 (m, 4H). LC-MS: (M+H)+=353.2; HPLC purity=90.44%.

Example 35

3-(4-chloro-1H-indol-3-yl)-1-(5-hydroxy-2-azatricyclo[3.3.1.1³,⁷]dec-2-yl)butan-1-one (35)

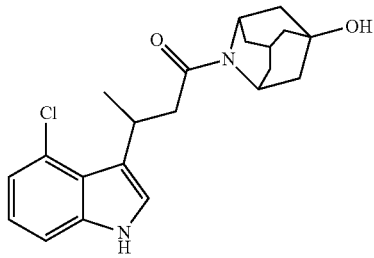

(35)

Synthesis of Compound (35)

Compound (35) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (35). 1H NMR (300 MHz, CDCl3): δ 8.44 (brs, 1H), 7.01-7.19 (m, 1H), 6.95-7.01 (m, 3H), 4.99 (brs, 1H), 4.23 (brs, 1H), 3.99-4.06 (m, 1H), 2.82-2.87 (m, 1H), 2.40-2.50 (m, 1H), 1.34-2.22 (m, 14H). LC-MS: (M+H)+=373.2; HPLC purity=93.64%.

Example 36

3-(4-chloro-1H-indol-3-yl)-1-(5-hydroxy-2-azatricyclo[3.3.1.1³,⁷]dec-2-yl)butan-1-one (36)

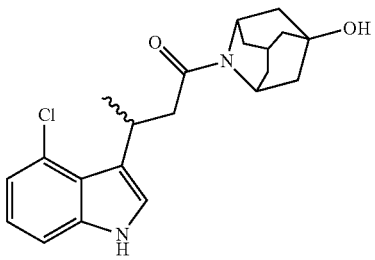

(36)

Synthesis of Compound (36) (Peak-1)

Racemate of Compound (35) was separated by using chiral HPLC to give enantiomer Compound (36) (peak-1). 1H NMR (300 MHz, CDCl3) δ 8.44 (brs, 1H), 7.01-7.19 (m, 1H), 6.95-7.01 (m, 3H), 4.99 (brs, 1H), 4.23 (brs, 1H), 3.99-4.06 (m, 1H), 2.82-2.87 (m, 1H), 2.40-2.50 (m, 1H), 1.34-2.22 (m, 14H). LC-MS: (M+H)+=373.2; HPLC purity=91.31%; Chiral purity=98.36% (RT=17.89 min).

Example 37

3-(4-chloro-1H-indol-3-yl)-1-(5-hydroxy-2-azatricyclo[3.3.1.1³,⁷]dec-2-yl)butan-1-one (37)

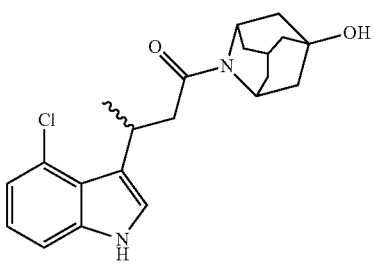

(37)

Synthesis of Compound (37) (peak-2)

Racemate of Compound (35) was separated by using chiral HPLC to give enantiomer Compound (37) (peak-2). 1H NMR (300 MHz, CDCl3) δ 8.44 (brs, 1H), 7.01-7.19 (m, 1H), 6.95-7.011 (m, 3H), 4.99 (brs, 1H), 4.23 (brs, 1H), 3.99-4.06 (m, 1H), 2.82-2.87 (m, 1H), 2.40-2.50 (m, 1H), 1.34-2.22 (m,

Example 38

1-[6-(cyclopropylmethoxy)-2-azatricyclo[3.3.1.1$^{3,7}$]dec-2-yl]-3-(1H-indol-3-yl)butan-1-one (38)

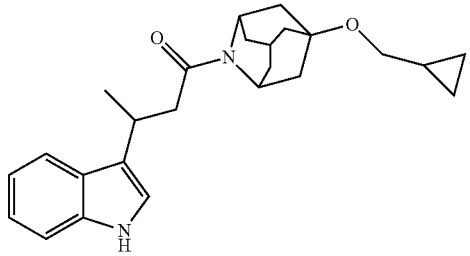

Synthesis of Compound (38)

Compound (38) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (38). 1H NMR (300 MHz, CDCl3): δ 7.92 (brs, 1H), 7.59-7.62 (d, 1H), 7.26-7.29 (d, 2H), 7.01-7.02 (m, 2H), 4.98 (brs, 1H), 4.09 (brs, 1H), 3.45-3.61 (m, 1H), 3.08-3.16 (dd, 2H), 2.55-2.64 (m, 2H), 2.09-2.36 (m, 2H), 1.61-1.82 (m, 9H), 1.41-1.43 (d, 3H), 0.86-0.89 (m, 1H), 0.41-0.47 (m, 2H), 0.07 (m, 2H). LC-MS: (M+H)+=393.3; HPLC purity=95.10%.

Example 39

3-(4-chloro-1H-indol-3-yl)-1-[5-(difluoromethoxy)-2-azatricyclo[3.3.1.1$^7$]dec-2-yl]butan-1-one (39)

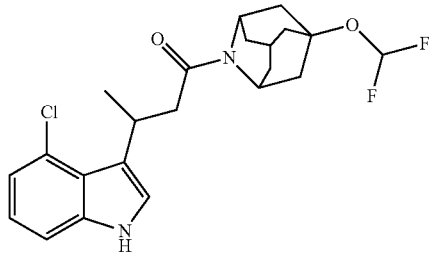

Synthesis of Compound (39)

Compound (39) was synthesized by following the procedure used to make and Compound (1) (Scheme 2) and Compound (13) (Scheme 8). The crude product was obtained by evaporating the organic layer under reduced pressure and was purified by silica gel column using Petroleum ether Ethyl acetate as eluent to obtain Compound (39). 1H NMR (300 MHz, CDCl3): δ 8.22 (brs, 1H), 7.06 (brs, 2H), 6.99-7.01 (m, 2H), 5.9-6.4 (t, 1H), 5.03 (brs, 1H), 4.26 (brs, 1H), 4.03-4.04 (m, 1H), 2.83-2.87 (m, 1H), 2.49-2.57 (m, 1H), 2.28 (brs, 1H), 1.93 (m, 1H), 1.62-2.01 (m, 10H), 1.38-1.41 (d, 3H). LC-MS: (M+H)+=423.2; HPLC purity=92.19%.

Example 40

3-(4-bromo-1H-indol-3-yl)-1-(6-hydroxy-2-azatricyclo[3.3.1.1$^{3,7}$]dec-2-yl)butan-1-one (40)

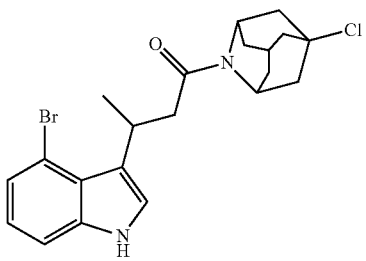

Synthesis of Compound (40)

Compound (40) was synthesized by following the procedure used to make Compound (1) (Scheme 2). The crude product was obtained by evaporating the organic layer under reduced pressure and was purified by silica gel column using Petroleum ether Ethyl acetate (1:4) as eluent to obtain Compound (40). 1H NMR (300 MHz, DMSO-d6): δ 11.21 (brs, 1H), 7.32-7.36 (m, 2H), 7.14-7.17 (d, 1H), 6.92-6.97 (t, 1H), 4.80 (brs, 1H), 4.66 (s, 1H), 4.33 (brs, 1H), 3.99-4.06 (m, 1H), 2.50-2.55 (m, 1H), 2.19 (brs, 1H), 1.69 (brs, 2H), 1.62-2.01 (m, 8H), 1.38-1.41 (d, 3H). LC-MS: (M+H)+=418.1; HPLC purity=92.77%.

Example 41

3-(4-cyclopropyl-1H-indol-3-yl)-1-(6-hydroxy-2-azatricyclo[3.3.1.1$^{3,7}$]dec-2-yl)butan-1-one (41)

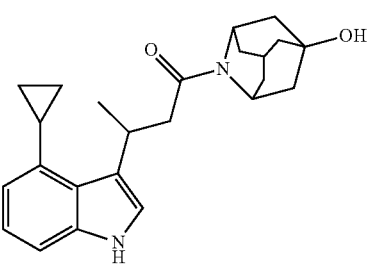

Synthesis of Compound (41)

Compound (41) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (41). 1H NMR (300 MHz, CDCl3): δ 7.97 (brs, 1H),

Example 42

3-[4-(6-hydroxy-2-azatricyclo[3.3.1.1$^{3,7}$]dec-2-yl)-4-oxobutan-2-yl]-1H-indole-4-carbonitrile (42)

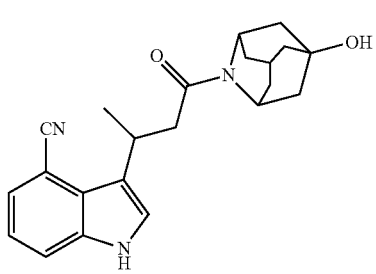

(42)

Synthesis of Compound (42)

Compound (42) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (42). 1H NMR (300 MHz, CDCl3): δ8.97 (s, 1H), 7.47-7.50 (d, 1H), 7.38-7.40 (d, 1H), 7.18 (m, 1H), 7.07-7.13 (m, 1H), 4.95 (s, 1H), 4.30 (s, 1H), 3.86-3.93 (m, 1H), 2.81-2.91 (m, 1H), 2.56-2.66 (m, 1H), 2.23 (s, 1H), 1.57-1.74 (m, 10H), 1.39-1.41 (d, 3H). LC-MS: (M+H)+=364.2; HPLC purity=97.36%.

Example 41

3-(4-cyclopropyl-1H-indol-3-yl)-1-5-hydroxy-2-azatricyclo[3.3.1.1$^{3,7}$]dec-2-yl)butan-1-one (41)

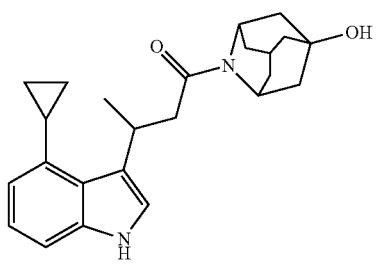

(41)

Synthesis of Compound (41)

Compound (41) was synthesized by following the procedure used to make Compound (1) (Scheme 2). The crude product was obtained by evaporating the organic layer under reduced pressure and was purified by silica gel column using Petroleum ether Ethyl acetate (1:4) as eluent to obtain Compound (41). 1H NMR (300 MHz, CDCl3): δ 7.97 (brs, 1H), 7.01-7.1 (d, 1H), 6.97-7.02 (m, 2H), 6.66-6.68 (d, 1H), 5.03 (brs, 1H), 4.19 (brs, 2H), 2.77-2.83 (m, 1H), 2.35-2.44 (m, 2H), 2.24 (brs, 1H), 1.75 (brs, 2H), 1.57-1.66 (m, 8H), 1.36-1.38 (d, 3H), 0.73-0.94 (m, 4H). LC-MS: (M+H)+=379.2; HPLC purity=97.64%.

Example 43

2-[3-(4-chloro-1H-indol-3-yl)butanoyl]-2-azatricyclo[3.3.1.1$^{3,7}$]decane-carboxylic acid (43)

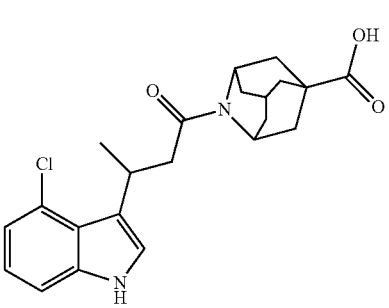

(43)

SYNTHETIC SCHEME 14

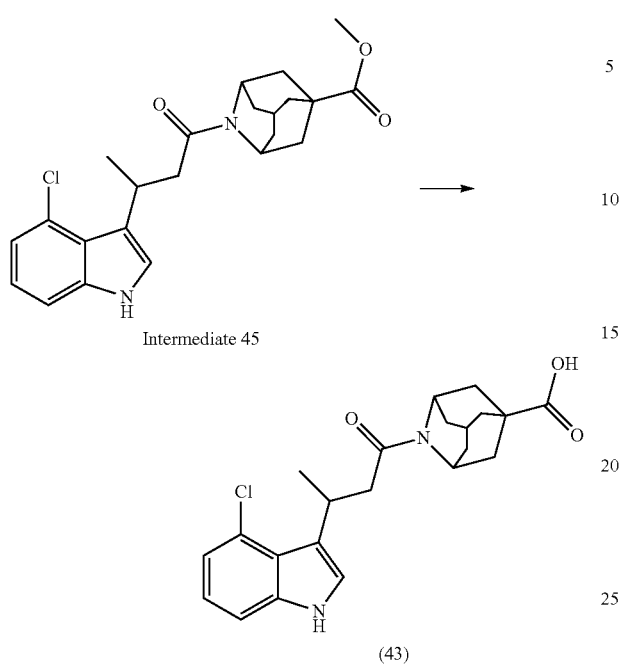

Intermediate 45

(43)

Synthesis of Compound (43)

Compound (43) was synthesized by following the procedure used to make Intermediate-26 (Scheme 4). The crude product was obtained by evaporating the organic layer under reduced pressure and was purified by silica gel column using DCM:MeOH as eluent to obtain Compound (43). 1H NMR (300 MHz, CDCl3): δ 12.25 (s, 1H), 11.20 (s, 1H), 7.29-7.31 (m, 2H), 6.96-7.04 (m, 2H), 4.78 (s, 1H), 4.28 (s, 1H), 3.92-3.99 (m, 1H), 2.55-2.76 (m, 2H), 2.11 (s, 1H), 1.59-1.89 (m, 10H), 1.26-1.28 (d, 3H). LC-MS: (M+H)+=401.1; HPLC purity=89.33%.

Example 44

3-[4-(4-chlorophenoxy)-1H-indol-3-yl]-1-(5-hydroxy-2-azatricyclo[3.3.1.1³,⁷]dec-2-yl)butan-1-one (44)

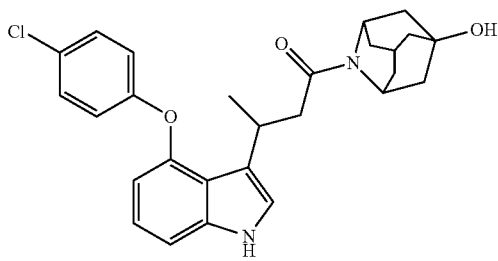

(44)

Synthesis of Compound (44)

Compound (44) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (44). 1H NMR (300 MHz, CDCl3): δ 8.12 (s, 1H), 7.21-7.24 (m, 2H), 7.04-7.07 (m, 2H), 6.94-7.01 (m, 2H), 6.92-6.93 (m, 1H), 6.40-6.43 (d, 1H), 4.94 (s, 1H), 4.11 (s, 1H), 3.57-3.63 (m, 1H), 2.78-2.85 (m, 1H), 2.32-2.42 (m, 1H), 2.16 (s, 1H), 1.66-1.69 (d, 3H), 1.43-1.47 (m, 7H), 1.38-1.39 (d, 3H). LC-MS: (M+H)+=465.2; HPLC purity=99.73%.

Example 45

2-[3-(4-chloro-1H-indol-3-yl)butanoyl]-N-(4-fluorophenyl)-2-azatricyclo[3.3.1.1³,⁷]decane-5-carboxamide (45)

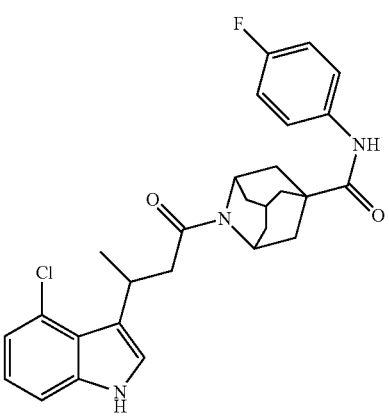

(45)

SYNTHETIC SCHEME 15

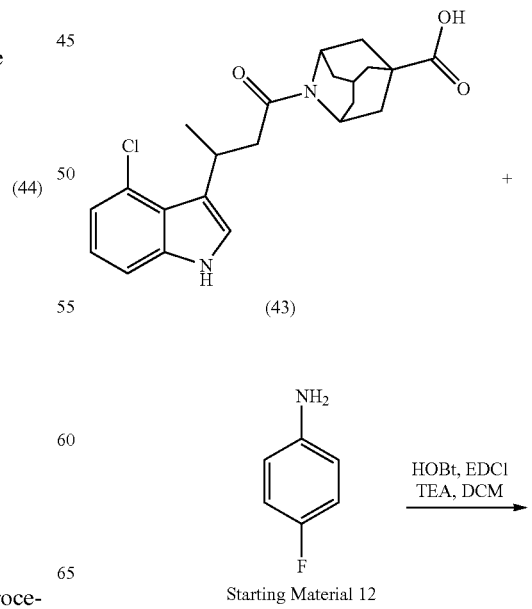

(43)

Starting Material 12

HOBt, EDCl
TEA, DCM

-continued

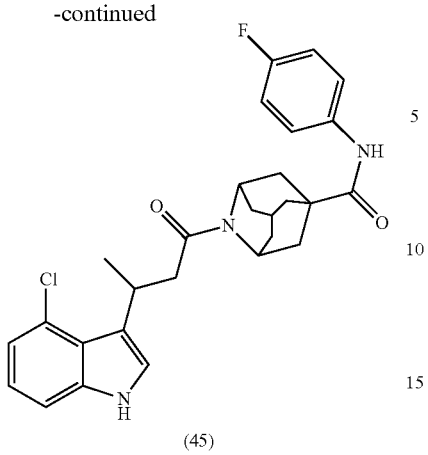

(45)

Synthesis of Compound (45)

Compound (45) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (45). 1H NMR (300 MHz, CDCl3): δ 8.21-8.24 (d, 1H), 7.34-7.42 (m, 2H), 7.19 (m, 2H), 6.91-7.04 (m, 5H), 4.96 (s, 1H), 4.18 (s, 1H), 4.01-4.12 (m, 1H), 2.80-2.89 (m, 1H), 2.41-2.59 (m, 1H), 2.19-2.26 (m, 1H), 1.60-1.97 m, 10H), 1.37-1.40 (m, 3H). LC-MS: (M+H)+=494.2; HPLC purity=98.06%.

Example 46

3-[4-chloro-1-(methylsulfonyl)-1H-indol-3-yl]-1-(5-hydroxy-2-azatricyclo[3.3.1.1$^{3,7}$]dec-2-yl)butan-1-one (46)

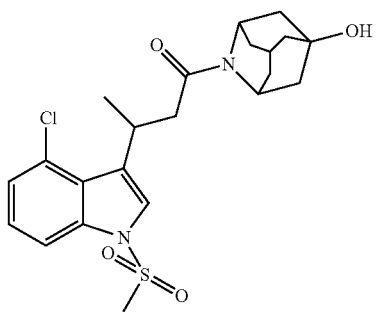

(46)

Synthesis of Compound (46)

Compound (46) was synthesized by following the procedure used to make Compound (1) (Scheme 2). The crude product was obtained by evaporating the organic layer under reduced pressure and was purified by silica gel column using Petroleum ether. Ethyl acetate (1:4) as eluent to obtain Compound (46). 1H NMR (300 MHz, CDCl3): δ 7.74-7.77 (m, 1H), 7.20-7.22 (m, 3H), 5.01 (s, 1H), 4.22 (s, 1H), 4.08 (s, 1H), 3.02 (s, 3H), 2.73-2.802 (m, 1H), 2.33-2.42 (m, 1H), 2.28 (s, 1H), 1.77 (s, 2H), 1.60-1.66 (m, 9H), 1.34-1.36 (d, 3H). LC-MS: (M+H)+=451.1; HPLC purity=94.52%.

Example 47

2-[3-(4-chloro-1H-indol-3-yl)butanoyl]-2-azatricyclo[3.3.1.1$^{3,7}$]decane-5-carboxamide (47)

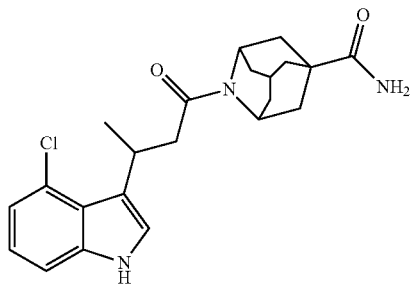

(47)

SYNTHETIC SCHEME 16

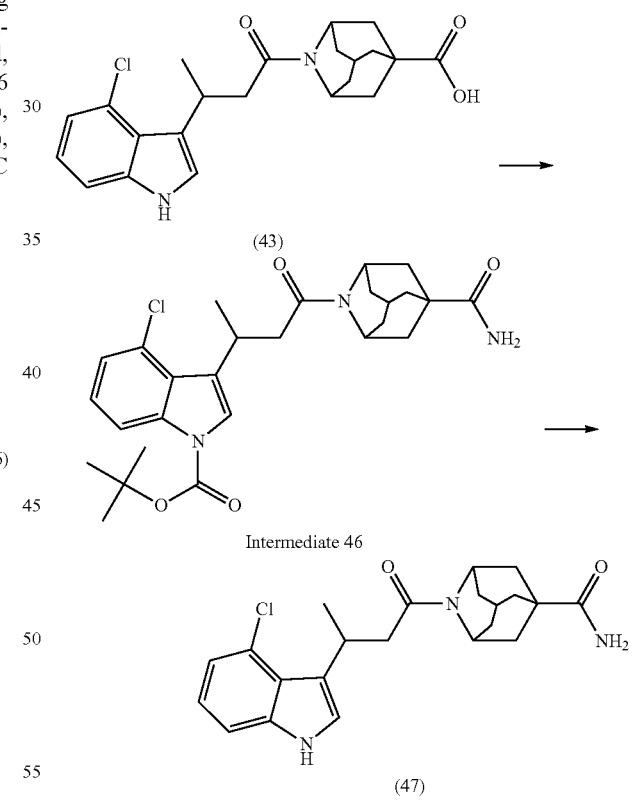

Synthesis of tert-butyl 3-(4-(5-carbamoyl-2-azaadamantan-2-yl)-4-oxobutan-2-yl)-4-chloro-1H-indole-1-carboxylate (Intermediate-46)

To a stirred solution of compound 43 (0.070 g, 0.17 mmol) in MeCN (2 mL), pyridine (0.016 g, 0.21 mmol) was added, followed by di-tert-butyl dicarbonate (0.045 g, 0.21 mmol) and stirred for 1 hour at room temperature. To this solution solid ammonium bicarbonate (0.021 g, 0.27 mmol) was added and stirred at room temperature for 12 hours. After completion of the reaction, the reaction mixture was quenched with $H_2O$ and extracted with EtOAc and concentrated to give Intermediate-46 (30 mg) as white solid.

Synthesis of Compound (47)

To a stirred solution of Intermediate-46 (0.030 g, 0.017 mmol) in DCM (1 mL), TFA (0.013 g, 0.11 mmol) was added at 0° C. and stirred at room temperature for 4 hours. After completion of the reaction, the reaction mixture was concentrated to remove DCM and TFA. The reaction mixture was further diluted with $H_2O$ and extracted with EtOAc and was then concentrated to give crude material which was purified by using Silica-gel column chromatography eluting with mixture of hexanes:EtOAc to give Compound (47) (145 mg) as white solid. 1H NMR (300 MHz, CDCl3): δ 11.20 (s, 1H), 7.29-7.31 (d, 2H), 6.96-7.04 (m, 3H), 6.81 (s, 1H), 4.74 (s, 1H), 4.28 (s, 1H), 3.89-4.02 (m, 1H), 2.68-2.72 (m, 2H), 2.10 (s, 1H), 1.62-1.85 (m, 10H), 1.26-1.28 (d, 3H). LC-MS: (M+H)+=400.2; HPLC purity=99.92%.

Example 48

1-(6-hydroxy-2-azatricyclo[3.3.1.1$^{3,7}$]dec-2-yl)-3-(4-methyl-1H-indol-3-yl)butan-1-one (48)

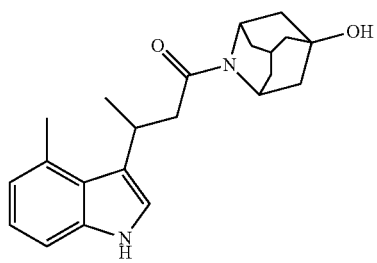

(48)

SYNTHETIC SCHEME 17

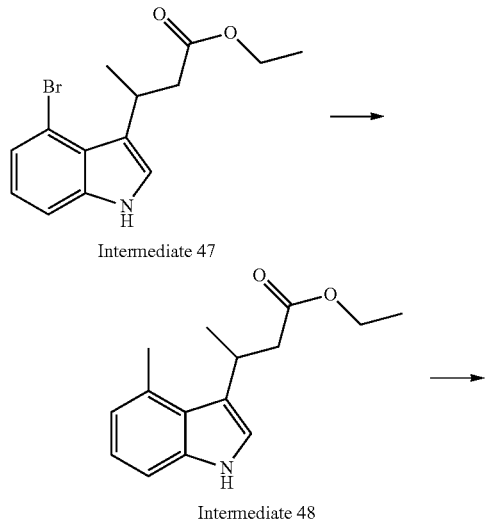

Intermediate 47

Intermediate 48

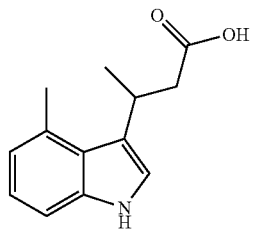

Intermediate 49

Synthesis of ethyl 3-(4-bromo-1H-indol-3-yl)butanoate (Intermediate-47)

Intermediate-47 was synthesized by following the procedure used to make Intermediate-41 (Scheme 11).

Synthesis of ethyl 3-(4-methyl-1H-indol-3-yl)butanoate (Intermediate-48)

A 100 mL RB flask fitted with magnetic stirrer and reflux condenser was charged with 25 mL of toluene and 5 mL of water. To the stirred solvent Intermediate-47 (4.4 g, 14.185 mmol) was added followed by the addition of methyl boronic acid (1.696 g, 28.37 mmol), Potassium phosphate tribasic (10.535 g, 49.647 mmol) and tricyclohexyl phosphine (0.397 g, 1.4185 mmol). The resulting mass was stirred at room temperature under argon purging for 30 minutes. Then Palladium acetate (0.159, 0.7092 mmol) was added and the resulting mixture was stirred at 100° C. for 16 hours. After completion of the reaction mass was diluted with 10 mL of water and was extracted with ethyl acetate (100 mL×3) and the combine organic layer was washed with brine solution and was dried over anhydrous sodium sulfate and solvent from the organic layer was removed under reduced pressure to yield the crude compound. Crude mass was purified by column chromatography using 60-120 silica gel and 8% of ethyl acetate in Pet ether as eluent to give Intermediate-48 (2.55 g).

Synthesis of 3-(4-methyl-1H-indol-3-yl)butanoic acid (Intermediate-49)

Compound Intermediate-49 was synthesized by following the procedure used to make Intermediate-42 (Scheme 11).

Synthesis of Compound (48)

Compound (48) was synthesized by following the procedure used to make Compound (1) (Scheme 2). The crude product was obtained by evaporating the organic layer under reduced pressure and was purified by silica gel column using Petroleum ether Ethyl acetate (1:4) as eluent to obtain Compound (48). 1H NMR (300 MHz, DMSO-d6): δ 10.78 (s, 1H), 7.12-7.15 (d, 2H), 6.87-6.92 (t, 1H), 6.67-6.69 (d, 1H), 4.80 (s, 1H), 4.64-4.65 (d, 1H), 4.33 (s, 1H), 3.69-3.76 (m, 1H), 2.63-2.68 (m, 2H), 2.60 (s, 3H), 2.15-2.19 (d, 1H), 1.68 (s, 2H), 1.42-1.63 (m, 8H), 1.23-1.25 (d, 3H). LC-MS: (M+H)+=353.2; HPLC purity=98.43%.

Example 49

1-(5-hydroxy-2-azatricyclo[3.3.1.1³,⁷]dec-2-yl)-3-(4-methyl-1H-indol-3-yl)butan-1-one (49)

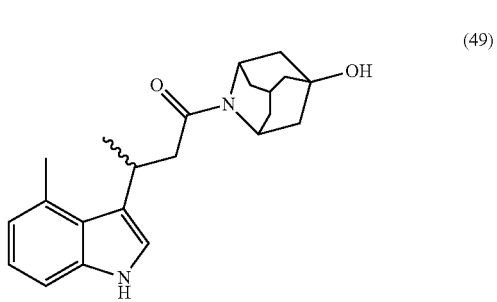 [SMILES: Cc1cccc2[nH]cc(C(C)CC(=O)N3C4CC5CC3CC(O)(C5)C4)c12]

(49)

Synthesis of Compound (49) (Peak-1)

Racemate of Compound (48) was separated by using chiral HPLC to give enantiomer Compound (49) (peak-1). 1H NMR (300 MHz, DMSO-d6): δ 10.78 (s, 1H), 7.12-7.15 (d, 2H), 6.87-6.92 (t, 1H), 6.67-6.69 (d, 1H), 4.80 (s, 1H), 4.64-4.65 (d, 1H), 4.33 (s, 1H), 3.69-3.76 (m, 1H), 2.63-2.68 (m, 2H), 2.60 (s, 3H), 2.15-2.19 (d, 1H), 1.68 (s, 2H), 1.42-1.63 (m, 8H), 1.23-1.25 (d, 3H). LC-MS: (M+H)+=353.2; HPLC purity=95.87%; Chiral purity=100% (RT=17.45 min), Column: Chiralpak IC 4.6 mm×250 mm, Mobile phase, hexane:IPA:DCM (75:15:10).

Example 50

1-(6-hydroxy-2-azatricyclo[3.3.1.1³,⁷]dec-2-yl)-3-(4-methyl-1H-indol-3-yl)butan-1-one (60)

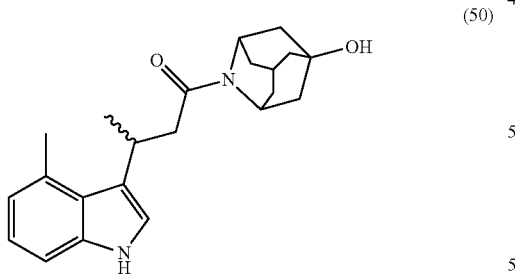

(50)

Synthesis of Compound (50) (Peak-2)

Racemate of Compound (48) was separated by using chiral HPLC to give enantiomer, Compound (50) (peak-2). 1H NMR (300 MHz, DMSO-d6): δ 10.78 (s, 1H), 7.12-7.15 (d, 2H), 6.87-6.92 (t, 1H), 6.67-6.69 (d, 1H), 4.80 (s, 1H), 4.64-4.65 (d, 1H), 4.33 (s, 1H), 3.69-3.76 (m, 1H), 2.63-2.68 (m, 2H), 2.60 (s, 3H), 2.15-2.19 (d, 1H), 1.68 (s, 2H), 1.42-1.63 (m, 8H), 1.23-1.25 (d, 3H). LC-MS: (M+H)+=353.2; HPLC purity=98.64%; Chiral purity=100% (RT=21.17 min), Column: Chiralpak IC 4.6 mm×250 mm, Mobile phase, hexane:IPA:DCM (75:15:10).

Example 51

2-[3-(4-cyclopropyl-1H-indol-3-yl)butanoyl]-2-azatricyclo[3.3.1.1³,⁷]decane-5-carboxylic acid (51)

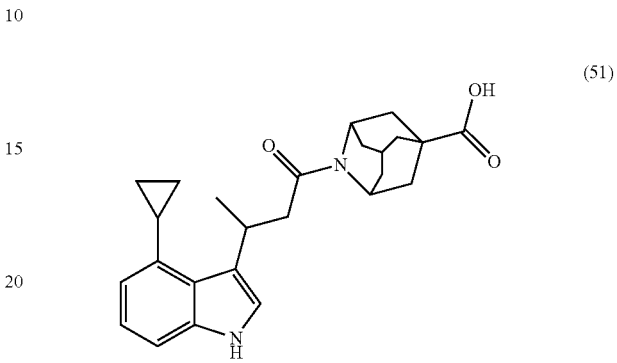

(51)

Synthesis of Compound (51)

Compound (51) was synthesized by following the procedure used to make Compound 43 (Scheme 14). The crude product was obtained by evaporating the organic layer under reduced pressure and was purified by silica gel column using Petroleum DCM:MeOH as eluent to obtain Compound (51). 1H NMR (300 MHz, DMSO-d6): δ 12.23 (s, 1H), 10.801 (s, 1H), 7.11-7.17 (m, 2H), 6.88-6.93 (t, 1H), 6.55-6.58 (d, 1H), 4.75 (s, 1H), 4.26 (s, 1H), 4.01-4.04 (m, 1H), 3.37-3.41 (m, 2H), 2.68-2.73 (m, 1H), 2.09 (s, 1H), 1.62-1.88 (m, 13H), 0.85-00.91 (m, 2H), 0.70-0.77 (m, 2H). LC-MS: (M+H)+=407.2; HPLC purity=91.19%.

Example 62

2-[3-(4-cyclopropyl-1H-indol-3-yl)butanoyl]-2-azatricyclo[3.3.1.1³,⁷]decane-6-carboxylic acid (52)

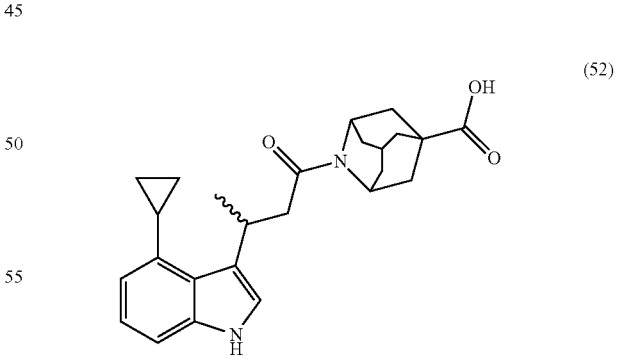

(52)

Synthesis of Compound (52) (Peak-1)

Racemate of Compound (51) was separated by using chiral HPLC to give enantiomer Compound (52) (peak-1). 1H NMR (300 MHz, DMSO-d6): δ 12.23 (s, 1H), 10.801 (s, 1H), 7.11-7.17 (m, 2H), 6.88-6.93 (t, 1H), 6.55-6.58 (d, 1H), 4.75 (s, 1H), 4.26 (s, 1H), 4.01-4.04 (m, 1H), 3.37-3.41 (m, 2H), 2.68-2.73 (m, 1H), 2.09 (s, 1H), 1.62-1.88 (m, 13H), 0.85-00.91 (m, 2H), 0.70-0.77 (m, 2H). LC-MS: (M+H)+=407.3; HPLC purity=89.77%; Chiral purity=100% (RT=8.29 min), Column: Chiralpak IC 4.6 mm×250 mm, Mobile phase, hexane:IPA:DCM (75:15:10).

Example 53

2-[3-(4-cyclopropyl-1H-indol-3-yl)butanoyl]-2-azatricyclo[3.3.1.1$^{3,7}$]decane-5-carboxylic acid (53)

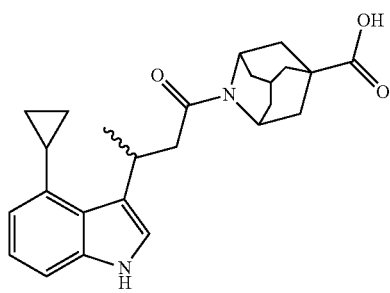
(53)

Synthesis of Compound (53) Peak-2

Racemate of Compound (51) was separated by using chiral HPLC to give enantiomer, Compound (53) (peak-2). 1H NMR (300 MHz, DMSO-6): δ 12.23 (s, 1H), 10.801 (s, 1H), 7.11-7.17 (m, 2H), 6.88-6.93 (t, 1H), 6.55-6.58 (d, 1H), 4.75 (s, 1H), 4.26 (s, 1H), 4.01-4.04 (m, 1H), 3.37-3.41 (m, 2H), 2.68-2.73 (m, 1H), 2.09 (s, 1H), 1.62-1.88 (m, 13H), 0.85-00.91 (m, 2H), 0.70-0.77 (m, 2H). LC-MS: (M+H)+=407.3; HPLC purity=86.37%; Chiral purity=94.78% (RT=11.60 min), Column: Chiralpak IC 4.6 mm×250 mm, Mobile phase, hexane:IPA:DCM (75:15:10).

Example 64

2-[3-(4-cyclopropyl-1H-indol-3-yl)butanoyl]-2-azatricyclo[3.3.1.1$^{3,7}$]decane-5-carboxylic acid sodium salt (sodium salt) (54)

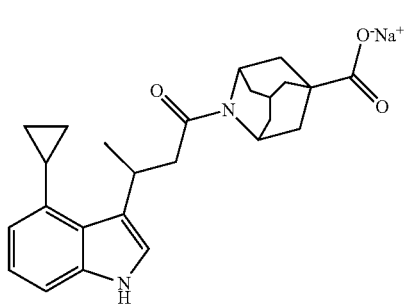
(54)

SYNTHETIC SCHEME 18

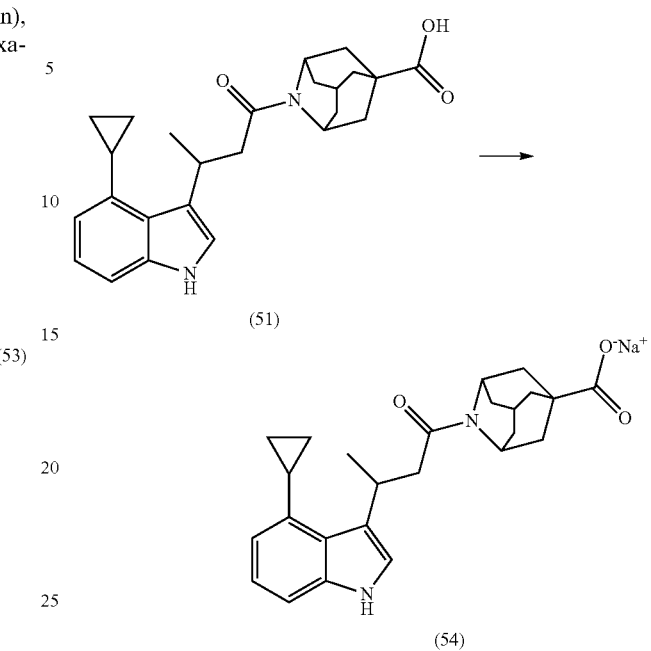

Synthesis of Compound (54) (Sodium Salt)

To a stirred solution of Compound (51) (306 mg, 0.72 mmol) in THF:MeOH:H$_2$O (2 mL: 3 mL: 1 mL), sodium hydroxide (26 mg, 0.65 mmol) was added at 0° C. Resulted reaction mixture was allowed to stir at room temperature for 16 hours. Then reaction mixture was concentrated, followed by trituration with mixture of hexane:ether to give Compound (54) (sodium salt) (25 mg) as a white solid. 1H NMR (300 MHz, DMSO-6): δ. 10.92 (s, 1H), 7.12-7.15 (m, 2H), 6.87-6.92 (t, 1H), 6.54-6.57 (d, 1H), 4.69 (s, 1H), 4.17 (s, 1H), 4.02-4.03 (m, 1H), 3.39-3.41 (m, 2H), 2.61-2.7 (m, 2H), 1.28-1.79 (m, 13H), 0.89-0.92 (m, 2H), 0.70-0.76 (m, 2H) LC-MS: (M+H)+=407.3; HPLC purity=96.31%.

Example 55

2-[3-(4-bromo-1H-indol-3-yl)butanoyl]-2-azatricyclo[3.3.1.1$^{3,7}$]decane-5-carboxylic acid (55)

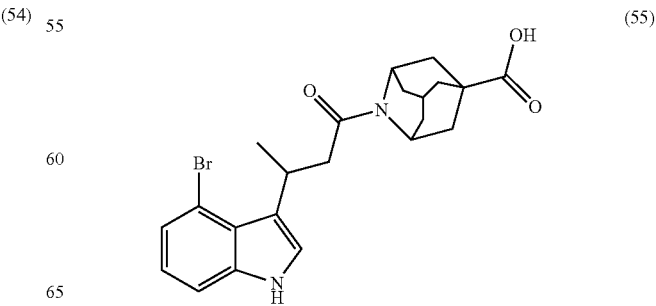
(55)

Synthesis of Compound (55)

Compound (55) was synthesized by following the procedure used to make Compound (43) (Scheme 14). The crude product was obtained by evaporating the organic layer under reduced pressure and was purified by silica gel column using Petroleum DCM:MeOH as eluent to obtain Compound (55). 1H NMR (300 MHz, DMSO-d6): δ 12.25 (s, 1H), 11.20 (s, 1H), 7.32-7.36 (m, 2H), 7.14-7.17 (d, 1H), 6.92-6.97 (t, 1H), 4.74 (s, 1H), 4.28 (s, 1H), 4.01-4.05 (m, 1H), 2.70-2.77 (m, 2H), 2.11 (s, 2H), 1.60-1.89 (m, 9H), 1.26-1.28 (d, 3H). LC-MS: (M+H)+=445.1; HPLC purity=90.50%.

Example 56

2-[3-(4-cyclopropyl-1H-indol-3-yl)butanoyl]-2-azatricyclo[3.3.1.1$^{3,7}$]decane-5-carboxamide (56)

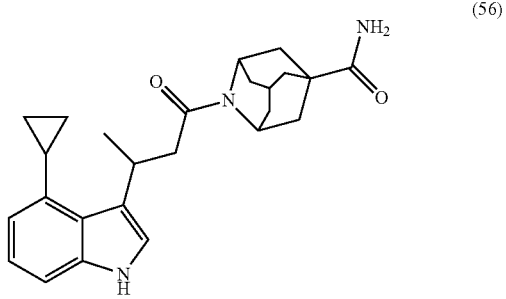 [SMILES: CC(CC(=O)N1C2CC3CC1CC(C(=O)O)(C3)C2)c1c[nH]c2cccc(C3CC3)c12]

(56)

Synthesis of Compound (56)

Compound (56) was synthesized by following the procedure used to make Compound (47) (Scheme 16). The crude product was obtained by evaporating the organic layer under reduced pressure and was purified by silica gel column using Petroleum ether:Ethyl acetate (1:4) as eluent to obtain Compound (56). 1H NMR (300 MHz, DMSO-d6): δ 10.79 (s, 1H), 9.50 (s, 2H), 7.01-7.17 (m, 1H), 6.88-6.93 (m, 1H), 6.79 (s, 1H), 6.55-6.58 (d, 1H), 4.74 (s, 1H), 4.26 (s, 1H), 4.01-4.04 (d, 1H), 2.6-2.8 (m, 3H), 2.07-2.08 (m, 2H), 1.15-1.98 (m, 12H), 0.83-0.95 (m, 2H), 0.70-0.95 (m, 2H). LC-MS: (M+H)+=406.2; HPLC purity=88.73%.

Example 57

2-[3-(4-methyl-1H-indol-3-yl)butanoyl]-2-azatricyclo[3.3.1.1$^{3,7}$]decane-5-carboxylic acid (57)

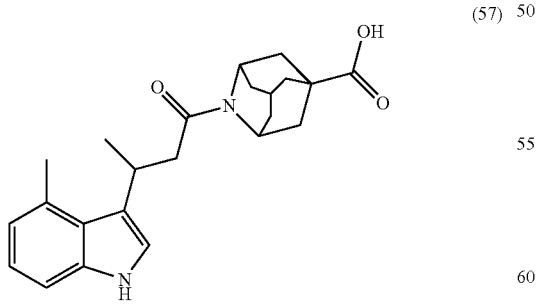

(57)

Synthesis of Compound (57)

Compound (57) was synthesized by following the procedure used to make Compound (43) (Scheme 14). The crude product was obtained by evaporating the organic layer under reduced pressure and was purified by silica gel column using DCM:MeOH as eluent to obtain Compound (57). 1H NMR (300 MHz, DMSO-d6): δ 12.25 (s, 1H), 10.78 (s, 1H), 7.12-7.15 (m, 2H), 6.87-6.92 (t, 1H), 6.67-6.69 (d, 1H), 4.74 (s, 1H), 4.28 (s, 1H), 3.76-3.80 (m, 1H), 2.61-2.68 (m, 5H), 2.08-2.11 (m, 1H), 1.48-1.88 (m, 10H), 1.24-1.26 (d, 3H). LC-MS: (M+H)+=381.2; HPLC purity=99.05%.

Example 58

3-(4-chloro-1H-indol-3-yl)-1-[5-(hydroxymethyl)-2-azatricyclo[3.3.1.1$^{3,7}$]dec-2-yl]butan-1-one (58)

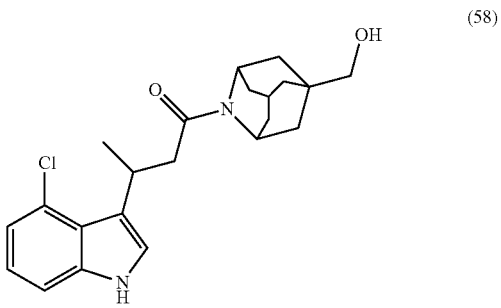 [SMILES: CC(CC(=O)N1C2CC3CC1CC(CO)(C3)C2)c1c[nH]c2cccc(Cl)c12]

(58)

Synthesis of Compound (58)

Compound (58) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (58). 1H NMR (300 MHz, CDCl3): δ 11.19 (s, 1H), 7.28-7.31 (m, 2H), 6.96-7.04 (m, 2H), 4.72 (s, 1H), 4.42-4.45 (m, 1H), 4.24 (s, 1H), 3.91-3.95 (m, 1H), 2.99-3.01 (m, 2H), 2.67-2.75 (m, 3H), 2.07 (s, 1H), 1.42-1.63 (m, 9H), 1.25-1.28 (d, 3H). LC-MS: (M+H)+=387.1; HPLC purity=97.41%.

Example 59

2-[3-(4-chloro-1H-indol-3-yl)butanoyl]-2-azatricyclo[3.3.1.1$^{3,7}$]decane-5-carbonitrile (59)

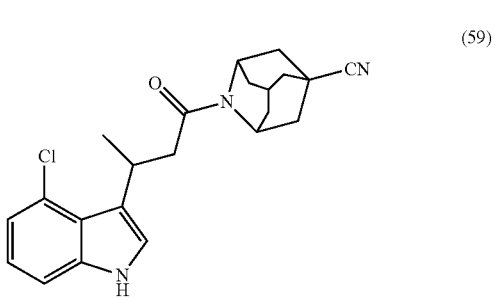 [SMILES: CC(CC(=O)N1C2CC3CC1CC(C#N)(C3)C2)c1c[nH]c2cccc(Cl)c12]

(59)

Synthesis of Compound (59)

Compound (59) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (59). 1H NMR (300 MHz, CDCl3): δ 8.10 (s, 1H), 7.21-7.25 (m, 1H), 7.00-7.03 (m, 3H), 4.90 (s, 1H), 4.02-4.12 (m, 2H), 2.77-2.87 (m, 1H), 2.37-2.49 (m, 1H), 2.06-2.12 (m, 3H), 1.60-1.94 (m, 8H), 1.37-1.40 (m, 3H). LC-MS: (M+H)+=382.3; HPLC purity=97.62%.

Example 60

3-(4-chloro-2-methyl-1H-indol-3-yl)-1-(5-hydroxy-2-azatricyclo[3.3.1.1$^{3,7}$]dec-2-yl)butan-1-one (60)

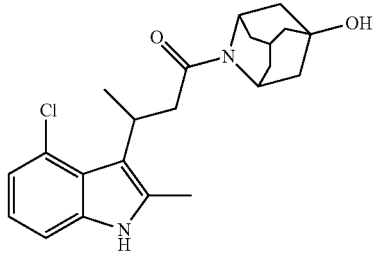

(60)

Synthesis of Compound (60)

Compound (60) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (60). 1H NMR (300 MHz, CDCl3): δ 7.86-7.89 (d, 1H), 7.08-7.10 (d, 1H), 6.99-7.03 (m, 1H), 6.88-6.94 (t, 1H), 4.91-5.00 (m, 1H), 4.00-4.33 (m, 2H), 2.56-2.67 (m, 1H), 2.40 (s, 3H), 2.21-2.24 (m, 1H), 1.74-1.80 (m, 2H), 1.54 (m, 9H), 1.36-1.38 (d, 3H). LC-MS: (M+H)+=387.1; HPLC purity=98.42%.

Example 61

2-[3-(1H-indol-3-yl)butanoyl]-2-azatricyclo[3.3.1.1$^{3,7}$]decane-5-carboxylic acid (61)

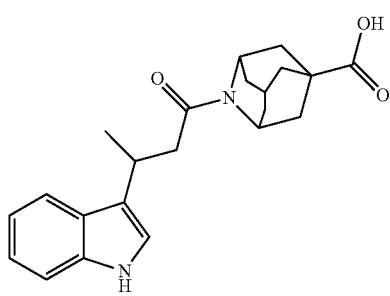

(61)

Synthesis of Compound (61)

Compound (61) was synthesized by following the procedure used to make Compound (43) (Scheme 14). The crude product was obtained by evaporating the organic layer under reduced pressure and was purified by silica gel column using DCM:MeOH as eluent to obtain Compound (61). 1H NMR (300 MHz, DMSO-d6): δ 12.21 (s, 1H), 10.77 (s, 1H), 7.51-7.54 (d, 1H), 7.29-7.32 (m, 1H), 7.12-7.13 (d, 1H), 7.01-7.06 (t, 1H), 6.92-6.97 (t, 1H), 4.72 (s, 1H), 4.20 (s, 1H), 3.39-3.45 (m, 1H), 2.65-2.72 (m, 1H), 2.09 (s, 1H), 1.85 (s, 2H), 1.73-1.77 (d, 3H), 1.43-1.66 (m, 6H), 1.29-1.31 (d, 3H). LC-MS: (M+H)+=367.2; HPLC purity=93.96%.

Example 62

2-{3-[4-(4-fluorophenyl)-1H-indol-3-yl]butanoyl}-2-azatricyclo[3.3.1.1$^{3,7}$]decane-5-carboxylic acid (62)

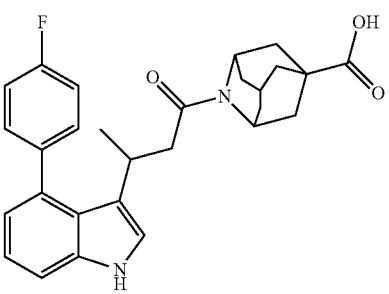

(62)

Synthesis of Compound (62)

Compound (62) was synthesized by following the procedure used to make Compound (43) (Scheme 14). The crude product was obtained by evaporating the organic layer under reduced pressure and was purified by silica gel column using DCM:MeOH as eluent to obtain Compound (62). 1H NMR (300 MHz, CDCl3): δ 8.30 (s, 1H), 7.31-7.39 (m, 2H), 7.25-7.29 (d, 1H), 7.08-7.12 (t, 1H), 7.04-7.05 (m, 3H), 6.82-6.85 (d, 1H), 4.75 (s, 1H), 3.56-3.68 (t, 1H), 3.13-3.14 (d, 1H), 2.25-2.30 (m, 2H), 1.88-1.92 (m, 3H), 1.71-1.75 (m, 6H), 1.58 (s, 3H), 1.48-1.54 (d, 2H). LC-MS: (M+H)+=461.2; HPLC purity=95.42%.

Example 63

4-{[({2-[3-(4-cyclopropyl-1H-indol-3-yl)butanoyl]-2-azatricyclo[3.3.1.1$^{3,7}$]dec-5-yl}carbonyl)amino]methyl}benzoic acid (63)

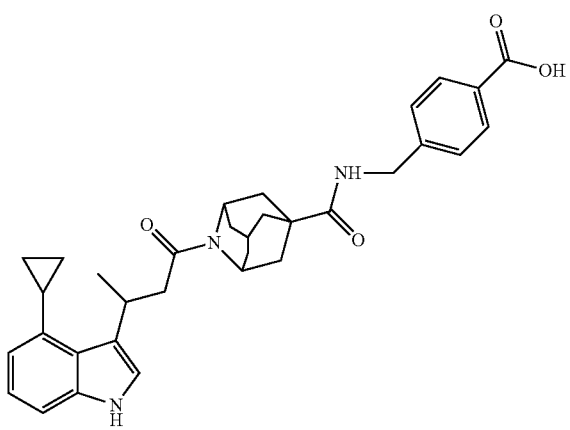

(63)

SYNTHETIC SCHEME 19

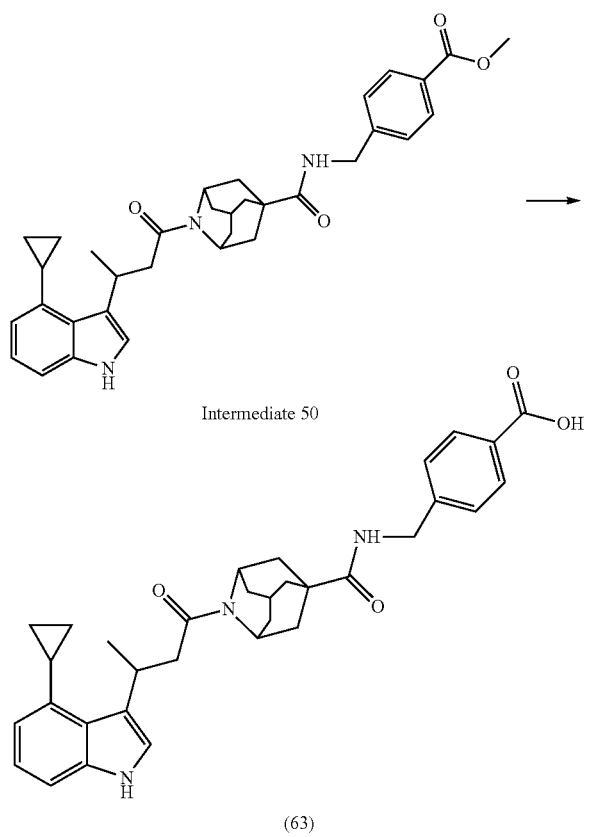

Intermediate 50

(63)

Synthesis of Compound (63)

Compound (63) was synthesized by following the procedure used to make Compound (43) (Scheme 14). The crude product was obtained by evaporating the organic layer under reduced pressure and was purified by silica gel column using DCM:MeOH as eluent to obtain Compound (63). 1H NMR (300 MHz, DMSO-d6): δ 12.80 (s, 1H), 10.81 (s, 1H), 8.12-8.20 (m, 1H), 7.86-7.89 (d, 2H), 7.28-7.31 (m, 2H), 7.12-7.17 (t, 2H), 6.88-6.93 (t, 1H), 6.55-6.58 (d, 1H), 4.77 (s, 1H), 4.30 (s, 2H), 4.04 (s, 1H), 2.61-2.80 (m, 1H), 2.50-2.54 (m, 2H), 2.08-2.13 (t, 1H), 1.86-1.91 (m, 4H), 1.63-1.78 (m, 6H), 1.50-1.55 (d, 1H), 1.28-1.31 (d, 3H), 0.89-0.91 (m, 2H), 0.69-0.74 (m, 2H). LC-MS: (M+H)+=540.3; HPLC purity=95.62%.

Example 64

1-(5-hydroxy-2-azatricyclo[3.3.1.1$^{3,7}$]dec-2-yl)-3-(1H-indol-3-yl)pentan-1-one (64)

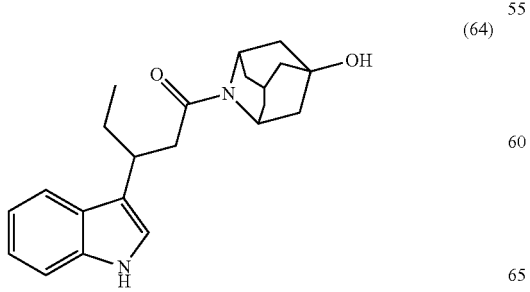

(64)

Synthesis of Compound (64)

Compound (64) was synthesized by following the procedure used to make Compound (1) (Scheme 2). The crude product was obtained by evaporating the organic layer under reduced pressure and was purified by silica gel column using Petroleum ether. Ethyl acetate (1:4) as eluent to obtain Compound (64). 1H NMR (300 MHz, CDCl3): δ 8.03 (s, 1H), 7.58-7.61 (d, 1H), 7.26-7.29 (d, 1H), 7.07-7.12 (t, 1H), 6.99-7.04 (t, 1H), 6.94 (s, 1H), 4.93 (s, 1H), 4.01-4.04 (d, 1H), 3.25-3.35 (m, 1H), 2.70-2.79 (m, 1H), 2.56-2.59 (m, 1H), 2.03-2.17 (d, 1H), 1.75-1.85 (m, 2H), 1.56-1.65 (m, 5H), 1.31-1.45 (m, 3H), 1.18-1.22 (m, 2H), 0.77-0.82 (m, 3H) LC-MS: (M+H)+=353.2; HPLC purity=94.01%.

Example 65

2-[3-1H-indol-3-yl)butanoyl]-2-azatricyclo[3.3.1.1$^{3,7}$]decane-5-carbonitrile (65)

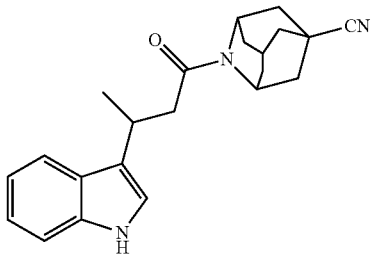

(65)

Synthesis of Compound (65)

Compound (65) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (65). 1H NMR (300 MHz, CDCl3): δ 7.92-7.95 (d, 1H), 7.58-7.61 (d, 1H), 7.27-7.32 (t, 1H), 7.09-7.13 (t, 1H), 7.01-7.06 (t, 1H), 6.95 (d, 1H), 4.83-4.87 (d, 1H), 3.83-3.94 (d, 1H), 3.55-3.62 (m, 1H), 2.69-2.77 (m, 1H), 2.42-2.50 (m, 1H), 2.07-2.10 (m, 1H), 1.93-2.00 (m, 4H), 1.86 (s, 1H), 1.74-1.79 (d, 1H), 1.57-1.64 (m, 4H), 1.40-1.43 (m, 3H). LC-MS: (M+H)+=348.2; HPLC purity=91.69%.

Example 66

3-cyclopropyl-1-(5-hydroxy-2-azatricyclo[3.3.1.1$^{3,7}$]dec-2-yl)-3-(1H-indol-3-yl)propan-1-one (66)

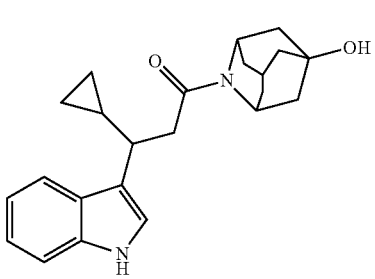

(66)

Synthesis of Compound (66)

Compound (66) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (66). 1H NMR (300 MHz, CDCl3): δ 8.01-8.05 (m, 1H), 7.59-7.62 (d, 1H), 7.26-7.29 (d, 1H), 7.07-7.12 (t, 1H), 6.98-7.04 (m, 2H), 4.93 (s, 1H), 4.60-4.61 (d, 1H), 4.08-4.11 (d, 1H), 2.84-2.91 (m, 1H), 2.65-2.78 (m, 2H), 2.04-2.18 (s, 1H), 1.65 (s, 2H), 1.57 (s, 2H), 1.44 (m, 2H), 1.32-1.34 (m, 3H), 0.47-0.56 (m, 1H), 0.35-0.39 (m, 1H), 0.25-0.32 (m, 1H), 0.06-0.13 (m, 2H). LC-MS: (M+H)+=365.2; HPLC purity=93.07%.

Example 67

1-(5-hydroxy-2-azatricyclo[3.3.1.1$^{3,7}$]dec-2-yl)-3-(1H-indol-3-yl)-3-phenylpropan-1-one (67)

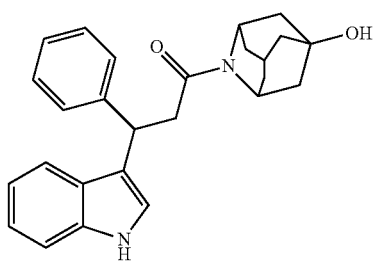

(67)

SYNTHETIC SCHEME 20

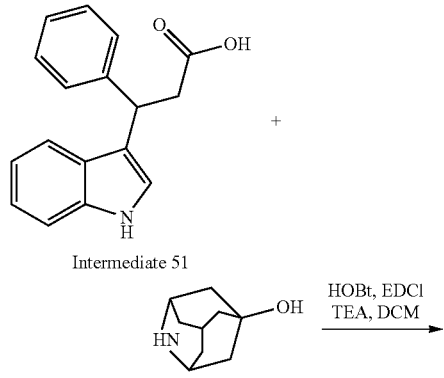

Synthesis of 3-(1H-indol-3-yl)-3-phenylpropanoic acid (Intermediate-61)

Intermediate-51 was synthesized by following the procedure used to make Intermediate-42 (Scheme 11).

Synthesis of Compound (67)

Compound (67) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (67). 1H NMR (300 MHz, DMSO-d6): δ 10.85 (s, 1H), 7.28-7.33 (m, 5H), 7.18-7.23 (t, 2H), 7.07-7.12 (t, 1H), 6.97-7.02 (t, 1H), 6.83-6.88 (t, 1H), 4.67-4.71 (m, 1H), 4.62-4.65 (m, 1H), 4.56 (s, 1H), 4.35 (s, 1H), 3.01-3.08 (m, 2H), 1.98-2.13 (d, 1H), 1.63 (s, 2H), 1.55 (s, 1H), 1.47-1.50 (d, 3H), 1.38-1.41 (m, 2H), 1.25-1.28 (m, 2H). LC-MS: (M+H)+=401.2; HPLC purity=94.67%.

Example 68

3-(5-chloro-1H-indol-3-yl)-1-(5-hydroxy-2-azatricyclo[3.3.1.1$^{3,7}$]dec-2-yl)butan-1-one (68)

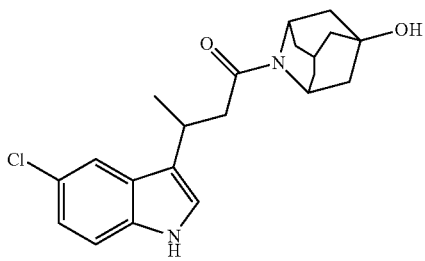

(68)

Synthesis of Compound (68)

Compound (68) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (68). 1H NMR (300 MHz, CDCl3): δ 8.10 (s, 1H), 7.55-7.56 (d, 1H), 7.21-7.25 (d, 1H), 7.04-7.07 (d, 1H), 6.99 (s, 1H), 4.97 (s, 1H), 4.03-4.13 (m, 1H), 3.54-3.62 (m, 1H), 2.64-2.72 (d, 1H), 2.44-2.54 (d, 1H), 2.15-2.30 (m, 2H), 1.76 (s, 4H), 1.70 (s, 3H), 1.62 (s, 2H), 1.38-1.40 (d, 3H). LC-MS: (M+H)+=373.1; HPLC purity=92.50%.

Example 69

3-(6-chloro-1H-indol-3-yl)-1-(5-hydroxy-2-azatricyclo[3.3.1.1$^{3,7}$]dec-2-yl)butan-1-one (69)

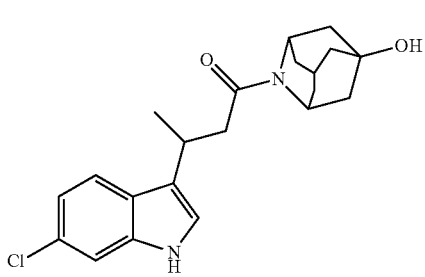

(69)

Synthesis of Compound (69)

Compound (69) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (69). 1H NMR (300 MHz, CDCl3): δ 8.03 (s, 1H), 7.49-7.51 (d, 1H), 7.27 (s, 1H), 6.95-7.01 (m, 2H), 4.91-5.01 (s, 1H), 4.08 (s, 1H), 3.56-3.58 (m, 1H), 2.69-2.73 (d, 1H), 2.54 (s, 1H), 2.11-2.27 (m, 1H), 1.8 (s, 1H), 1.68 (s, 9H), 1.37-1.40 (d, 3H). LC-MS: (M+H)+=373.1; HPLC purity=91.91%.

Example 70

2-[3-(4-methyl-1H-indol-3-yl)butanoyl]-2-azatricyclo[3.3.1.1$^{3,7}$]decane-5-carbonitrile (70)

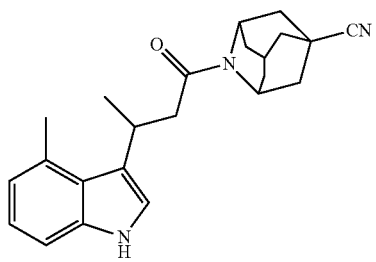

(70)

Synthesis of Compound (70)

Compound (70) was synthesized by following the procedure used to make Compound (1) (Scheme 2). The crude product was obtained by evaporating the organic layer under reduced pressure and was purified by silica gel column using Petroleum ether. Ethyl acetate (1:4) as eluent to obtain Compound (70). 1H NMR (300 MHz, CDCl3): δ 7.94 (s, 1H), 7.12-7.14 (d, 1H), 6.96-7.02 (m, 2H), 6.77-6.79 (d, 1H), 4.91 (s, 1H), 4.04 (s, 1H), 3.89 (s, 1H), 2.65 (s, 3H), 2.37-2.48 (m, 1H), 2.25-2.30 (m, 1H), 2.12 (s, 2H), 2.06 (s, 2H), 1.98-2.02 (d, 2H), 1.86-1.94 (s, 2H), 1.71-1.77 (m, 3H), 1.34-1.36 (d, 3H). LC-MS: (M+H)+=362.2; HPLC purity=95.85%.

Example 71

3-(4-chlorophenyl)-1-(5-hydroxy-2-azatricyclo[3.3.1.1$^{3,7}$]dec-2-yl)-3-(1H-indol-3-yl)propan-1-one (71)

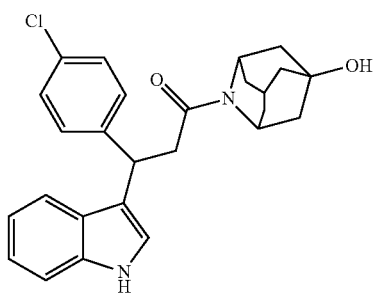

(71)

Synthesis of Compound (71)

Compound (71) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (71). 1H NMR (300 MHz, CDCl3): δ 8.01-8.13 (t, 1H), 7.25-7.28 (d, 2H), 7.18 (m, 4H), 7.05-7.10 (t, 1H), 6.93-6.96 (d, 2H), 4.92 (s, 1H), 4.79 (s, 1H), 4.11 (s, 1H), 2.97-3.05 (m, 2H), 2.15 (s, 1H), 1.69 (s, 7H), 1.45 (d, 3H). LC-MS: (M+H)+=435.1; HPLC purity=95.96%.

Example 72

1-(5-hydroxy-2-azatricyclo[3.3.1.1$^{3,7}$]dec-2-yl)-3-(4-methyl-1H-indol-3-yl)-3-phenylpropan-1-one (72)

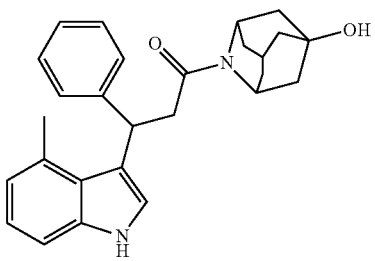

(72)

Synthesis of Compound (72)

Compound (72) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (72). 1H NMR (300 MHz, CDCl3): δ 8.13-8.21 (d, 1H), 7.14-7.15 (d, 4H), 7.04-7.11 (m, 2H), 6.99 (s, 1H), 6.90-6.96 (m, 1H), 6.64-6.66 (d, 1H), 5.08-5.13 (t, 1H), 4.92 (s, 1H), 4.13 (s, 1H), 2.89-3.02 (m, 2H), 2.4 (d, 3H), 2.08-2.21 (m, 1H), 1.81 (s, 1H), 1.68 (s, 2H), 1.62 (s, 2H), 1.39 (s, 2H), 0.78-0.90 (m, 3H). LC-MS: (M+H)+=415.2; HPLC purity=99.51%.

Example 73

3-(4-fluorophenyl)-1-(5-hydroxy-2-azatricyclo[3.3.1.1$^{3,7}$]dec-2-yl)-3-(1H-indol-3-yl)propan-1-one (73)

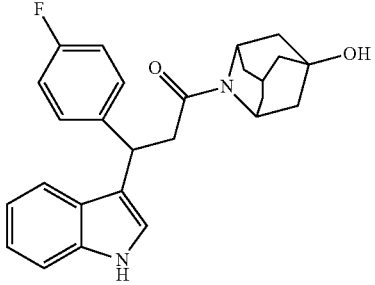

(73)

Synthesis of Compound (73)

Compound (73) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (73). 1H NMR (300 MHz, DMSO-d6): δ 10.87 (s, 1H), 7.28-7.31 (m, 5H), 6.98-7.05 (m, 3H), 6.84-6.89 (t, 1H), 4.58-4.71 (m, 3H), 4.36 (s, 1H), 2.97-3.12 (m, 2H), 2.08-2.13 (d, 1H), 1.64 (s, 2H), 1.41-1.55 (m, 6H), 1.20.-1.35 (m, 2H). LC-MS: (M+H)+=419.2; HPLC purity=95.83%.

Example 74

1-(5-hydroxy-2-azatricyclo[3.3.1.1$^7$]dec-2-yl)-4-methyl-3-(4-methyl-1H-indol-3-yl)pentan-1-one (74)

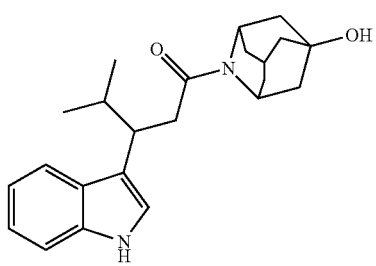

(74)

Synthesis of Compound (74)

Compound (74) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (74). 1H NMR (300 MHz, DMSO-d6): δ 10.77 (s, 1H), 7.11-7.13 (d, 2H), 6.85-6.90 (t, 1H), 6.64-6.66 (d, 1H), 4.66 (s, 1H), 4.58-4.62 (d, 1H), 4.38-4.40 (d, 1H), 3.70 (s, 1H), 2.67-2.76 (m, 2H), 2.64 (s, 3H), 2.05-2.16 (d, 1H), 1.84-1.86 (m, 1H), 1.52-1.64 (m, 5H), 0.1.36-1.48 (m, 5H), 0.82-0.90 (m, 6H). LC-MS: (M+H)+=381.2; HPLC purity=97.77%.

Example 76

3-(5-fluoro-1H-indol-3-yl)-1-(5-hydroxy-2-azatricyclo[3.3.1.1$^{3,7}$]dec-2-yl)butan-1-one (75)

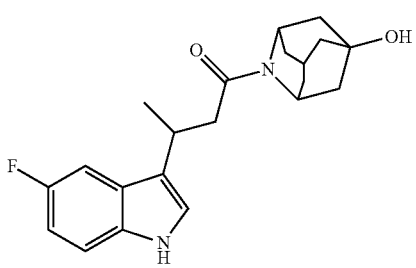

(75)

Synthesis of Compound (75)

Compound (75) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (75). 1H NMR (300 MHz, DMSO-d6): δ 10.88 (s, 1H), 7.28-7.32 (m, 2H), 7.21-7.24 (m, 1H), 6.85-6.91 (m, 1H), 4.78 (s, 1H), 4.58-4.64 (d, 1H), 4.23-4.25 (d, 1H), 3.16-3.39 (m, 2H), 2.53-2.69 (m, 2H), 2.15-2.17 (m, 1H), 1.65 (s, 2H), 1.54-1.57 (m, 3H), 1.36-1.49 (m, 4H), 1.29-1.30 (d, 3H). LC-MS: (M+H)+=356.1; HPLC purity=98.0%.

Example 76

3-(4-chloro-1H-indol-3-yl)-1-[5-(1H-tetrazol-5-yl)-2-azatricyclo[3.3.1.1$^{3,7}$]dec-2-yl]butan-1-one (76)

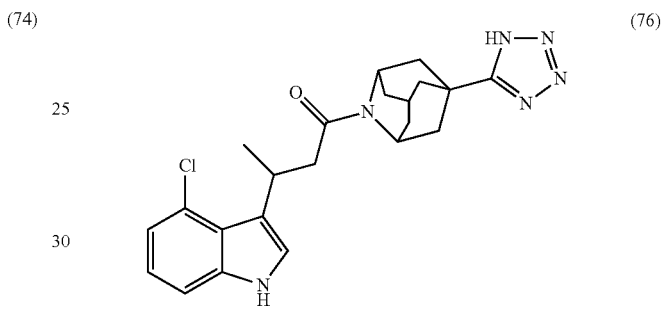

(76)

Synthesis of Compound (76)

Compound (76) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (76). 1H NMR (300 MHz, CD3OD): δ 7.10-7.21 (m, 3H), 6.93 (s, 2H), 4.30-4.35 (d, 1H), 4.08 (s, 1H), 2.89 (s, 1H), 2.54-2.61 (m, 2H), 1.90-1.94 (m, 4H), 1.74-1.77 (m, 5H), 1.24-1.37 (m, 6H). LC-MS: (M+H)+=426.1; HPLC purity=99.36%.

Example 77

3-(4-methyl-1H-indol-3-yl)-1-[5-(1H-tetrazol-5-yl)-2-azatricyclo[3.3.1.1$^{3,7}$]dec-2-yl]butan-1-one (77)

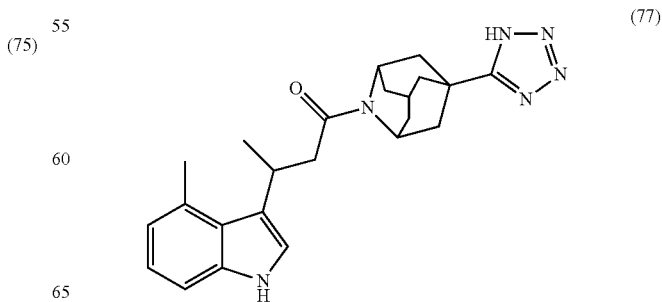

(77)

SYNTHETIC SCHEME 21

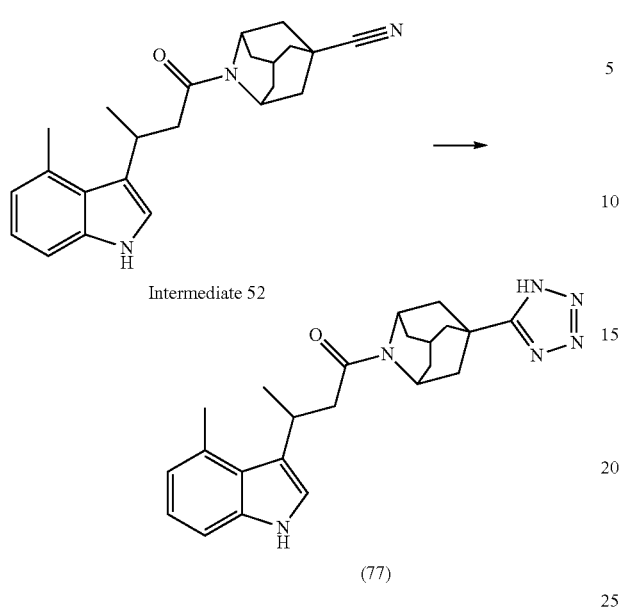

Synthesis of Compound (77)

To a stirred solution of Intermediate-52 (20 mg, 0.05 mmol) in toluene (10 mL) $NaN_3$ (37 mg, 0.5 mmol) was added along with trimethyltin chloride (49 mg, 0.25 mmol) under $N_2$ atmosphere, Resulted reaction mixture was heated at 110° C. for 12 hours. After completion of the reaction (monitored by TLC), the reaction mixture was quenched with water and was extracted with ethyl acetate (3×10 mL). The combined organic layer was concentrated to obtain a crude product. The resulted crude product was purified by prep. TLC eluted with DCM:MeOH to give Compound (77) (8 mg) as white solid. 1H NMR (300 MHz, CD3OD): δ 7.06-7.15 (m, 2H), 6.84-6.94 (m, 11H), 6.67-6.72 (m, 1H), 4.69-4.81 (m, 1H), 4.30-4.35 (d, 1H), 3.92-3.98 (m, 1H), 2.82-2.90 (m, 1H), 2.68 (d, 3H), 2.57-2.64 (m, 1H), 2.21 (s, 1H), 1.96-2.11 (m, 5H), 1.8 (s, 3H), 1.70-1.74 (m, 2H), 1.57-1.61 (d, 1H), 1.38-1.40 (d, 3H). LC-MS: (M+H)+=405.2; HPLC purity=98.31%.

Example 78

1-(5-hydroxy-2-azatricyclo[3.3.1.1$^{3,7}$]dec-2-yl)-3-(7-methyl-1H-indol-3-yl)butan-1-one (78)

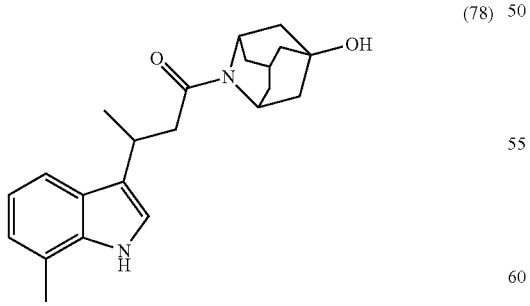
(78)

Synthesis of Compound (78)

Compound (78) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (78). 1H NMR (300 MHz, CDCl3): δ 7.88 (s, 1H), 7.44-7.46 (d, 1H), 6.90-7.03 (m, 3H), 3.52-3.61 (m, 1H), 2.72-2.79 (m, 1H), 2.40-2.50 (m, 1H), 2.40 (m, 3H), 2.22-2.23 (m, 1H), 1.70 (s, 3H), 1.49-1.61 (m, 6H), 1.45 (s, 3H), 1.40-1.43 (m, 3H). LC-MS: (M+H)+=353.2; HPLC purity=97.30%.

Example 79

3-(6-fluoro-1H-indol-3-yl)-1-(5-hydroxy-2-azatricyclo[3.3.1.1$^{3,7}$]dec-2-yl)butan-1-one (79)

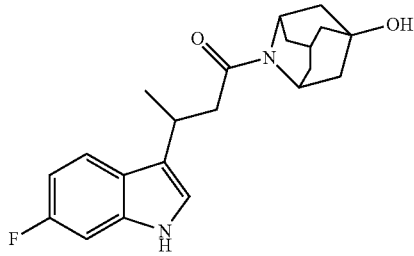
(79)

Synthesis of Compound (79)

Compound (79) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (79). 1H NMR (300 MHz, CDCl3): δ 7.99 (s, 1H), 7.55-7.60 (m, 1H), 6.98-7.04 (m, 2H), 6.84-6.91 (m, 1H), 5.04 (s, 1H), 4.15 (s, 1H), 3.56-3.68 (m, 1H), 2.74-2.82 (m, 1H), 2.48-2.55 (m, 1H), 2.29-2.18 (s, 1H), 1.76 (s, 2H), 1.67 (s, 2H), 1.57-1.62 (m, 4H), 1.48-1.50 (m, 2H), 1.43-1.46 (m, 3H). LC-MS: (M+H)+=357.2; HPLC purity=91.94%.

Example 80

3-[4-cyclopropyl-1-(2-hydroxyethyl)-1H-indol-3-yl]-1-(5-hydroxy-2-azatricyclo[3.3.1.1$^{3,7}$]dec-2-yl)butan-1-one (80)

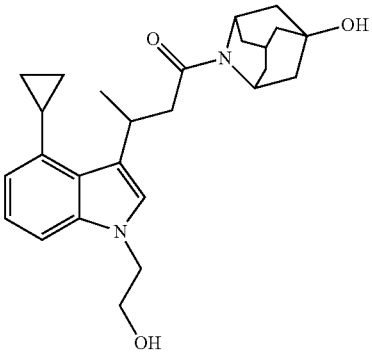
(80)

Synthesis of Compound (80)

Compound (80) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (80). 1H NMR (300 MHz, CDCl3): δ 7.14-7.19 (m, 1H), 7.06-7.11 (m, 1H), 7.00 (s, 1H), 6.73-6.75 (d, 1H), 5.06 (s, 1H), 4.27 (s, 1H), 4.20-4.24 (m, 3H), 3.91-3.95 (m, 2H), 2.76-2.90 (m, 1H), 2.56-2.64 (m, 1H), 2.43-2.51 (m, 1H), 2.31 (s, 1H), 1.79 (s, 2H), 1.68 (s, 2H), 1.63-1.65 (d, 4H), 1.57 (s, 3H), 1.42-1.46 (m, 3H), 0.97-1.02 (m, 2H), 0.79-0.90 (m, 2H). LC-MS: (M+H)+=423.2; HPLC purity=97.26%.

Example 81

3-(4-fluorophenyl)-1-(5-hydroxy-2-azatricyclo[3.3.1.1$^{3,7}$]dec-2-yl)-3-(1H-indol-3-yl)propan-1-one (81)

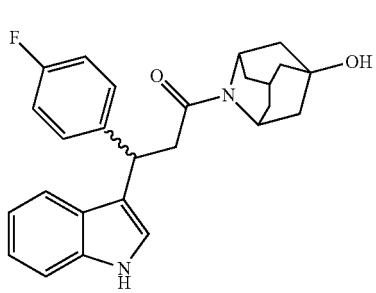
(81)

Synthesis of Compound (81) (Peak-1)

Racemate of Compound (73) was separated by using chiral HPLC to give enantiomer Compound (81) (peak-1) 1H NMR (300 MHz, CDCl3): δ 10.87 (s, 1H), 7.20 (m, 5H), 7.00-7.05 (m, 3H), 6.83 (m, 1H), 4.66-4.68 (m, 1H), 4.58 (m, 2H), 4.40 (s, 1H), 3.10 (s, 2H), 2.08-2.13 (d, 1H), 1.61.23-1.55 (m, 8H), 1.11-1.15 (m, 2H). LC-MS: (M+H)+=419.2; HPLC purity=94.26%; Chiral purity=100% (RT=8.57 min), Chiral column: Chiralpak IC 4.6 mm×250 mm, Mobile phase hexane:EtOH:DCM (75:15:10).

Example 82

3-(4-fluorophenyl)-1-(6-hydroxy-2-azatricyclo[3.3.1.1$^{3,7}$]dec-2-yl)-3-(1H-indol-3-yl)propan-1-one (82)

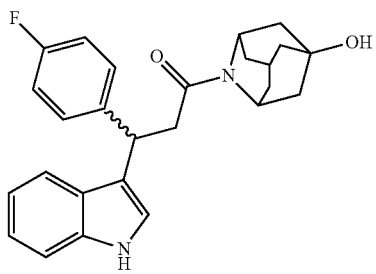
(82)

Synthesis of Compound (82) (Peak-2)

Racemate of Compound (73) was separated by using chiral HPLC to give enantiomer Compound (82) (peak-2). 1H NMR (300 MHz, CDCl3): δ 10.87 (s, 1H), 7.20 (m, 5H), 7.00-7.05 (m, 3H), 6.83 (m, 1H), 4.66-4.68 (m, 1H), 4.58 (m, 2H), 4.40 (s, 1H), 3.10 (s, 2H), 2.08-2.13 (d, 1H), 1.61.23-1.55 (m, 8H), 1.11-1.15 (m, 2H). LC-MS: (M+H)+=419.2; HPLC purity=97.71%; Chiral purity=100% (RT=10.56 min), Chiral column: Chiralpak IC 4.6 mm×250 mm, Mobile phase hexane:EtOH:DCM (75:15:10).

Example 83

3-(4-fluoro-1H-indol-3-yl)-1-(5-hydroxy-2-azatricyclo[3.3.1.1$^{3,7}$]dec-2-yl)-3-phenylpropan-1-one (83)

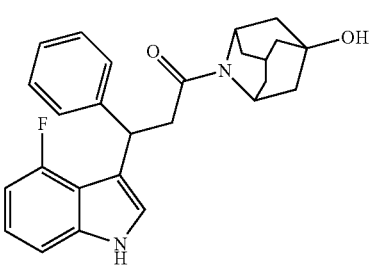
(83)

Synthesis of Compound (83)

Compound (83) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (83). 1H NMR (300 MHz, DMSO-d6): 511.17 (s, 1H), 7.35-7.37 (m, 1H), 7.14-7.27 (m, 4H), 7.06-7.11 (m, 2H), 6.93-7.00 (m, 1H), 6.58-6.64 (m, 1H), 4.80-4.85 (t, 1H), 4.70 (s, 1H), 4.60-4.65 (d, 1H), 4.37 (s, 1H), 2.93-3.17 (m, 2H), 2.07-2.27 (m, 2H), 1.64 (s, 2H), 1.40-1.53 (m, 3H), 1.36 (m, 2H), 1.23-1.28 (m, 2H). LC-MS: (M+H)+=419.2; HPLC purity=96.72%.

Example 84

3-(1,3-benzothiazol-2-yl)-1-(5-hydroxy-2-azatricyclo[3.3.1.1$^{3,7}$]dec-2-yl)butan-1-one (84)

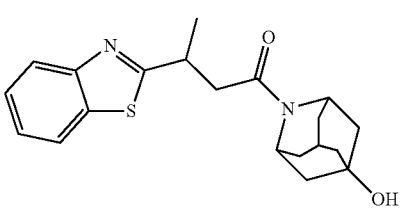
(84)

163

SYNTHETIC SCHEME 22

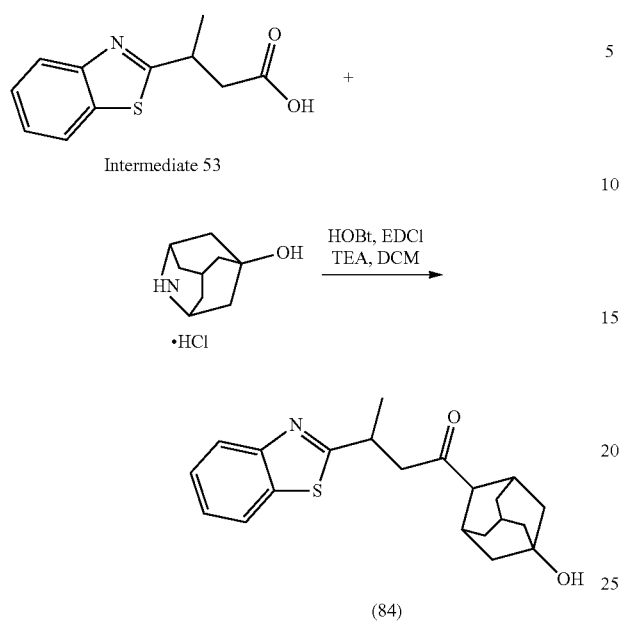

(84)

Synthesis of Compound (84)

Intermediate-53 was synthesized by following the procedure used to make Intermediate-36 (Scheme 7). Compound (84) was synthesized by following the procedure used to make Compound (1) (Scheme 2). The crude product was obtained by evaporating the organic layer under reduced pressure and was purified by silica gel column using DCM:MeOH as eluent to obtain (84). 1H NMR (300 MHz, CDCl3): δ 7.90-7.93 (d, 1H), 7.76-7.79 (d, 1H), 7.36-7.41 (t, 1H), 7.26-7.31 (t, 1H), 4.96 (s, 1H), 4.33 (s, 1H), 3.84-3.86 (d, 1H), 3.04-3.11 (m, 1H), 2.58-2.73 (m, 1H), 2.23-2.27 (d, 1H), 1.72-1.76 (d, 4H), 1.55-1.65 (m, 6H), 1.45-1.47 (d, 3H). LC-MS: (M+H)+=357.1; HPLC purity=98.96%.

Example 86

1-(2-azatricyclo[3.3.1.1$^{3,7}$]dec-2-yl)-3-1H-pyrrolo[2,3-b]pyridin-3-yl)butan-1-one (86)

164

SYNTHETIC SCHEME 23

Synthesis of 3-(1H-pyrrolo[2,3-b]pyridin-3-yl)butanoic acid (Intermediate-64)

Intermediate-54 was synthesized by following the procedure used to make Intermediate-42 (Scheme 11).

Synthesis of Compound (85)

Compound (85) was synthesized by following the procedure used to make Compound (1) (Scheme 2). The crude product was obtained by evaporating the organic layer under reduced pressure and was purified by silica gel column using Petroleum ether Ethyl acetate as eluent to obtain Compound (85). 1H NMR (300 MHz, CDCl3): δ 9.29 (s, 1H), 8.19-8.21 (m, 1H), 7.93-7.96 (m, 1H), 7.07 (s, 1H), 6.97-7.01 (m, 1H), 4.76 (s, 1H), 3.89 (s, 1H), 3.52-3.66 (m, 1H), 2.65-2.73 (m, 1H), 2.42-2.49 (m, 1H), 1.97 (s, 11H), 1.84 (s, 1H), 1.65-1.68 (m, 4H), 1.61-1.65 (m, 3H), 1.56-1.57 (d, 2H), 1.41-1.49 (m, 1H), 1.35 (d, 3H). LC-MS: (M+H)+=324.2; HPLC purity=94.58%.

Example 86

1-(5-hydroxy-2-azatricyclo[3.3.1.1]dec-2-yl)-3-(1H-pyrrolo[2,3-b]pyridin-3-yl)butan-1-one (86)

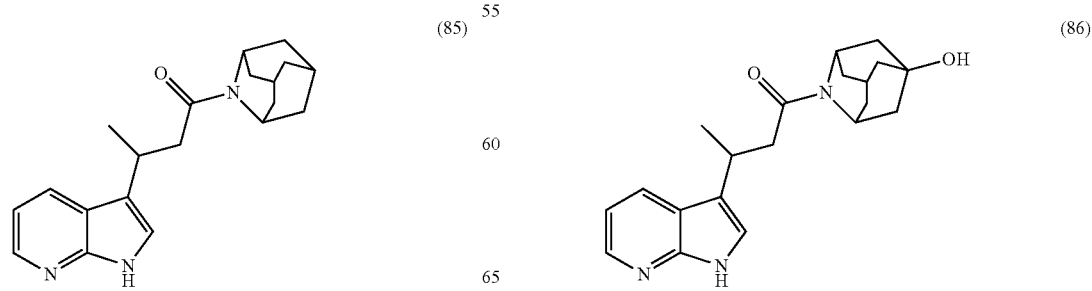

Synthesis of Compound (86)

Compound (86) was synthesized by following the procedure used to make Compound (1) (Scheme 2). The crude product was obtained by evaporating the organic layer under reduced pressure and was purified by silica gel column using DCM:MeOH as eluent to obtain Compound (86). 1H NMR (300 MHz, CDCl3): δ 8.82-9.01 (m, 1H), 8.19-8.21 (d, 1H), 7.94-7.96 (m, 1H), 7.05 (s, 1H), 6.98-7.02 (m, 1H), 4.96 (s, 1H), 4.08 (s, 1H), 3.55-3.62 (m, 1H), 2.65-2.72 (m, 1H), 2.42-2.55 (m, 1H), 2.09-2.29 (m, 1H), 1.69 (s, 3H), 1.50 (s, 2H), 1.18-1.44 (m, 5H), 1.18 (s, 1H), 0.78-0.98 (m, 2H). LC-MS: (M+H)+=340.2; HPLC purity=99.20%.

Example 87

3-(4-chloro-1H-pyrrolo[2,3-b]pyridin-3-yl)-1-(5-hydroxy-2-azatricyclo[3.3.1.1$^{3,7}$]dec-2-yl)butan-1-one (87)

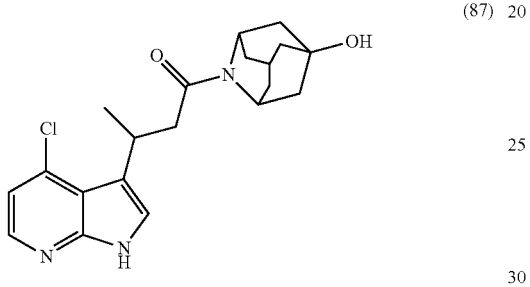

(87)

Synthesis of Compound (87)

Compound (87) was synthesized by following the procedure used to make Compound (1) (Scheme 2). The crude product was obtained by evaporating the organic layer under reduced pressure and was purified by silica gel column using DCM:MeOH as eluent to obtain Compound (87). 1H NMR (300 MHz, DMSO-d6): δ11.77 (s, 1H), 8.09-8.11 (d, 1H), 7.38-7.43 (m, 1H), 7.10-7.11 (d, 1H), 4.80 (s, 1H), 4.66 (s, 1H), 4.35 (s, 1H), 3.84 (s, 1H), 2.69 (m, 3H), 2.18 (s, 1H), 1.45-1.68 (m, 9H), 1.23-1.30 (m, 3H). LC-MS: (M+H)+=374.2; HPLC purity=96.68%.

Example 88

1-(5-hydroxy-2-azatricyclo[3.3.1.1$^{3,7}$]dec-2-yl)-3-(4-methyl-1H-pyrrolo[2,3-b]pyridin-3-yl)butan-1-one (88)

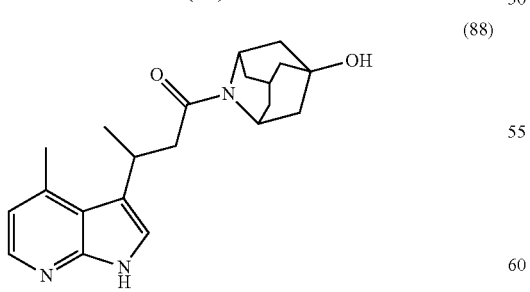

(88)

Synthesis of Compound (88)

Compound (88) was synthesized by following the procedure used to make Compound (1) (Scheme 2). The crude product was obtained by evaporating the organic layer under reduced pressure and was purified by silica gel column using Petroleum ether. Ethyl acetate (1:4) as eluent to obtain Compound (88). 1H NMR (300 MHz, CDCl3): δ11.91-11.95 (d, 1H), 7.97-7.99 (d, 1H), 7.26-7.29 (d, 1H), 7.05-7.06 (d, 1H), 4.89-4.94 (d, 1H), 4.26 (s, 1H), 3.91 (s, 1H), 3.04-3.06 (m, 1H), 2.90 (s, 3H), 2.50-2.66 (m, 2H)(, 2.27 (s, 1H), 1.36-1.78 (m, 9H), 1.29-1.32 (d, 3H). LC-MS: (M+H)+=354.2; HPLC purity=99.38%.

Example 89

1-(6-hydroxy-2-azatricyclo[3.3.1.1$^{3,7}$]dec-2-yl)-3-phenyl-3-(1H-pyrrolo[2,3-b]pyridin-3-yl)propan-1-one (89)

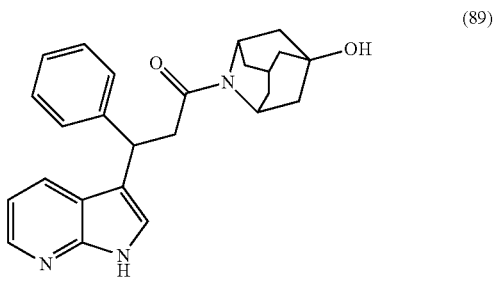 [SMILES: O=C(CC(c1ccccc1)c1c[nH]c2ncccc12)N1C2CC3CC1CC(O)(C3)C2]

(89)

Synthesis of Compound (89)

Compound (89) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (89). LC-MS: (M+H)+=402.2; HPLC purity=95.83%.

Example 90

1-(5-hydroxy-2-azatricyclo[3.3.1.1$^{3,7}$]dec-2-yl)-4-methyl-3-(1H-pyrrolo[2,3-b]pyridin-3-yl)pentan-1-one (90)

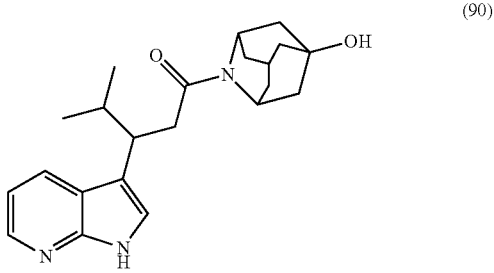 [SMILES: CC(C)C(CC(=O)N1C2CC3CC1CC(O)(C3)C2)c1c[nH]c2ncccc12]

(90)

Synthesis of Compound (90)

Compound (90) was synthesized by following the procedure used to make Compound (1) (Scheme 2). The crude product was obtained by evaporating the organic layer under reduced pressure and was purified by silica gel column using Petroleum ether:Ethyl acetate (1:4) as eluent to obtain Compound (90). 1H NMR (300 MHz, CDCl3): δ11.48-11.50 (d, 1H), 8.28-8.33 (t, 1H), 8.14-8.16 (d, 1H), 7.22 (m, 2H), 4.75-4.80 (d, 1H), 4.13 (s, 1H), 3.32-3.37 (m, 1H), 2.63-2.69 (m, 3H), 2.12-2.20 (d, 1H), 1.95-2.04 (m, 1H), 1.36-1.70 (m, 9H), 0.89-0.93 (m, 3H), 0.77-0.81 (m, 3H). LC-MS: (M+H)+=368.2; HPLC purity=94.67%.

Example 91

2-[3-(1H-pyrrolo[2,3-b]pyridin-3-yl)butanoyl]-2-azatricyclo[3.3.1.1$^{3,7}$]decane-5-carboxylic acid (91)

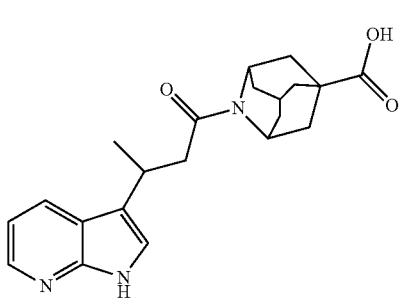

(91)

Synthesis of Compound (91)

Compound (91) was synthesized by following the procedure used to make Intermediate-26 (Scheme 4). The crude product was obtained by evaporating the organic layer under reduced pressure and was purified by silica gel column using DCM:MeOH as eluent to obtain Compound (91). 1H NMR (300 MHz, CDCl3): δ 11.09 (s, 1H), 8.08-8.13 (m, 2H), 7.06-7.10 (m, 2H), 4.71 (s, 1H), 3.64-3.72 (m, 2H), 2.66-2.74 (t, 1H), 2.36-2.41 (m, 1H), 2.01-2.04 (d, 1H), 1.80-1.84 (d, 1H), 1.48-1.70 (m, 8H), 1.43-1.45 (d, 3H), 1.18-1.22 (m, 1H). LC-MS: (M+H)+=368.2; HPLC purity=98.93%.

Example 92

2-[4-methyl-3-(1H-pyrrolo[2,3-b]pyridin-3-yl)pentanoyl]-2-azatricyclo[3.3.1.1$^{3,7}$]decane-5-carbonitrile (92)

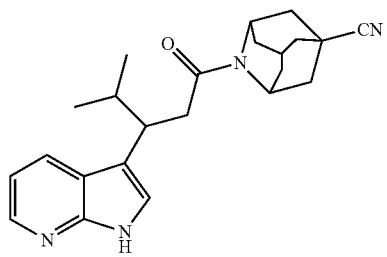

(92)

Synthesis of Compound (92)

Compound (92) was synthesized by following the procedure used to make Compound (1) (Scheme 2). The crude product was obtained by evaporating the organic layer under reduced pressure and was purified by silica gel column using DCM:MeOH as eluent to obtain Compound (92). 1H NMR (300 MHz, CDCl3): δ 10.75-10.78 (d, 1H), 8.18-8.25 (m, 2H), 7.19-7.20 (m, 2H), 4.72 (s, 1H), 4.03 (s, 1H), 3.33-3.35 (m, 1H), 2.61-2.70 (m, 2H), 2.13 (s, 1H), 1.97-2.02 (m, 4H), 1.81-1.90 (m, 2H), 1.09-1.68 (m, 5H), 0.90-0.92 (m, 3H), 0.77-0.79 (d, 3H). LC-MS: (M+H)+=377.2; HPLC purity=97.71%.

Example 93

3-(4-fluorophenyl)-1-(5-hydroxy-2-azatricyclo[3.3.1.1$^{3,7}$]dec-2-yl)-3-(4-methyl-1H-indol-3-yl)propan-1-one (93)

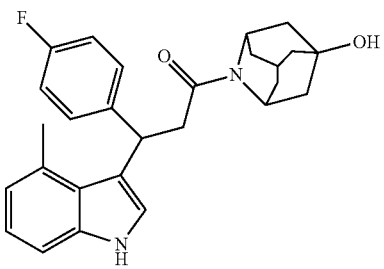

(93)

Synthesis of Compound (93)

Compound (93) was synthesized by following the procedure used to make Compound (1) (Scheme 2). The crude product was obtained by evaporating the organic layer under reduced pressure and was purified by silica gel column using DCM:MeOH as eluent to obtain Compound (93). 1H NMR (300 MHz, DMSO-d6): δ 10.91 (s, 1H), 7.36 (m, 1H), 7.18-7.23 (m, 2H), 7.12-7.15 (d, 1H), 7.01-7.06 (t, 2H), 6.85-6.902 (t, 1H), 6.58-6.60 (d, 1H), 4.99-5.02 (m, 1H), 4.74 (m, 1H), 4.58-4.66 (d, 1H), 4.36 (m, 1H), 2.95-2.97 (m, 2H), 2.42 (s, 3H), 2.07-2.17 (m, 1H), 1.28-1.65 (m, 10H). LC-MS: (M+H)+=433.2; HPLC purity=94.79%.

Example 94

3-(6-fluoro-1H-indol-3-yl)-1-(5-hydroxy-2-azatricyclo[3.3.1.1$^{3,7}$]dec-2-yl)-3-phenylpropan-1-one (94)

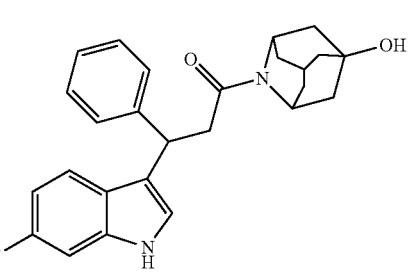

(94)

Synthesis of Compound (94)

Compound (94) was synthesized by following the procedure used to make Compound (1) (Scheme 2). The crude product was obtained by evaporating the organic layer under reduced pressure and was purified by silica gel column using DCM:MeOH as eluent to obtain Compound (94). 1H NMR (300 MHz, DMSO-d6): δ 10.94 (s, 1H), 7.30-7.32 (m, 4H), 7.19-7.26 (m, 2H), 7.04-7.13 (m, 2H), 6.69-6.75 (t, 1H), 4.71 (s, 1H), 4.56-4.65 (m, 2H), 4.35 (s, 1H), 3.02-3.05 (m, 2H), 2.06-2.13 (d, 1H), 1.63 (s, 2H), 1.20-1.59 (m, 8H). LC-MS: (M+H)+=419.1; HPLC purity=93.86%.

Example 95

3-cyclopropyl-3-(4-fluoro-1H-indol-3-yl)-1-(5-hydroxy-2-azatricyclo[3.3.1.1$^{3,7}$]dec-2-yl)propan-1-one (95)

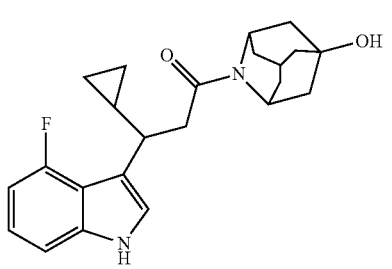

(95)

Synthesis of Compound (95)

Compound (95) was synthesized by following the procedure used to make Compound (1) (Scheme 2). The crude product was obtained by evaporating the organic layer under reduced pressure and was purified by silica gel column using DCM:MeOH as eluent to obtain Compound (95). 1H NMR (300 MHz, CDCl3): δ 8.13 (s, 1H), 6.93-7.08 (m, 3H), 6.66-6.73 (m, 1H), 4.93 (s, 1H), 4.24 (s, 1H), 2.94-3.04 (m, 1H), 2.66-2.75 (m, 1H), 2.60 (s, 1H), 2.08-2.20 (d, 1H), 1.21-1.67 (m, 10H), 0.76-0.97 (m, 1H), 0.49-0.53 (m, 1H), 0.26-0.32 (m, 2H), 0.05-0.07 (m, 1H). LC-MS: (M+H)+=383.1; HPLC purity=96.02%.

Example 96

3-(2,4-difluorophenyl)-1-(5-hydroxy-2-azatricyclo[3.3.1.1$^{3,7}$]dec-2-yl)-3-(1H-indol-3-yl)propan-1-one (96)

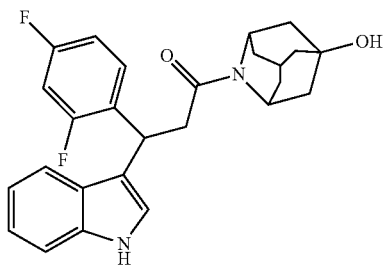

(96)

Synthesis of Compound (96)

Compound (96) was synthesized by following the procedure used to make Compound (1) (Scheme 2). The crude product was obtained by evaporating the organic layer under reduced pressure and was purified by silica gel column using DCM:MeOH as eluent to obtain Compound (96). 1H NMR (300 MHz, DMSO-d6): δ 10.90 (s, 1H), 7.36-7.41 (m, 1H), 7.32 (m, 2H), 7.29 (m, 1H), 7.11-7.15 (t, 1H), 6.97-7.05 (t, 1H), 6.88-6.95 (m, 2H), 4.93 (t, 1H), 4.69 (s, 1H), 4.62-4.64 (d, 1H), 4.40 (s, 1H), 2.72-3.11 (m, 2H), 2.14-2.27 (m, 1H), 1.24-1.66 (m, 10H). LC-MS: (M+H)=437.1; HPLC purity=92.20%.

Example 97

3-(6-fluoro-1H-indol-3-yl)-1-(5-hydroxy-2-azatricyclo[3.3.1.1$^{3,7}$]dec-2-yl)butan-1-one Peak-1 (97)

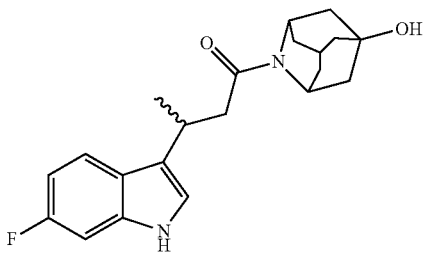

(97)

Synthesis of Compound (97) (Peak-1)

Racemate of (79) was separated by chiral HPLC column chromatography to give Compound (97) (peak-1). 1H NMR (300 MHz, CDCl3): δ 7.90 (S, 1H), 7.48-7.53 (m, 1H), 6.92-6.97 (m, 2H), 6.78-6.84 (t, 1H), 4.97 (s, 1H), 4.09 (s, 1H), 3.52-3.96 (m, 1H), 2.67-2.75 (m, 1H), 2.41-2.48 (m, 1H), 2.11-2.22 (d, 1H), 1.60 (m, 6H), 1.36-1.39 (m, 6H). LC-MS: (M+H)+=357.1; HPLC purity=93.22%; Chiral purity: 100% (RT=15.45 min); Column: Chiralpak IC, 4.6 mm×250 mm; Mobile phase: hexanes:i-PrOH:DCM (7.5:1.5:1.0).

Example 98

3-(6-fluoro-1H-indol-3-yl)-1-(5-hydroxy-2-azatricyclo[3.3.1.1$^{3,7}$]dec-2-yl)butan-1-one Peak-) (98)

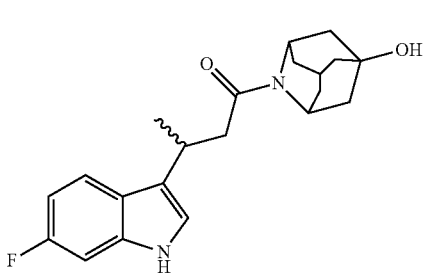

(98)

Synthesis of Compound (98) (Peak-2)

Racemate of Compound (79) was separated by chiral HPLC column chromatography to give Compound (98) (peak-2). 1H NMR (300 MHz, CDCl3): δ 7.89 (S, 1H), 7.48-7.53 (m, 1H), 6.93-6.97 (m, 2H), 6.78-6.84 (t, 1H), 4.97 (s, 1H), 4.08 (s, 1H), 3.52-3.59 (m, 1H); 2.67-2.75 (m, 1H), 2.41-2.48 (m, 1H), 2.11-2.22 (d, 1H), 1.54-1.69 (m, 9H), 1.36-1.38 (d, 3H). LC-MS: (M+H)⁺=357.2; HPLC purity=95.14%; Chiral purity: 99.35% (RT=19.0 min); Column: Chiralpak IC, 4.6 mm×250 mm; Mobile phase: hexanes:i-PrOH:DCM (7.5:1.5:1.0).

Example 99

3-(4-fluoro-1H-indol-3-yl)-3-(4-fluorophenyl)-1-(5-hydroxy-2-azatricyclo[3.3.1.1$^{3,7}$]dec-2-yl)propan-1-one (99)

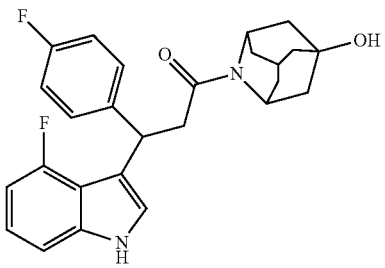

(99)

Synthesis of Compound (99)

Compound (99) was synthesized by following the procedure used to make Compound (1) (Scheme 2). The crude product was obtained by evaporating the organic layer under reduced pressure and was purified by silica gel column using DCM:MeOH as eluent to obtain Compound (99). 1H NMR (300 MHz, DMSO-d6): δ 11.19-11.23 (d, 1H), 7.37 (s, 1H), 7.27-7.29 (t, 2H), 7.12-7.14 (d, 1H), 6.93-7.05 (m, 3H), 6.58-6.65 (m, 1H), 4.80-4.84 (m, 1H), 4.70 (s, 1H), 4.59-4.65 (d, 1H), 4.37 (s, 1H), 2.96-3.11 (m, 2H), 2.08-2.16 (d, 1H), 1.29-1.65 (m, 1 OH). LC-MS: (M+H)⁺=437.1; HPLC purity=99.01%.

Example 100

2-[3-(4-chloro-1H-indol-3-yl)butanoyl]-2-azatricyclo[3.3.1.1$^{3,7}$]decane-6-carbonitrile Peak-1 (100)

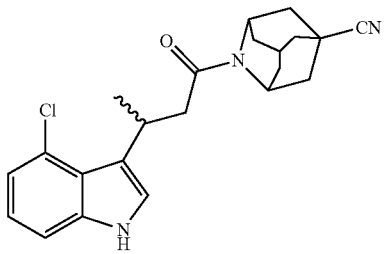

(100)

Synthesis of Compound (100) (Peak-1)

Racemate of Compound (59) was separated by preparative chiral column to give Compound (100) (peak-1). 1H NMR (300 MHz, CDCl3): δ 8.06 (s, 1H), 7.32 (m, 1H), 7.00-7.02 (m, 3H), 4.90 (s, 1H), 3.96-4.11 (m, 2H), 2.77-2.87 (m, 1H), 2.40-2.48 (m, 1H), 1.60-2.12 (m, 11H), 1.37-1.40 (m, 3H). LC-MS: (M+H)⁺=382.1; HPLC purity=98.74%; Chiral purity: 100% (RT=16.17 min); Column: Chiralpak IC, 4.6 mm×250 mm; Mobile phase: hexanes:i-PrOH:DCM (7.5:1.5:1.0).

Example 101

2-[3-(4-chloro-1H-indol-3-yl)butanoyl]-2-azatricyclo[3.3.1.1$^{3,7}$]decane-6-carbonitrile Peak-2 (101)

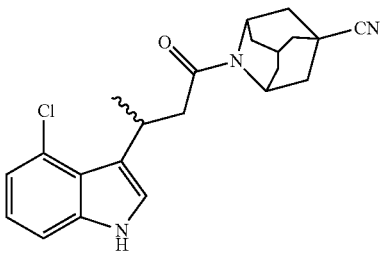

(101)

Synthesis of Compound (101) (Peak-2)

Racemate of Compound (59) was separated by preparative chiral column to give Compound (101) (peak-2). 1H NMR (300 MHz, CDCl3): δ 8.07 (s, 1H), 7.00-7.04 (m, 4H), 4.90 (s, 1H), 3.96-4.11 (m, 2H), 2.77-2.87 (m, 1H), 2.40-2.48 (m, 1H), 1.60-2.12 (m, 11H), 1.37-1.40 (m, 3H). LC-MS: (M+H)⁺=382.1; HPLC purity=98.08%; Chiral purity: 100% (RT=30.89 min); Column: Chiralpak IC, 4.6 mm×250 mm; Mobile phase: hexanes:i-PrOH:DCM (7.5:1.5:1.0).

Example 102

3-(4-cyclopropyl-1H-indol-3-yl)-1-(5-hydroxy-2-azatricyclo[3.3.1.1$^{3,7}$]dec-2-yl)butan-1-one Peak-1 (102)

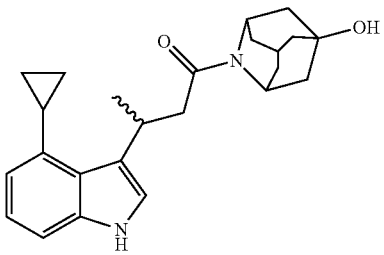

(102)

Synthesis of Compound (102) (Peak-1)

Racemate of Compound (41) was separated by preparative chiral column to give Compound (102) (peak-1). 1H NMR (300 MHz, DMSO-d6): δ 10.80 (s, 1H), 7.12-7.16 (m, 2H), 6.88-6.963 (t, 1H), 6.55-6.58 (d, 1H), 4.81 (s, 1H), 4.65 (d, 1H), 4.32 (s, 1H), 4.01-4.06 (m, 1H), 2.67-2.72 (m, 2H), 2.17 (s, 1H), 1.43-1.68 (m, 11H), 1.27-1.30 (d, 3H), 0.89-0.95 (m, 2H), 0.73-0.86 (m, 2H). LC-MS: (M+H)⁺=379.2; HPLC purity=98.53%; Chiral purity: 100% (RT=15.36 min); Column: Chiralpak IC, 4.6 mm×250 mm; Mobile phase: hexanes:i-PrOH:DCM (7.5:1.5:1.0).

Example 103

3-(4-cyclopropyl-1H-indol-3-yl)-1-(5-hydroxy-2-azatricyclo[3.3.1.1³,⁷]dec-2-yl)butan-1-one Peak-2 (103)

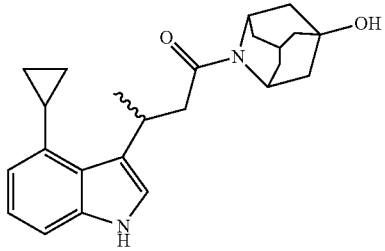

(103)

Synthesis of Compound (103) (Peak-2)

Racemate of Compound (41) was separated by preparative chiral column to give Compound (103) (peak-2). 1H NMR (300 MHz, DMSO-d6): δ 10.80 (s, 1H), 7.12-7.16 (m, 2H), 6.88-6.93 (t, 1H), 6.55-6.58 (d, 1H), 4.81 (s, 1H), 4.65 (d, 1H), 4.32 (s, 1H), 3.97-4.05 (m, 1H), 2.67-2.72 (m, 2H), 2.17 (s, 1H), 1.43-1.68 (m, 11H), 1.27-1.30 (d, 3H), 0.83-0.95 (m, 2H), 0.70-0.74 (m, 2H). LC-MS: $(M+H)^+$=379.2; HPLC purity=99.43%; Chiral purity: 100% (RT=22.17 min); Column: Chiralpak IC, 4.6 mm×250 mm; Mobile phase: hexanes:i-PrOH:DCM (7.5:1.5:1.0).

Example 104

1-(5-fluoro-2-azatricyclo[3.3.1.1³,⁷]dec-2-yl)-3-(4-methyl-1H-indol-3-yl)butan-1-one (104)

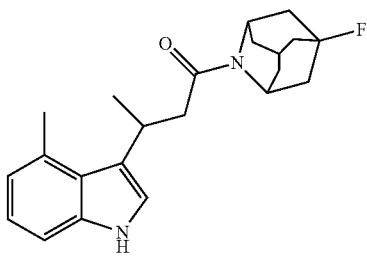

(104)

Synthesis of Compound (104)

Compound (104) was synthesized by following the procedure used to make Compound (24) (Scheme 12). The crude product was obtained by evaporating the organic layer under reduced pressure and was purified by silica gel column using hexane:EtOAc as eluent to obtain Compound (104). 1H NMR (300 MHz, DMSO-d6): δ 10.79 (s, 1H), 7.12-7.16 (m, 2H), 6.87-6.92 (mt, 1H), 6.67-6.69 (d, 1H), 4.92 (s, 1H), 4.48 (s, 1H), 3.73-3.80 (m, 1H), 2.65-2.72 (m, 1H), 2.61 (s, 3H), 2.27-2.36 (m, 2H), 1.42-1.93 (m, 10H), 1.24-1.26 (d, 3H). LC-MS: $(M+H)^+$=355.2; HPLC purity=98.31%.

Example 106

1-(2-azatricyclo[3.3.1.1³,⁷]dec-2-yl)-3-(1,3-benzothiazol-2-yl)butan-1-one (106)

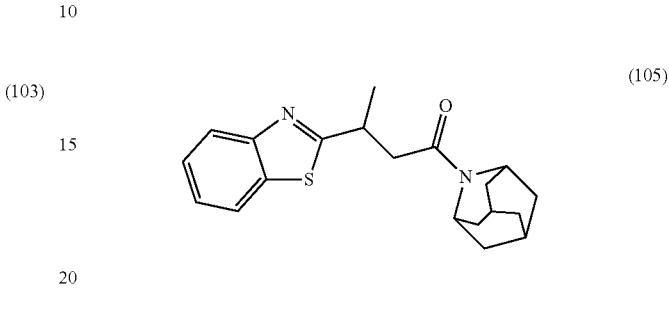

(105)

Synthesis of Compound (105)

Compound (105) was synthesized by following the procedure used to make Compound (1) (Scheme 2). The crude product was obtained by evaporating the organic layer under reduced pressure and was purified by silica gel column using hexane:EtOAc as eluent to obtain Compound (105). 1H NMR (300 MHz, CDCl3): δ 7.87-7.89 (d, 1H), 7.74-7.77 (d, 1H), 7.33-7.38 (tm 1H), 7.23-7.28 (t, 1H), 4.77 (s, 1H), 4.05 (s, 1H), 3.65-3.89 (m, 1H), 2.96-3.03 (m, 1H), 2.55-2.57 (m, 1H), 1.66-2.01 (m, 12H), 1.33-1.35 (d, 3H). LC-MS: $(M+H)^+$=341.1; HPLC purity=98.67%.

Example 106

3-(1,3-benzothiazol-2-yl)-1-(5-fluoro-2-azatricyclo[3.3.1.1³,⁷]dec-2-yl)butan-1-one (106)

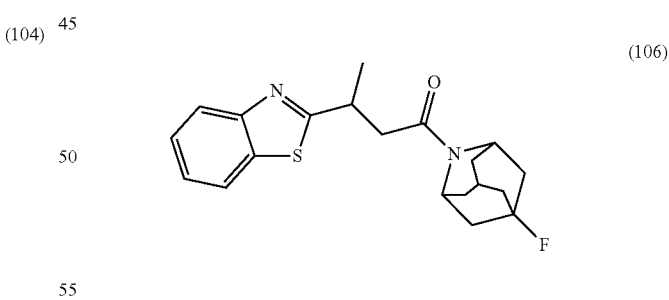

(106)

Synthesis of Compound (106)

Compound (106) was synthesized by following the procedure used to make Compound (24) (Scheme 12). The crude product was obtained by evaporating the organic layer under reduced pressure and was purified by silica gel column using hexane:EtOAc as eluent to obtain Compound (106). 1H NMR (300 MHz, CDCl3): δ 7.85-7.88 (d, 1H), 7.75-7.78 (m, 1H), 7.33-7.39 (m, 1H), 7.23-7.29 (m, 1H), 5.04 (s, 1H), 4.40 (s, 1H), 3.79-3.88 (m, 1H), 3.01-3.09 (m, 1H), 2.53-2.61 (m, 1H), 2.36 (d, 1H), 1.50-1.88 (m, 10H), 1.42-1.47 (d, 3H). LC-MS: (M+H)⁺=359.1; HPLC purity=95.97%.

Example 107

3-(1,3-benzothiazol-2-yl)-1-(5-hydroxy-2-azatricyclo[3.3.1.1$^{3,7}$]dec-2-yl)-3-phenylpropan-1-one (107)

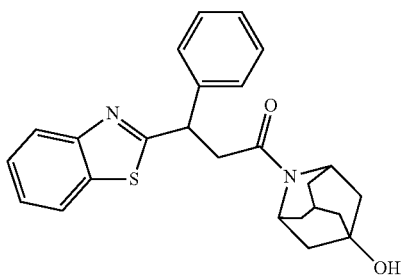

(107)

Synthesis of (107)

Compound (107) was synthesized by following the procedure used to make Compound (1) (Scheme 2). The crude product was obtained by evaporating the organic layer under reduced pressure and was purified by silica gel column using DCM:MeOH as eluent to obtain Compound (107). 1H NMR (300 MHz, DMSO-d6): δ 7.91-8.00 (m, 2H), 7.22-7.50 (m, 7H), 4.95-5.00 (m, 1H), 4.64-4.69 (m, 2H), 4.43 (s, 1H), 3.52-3.59 (m, 1H), 2.95-3.04 (m, 1H), 2.08-2.20 (m, 1H), 1.23-1.79 (m, 10H). LC-MS: (M+H)⁺=419.1; HPLC purity=99.70%.

Example 108

3-(1,3-benzothiazol-2-yl)-1-(5-fluoro-2-azatricyclo[3.3.1.1$^{3,7}$]dec-2-yl)-3-phenylpropan-1-one (108)

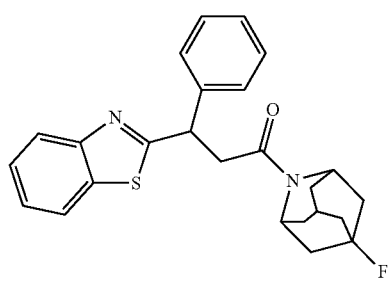

(108)

Synthesis of Compound (108)

Compound (108) was synthesized by following the procedure used to make Compound (24) (Scheme 12). The crude product was obtained by evaporating the organic layer under reduced pressure and was purified by silica gel column using hexane:EtOAc as eluent to obtain Compound (108). 1H NMR (300 MHz, DMSO-d6): δ7.90-8.00 (m, 2H), 7.22-7.50 (m, 7H), 4.95-5.01 (m, 1H), 4.82 (s, 1H), 4.60 (s, 1H), 3.53-3.61 (m, 1H), 2.96-3.09 (m, 1H), 2.27-2.35 (m, 1H), 1.23-1.79 (m, 10H). LC-MS: (M+H)⁺=421.1; HPLC purity=92.61%.

Example 109

1-(5-hydroxy-2-azatricyclo[3.3.1.1$^{3,7}$]dec-2-yl)-3-(5-methoxy-1H-indol-3-yl)butan-1-one (109)

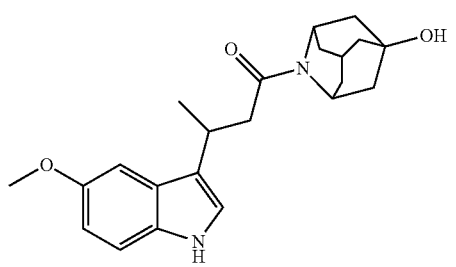

(109)

Synthesis of Compound (109)

Compound (109) was synthesized by following the procedure used to make Compound (1) (Scheme 2). The crude product was obtained by evaporating the organic layer under reduced pressure and was purified by silica gel column using DCM:MeOH as eluent to obtain Compound (109). 1H NMR (300 MHz, DMSO-d6): δ 10.61 (s, 1H), 7.18-7.22 (d, 1H), 7.09 (s, 1H), 6.96 (s, 1H), 6.68-6.71 (m, 1H), 4.79 (s, 1H), 4.59-4.64 (d, 1H), 4.25-4.28 (m, 1H), 3.74 (s, 3H), 3.37-3.40 (m, 1H), 2.63-2.72 (m, 2H), 2.07-2.37 (m, 1H), 1.27-1.65 (m, 13H). LC-MS: (M+H)⁺=369.2; HPLC purity=98.14%.

Example 110

1-(5-hydroxy-2-azatricyclo[3.3.1.1$^{3,7}$]dec-2-yl)-3-(5-methyl-1H-indol-3-yl)butan-1-one (110)

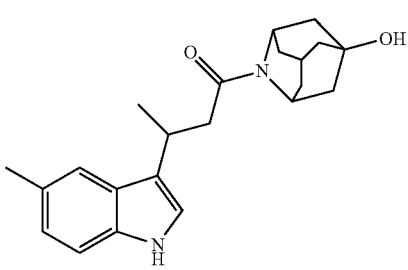

(110)

Synthesis of Compound (110)

Compound (110) was synthesized by following the procedure used to make Compound (1) (Scheme 2). The crude product was obtained by evaporating the organic layer under reduced pressure and was purified by silica gel column using DCM:MeOH as eluent to obtain Compound (110). 1H NMR (300 MHz, DMSO-d6): δ 10.62 (s, 1H), 7.29 (s, 1H), 7.18-7.21 (d, 1H), 7.06 (s, 1H), 6.85-6.88 (d, 1H), 4.80 (s, 1H), 4.61-4.65 (d, 1H), 4.28 (s, 1H), 3.39 (m, 1H), 2.62-2.72 (m, 2H), 2.36 (s, 3H), 2.10-2.27 (m, 1H), 1.27-1.66 (m, 13H). LC-MS: (M+H)⁺=353.2; HPLC purity=95.0%.

Example 111

2-[3-(4-fluoro-1H-indol-3-yl)-3-phenylpropanoyl]-2-azatricyclo[3.3.1.1³,⁷]decane-5-carboxylic acid (111)

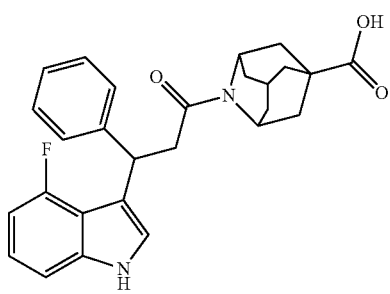

(111)

Synthesis of Compound (111)

Compound (111) was synthesized by following the procedure used to make Compound (43) (Scheme 14). The crude product was obtained by evaporating the organic layer under reduced pressure and was purified by silica gel column using DCM:MeOH as eluent to obtain Compound (111). 1H NMR (300 MHz, DMSO-d6): δ 12.17 (s, 1H), 11.18 (s, 1H), 7.37 (s, 1H), 7.17-7.31 (m, 4H), 7.05-7.14 (m, 2H), 6.92-6.99 (m, 1H), 6.57-6.64 (m, 1H), 4.81-4.86 (t, 1H), 4.64 (s, 1H), 4.31 (s, 1H), 3.00-3.07 (m, 2H), 1.30-2.07 (m, 11H). LC-MS: (M+H)⁺=447.3; HPLC purity=98.60%.

Example 112

2-[3-(6-fluoro-1H-indol-3-yl)-3-phenylpropanoyl]-2-azatricyclo[3.3.1.1³,⁷]decane-5-carboxylic acid (112)

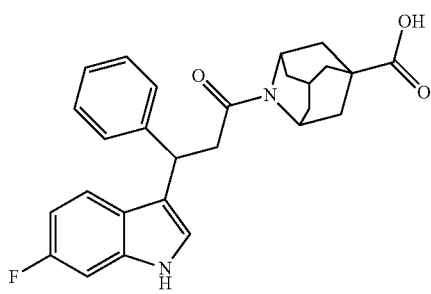

(112)

Synthesis of Compound (112)

Compound (112) was synthesized by following the procedure used to make Compound (43) (Scheme 14). The crude product was obtained by evaporating the organic layer under reduced pressure and was purified by silica gel column using DCM:MeOH as eluent to obtain Compound (112). 1H NMR (300 MHz, DMSO-d6): δ 12.19 (s, 1H), 10.94 (s, 1H), 7.30-7.33 (m, 4H), 7.18-7.27 (m, 2H), 7.03-7.13 (m, 2H), 6.69-6.74 (m, 1H), 4.61-4.66 (m, 2H), 4.29 (s, 1H), 3.02-3.05 (d, 2H), 2.72 (m, 2H), 1.32-2.08 (m, 9H). LC-MS: (M+H)⁺=447.2; HPLC purity=96.93%.

Example 113

3-(5-fluoro-2-methyl-1H-indol-3-yl)-1-(5-hydroxy-2-azatricyclo[3.3.1.1³,⁷]dec-2-yl)butan-1-one (113)

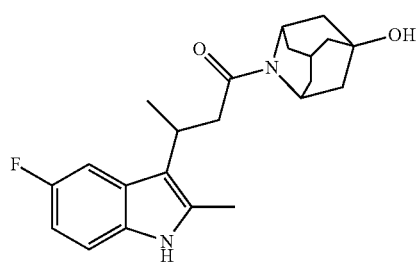

(113)

Synthesis of Compound (113)

Compound (113) was synthesized by following the procedure used to make Compound (1) (Scheme 2). The crude product was obtained by evaporating the organic layer under reduced pressure and was purified by silica gel column using DCM:MeOH as eluent to obtain Compound (113). 1H NMR (300 MHz, DMSO-d6): δ 10.74 (s, 1H), 7.26-7.31 (m, 1H), 7.15-7.20 (m, 1H), 6.73-6.80 (m, 1H), 4.72 (s, 1H), 4.51-4.61 (m, 1H), 4.09 (s, 1H), 3.35-3.39 (m, 1H), 2.70-2.80 (m, 2H), 2.29 (s, 3H), 1.97-2.14 (d, 1H), 0.74-1.60 (m, 13H). LC-MS: (M+H)⁺=371.2; HPLC purity=97.40%.

Example 114

3-(1,3-benzothiazol-2-yl)-1-(6-hydroxy-2-azatricyclo[3.3.1.1³,⁷]dec-2-yl)butan-1-one Peak-1 (114)

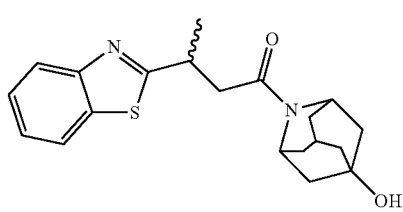

(114)

Synthesis of Compound (114) (Peak-1)

Racemate of Compound (84) was separated by preparative chiral HPLC column to give Compound (114) (peak-1). 1H NMR (300 MHz, CDCl3): δ 7.86-7.89 (d, 1H), 7.75-7.78 (d, 1H), 7.34-7.39 (t, 1H), 7.24-7.29 (t, 1H), 4.96 (s, 1H), 4.31 (s, 1H), 3.79-3.86 (m, 1H), 2.99-3.07 (m, 1H), 2.54-2.62 (m, 1H), 2.22-2.27 (m, 1H), 1.43-1.75 (m, 14H). LC-MS: (M+H)⁺=357.1; HPLC purity=99.8%; Chiral purity: 100%

(RT=16.99 min); Column: Chiralpak IC, 4.6 mm×250 mm; Mobile phase: hexanes:i-PrOH:DCM (7:2:1).

Example 115

3-(1,3-benzothiazol-2-yl)-1-(5-hydroxy-2-azatricyclo[3.3.1.1³,⁷]dec-2-yl)butan-1-one Peak-2 (115)

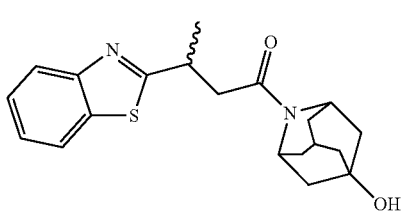

(115)

Synthesis of Compound (115) (Peak-2)

Racemate of Compound (84) was separated by preparative chiral HPLC column to give Compound (115) (peak-2). 1H NMR (300 MHz, CDCl3): δ 7.86-7.89 (d, 1H), 7.75-7.78 (d, 1H), 7.34-7.39 (t, 1H), 7.24-7.29 (t, 1H), 4.96 (s, 1H), 4.31 (s, 1H), 3.79-3.86 (m, 1H), 2.99-3.07 (m, 1H), 2.54-2.62 (m, 1H), 2.22-2.27 (m, 1H), 1.43-1.76 (m, 14H). LC-MS: (M+H)$^+$=357.1; HPLC purity=99.85%; Chiral purity: 100% (RT=23.47 min); Column: Chiralpak IC, 4.6 mm×250 mm; Mobile phase: hexanes:i-PrOH:DCM (7:2:1).

Example 116

1-(5-hydroxy-2-azatricyclo[3.3.1.1³,⁷]dec-2-yl)-3-(4-methyl-1H-indol-3-yl)propan-1-one (116)

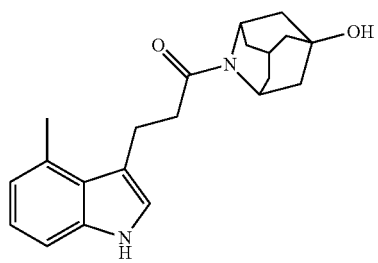

(116)

Synthesis of Compound (116)

Compound (116) was synthesized by following the procedure used to make Compound (1) (Scheme 2). The crude product was obtained by evaporating the organic layer under reduced pressure and was purified by silica gel column using DCM:MeOH as eluent to obtain Compound (116). 1H NMR (300 MHz, CDCl3): δ 7.90 (s, 1H), 7.10-7.13 (d, 1H), 6.96-7.01 (t, 1H), 6.92 (d, 1H), 6.76-6.78 (d, 1H), 5.02 (s, 1H), 4.13 (s, 1H), 3.18-3.23 (m, 2H), 2.64 (s, 3H), 2.58-2.63 (m, 2H), 2.24 (s, 1H), 1.49-1.74 (m, 11H). LC-MS: (M+H)=339.3; HPLC purity=91.46%.

Example 117

3-(6-chloro-5-methoxy-1H-indol-3-yl)-1-(5-hydroxy-2-azatricyclo[3.3.1.1³,⁷]dec-2-yl)butan-1-one (117)

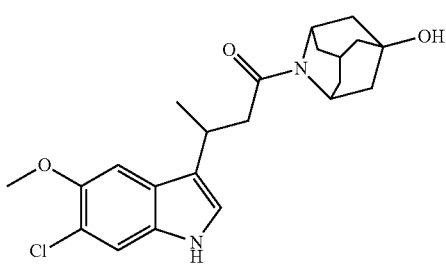

(117)

Synthesis of Compound (117)

Compound (117) was synthesized by following the procedure used to make Compound (1) (Scheme 2). The crude product was obtained by evaporating the organic layer under reduced pressure and was purified by silica gel column using DCM:MeOH as eluent to obtain Compound (117). 1H NMR (300 MHz, CDCl3): δ 7.85 (brs, 1H), 7.30-7.31 (d, 1H), 7.09 (brs, 1H), 6.92-6.93 (m, 1H), 4.98 (brs, 1H), 4.09 (brs, 1H), 3.87 (s, 3H), 3.52-3.59 (m, 1H), 2.63-2.71 (m, 1H), 2.40-2.44 (m, 1H), 2.10 (brs, 1H), 1.41-1.70 (m, 10H), 1.35-1.38 (d, 3H). LC-MS: (M+H)$^+$=403.2; HPLC purity=99.36%.

Example 118

2-[3-(1,3-benzothiazol-2-yl)butanoyl]-2-azatricyclo[3.3.1.1³,⁷]decane-5-carbonitrile (118)

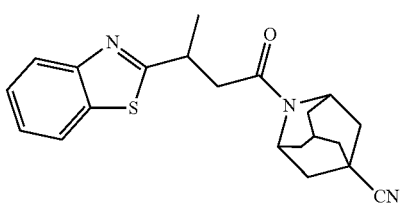

(118)

Synthesis of Compound (118)

Compound (118) was synthesized by following the procedure used to make Compound (1) (Scheme 2). The crude product was obtained by evaporating the organic layer under reduced pressure and was purified by silica gel column using DCM:MeOH as eluent to obtain Compound (118). 1H NMR (300 MHz, CDCl3): δ 7.84-7.89 (dd, 1H), 7.76-7.78 (d, 1H), 7.34-7.40 (m, 1H), 7.25-7.30 (m, 1H), 4.86 (brs, 1H), 4.23 (brs, 1H), 3.79-3.87 (m, 1H), 3.00-3.09 (m, 1H), 2.49-2.59

(m, 1H), 1.90-2.18 (m, 8H), 1.63-1.76 (m, 3H), 1.45 (d, 3H). LC-MS: (M+H)+=366.2; HPLC purity=93.68%.

Example 119

1-(2-azatricyclo[3.3.1.1³,⁷]dec-2-yl)-3-(4-chloro-1,3-benzothiazol-2-yl)butan-1-one (119)

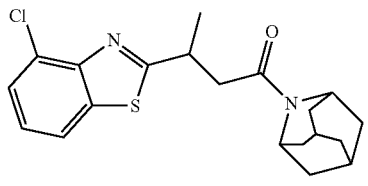

(119)

Synthesis of Compound (119)

Compound (119) was synthesized by following the procedure used to make Compound (1) (Scheme 2). The crude product was obtained by evaporating the organic layer under reduced pressure and was purified by silica gel column using hexane:EtOAc as eluent to obtain Compound (119). 1H NMR (300 MHz, CDCl3): δ 7.64-7.67 (d, 1H), 7.36-7.39 (d, 1H), 7.15-7.21 (dd, 1H), 4.74 (brs, 1H), 4.10 (brs, 1H), 3.85-3.92 (q, 1H), 3.04-3.11 (dd, 1H), 2.53-2.61 (dd, 1H), 1.98-2.02 (m, 2H), 1.65-1.79 (m, 10H), 1.45 (d, 3H). LC-MS: (M+H)+=375.1; HPLC purity=98.71%.

Example 120

3-(4-chloro-1,3-benzothiazol-2-yl)-1-(5-hydroxy-2-azatricyclo[3.3.1.1³,⁷]dec-2-yl)butan-1-one (120)

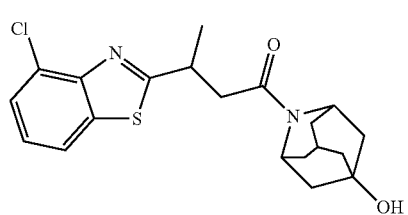

(120)

Synthesis of Compound (120)

Compound (120) was synthesized by following the procedure used to make Compound (1) (Scheme 2). The crude product was obtained by evaporating the organic layer under reduced pressure and was purified by silica gel column using DCM:MeOH as eluent to obtain Compound (120). 1H NMR (300 MHz, DMSO-d6): δ 8.02-8.05 (d, 1H), 7.56-7.58 (d, 1H), 7.36-7.41 (t, 1H), 4.65-4.72 (m, 2H), 4.34 (s, 1H), 3.80 (m, 1H), 2.80-3.20 (m, 2H), 1.45-2.22 (m, 11H), 1.39-1.42 (d, 3H). LC-MS: (M+H)+=391.1; HPLC purity=98.58%.

Example 121

3-(1H-benzotriazol-1-yl)-1-(5-hydroxy-2-azatricyclo[3.3.1.1³,⁷]dec-2-yl)-3-phenylpropan-1-one (121)

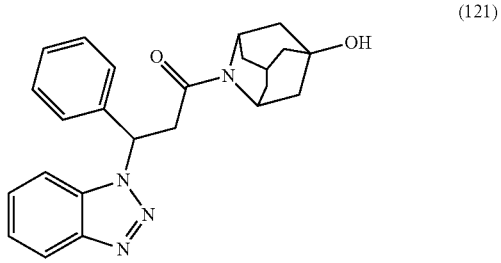 [SMILES: O=C(CC(c1ccccc1)n1nnc2ccccc21)N1C2CC3CC1CC(O)(C3)C2]

(121)

SYNTHETIC SCHEME 24

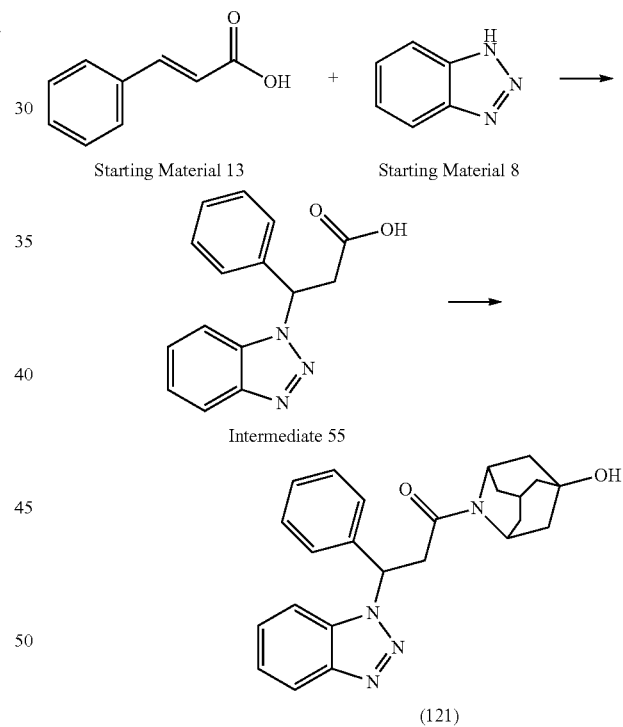

Synthesis of 3-(1H-benzotriazol-1-yl)-3-phenylpropanoic acid (Intermediate-55)

A 30 mL ACE pressure tube fitted with magnetic stirrer was charged with Starting Material-13 (2 g, 13.4 mmol) and Starting Material-8 (4.8 g, 40.4 mmol). Reaction mixture was heated at 150° C. for 12 hours. After completion of reaction, the mixture was diluted with ethyl acetate and concentrated. Resulted crude product was purified by Combiflash column chromatography eluting with hexanes:EtOAc to give Intermediate-55 (2.1 g).

Synthesis of Compound (121)

To a stirred solution of Intermediate-55 (75 mg, 0.28 mmol) in THF (4 mL) Intermediate-7 (43 mg, 0.28 mmol) and HBTU (126 mg, 0.3 mmol) was added. This was followed by addition of DIPEA (108 mg, 0.84 mmol) at 0° C. Resulted reaction mixture was stirred at room temperature for 1 hour. After completion of reaction, the resultant mass was first quenched with water, then extracted with ethyl acetate and then concentrated. Resulted crude product was purified by preparative TLC eluting with hexanes:EtOAc to give compound (121)(40 mg) as white solid. 1H NMR (300 MHz, DMSO-d6): δ 7.99-8.02 (d, 1H), 7.88-7.91 (d, 1H), 7.45-7.52 (m, 3H), 7.24-7.39 (m, 3H), 6.52-6.54 (d, 1H), 4.66-4.67 (d, 1H), 4.62 (s, 1H), 4.46 (s, 1H), 4.01-4.10 (m, 1H), 3.23-3.25 (m, 1H), 2.16 (s, 1H), 1.23-1.67 (m, 11H). LC-MS: (M+H)+=403.2; HPLC purity=93.95%.

Example 122

2-[3-(4-fluoro-1H-indol-3-yl)-3-(thiophen-2-yl)propanoyl]-2-azatricyclo[3.3.1.1$^{3,7}$]decane-4-carboxylic acid (122)

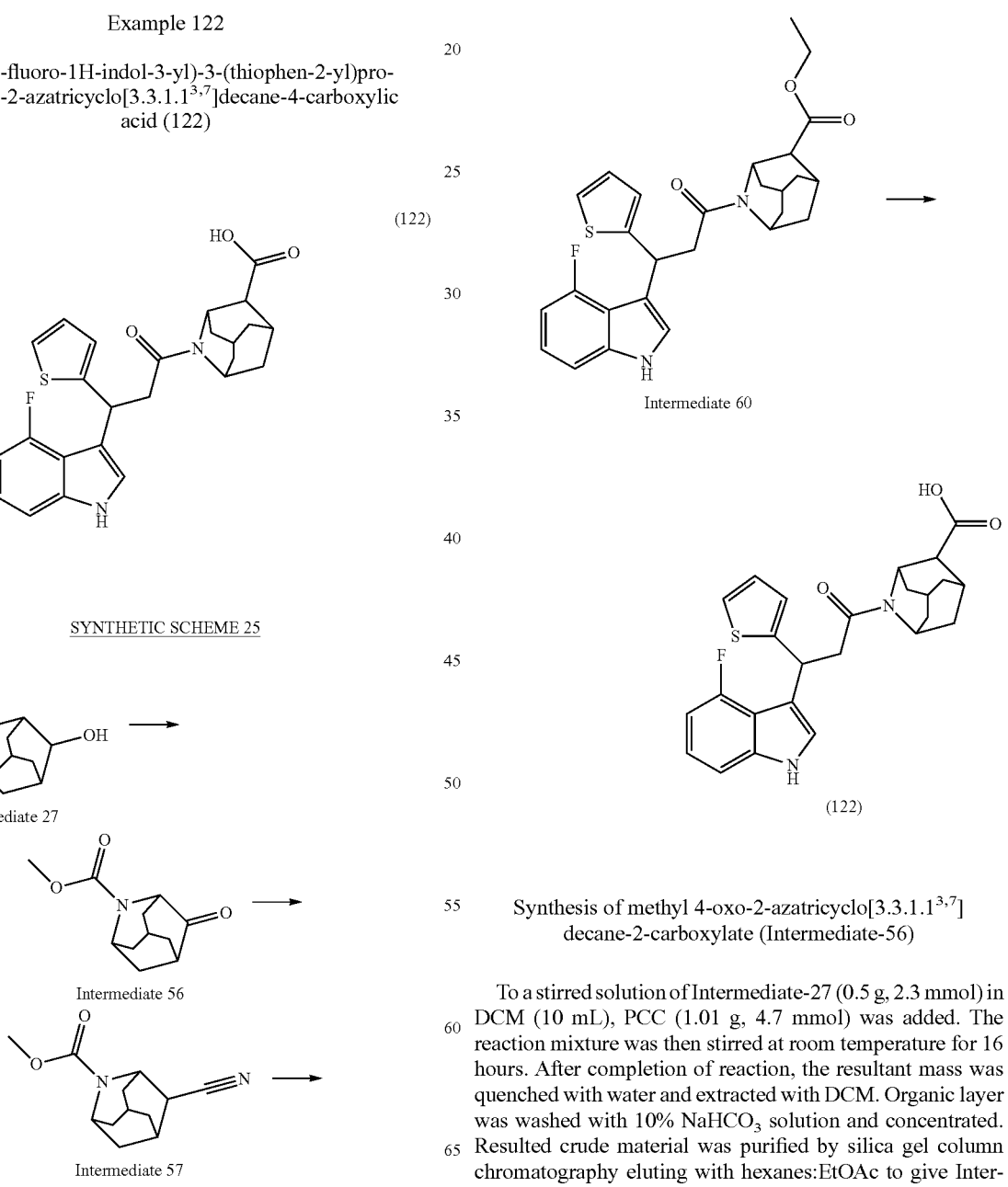

SYNTHETIC SCHEME 25

Synthesis of methyl 4-oxo-2-azatricyclo[3.3.1.1$^{3,7}$]decane-2-carboxylate (Intermediate-56)

To a stirred solution of Intermediate-27 (0.5 g, 2.3 mmol) in DCM (10 mL), PCC (1.01 g, 4.7 mmol) was added. The reaction mixture was then stirred at room temperature for 16 hours. After completion of reaction, the resultant mass was quenched with water and extracted with DCM. Organic layer was washed with 10% NaHCO$_3$ solution and concentrated. Resulted crude material was purified by silica gel column chromatography eluting with hexanes:EtOAc to give Intermediate-56 (230 mg).

Synthesis of methyl 4-cyano-2-azatricyclo[3.3.1.1³,⁷]decane-2-carboxylate (Intermediate-57)

To a stirred solution of Intermediate-56 (0.23 g, 1.1 mmol) and Tos MIC (0.3 g, 1.5 mmol) in DME:EtOH (5 mL: 0.2 mL), t-BuOK (0.37 g, 3.30 mmol) was added at 0° C. The reaction mixture was stirred at room temperature for 2 hours. Then reaction mixture was filtered. Filtrate portion was concentrated to give Intermediate-57 (230 mg).

Synthesis of 2-tert-butyl 4-ethyl 2-azatricyclo[3.3.1.1³,⁷]decane-2,4-dicarboxylate (Intermediate-58)

A 100 mL RB fitted with magnetic stirrer was charged with Intermediate-57 (0.23 g, 1.04 mmol), and 5N H$_2$SO$_4$ (25 mL). The reaction mixture was heated at 100° C. for 36 hours. After completion of reaction (monitored by LC-MS), the mixture was cooled to 0° C. Conc. HCl was added to the cooled mixture, followed by addition of EtOH. The mixture was then heated at 90° C. for 16 hours. The resultant mass was quenched with water, basified with sodium carbonate and washed with DCM. The aqueous layer was diluted with THF (40 mL) to which TEA (5 mL) and Boc-anhydride (0.360 g, 1.4 mmol) was added. The resulting mixture was stirred at room temperature for 12 hours. Then reaction mixture was extracted with ethyl acetate and concentrated. Resulted crude material was purified by silica gel column chromatography eluting with hexanes:EtOAc to give Intermediate-58 (130 mg).

Synthesis of ethyl 2-azatricyclo[3.3.1.1³,⁷]decane-4-carboxylate. Trifluoroacetic acid salt (Intermediate-59)

To a stirred solution of Intermediate-58 (0.13 g, 0.4 mmol) in DCM (5 mL), TFA (0.1 g, 0.8 mmol) was added at 0° C. Resulted reaction mixture was stirred for 4 hours at room temperature. After completion of the reaction (reaction was monitored by LC-MS), the resultant mass was concentrated followed by trituration with mixture of hexanes:ether (1:1) to give Intermediate-59 (130 mg).

Synthesis of ethyl 2-[3-(4-fluoro-1H-indol-3-yl)-3-(thiophen-2-yl)propanoyl]-2-azatricyclo[3.3.1.1³,⁷]decane-4-carboxylate (Intermediate-60)

Intermediate-60 was synthesized by following the procedure used to make Compound (1) (Scheme 2). The crude product was obtained by evaporating the organic layer under reduced pressure and was purified by silica gel column using hexanes:EtOAc as eluent to obtain Intermediate-60.

Synthesis of Compound (122)

Compound (122) was synthesized by following the procedure used to make Compound (43) (Scheme 14). 1H NMR (300 MHz, CDCl3): δ 8.30-9.30 (m, 1H), 7.00-7.02 (m, 2H), 6.87-6.89 (m, 1H), 6.77-6.79 (m, 2H), 6.62-6.65 (m, 1H), 6.46-6.56 (m, 1H), 5.02-5.33 (m, 1H), 4.34-4.73 (m, 1H), 3.99-4.12 (m, 1H), 2.92-3.61 (m, 2H), 1.45-2.64 (m, 11H). LC-MS: (M+H)+=453.2; HPLC purity=98.96%.

Example 123

2-[3-(4-chloro-1,3-benzothiazol-2-yl)butanoyl]-2-azatricyclo[3.3.1.1³,⁷]decane-5-carbonitrile (123)

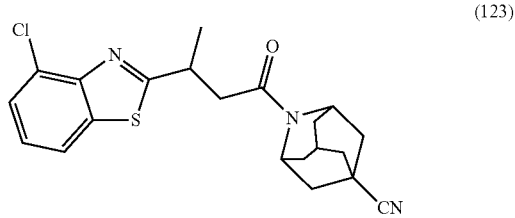 [SMILES: CC(CC(=O)N1C2CC3CC1CC(C#N)(C3)C2)c1nc2c(Cl)cccc2s1]

(123)

Synthesis of Compound (123)

Compound (123) was synthesized by following the procedure used to make Compound (1) (Scheme 2). The crude product was obtained by evaporating the organic layer under reduced pressure and was purified by silica gel column using hexanes:EtOAc as eluent to obtain Compound (123). 1H NMR (300 MHz, CDCl3): δ 7.65-7.67 (d, 1H), 7.36-7.40 (m, 1H), 7.22 (m, 1H), 4.84 (s, 1H), 4.26 (s, 1H), 3.84-3.91 (m, 1H), 3.11-3.20 (m, 1H), 2.48-2.58 (m, 1H), 1.55-2.15 (m, 11H), 1.45-1.47 (m, 3H). LC-MS: (M+H)+=400.1; HPLC purity=96.66%.

Example 124

2-[3-(4-chloro-1,3-benzothiazol-2-yl)butanoyl]-2-azatricyclo[3.3.1.1³,⁷]decane-5-carbonitrile Compound (124) peak 1

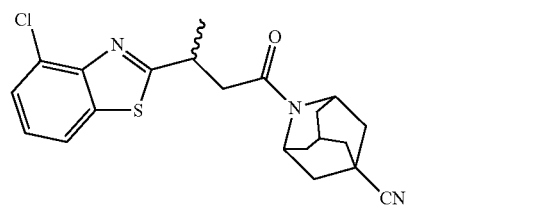

(124) Peak 1

Synthesis of Compound (124) (Peak-1)

Racemic compound (123) was separated by chiral preparative HPLC to give Compound (124) (peak-1). LC-MS: (M+H)+=400.1; HPLC purity=91.31%; Chiral column, Chiralpak IC, 4.6 mm×250 m; Mobile Phase: hexane:i-PrOH:DCM (7:2:1); RT=23.47 minutes.

Example 126

2-[3-(4-chloro-1,3-benzothiazol-2-yl)butanoyl]-2-azatricyclo[3.3.1.1$^{3,7}$]decane-5-carbonitrile Compound (125) peak 2

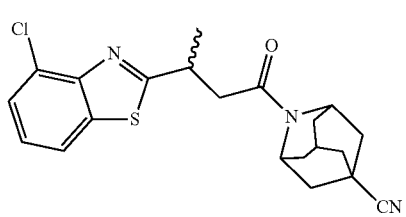
(125) Peak 2

Synthesis of Compound (126) (Peak-2)

Racemate of Compound (123) was separated by chiral preparative HPLC to give Compound (125) peak-2 (125). LC-MS: (M+H)+=400.1; HPLC purity=97.74%; Chiral column, Chiralpak IC, 4.6 mm×250 m; Mobile Phase: hexane:i-PrOH:DCM (7:2:1); RT=27.72 minutes.

Example 126

3-(4-cyclopropyl-1H-indol-3-yl)-1-(5-hydroxy-2-azatricyclo[3.3.1.1$^{3,7}$]dec-2-yl)propan-1-one (126)

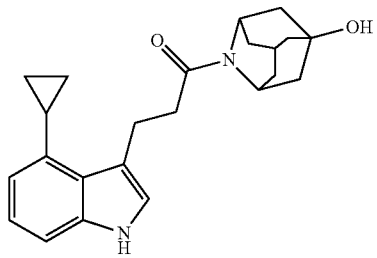
(126)

Synthesis of Compound (126)

Compound (126) was synthesized by following the procedure used to make Compound (1) (Scheme 2). The crude product was obtained by evaporating the organic layer under reduced pressure and was purified by silica gel column using DCM:MeOH as eluent to obtain Compound (126). 1H NMR (300 MHz, CDCl3): δ 8.00 (brs, 1H), 7.09-7.12 (d, 1H), 6.96-7.01 (t, 1H), 6.93-6.94 (d, 1H), 6.64-6.66 (1H, d), 5.01 (brs, 1H), 4.14 (brs, 1H), 3.31-3.36 (t, 2H), 2.65-2.70 (m, 2H), 2.32-2.41 (m, 1H), 2.23 (brs, 1H), 1.45-1.73 (m, 10H), 0.88-0.94 (m, 2H), 0.74-0.81 (M, 2H). LC-MS: (M+H)+=365.2; HPLC purity=98.22%.

Example 127

3-(4-fluoro-1H-indol-3-yl)-1-(5-hydroxy-2-azatricyclo[3.3.1.1$^{3,7}$]dec-2-yl)-3-(thiophen-2-yl)propan-1-one (127)

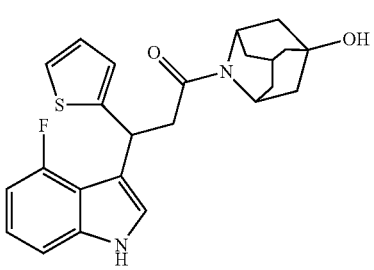
(127)

Synthesis of Compound (127)

Compound (127) was synthesized by following the procedure used to make Compound (1) (Scheme 2). The crude product was obtained by evaporating the organic layer under reduced pressure and was purified by silica gel column using DCM:MeOH as eluent to obtain Compound (127). 1H NMR (300 MHz, CDCl3): δ 8.34 (brs, 0.5H), 8.30 (brs, 0.5H), 6.99-7.06 (m, 2H), 6.96-6.97 (m, 2H), 6.81-6.83 (m, 2H), 6.61-6.68 (m, 1H), 5.14-5.20 (m, 1H), 4.94 (brs, 1H), 4.23 (brs, 1H), 3.02-3.20 (m, 2H), 2.14 (brs, 1H), 1.35-1.70 (m, 10H). LC-MS: (M+H)+=425.2; HPLC purity=99.56%.

Example 128

1-(5-hydroxy-2-azatricyclo[3.3.1.1$^{3,7}$]dec-2-yl)-3-(4-propyl-1H-indol-3-yl)propan-1-one (128)

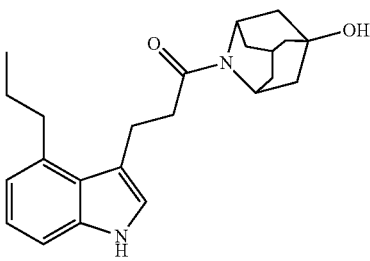
(128)

Synthesis of Compound (128)

Compound (128) was synthesized by following the procedure used to make Compound (1) (Scheme 2). The crude product was obtained by evaporating the organic layer under reduced pressure and was purified by silica gel column using DCM:MeOH as eluent to obtain Compound (128). 1H NMR (300 MHz, CDCl3): δ 7.99 (brs, 1H), 7.10-7.13 (d, 1H), 6.99-7.04 (t, 1H), 6.91-6.92 (d, 1H), 6.80-6.82 (d, 1H), 5.02

(brs, 1H), 4.13 (brs, 1H), 3.14-3.19 (t. 2H), 2.87-2.92 (t, 2H), 2.59-2.64 (m, 2H), 2.24 (brs, 1H), 1.53-1.74 (m, 12H), 0.93-0.98 (t, 3H). LC-MS: (M+H)+=367.2; HPLC purity=96.54%.

Example 129

3-(6-chloro-5-methoxy-1H-indol-3-yl)-1-(5-hydroxy-2-azatricyclo[3.3.1.1³,⁷]dec-2-yl)butan-1-one (129) peak 1

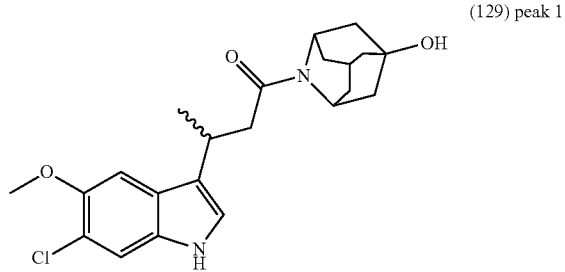

(129) peak 1

Synthesis of Compound (129) (Peak-1)

Racemate of Compound (117) was separated by chiral preparative HPLC to give Compound (129) (peak-1). 1H NMR (300 MHz, CDCl3): δ 7.85 (brs, 1H), 7.30-7.31 (d, 1H), 7.09 (brs, 1H), 6.92-6.93 (m, 1H), 4.98 (brs, 1H), 4.09 (brs, 1H), 3.87 (s, 3H), 3.52-3.59 (m, 1H), 2.63-2.71 (m, 1H), 2.40-2.44 (m, 1H), 2.10 (brs, 1H), 1.41-1.70 (m, 10H), 1.35-1.38 (d, 3H). LC-MS: (M+H)+=403.2; HPLC purity=99.32%; Chiral Column: Chiralpak IC, 4.6 mm×250 mm; Mobile phase: hexane:i-PrOH:DCM (7:2:1); RT=11.65 minutes.

Example 130

3-(6-chloro-5-methoxy-1H-indol-3-yl)-1-(5-hydroxy-2-azatricyclo[3.3.1.1³,⁷]dec-2-yl)butan-1-one (130) peak 2

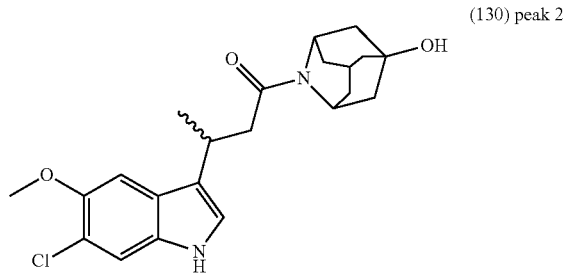

(130) peak 2

Synthesis of Compound (130) (Peak-2)

Racemate of compound (117) was separated by chiral preparative HPLC to give Compound (130) (peak-2). 1H NMR (300 MHz, CDCl3): δ 7.85 (brs, 1H), 7.30-7.31 (d, 1H), 7.09 (brs, 1H), 6.92-6.93 (m, 1H), 4.98 (brs, 1H), 4.09 (brs, 1H), 3.87 (s, 3H), 3.52-3.59 (m, 1H), 2.63-2.71 (m, 1H), 2.40-2.44 (m, 1H), 2.10 (brs, 1H), 1.41-1.70 (m, 10H), 1.35-1.38 (d, 3H). LC-MS: (M+H)+=403.2; HPLC purity=99.76%; Chiral Column: Chiralpak IC, 4.6 mm×250 mm; Mobile phase: hexane:i-PrOH:DCM (7:2:1); RT=14.60 minutes.

Example 131

1-(5-hydroxy-2-azatricyclo[3.3.1.1³,⁷]dec-2-yl)-4-methyl-3-(4-methyl-1H-benzotriazol-1-yl)pentan-1-one (131)

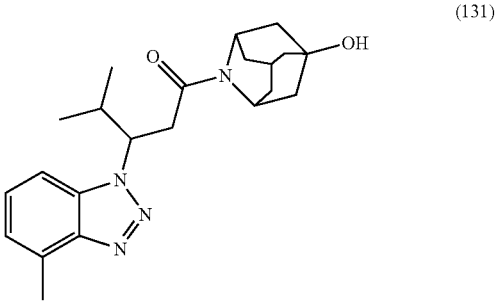

(131)

Synthesis of Compound (131)

Compound (131) was synthesized by following the procedure used to make Compound (1) (Scheme 2). The crude product was obtained by evaporating the organic layer under reduced pressure and was purified by silica gel column using DCM:MeOH as eluent to obtain Compound (131). 1H NMR (300 MHz, CDCl3): δ 7.37-7.40 (d, 1H), 7.26-7.31 (t, 1H), 7.02-7.04 (d, 1H), 5.00-5.06 (m, 1H), 4.81 (brs, 1H), 4.25 (brs, 1H), 3.47-3.65 (m, 2H), 2.72 (s, 3H), 2.2-2.34 (m, 1H), 2.10 brs, 1H), 1.35-1.75 (m, 10H), 0.96-0.98 (d, 3H), 0.72-0.74 (d, 3H). LC-MS: (M+H)+=383.2; HPLC purity=94.65%.

Example 132

3-(4-cyclopropyl-1H-pyrrolo[2,3-b]pyridin-3-yl)-1-(5-hydroxy-2-azatricyclo[3.3.1.1³,⁷]dec-2-yl)butan-1-one (132)

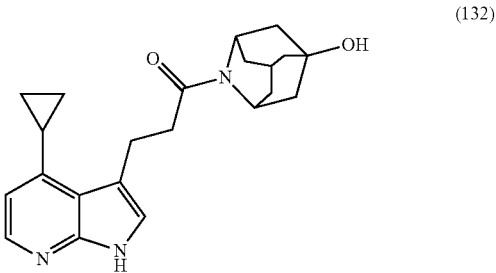

(132)

Synthesis of Compound (132)

Compound (132) was synthesized by following the procedure used to make Compound (1) (Scheme 2). The crude product was obtained by evaporating the organic layer under reduced pressure and was purified by silica gel column using DCM:MeOH as eluent to obtain Compound (132). 1H NMR (300 MHz, CDCl3): δ 9.30 (brs, 1H), 8.03-8.05 (d, 1H), 7.03 (s, 1H), 6.47-6.49 (d, 1-1H), 5.02 (brs, 1H), 4.21 (brs, 1H), 4.01 (brs, 1H), 2.73-2.78 (m, 1H), 2.33-2.49 (m, 2H), 2.26 (brs, 1H), 1.42-1.75 (m, 10H), 1.35-1.37 (d, 3H). LC-MS: (M+H)+=380.2; HPLC purity=98.45%.

Example 133

3-(6-chloro-5-fluoro-1H-indol-3-yl)-1-(5-hydroxy-2-azatricyclo[3.3.1.1$^{3,7}$]dec-2-yl)butan-1-one (133)

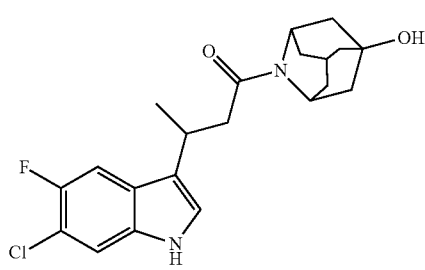

Synthesis of Compound (133)

Compound (133) was synthesized by following the procedure used to make Compound (1) (Scheme 2). The crude product was obtained by evaporating the organic layer under reduced pressure and was purified by silica gel column using DCM:MeOH as eluent to obtain Compound (133). 1H NMR (300 MHz, CDCl3): δ 7.91 (brs, 1H), 7.31-7.34 (d, 1H), 7.28-7.30 (d, 1H), 6.99-7.00 (d, 1H), 4.98 (brs, 1H), 4.10 (brs, 1H), 3.47-3.54 (q, 11H), 2.63-2.71 (m, 1H), 2.40-2.44 (m, 1H), 2.15 (brs, 11H), 1.40-1.71 (m, 10H), 1.34-1.36 (d, 3H). LC-MS: (M+H)+=391.2; HPLC purity=97.57%.

Example 134

2-[3-(6-chloro-1H-indol-3-yl)-3-phenylpropanoyl]-2-azatricyclo[3.3.1.1$^{3,7}$]decane-5-carboxylic acid (134)

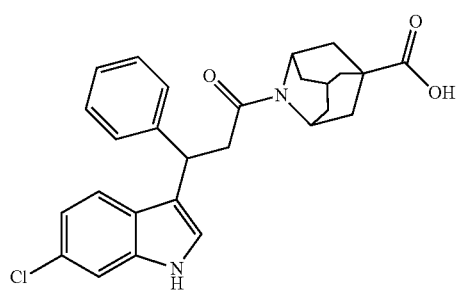

Synthesis of Compound (134)

Compound (134) was synthesized by following the procedure used to make Compound (43) (Scheme 14). The crude product was obtained by evaporating the organic layer under reduced pressure and was purified by silica gel column using DCM:MeOH as eluent to obtain Compound (134). 1H NMR (300 MHz, DMSO-d6): δ 12.34 (brs, 1H), 11.03 (s, 1H), 7.10-7.40 (m, 8H), 6.84-6.91 (m, 1H), 4.66 (brs, 2H), 4.30 (brs, 1H), 3.01-3.10 (m, 2H), 2.05 (brs, 1H), 1.55-1.98 (m, 10H). LC-MS: (M+H)+=463.2; HPLC purity=99.58%.

Example 135

3-(5-chloro-1H-pyrrolo[2,3-b]pyridin-3-yl)-1-(5-hydroxy-2-azatricyclo[3.3.1.1$^{3,7}$]dec-2-yl)butan-1-one (135)

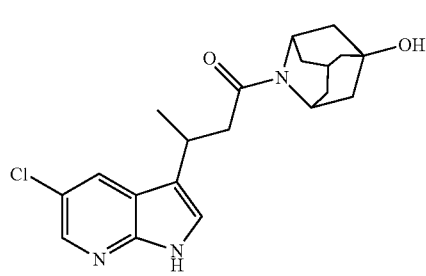

Synthesis of Compound (135)

Compound (135) was synthesized by following the procedure used to make Compound (1) (Scheme 2). The crude product was obtained by evaporating the organic layer under reduced pressure and was purified by silica gel column using DCM:MeOH as eluent to obtain Compound (135). 1H NMR (300 MHz, CDCl3): δ 9.15 (brs, 0.5H), 9.01 (brs, 1H), 8.15-8.16 (d, 1H), 7.91 (s, 1H), 7.09-7.10 (d, 1H), 4.97 (brs, 1H), 4.10 (brs, 1H), 3.51-3.58 (q, 1H), 2.61-2.68 (dd, 1H), 2.42-2.50 (dd, 1H), 2.24 (brs, 0.5H), 2.14 (brs, 0.5H), 1.44 (1.71 (m, 10H), 1.35-1.38 (d, 3H). LC-MS: (M+H)+=374.2; HPLC purity=98.36%.

Example 136

2-[3-(4-cyclopropyl-1H-pyrrolo[2,3-b]pyridin-3-yl)butanoyl]-2-azatricyclo[3.3.1.1$^{3,7}$]decane-5-carbonitrile (136)

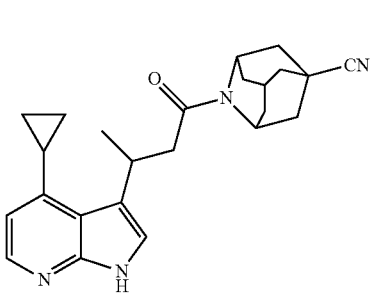

Synthesis of Compound (136)

Compound (136) was synthesized by following the procedure used to make Compound (1) (Scheme 2). The crude product was obtained by evaporating the organic layer under reduced pressure and was purified by silica gel column using DCM:MeOH as eluent to obtain Compound (136). 1H NMR (300 MHz, DMSO-d6): δ 11.28 (brs, 1H), 7.99-8.00 (d, 1H), 7.25 (s, 1H), 6.52-6.53 (d, 1H), 4.72 (brs, 1H), 4.29 (brs, 1H), 3.85-3.89 (m, 11H), 2.55.-2.72 (m, 3H), 2.09 (brs, 1H), 1.45-1.99 (m, 10H), 1.28-1.30 (d, 3H), 1.00-1.05 (m, 2H), 0.83-0.88 (m, 2H). LC-MS: (M+H)+=389.3; HPLC purity=98.69%.

Example 137

2-[3-(6-chloro-1H-pyrrolo[2,3-b]pyridin-3-yl)butanoyl]-2-azatricyclo[3.3.1.1$^{3,7}$]decane-5-carbonitrile (137)

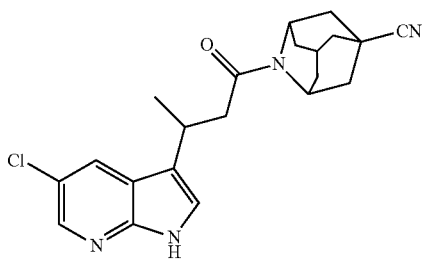

(137)

Synthesis of Compound (137)

Compound (137) was synthesized by following the procedure used to make Compound (1) (Scheme 2). The crude product was obtained by evaporating the organic layer under reduced pressure and was purified by silica gel column using DCM:MeOH as eluent to obtain Compound (137). 1H NMR (300 MHz, CDCl3): δ 8.98 (brs, 0.5H), 8.88 (brs, 0.5H), 8.15-8.20 (m, 1H), 7.90 (s, 1H), 7.10 (s, 1H), 4.90 (brs, 1H), 4.00 (brs, 1H), 3.50-3.60 (m, 1H), 2.58-2.62 (dd, 1H), 2.40-2.45 (m, 1H), 2.13-2.16 (m, 1H), 1.60-1.93 (m, 10H), 1.38-1.40 (d, 3H). LC-MS: (M+H)+=383.2; HPLC purity=97.99%.

Example 138

3-(6-chloro-5-cyclopropyl-1H-indol-3-yl)-1-(5-hydroxy-2-azatricyclo[3.3.1.1$^{3,7}$]dec-2-yl)butan-1-one (138)

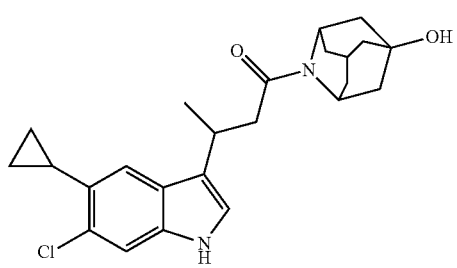

(138)

Synthesis of Compound (138)

Compound (138) was synthesized by following the procedure used to make Compound (1) (Scheme 2). The crude product was obtained by evaporating the organic layer under reduced pressure and was purified by silica gel column using DCM:MeOH as eluent to obtain Compound (138). 1H NMR (300 MHz, CDCl3): δ 7.98 (brs, 0.5H), 7.95 (brs, 0.5H), 7.29 (s, 1H), 7.23 (s, 1H), 6.88 (s, 1H), 4.96 (brs, 1H), 4.09 (brs, 1H), 3.46-3.52 (q, 1H), 2.64-2.72 (dd, 1H), 2.38-2.45 (dd, 1H), 2.21-2.24 (m, 1H), 2.08-2.14 (m, 2H), 1.40-1.70 (m, 9H), 1.34-1.36 (d, 3H), 0.83-0.95 (m, 2H), 0.58-0.63 (m, 2H). LC-MS: (M+H)+=413.3; HPLC purity=95.14%.

Example 139

3-(5-fluoro-4-methyl-1H-indol-3-yl)-1-(5-hydroxy-2-azatricyclo[3.3.1.1$^{3,7}$]dec-2-yl)butan-1-one Compound (139)

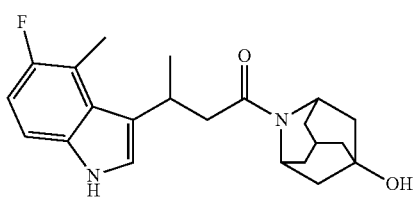

(139)

Synthesis of Compound (139)

Compound (139) was synthesized by following the procedure used to make Compound (1) (Scheme 2). The crude product was obtained by evaporating the organic layer under reduced pressure and was purified by silica gel column using DCM:MeOH as eluent to obtain Compound (139). 1H NMR (300 MHz, CDCl3): δ 7.89 (br s, 1H), 7.00-7.05 (dd, 1H), 6.98-6.99 (d, 1H), 6.81-6.87 (t, 1H), 5.04 (br s, 1H), 4.20 (br s, 1H), 3.84-3.93 (m, 1H), 2.65-2.71 (dd, 1H), 2.54-2.55 (d, 3H), 2.37-2.48 (dd, 1H), 2.26 (br s, 1H), 1.54-1.66 (m, 8H), 1.75 (br s, 2H), 1.39-1.43 (d, 3H). LC-MS: (M+H)+=371.2; HPLC purity=96.42%.

Example 140

2-[3-(6-chloro-1H-indol-3-yl)-3-phenylpropanoyl]-2-azatricyclo[3.3.1.1$^{3,7}$]decane-6-carboxylic acid (Peak-1) (140)

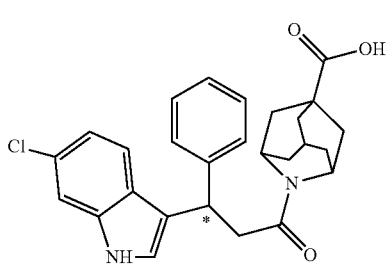

(140)

Synthesis of Compound (140)

Racemate of compound (134) was separated by chiral preparative HPLC to give Compound (140). 1H NMR (300 MHz, DMSO-d6): δ 12.34 (brs, 1H), 11.03 (s, 1H), 7.10-7.40 (m, 8H), 6.84-6.91 (m, 1H), 4.66 (brs, 2H), 4.30 (brs, 1H), 3.01-3.10 (m, 2H), 2.05 (brs, 1H), 1.55-1.98 (m, 10H). LC-MS: (M+H)+=463.1; HPLC purity=99.56%; Chiral RT=7.95 min [column: ChiralPak IC, Mobile phase: hexane:IPA:DCM (7:2:1)].

Example 141

2-[3-(6-chloro-1H-indol-3-yl)-3-phenylpropanoyl]-2-azatricyclo[3.3.1.1$^{3,7}$]decane-5-carboxylic acid (Peak-2) (141)

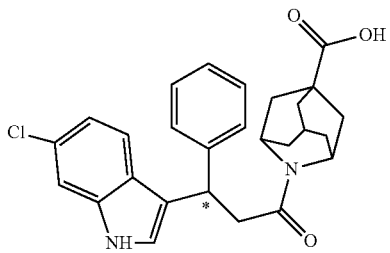

(141)

Synthesis of Compound (141)

Racemate of compound (134) was separated by chiral preparative HPLC to give Compound (141). 1H NMR (300 MHz, DMSO-d6): δ 12.34 (brs, 1H), 11.03 (s, 1H), 7.10-7.40 (m, 8H), 6.84-6.91 (m, 1H), 4.66 (brs, 2H), 4.30 (brs, 1H), 3.01-3.10 (m, 2H), 2.05 (brs, 1H), 1.55-1.98 (m, 10H). LC-MS: (M+H)+=463.1; HPLC purity=99.15%; Chiral RT=11.99 min [column: ChiralPak IC, Mobile phase: hexane:IPA:DCM (7:2:1)].

Example 142

2-[3-(5-phenyl-1H-indol-3-yl)butanoyl]-2-azatricyclo[3.3.1.1$^{3,7}$]decane-5-carboxylic acid (142)

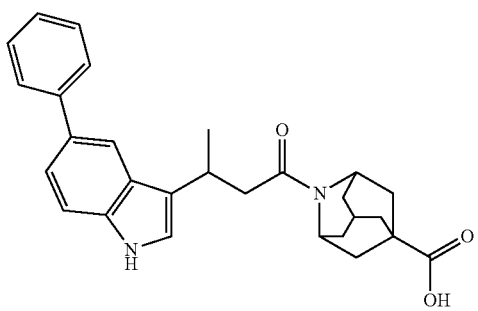

(142)

Synthesis of Compound (142)

Compound (142) was synthesized by following the procedure used to make Compound (43) (Scheme 14). The crude product was obtained by evaporating the organic layer under reduced pressure and was purified by silica gel column using DCM:MeOH as eluent to obtain Compound (142). 1H NMR (300 MHz, CDCl3): δ 7.96 (br s, 1H), 7.80 (br s, 1H), 7.56-7.59 (d, 2H), 7.32-7.39 (m, 4H), 7.24-7.29 (dd, 1H), 6.97-6.99 (m, 1H), 4.89 (br s, 1H), 4.04 (br s, 1H), 3.61-3.63 (m, 1H), 2.75-2.81 (dd, 1H), 2.48-2.52 (dd, 1H), 1.54-2.09 (m, 11H), 1.41-1.44 (dd, 3H). LC-MS: (M+H)+=443.2; HPLC purity=98.51%.

Example 143

2-[3-(6-chloro-1H-indol-3-yl)butanoyl]-2-azatricyclo[3.3.1.1$^{3,7}$]decane-6-carboxylic acid (143)

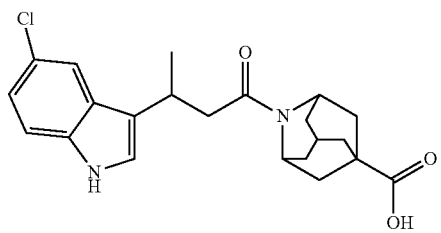

(143)

Synthesis of Compound (143)

Compound (143) was synthesized by following the procedure used to make Compound (43) (Scheme 14). The crude product was obtained by evaporating the organic layer under reduced pressure and was purified by silica gel column using DCM:MeOH as eluent to obtain Compound (143). 1H NMR (300 MHz, DMSO-d6): δ 12.20 (br s, 1H), 11.00 (br s, 1H), 7.54 (br s, 1H), 7.30-7.34 (dd, 1H), 7.23 (br s, 1H), 7.01-7.05 (m, 1H), 4.71 (br s, 1H), 4.18 (br s, 1H), 3.67-3.78 (m, 1H), 2.62-2.68 (m, 1H), 2.43-2.47 (m, 1H), 1.39-1.97 (m, 11H), 1.29-1.31 (d, 3H). LC-MS: (M+H)+=401.2; HPLC purity=97.21%.

Example 144

3-(6-chloro-4-methyl-1H-indol-3-yl)-1-(5-hydroxy-2-azatricyclo[3.3.1.1$^{3,7}$]dec-2-yl)butan-1-one (144)

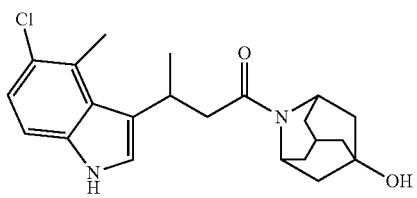

(144)

Synthesis of Compound (144)

Compound (144) was synthesized by following the procedure used to make Compound (1) (Scheme 2). The crude product was obtained by evaporating the organic layer under reduced pressure and was purified by silica gel column using DCM:MeOH as eluent to obtain Compound (144). 1H NMR (300 MHz, CDCl3): δ 7.95 (br s, 1H), 7.09-7.12 (d, 1H), 7.03-7.06 (d, 1H), 6.93-6.98 (d, 1H), 5.03 (br s, 1H), 4.19 (br s, 1H), 3.88-3.90 (m, 1H), 2.68 (s, 3H), 2.62-2.65 (m, 1H), 2.37-2.45 (m, 1H), 2.27 (br s, 1H), 1.54-1.76 (m, 10H), 1.32-1.34 (d, 3H). LC-MS: (M+H)+=387.2; HPLC purity=97.47%.

Example 145

{2-[3-(4-chloro-1H-indol-3-yl)butanoyl]-2-azatricyclo[3.3.1.1$^{3,7}$]dec-5-yl}acetic acid (145)

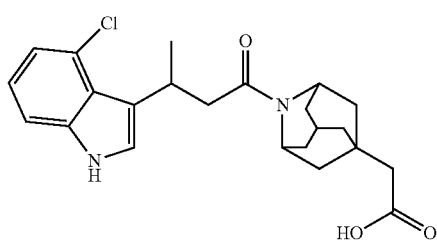
(145)

Synthesis of Compound (145)

Compound (145) was synthesized by following the procedure used to make Compound (43) (Scheme 14). The crude product was obtained by evaporating the organic layer under reduced pressure and was purified by silica gel column using DCM:MeOH as eluent to obtain Compound (145). 1H NMR (300 MHz, CDCl3): δ 8.39 (br s, 1H), 7.16-7.20 (m, 1H), 6.92-6.97 (m, 3H), 4.88 (br s, 1H), 4.20 (br s, 1H), 3.98-4.13 (m, 1H), 2.76-2.94 (m, 1H), 2.52-2.59 (m, 1H), 2.08 (br s, 2H), 2.04 (br s, 1H), 1.52-1.68 (m, 10H), 1.37-1.39 (d, 3H). LC-MS: (M+H)+=415.2; HPLC purity=97.51%.

Example 146

3-{2-[3-(4-cyclopropyl-1H-indol-3-yl)butanoyl]-2-azatricyclo[3.3.1.1$^{3,7}$]dec-6-yl}propanoic acid (146)

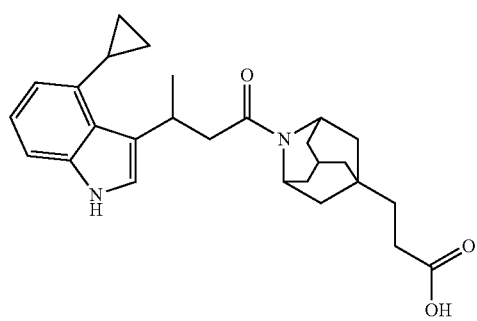
(146)

Synthesis of Compound (146)

Compound (146) was synthesized by following the procedure used to make Compound (43) (Scheme 14). The crude product was obtained by evaporating the organic layer under reduced pressure and was purified by silica gel column using DCM:MeOH as eluent to obtain Compound (146). 1H NMR (300 MHz, DMSO-d6): δ 12.01 (br s, 1H), 10.81 (br s, 1H), 7.17 (br s, 1H), 7.12-7.15 (d, 1H), 6.88-6.93 (t, 1H), 6.56-6.58 (d, 1H), 4.71 (br s, 1H), 4.20 (br s, 1H), 4.02-4.04 (m, 1H), 2.26-2.28 (m, 1H), 2.06-2.16 (m, 5H), 1.32-1.60 (m, 12H), 1.25-1.29 (d, 3H). LC-MS: (M+H)+=435.2; HPLC purity=98.38%.

Example 147

3-(5-fluoro-4-methyl-1H-indol-3-yl)-1-(5-hydroxy-2-azatricyclo[3.3.1.1$^{3,7}$]dec-2-yl)butan-1-one (Peak-1) (147)

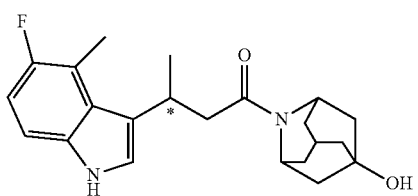
(147)

Synthesis of Compound (147)

Racemic compound (139) was separated by using chiral preparative column chromatography to give Compound (147). 1H NMR (300 MHz, CDCl3): δ 7.89 (br s, 1H), 7.00-7.05 (dd, 1H), 6.98-6.99 (d, 1H), 6.81-6.87 (t, 1H), 5.04 (br s, 1H), 4.20 (br s, 1H), 3.84-3.93 (m, 1H), 2.65-2.71 (dd, 1H), 2.54-2.55 (d, 3H), 2.37-2.48 (dd, 1H), 2.26 (br s, 1H), 1.54-1.66 (m, 8H), 1.75 (br s, 2H), 1.39-1.43 (d, 3H). LC-MS: (M+H)+=371.2; HPLC purity=96.98%. Chiral RT=10.82 min [Column: ChiralPak IC, Mobile phase: hexane:THF (7:3)].

Example 148

3-(5-fluoro-4-methyl-1H-indol-3-yl)-1-(5-hydroxy-2-azatricyclo[3.3.1.1$^{3,7}$]dec-2-yl)butan-1-one (Peak-2) (148)

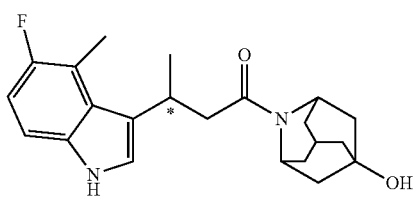
(148)

Synthesis of Compound (148)

Racemic compound (139) was separated by using chiral preparative column chromatography to give Compound (148). 1H NMR (300 MHz, CDCl3): δ 7.89 (br s, 1H), 7.00-7.05 (dd, 1H), 6.98-6.99 (d, 1H), 6.81-6.87 (t, 1H), 5.04 (br s, 1H), 4.20 (br s, 1H), 3.84-3.93 (m, 1H), 2.65-2.71 (dd, 1H), 2.54-2.55 (d, 3H), 2.37-2.48 (dd, 1H), 2.26 (br s, 1H), 1.54-1.66 (m, 8H), 1.75 (br s, 2H), 1.39-1.43 (d, 3H). LC-MS:

(M+H)+=371.2; HPLC purity=99.16%; Chiral RT=9.69 min [Column: ChiralPak IC, Mobile phase: hexane:THF (7:3)].

Example 149

3-(4-cyclopropyl-1H-indol-3-yl)-1-[5 (1H-tetrazol-5-yl)-2-azatricyclo[3.3.1.1³,⁷]dec-2-yl]butan-1-one (149)

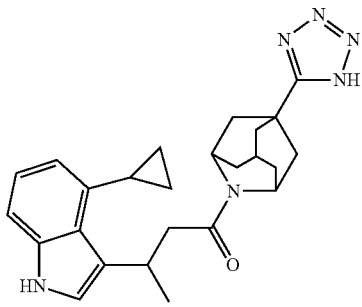

(149)

Synthesis of Compound (149)

Compound (149) was synthesized by following the procedure used to make Compound (77) (Scheme 21). The crude product was obtained by evaporating the organic layer under reduced pressure and was purified by silica gel column using DCM:MeOH as eluent to obtain Compound (149). 1H NMR (300 MHz, CDCl3): δ 8.38 (br s, 0.5H), 8.25 (br s, 0.5H), 7.02-7.07 (t, 1H), 6.98-7.00 (d, 1H), 6.89-6.94 (m, 1H), 6.56-6.66 (dd, 1H), 4.88-4.92 (d, 1H), 4.20 (br s, 1H), 3.47-3.50 (m, 1H), 2.78-2.85 (m, 1H), 2.46-2.59 (m, 1H), 2.29-2.34 (m, 1H), 2.17-2.19 (m, 1H), 1.61-2.01 (m, 10H), 1.32-1.38 (m, 3H), 0.72-0.79 (m, 2H), 0.63-0.65 (m, 2H). LC-MS: (M+H)+=431.2; HPLC purity=92.97%.

Example 150

3-(4-cyclopropyl-5-fluoro-1H-indol-3-yl)-1-(6-hydroxy-2-azatricyclo[3.3.1.1³,⁷]dec-2-yl)butan-1-one (150)

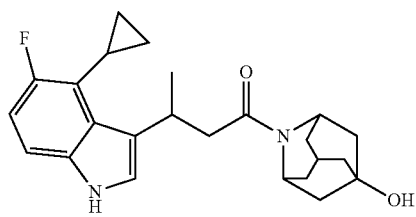

(150)

Synthesis of Compound (150)

Compound (150) was synthesized by following the procedure used to make Compound (1) (Scheme 2). The crude product was obtained by evaporating the organic layer under reduced pressure and was purified by silica gel column using DCM:MeOH as eluent to obtain Compound (150). 1H NMR (300 MHz, CDCl3): δ 7.93 (br s, 1H), 7.04-7.06 (d, 1H), 7.01-7.02 (d, 1H), 6.74-6.84 (dd, 1H), 5.02 (br s, 1H), 4.21-4.24 (m, 1H), 4.20 (br s, 1H), 2.68-2.75 (dd, 1H), 2.34-2.43 (dd, 1H), 2.22-2.25 (m, 1H), 2.00-2.09 (m, 1H), 1.52-1.75 (m, 10H), 1.31-1.34 (d, 3H), 0.99-1.03 (m, 2H), 0.83-0.87 (m, 2H). LC-MS: (M+H)+=397.2; HPLC purity=97.0%.

Example 151

3-(6-chloro-4-cyclopropyl-1H-indol-3-yl)-1-(5-hydroxy-2-azatricyclo[3.3.1.1³,⁷]dec-2-yl)butan-1-one (151)

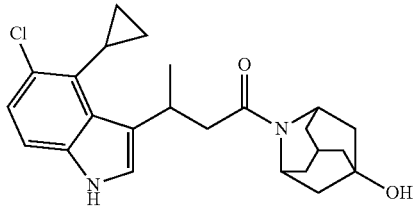

(151)

Synthesis of Compound (151)

Compound (151) was synthesized by following the procedure used to make Compound (1) (Scheme 2). The crude product was obtained by evaporating the organic layer under reduced pressure and was purified by silica gel column using DCM:MeOH as eluent to obtain Compound (151). 1H NMR (300 MHz, DMSO-d6): δ 11.04 (br s, 11H), 7.29 (br s, 1H), 7.17-7.20 (d, 1H), 6.98-7.00 (d, 1H), 4.79 (br s, 1H), 4.64-4.65 (d, 1H, OH group), 4.31 (br s, 1H), 4.22-4.23 (m, 1H), 2.60-2.72 (m, 2H), 2.07-2.27 (m, 2H), 1.38-1.68 (m, 10H), 1.24-1.27 (d, 3H), 0.80-0.85 (m, 2H), 0.70-0.75 (m, 2H). LC-MS: (M+H)+=413.1; HPLC purity=95.99%.

Example 152

{2-[3-(4-cyclopropyl-1H-indol-3-yl)butanoyl]-2-azatricyclo[3.3.1.1³,⁷]dec-5-yl}acetic acid (152)

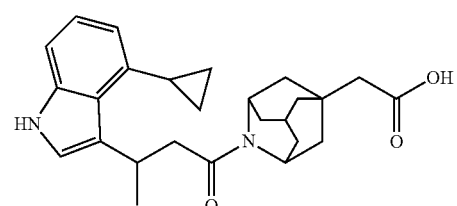

(152)

Synthesis of Compound (152)

Compound (152) was synthesized by following the procedure used to make Compound (43) (Scheme 14). The crude product was obtained by evaporating the organic layer under reduced pressure and was purified by silica gel column using DCM:MeOH as eluent to obtain Compound (152). 1H NMR (300 MHz, DMSO-d6): δ 10.82 (br s, 1H), 7.17 (br s, 1H), 7.12-7.15 (d, 1H), 6.88-6.93 (t, 1H), 6.56-6.58 (d, 1H), 4.72

(br s, 1H), 4.22 (br s, 1H), 4.00-4.06 (m, 1H), 2.68-2.73 (m, 2H), 2.43-2.46 (m, 3H), 1.99-2.05 (m, 1H), 1.45-1.68 (m, 10H), 1.28-1.30 (d, 3H), 0.85-0.90 (m, 2H), 0.70-0.75 (m, 2H). LC-MS: (M+H)+=421.2; HPLC purity=98.6%.

Example 153

1-(5-hydroxy-2-azatricyclo[3.3.1.1³,⁷]dec-2-yl)-3-[4-(thiophen-2-yl)-1H-indol-3-yl]butan-1-one (153)

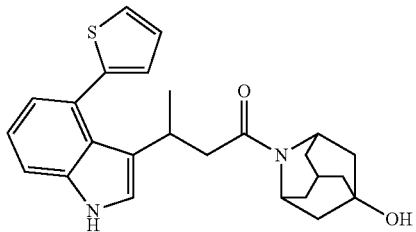

(153)

Synthesis of Compound (153)

Compound (153) was synthesized by following the procedure used to make Compound (1) (Scheme 2). The crude product was obtained by evaporating the organic layer under reduced pressure and was purified by silica gel column using DCM:MeOH as eluent to obtain Compound (153). 1H NMR (300 MHz, CDCl3): δ 8.16 (br s, 1H), 7.31-7.34 (d, 1H), 7.23-7.26 (m, 1H), 7.10-7.15 (t, 1H), 7.02-7.08 (m, 4H), 4.89 (br s, 1H), 3.80 (br s, 1H), 3.38-3.40 (m, 1H), 2.38-2.43 (m, 1H), 2.19-2.22 (m, 1H), 1.97-2.01 (m, 1H), 1.45-1.71 (m, 10H), 1.37-1.39 (d, 3H). LC-MS: (M+H)+=421.1; HPLC purity=96.43%.

Example 154

(2-{3-[4-(thiophen-2-yl)-1H-indol-3-yl]butanoyl}-2-azatricyclo[3.3.1.1³,⁷]dec-5-yl)acetic acid (154)

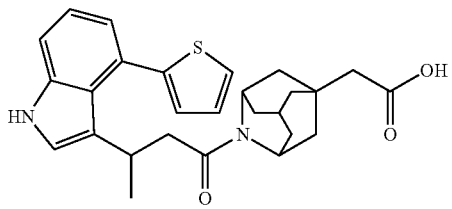

(154)

Synthesis of Compound (154)

Compound (154) was synthesized by following the procedure used to make Compound (43) (Scheme 14). The crude product was obtained by evaporating the organic layer under reduced pressure and was purified by silica gel column using DCM:MeOH as eluent to obtain Compound (154). 1H NMR (300 MHz, CDCl3): δ 8.68 (br s, 0.5H), 8.57 (br s, 0.5H), 7.22-7.30 (m, 2H), 7.01-7.09 (m, 5H), 4.77 (br s, 1H), 3.46 (br s, 1 1H), 3.31-3.35 (m, 1H), 2.35-2.48 (m, 2H), 2.07 (br s, 1H), 1.40-1.78 (m, 13H). LC-MS: (M+H)+=463.1; HPLC purity=92.86%.

Example 155

{2-[3-(4-cyclopropyl-1H-indol-3-yl)butanoyl]-2-azatricyclo[3.3.1.1³,⁷]dec-5-yl}acetic acid (Peak-1) (155)

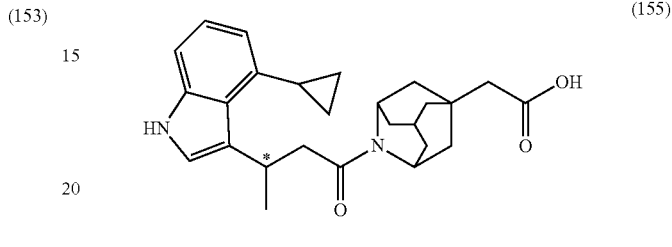

(155)

Synthesis of Compound (155)

Racemic compound (152) was purified by using chiral preparative HPLC chromatography to give Compound (155). 1H NMR (300 MHz, CDCl3): δ 7.98 (br s, 1H), 7.09-7.12 (d, 1H), 6.99-7.01 (d, 1H), 6.97 (br s, 1H), 6.66-6.78 (d, 1H), 4.89 (br s, 1H), 4.14-4.16 (m, 1H), 4.06 (br s, 1H), 2.75-2.82 (dd, 1H), 2.37-2.45 (m, 2H), 2.08 (s, 2H), 2.04 (br s, 1H), 1.52-1.71 (m, 10H), 1.36-1.38 (d, 3H), 0.90-0.95 (m, 2H), 0.76-0.81 (m, 2H). LC-MS: (M+H)+=421.2; HPLC purity=98.67%; Chiral RT=9.07 min [column: ChiralPak IC, mobile phase: hexane:IPA:DCM (7.5:1.5:1)].

Example 156

{2-[3-(4-cyclopropyl-1H-indol-3-yl)butanoyl]-2-azatricyclo[3.3.1.1³,⁷]dec-5-yl}acetic acid (Peak-2) (156)

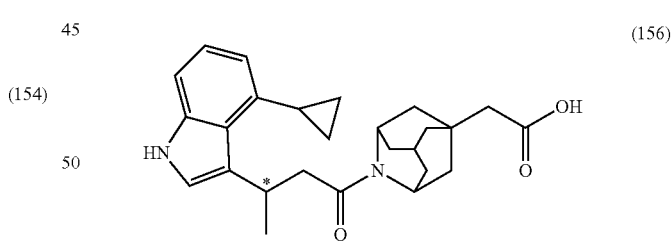

(156)

Synthesis of Compound (156)

Racemic compound (152) was purified by using chiral preparative HPLC chromatography to give Compound (156). 1H NMR (300 MHz, DMSO-d6): δ 10.82 (br s, 1H), 7.17 (br s, 1H), 7.12-7.15 (d, 1H), 6.88-6.93 (t, 1H), 6.56-6.58 (d, 1H), 4.72 (br s, 1H), 4.22 (br s, 1H), 4.00-4.06 (m, 1H), 2.68-2.73 (m, 2H), 2.43-2.46 (m, 3H), 1.99-2.05 (m, 1H), 1.45-1.68 (m, 10H), 1.28-1.30 (d, 3H), 0.85-0.90 (m, 2H), 0.70-0.75 (m, 2H). LC-MS: (M+H)+=421.2; HPLC purity=99.66%; Chiral RT=12.93 min [column: ChiralPak IC, mobile phase: hexane: IPA:DCM (7.5:1.5:1)].

Example 157

3-(4-cyclopropyl-6-fluoro-1H-indol-3-yl)-1-(5-hydroxy-2-azatricyclo[3.3.1.1³,⁷]dec-2-yl)butan-1-one (Peak-1) (157)

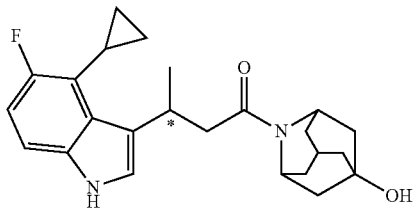
(157)

Synthesis of Compound (157) (Peak-1)

Racemic compound (150) was purified by using chiral preparative HPLC chromatography to give Compound (157). LC-MS: (M+H)+=397.2; Chiral RT=10.98 min [column: ChiralPak IC, mobile phase: hexane:IPA:DCM (7.5:1.5:1)].

Example 158

3-(4-cyclopropyl-5-fluoro-1H-indol-3-yl)-1-(5-hydroxy-2-azatricyclo[3.3.1.1³,⁷]dec-2-yl)butan-1-one (Peak-2) (158)

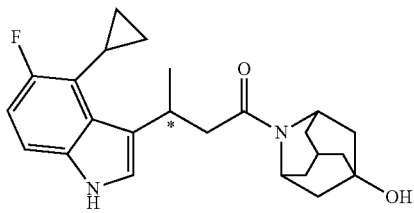
(158)

Synthesis of Compound (158) (Peak 2)

Racemic compound (150) was purified by using chiral preparative HPLC chromatography to give Compound (157). LC-MS: (M+H)+=397.2; HPLC purity=98.48%; Chiral RT=14.93 min [column: ChiralPak IC, mobile phase: hexane:IPA:DCM (7.5:1.5:1)].

Example 159

{2-[3-(4-fluoro-1H-indol-3-yl)-3-(thiophen-2-yl)propanoyl]-2-azatricyclo[3.3.1.1⁷]dec-5-yl}acetic acid (159)

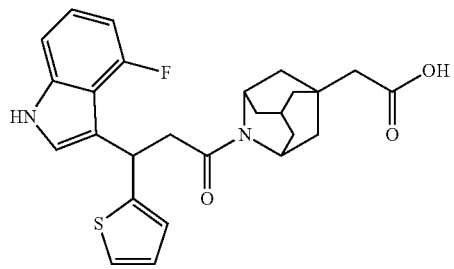
(159)

Synthesis of Compound (159)

Compound (159) was synthesized by following the procedure used to make Compound (43) (Scheme 14). The crude product was obtained by evaporating the organic layer under reduced pressure and was purified by silica gel column using DCM:MeOH as eluent to obtain Compound (159). 1H NMR (300 MHz, DMSO-d6): δ 11.93 (br s, 1H), 11.21 (br s, 1H), 7.35 (s, 1H), 7.21-7.23 (m, 1H), 7.15-7.18 (d, 1H), 6.97-7.04 (m, 1H), 6.85-6.88 (m, 1H), 6.81-6.83 (m, 1H), 6.63-6.70 (dd, 1H), 5.09-5.11 (t, 1H), 4.65 (br s, 1H), 4.27 (br s, 1H), 3.10-3.17 (m, 1H), 2.95-3.05 (m, 1H), 2.01 (s, 2H), 1.97 (s, 2H), 1.40-1.66 (m, 10H). LC-MS: (M+H)+=467.1; HPLC purity=99.63%.

Example 160

3-(4-cyclopropyl-5-methyl-1H-indol-3-yl)-1-(5-hydroxy-2-azatricyclo[3.3.1.1³,⁷]dec-2-yl)butan-1-one (160)

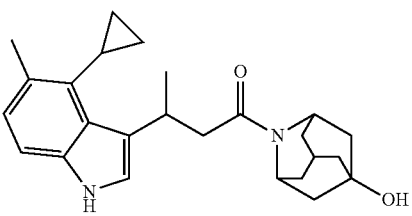
(160)

Synthesis of Compound (160)

Compound (160) was synthesized by following the procedure used to make Compound (1) (Scheme 2). The crude product was obtained by evaporating the organic layer under reduced pressure and was purified by silica gel column using DCM:MeOH as eluent to obtain Compound (160). 1H NMR (300 MHz, CDCl3): δ 7.84 (br s, 1H), 7.04-7.07 (d, 1H), 6.97 (br s, 1H), 6.88-6.91 (d, 1H), 5.00 (br s, 1H), 4.34-4.47 (m, 1H), 4.20 (br s, 1H), 2.67-2.73 (dd, 1H), 2.43 (s, 3H), 2.29-2.37 (dd, 1H), 2.15-2.22 (m, 1H), 2.00-2.05 (m, 1H), 1.45-1.78 (m, 10H), 1.33-1.36 (m, 3H), 1.04-1.10 (M, 2H), 0.64-0.69 (m, 2H). LC-MS: (M+H)+=393.3; HPLC purity=98.30%.

Example 161

3-(4-chloro-6-cyclopropyl-1H-indol-3-yl)-1-(5-hydroxy-2-azatricyclo[3.3.1.1³,⁷]dec-2-yl)butan-1-one (161)

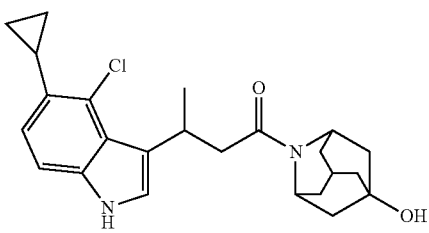
(161)

Synthesis of Compound (161)

Compound (161) was synthesized by following the procedure used to make Compound (1) (Scheme 2). The crude product was obtained by evaporating the organic layer under reduced pressure and was purified by silica gel column using DCM:MeOH as eluent to obtain Compound (161). 1H NMR (300 MHz, CDCl3): δ 8.03 (br s, 1H), 7.08-7.10 (d, 1H), 7.01-7.01 (d, 1H), 6.74-6.77 (d, 1H), 5.02 (br s, 1H), 4.26 (br s, 1H), 4.10-4.12 (m, 1H), 2.37-2.46 (m, 1H), 2.26-2.29 (m, 1H), 2.15-2.24 (m, 1H), 1.45-1.75 (m, 11H), 1.36-1.39 (d, 3H), 0.89-0.96 (m, 2H), 0.59-0.62 (m, 2H). LC-MS: (M+H)+=413.1; HPLC purity=98.97%.

Example 162

{2-[3-(4-bromo-5-chloro-1H-indol-3-yl)butanoyl]-2-azatricyclo[3.3.1.1$^{3,7}$]dec-5-yl}acetic acid (162)

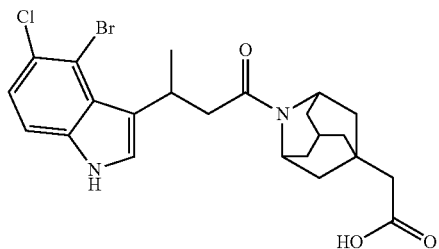

(162)

Synthesis of Compound (162)

Compound (162) was synthesized by following the procedure used to make Compound (43) (Scheme 14). The crude product was obtained by evaporating the organic layer under reduced pressure and was purified by silica gel column using DCM:MeOH as eluent to obtain Compound (162). 1H NMR (300 MHz, CDCl3): δ 8.70 (br s, 0.5H), 8.62 (br s, 0.5H), 7.12-7.15 (d, 1H), 7.07-7.09 (d, 1H), 7.01 (s, 1H), 4.87 (br s, 1H), 4.15-4.21 (m, 1H), 4.01 (br s, 1H), 2.72-2.85 (m, 1H), 2.45-2.60 (m, 1H), 2.29 (s, 2H), 2.04 (s, 1H), 1.50-1.75 (m, 10H). LC-MS: (M+H)+=493.2; HPLC purity=91.99%.

Example 163

3-(5-chloro-4-cyclopropyl-1H-indol-3-yl)-1-(5,7-dihydroxy-2-azatricyclo[3.3.1.1$^{3,7}$]dec-2-yl)butan-1-one (163)

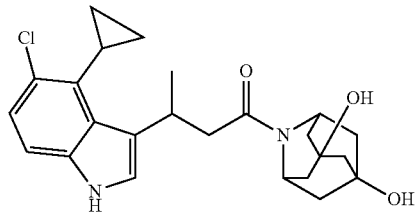

(163)

Synthesis of Compound (163)

Compound (163) was synthesized by following the procedure used to make Compound (1) (Scheme 2). The crude product was obtained by evaporating the organic layer under reduced pressure and was purified by silica gel column using DCM:MeOH as eluent to obtain Compound (163). 1H NMR (300 MHz, CDCl3): δ 8.01 (br s, 1H), 7.06 (s, 2H), 7.01-7.02 (d, 1H), 4.27-4.42 (m, 1H), 3.50 (br s, 1H), 3.43 (br s, 1H), 2.62-2.77 (dd, 1H), 2.37-2.46 (dd, 1H), 2.11-2.13 (m, 1H), 1.83-1.98 (m, 4H), 1.62-1.68 (m, 4H), 1.55-1.58 (m, 2H), 1.33-1.35 (d, 3H), 1.12-1.16 (m, 2H), 0.76-0.84 (m, 2H). LC-MS: (M+H)+=429.1; HPLC purity=99.90%.

Example 164

3-(4,5-dimethyl-1H-indol-3-yl)-1-(5-hydroxy-2-azatricyclo[3.3.1.1$^{3,7}$]dec-2-yl)butan-1-one (164)

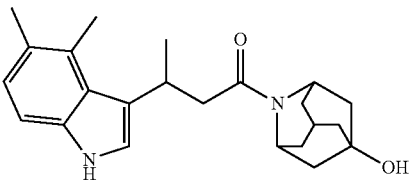

(164)

Synthesis of Compound (164)

Compound (164) was synthesized by following the procedure used to make Compound (1) (Scheme 2). The crude product was obtained by evaporating the organic layer under reduced pressure and was purified by silica gel column using DCM:MeOH as eluent to obtain Compound (164). 1H NMR (300 MHz, CDCl3): δ 7.92 (br s, 1H), 7.01-7.03 (d, 1H), 6.91-6.93 (d, 1H), 6.90 (s, 1H), 5.03 (br s, 1H), 4.18 (br s, 1H), 3.92-3.95 (m, 1H), 2.68-2.74 (dd, 1H), 2.54 (s, 3H), 2.35-2.43 (dd, 1H), 2.29 (s, 3H), 2.20-2.25 (m, 1H), 1.52-1.75 (m, 11H), 1.33-1.35 (d, 3H). LC-MS: (M+H)+=367.2; HPLC purity=97.04%.

Example 165

1-(5-hydroxy-2-azatricyclo[3.3.1.1$^{3,7}$]dec-2-yl)-3-(5-methoxy-4-methyl-1H-indol-3-yl)butan-1-one (165)

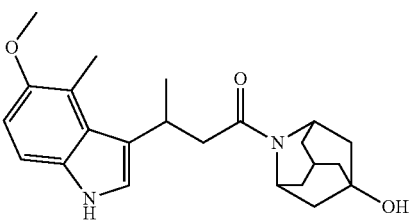

(165)

Synthesis of Compound (165)

Compound (165) was synthesized by following the procedure used to make Compound (1) (Scheme 2). The crude product was obtained by evaporating the organic layer under reduced pressure and was purified by silica gel column using DCM:MeOH as eluent to obtain Compound (165). 1H NMR (300 MHz, CDCl3): δ 7.77 (br s, 1H), 7.05-7.08 (d, 1H), 6.95-6.96 (d, 1H), 6.82-6.85 (d, 1H), 5.04 (br s, 1H), 4.19 (br s, 1H), 3.87-3.89 (m, 1H), 3.77 (s, 3H0, 2.67-2.73 (dd, 1H), 2.54 (s, 3H), 2.36-2.44 (dd, 1H), 2.24-2.26 (m, 1H), 1.55-1.75 (m, 10H), 1.33-1.35 (d, 3H). LC-MS: (M+H)+=383.2; HPLC purity=95.78%.

Example 166

3-(4-chloro-5-methyl-1H-indol-3-yl)-1-(5-hydroxy-2-azatricyclo[3.3.1.1$^{3,7}$]dec-2-yl)butan-1-one (166)

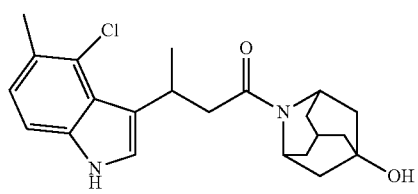
(166)

Synthesis of Compound (166)

Compound (166) was synthesized by following the procedure used to make Compound (1) (Scheme 2). The crude product was obtained by evaporating the organic layer under reduced pressure and was purified by silica gel column using DCM:MeOH as eluent to obtain Compound (166). 1H NMR (300 MHz, CDCl3): δ 8.00 (br s, 1H), 7.08-7.10 (d, 1H), 6.98-7.00 (d, 1H), 6.95 (s, 1H), 5.02 (br s, 1H), 4.25 (br s, 1H), 4.09-4.11 (m, 1H), 2.82-2.87 (m, 1H), 2.40-2.44 (m, 1H), 2.38 (s, 3H), 2.23-2.25 (m, 1H), 1.55-1.78 (m, 11H). LC-MS: (M+H)+=388.2; HPLC purity=99.97%.

Example 167

2-{2-[3-(4-cyclopropyl-1H-indol-3-yl)butanoyl]-2-azatricyclo[3.3.1.1$^{3,7}$]dec-5-yl}propanoic acid (167)

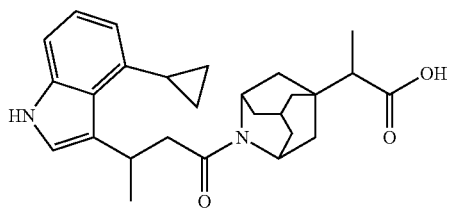
(167)

Synthesis of Compound (167)

Compound (167) was synthesized by following the procedure used to make Compound (43) (Scheme 14). The crude product was obtained by evaporating the organic layer under reduced pressure and was purified by silica gel column using DCM:MeOH as eluent to obtain Compound (167). 1H NMR (300 MHz, DMSO-d6): δ 12.01 (br s, 1H), 10.81 (s, 1H), 7.16-7.17 (d, 1H), 7.12-7.15 (d, 1H), 6.88-6.93 (t, 1H), 6.55-6.58 (d, 1H), 4.72 (br s, 1H), 4.24 (br s, 1H), 4.02-4.04 (m, 1H), 2.67-2.723 (m, 2H), 2.38-2.43 (m, 1H), 2.05-2.07 (m, 1H), 1.99-2.02 (m, 1H), 1.46-1.74 M, 10H), 1.28-1.30 (d, 3H), 0.95-0.98 (d, 3H), 0.83-0.88 (m, 2H), 0.70-0.74 (m, 2H). LC-MS: (M+H)+=435.2; HPLC purity=96.54%.

Example 168

3-(4,5-dichloro-1H-indol-3-yl)-1-(5-hydroxy-2-azatricyclo[3.3.1.1$^{3,7}$]dec-2-yl)butan-1-one (168)

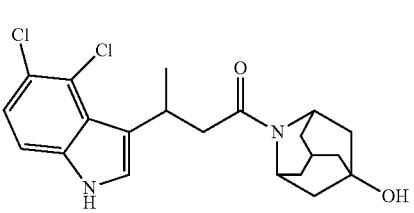
(168)

Synthesis of Compound (168)

Compound (168) was synthesized by following the procedure used to make Compound (1) (Scheme 2). The crude product was obtained by evaporating the organic layer under reduced pressure and was purified by silica gel column using DCM:MeOH as eluent to obtain Compound (168). 1H NMR (300 MHz, CDCl3): δ 8.18 (br s, 1H), 7.10-7.13 (d, 2H), 7.06-7.07 (d, 1H), 5.00 (br s, 1H), 4.24 (br s, 1H), 4.04-4.07 (m, 11-1H), 2.78-2.84 (m, 1H), 2.37-2.47 (dd, 1H), 2.24-2.26 (m, 1H), 1.73-1.78 (m, 3H), 1.61-1.65 (m, 7H), 1.35-1.38 (d, 3H). LC-MS: (M+H)+=407.1; HPLC purity=99.28%

Example 169

3-(4,5-dimethyl-1H-indol-3-yl)-1-(5-hydroxy-2-azatricyclo[3.3.1.1$^{3,7}$]dec-2-yl)butan-1-one (Peak-1) (169)

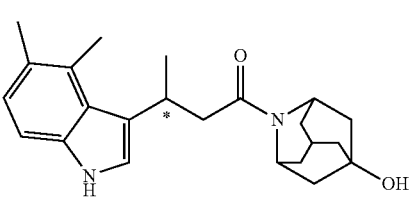
(169)

Synthesis of Compound (169)

Racemic compound (164) was purified by using chiral preparative HPLC chromatography to give Compound (169). 1H NMR (300 MHz, CDCl3): δ 7.92 (br s, 1H), 7.01-7.03 (d, 1H), 6.91-6.93 (d, 1H), 6.90 (s, 1H), 5.03 (br s, 1H), 4.18 (br s, 1H), 3.92-3.95 (m, 1H), 2.68-2.74 (dd, 1H), 2.54 (s, 3H), 2.35-2.43 (dd, 1H), 2.29 (s, 3H), 2.20-2.25 (m, 1H), 1.52-1.75 (m, 11H), 1.33-1.35 (d, 3H). LC-MS: (M+H)+=367.2; HPLC purity=93.27%; Chiral RT=20.93 min [column: ChiralPak IC, mobile phase: hexane:IPA:DCM (7.5:1.5:1)].

Example 170

3-(4,5-dimethyl-1H-indol-3-yl)-1-(6-hydroxy-2-azatricyclo[3.3.1.1$^{3,7}$]dec-2-yl)butan-1-one (Peak-2) (170)

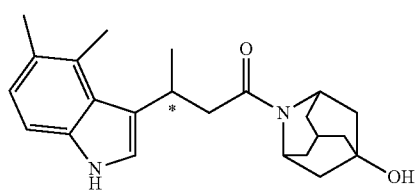
(170)

Synthesis of Compound (170)

Racemic compound (164) was purified by using chiral preparative HPLC chromatography to give Compound (170). 1H NMR (300 MHz, CDCl3): δ 7.92 (br s, 1H), 7.01-7.03 (d, 1H), 6.91-6.93 (d, 1H), 6.90 (s, 1H), 5.03 (br s, 1H), 4.18 (br s, 1H), 3.92-3.95 (m, 1H), 2.68-2.74 (dd, 1H), 2.54 (s, 3H), 2.35-2.43 (dd, 1H), 2.29 (s, 3H), 2.20-2.25 (m, 1H), 1.52-1.75 (m, 11H), 1.33-1.35 (d, 3H). LC-MS: (M+H)+=367.2; HPLC purity=99.81%; Chiral RT=25.61 min [column: ChiralPak IC, mobile phase: hexane:IPA:DCM (7.5:1.5:1)].

Example 171

3-(4-cyclopropyl-5-methoxy-1H-indol-3-yl)-1-(5-hydroxy-2-azatricyclo[3.3.1.1$^{3,7}$]dec-2-yl)butan-1-one (171)

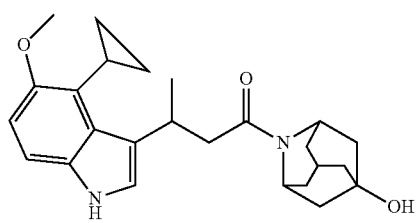
(171)

Synthesis of Compound (171)

Compound (171) was synthesized by following the procedure used to make Compound (1) (Scheme 2). The crude product was obtained by evaporating the organic layer under reduced pressure and was purified by silica gel column using DCM:MeOH as eluent to obtain Compound (171). 1H NMR (300 MHz, CDCl3): δ 7.83 (br s, 1H), 7.06-7.09 (d, 1H), 6.98-6.99 (d, 1H), 6.78-6.81 (d, 1H), 5.02 (br s, 1H), 4.26-4.29 (m, 1H), 4.19 (br s, 1H), 3.78 (s, 3H), 2.69-2.76 (dd, 1H), 2.31-2.39 (dd, 1H), 2.22-2.25 (m, 1H), 1.95-1.99 (m, 2H), 1.45-1.75 (m, 9H), 1.34-1.36 (d, 3H), 0.99-1.01 (m, 2H), 0.79-0.81 (m, 2H). LC-MS: (M+H)+=409.2; HPLC purity=92.57%.

Example 172

3-(4,5-dichloro-1H-indol-3-yl)-1-(5-hydroxy-2-azatricyclo[3.3.1.1$^{3,7}$]dec-2-yl)butan-1-one (Peak-1) (172)

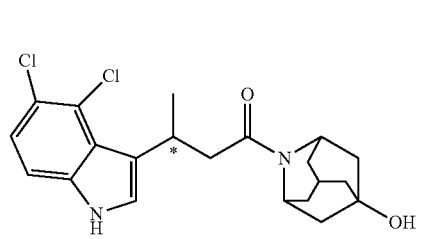
(172)

Synthesis of Compound (172)

Racemic compound (168) was purified by using chiral preparative HPLC chromatography to give Compound (172). 1H NMR (300 MHz, CDCl3): δ 8.18 (br s, 1H), 7.10-7.13 (d, 2H), 7.06-7.07 (d, 1H), 5.00 (br s, 1H), 4.24 (br s, 1H), 4.04-4.07 (m, 1H), 2.78-2.84 (m, 1H), 2.37-2.47 (dd, 1H), 2.24-2.26 (m, 1H), 1.73-1.78 (m, 3H), 1.61-1.65 (m, 7H), 1.35-1.38 (d, 3H). LC-MS: (M+H)+=407.0; HPLC purity=94.74%; Chiral RT=8.15 min [column: ChiralPak IC, mobile phase: hexane:IPA:DCM (7:2:1)].

Example 173

3-(4,6-dichloro-1H-indol-3-yl)-1-(5-hydroxy-2-azatricyclo[3.3.1.1$^{3,7}$]dec-2-yl)butan-1-one (Peak-2) (173)

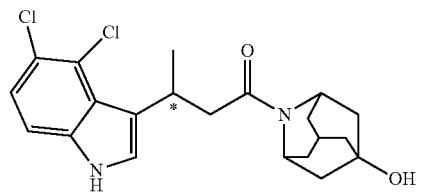
(173)

Synthesis of Compound (173)

Racemic compound (168) was purified by using chiral preparative HPLC chromatography to give Compound (173). 1H NMR (300 MHz, CDCl3): δ 8.18 (br s, 1H), 7.10-7.13 (d, 2H), 7.06-7.07 (d, 1H), 5.00 (br s, 1H), 4.24 (br s, 1H), 4.04-4.07 (m, 1H), 2.78-2.84 (m, 1H), 2.37-2.47 (dd, 1H), 2.24-2.26 (m, 1H), 1.73-1.78 (m, 3H), 1.61-1.65 (m, 7H), 1.35-1.38 (d, 3H). LC-MS: (M+H)+=407.0; HPLC purity=99.34%; Chiral RT=11.31 min [column: ChiralPak IC, mobile phase: hexane:IPA:DCM (7:2:1)].

Example 174

3-(4-chloro-5-methyl-1H-indol-3-yl)-1-(5-hydroxy-2-azatricyclo[3.3.1.1$^{3,7}$]dec-2-yl)butan-1-one (Peak-1) (174)

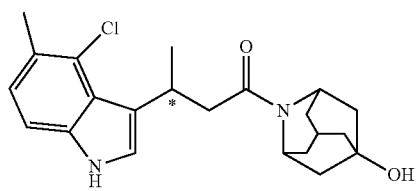

(174)

Synthesis of Compound (174)

Racemic compound (166) was purified by using chiral preparative HPLC chromatography to give Compound (174). 1H NMR (300 MHz, CDCl3): δ 8.00 (br s, 1H), 7.08-7.10 (d, 1H), 6.98-7.00 (d, 1H), 6.95 (s, 1H), 5.02 (br s, 1H), 4.25 (br s, 1H), 4.09-4.11 (m, 1H), 2.82-2.87 (m, 1H), 2.40-2.44 (m, 1H), 2.38 (s, 3H), 2.23-2.25 (m, 1H), 1.55-1.78 (m, 11H). LC-MS: (M+H)+=387.1; HPLC purity=95.57%; Chiral RT=15.30 min [column: ChiralPak IC, mobile phase: hexane:THF (7:3)].

Example 175

3-(4-chloro-5-methyl-1H-indol-3-yl)-1-(5-hydroxy-2-azatricyclo[3.3.1.1$^{3,7}$]dec-2-yl)butan-1-one (peak 2) (175)

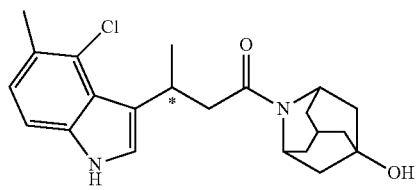

(175)

Synthesis of Compound (176)

Racemic compound 166) was purified by using chiral preparative HPLC chromatography to give Compound (175). 1H NMR (300 MHz, CDCl3): δ 8.00 (br s, 1H), 7.08-7.10 (d, 1H), 6.98-7.00 (d, 1H), 6.95 (s, 1H), 5.02 (br s, 1H), 4.25 (br s, 1H), 4.09-4.11 (m, 1H), 2.82-2.87 (m, 1H), 2.40-2.44 (m, 1H), 2.38 (s, 3H), 2.23-2.25 (m, 1H), 1.55-1.78 (m, 11H). LC-MS: (M+H)+=387.1; HPLC purity=98.33%; Chiral RT=17.15 min [column: ChiralPak IC, mobile phase: hexane:THF (7:3)].

Example 176

3-(4,5-dimethyl-1H-indol-3-yl)-1-(5-fluoro-2-azatricyclo[3.3.1.1$^{3,7}$]dec-2-yl)butan-1-one (176)

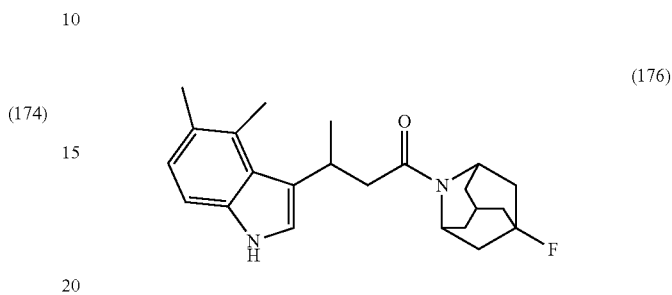

(176)

Synthesis of Compound (176)

Compound (176) was synthesized by following the procedure used to make Compound (1) (Scheme 2). The crude product was obtained by evaporating the organic layer under reduced pressure and was purified by silica gel column using DCM:MeOH as eluent to obtain Compound (176). 1H NMR (300 MHz, CDCl3): δ 8.06 (br s, 1H), 8.02-8.04 (d, 1H), 7.31-7.34 (d, 1H), 7.11-7.13 (d, 1H), 4.99-5.05 (m, 1H), 4.70-4.71 (m, 1H), 4.61-4.62 (m, 1H), 2.57-2.62 (m, 1H), 2.33-2.41 (m, 1H), 2.25 (s, 3H), 2.10 (s, 3H), 1.33-1.87 (m, 14H). LC-MS: (M−19)+=413.3; HPLC purity=90.92%.

Example 177

1-(6-hydroxy-2-azatricyclo[3.3.1.1$^{3,7}$]dec-2-yl)-3-[4-(propan-2-yloxy)-1H-indol-3-yl]butan-1-one (177)

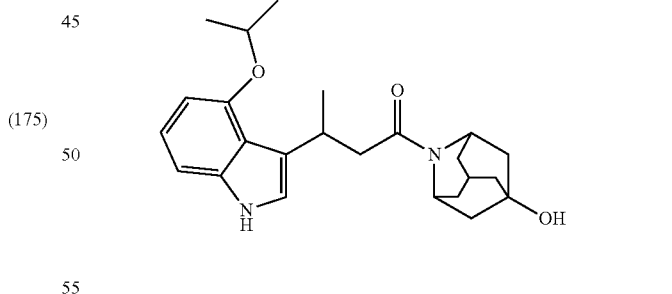

(177)

Synthesis of Compound (177)

Compound (177) was synthesized by following the procedure used to make Compound (1) (Scheme 2). The crude product was obtained by evaporating the organic layer under reduced pressure and was purified by silica gel column using DCM:MeOH as eluent to obtain Compound (177). 1H NMR (300 MHz, CDCl3): δ 7.91 (br s, 1H), 7.03-7.08 (t, 1H), 6.91-6.93 (d, 1H), 6.90 (s, 1H), 6.46-6.49 (d, 1H), 5.06 (br s, 1H), 4.74-4.80 (m, 1H), 4.22 (br s, 1H), 3.76-3.88 (m, 1H), 2.97-3.06 (m, 1H), 2.52-2.56 (m, 1H), 2.22-2.27 (m, 1H), 1.55-1.77 (m, 10H), 1.42-1.45 (m, 9H). LC-MS: (M+H)+=397.2; HPLC purity=90.56%.

Example 178

1-(6-hydroxy-2-azatricyclo[3.3.1.1³,⁷]dec-2-yl)-3-[4-(propan-2-yloxy)-1H-indol-3-yl]butan-1-one (Peak-1) (178)

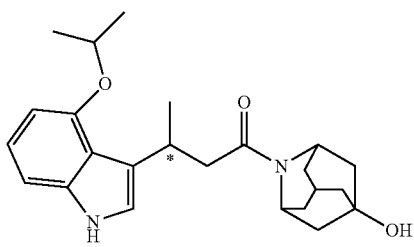

(178)

Synthesis of Compound (178)

Racemic compound (177) was purified by using chiral preparative HPLC chromatography to give Compound (178). LC-MS: (M+H)+=397.2; HPLC purity=99.12%. Chiral RT=9.72 min [column: ChiralPak IC, mobile phase: hexane:IPA:DCM (8:1:1)].

Example 179

1-(5-hydroxy-2-azatricyclo[3.3.1.1³,⁷]dec-2-yl)-3-[4-(propan-2-yloxy)-1H-indol-3-yl]butan-1-one (Peak-2) (179)

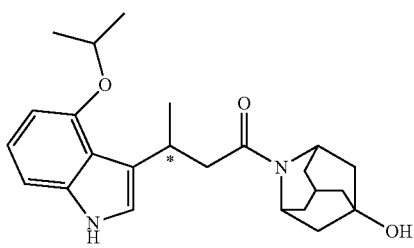

(179)

Synthesis of Compound (179)

Racemic compound (177) was purified by using chiral preparative HPLC chromatography to give Compound (179). LC-MS: (M+H)+=397.2; HPLC purity=99.65%. Chiral RT=11.97 min [column: ChiralPak IC, mobile phase: hexane:IPA:DCM (8:1:1)].

Example 180

1-(5-hydroxy-2-azatricyclo[3.3.1.1³,⁷]dec-2-yl)-3-[4-(piperidin-1-yl)-1H-indol-3-yl]butan-1-one (180)

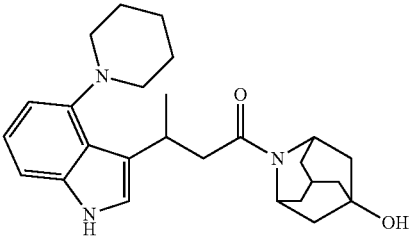

(180)

Synthesis of Compound (180)

Compound (180) was synthesized by following the procedure used to make Compound (1) (Scheme 2). The crude product was obtained by evaporating the organic layer under reduced pressure and was purified by silica gel column using DCM:MeOH as eluent to obtain Compound (180). 1H NMR (300 MHz, CDCl3): δ 7.90 (br s, 1H), 7.00-7.04 (m, 2H), 6.90-6.94 (m, 1H), 6.73-6.76 (m, 1H), 5.03 (br s, 1H), 4.13 (br s, 1H), 3.76-3.79 (m, 1H), 3.64-3.66 (m, 1H), 3.15-3.25 (m, 2H0, 2.86-2.92 (m, 1H), 2.76-2.77 (m, 1H), 2.37-2.41 (m, 1H), 2.19-2.21 (m, 1H), 1.34-1.98 (m, 19H). LC-MS: (M+H)+=422.2; HPLC purity=97.45%.

Example 181

1-(2-azatricyclo[3.3.1.1³,⁷]dec-2-yl)-3-[4-(propan-2-yloxy)-1H-indol-3-yl]butan-1-one (181)

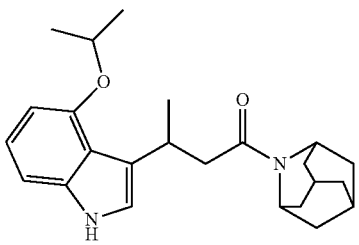

(181)

Synthesis of Compound (181)

Compound (181) was synthesized by following the procedure used to make Compound (1) (Scheme 2). The crude product was obtained by evaporating the organic layer under reduced pressure and was purified by silica gel column using DCM:MeOH as eluent to obtain Compound (181). 1H NMR (300 MHz, CDCl3): δ 7.85 (br s, 1H), 7.04-7.07 (m, 1H), 6.89-6.92 (m, 2H), 6.46-6.48 (m, 1H), 4.87 (br s, 1H), 4.75-4.79 (m, 1H), 4.04 (br s, 1H), 3.80-3.84 (m, 1H), 2.49-2.54

(m, 1H), 2.31-2.35 (m, 1H), 2.00-2.05 (m, 1H), 1.55-1.80 (m, 11H), 1.42-1.45 (m, 9H). LC-MS: (M+H)+=381.2; HPLC purity=99.41%

Example 182

1-(5-fluoro-2-azatricyclo[3.3.1.1$^{3,7}$]dec-2-yl)-3-[4-(propan-2-yloxy)-1H-indol-3-yl]butan-1-one (182)

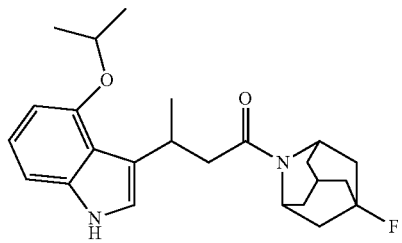

(182)

Synthesis of Compound (182)

Compound (182) was synthesized by following the procedure used to make Compound (1) (Scheme 2). The crude product was obtained by evaporating the organic layer under reduced pressure and was purified by silica gel column using DCM:MeOH as eluent to obtain Compound (182). 1H NMR (300 MHz, CDCl3): δ 7.82 (br s, 1H), 6.97-7.02 (t, 1H), 6.84-6.86 (d, 1H), 6.83 (s, 1H), 6.40-6.42 (d, 1H), 5.07 (br s, 1H), 4.65-4.73 (m, 1H), 4.21 (br s, 1H), 3.71-3.78 (m, 1H), 2.90-3.00 (m, 1H), 2.39-2.50 (m, 1H), 2.21-2.24 (m, 1H), 1.53-1.90 (m, 10H), 1.35-1.39 (m, 9H). LC-MS: (M+H)+=399.2; HPLC purity=93.52%.

Example 183

1-{3-[4-(2-azatricyclo[3.3.1.1$^{3,7}$]dec-2-yl)-4-oxobutan-2-yl]-1H-indol-4-yl}piperidine-4-carboxylic acid (183)

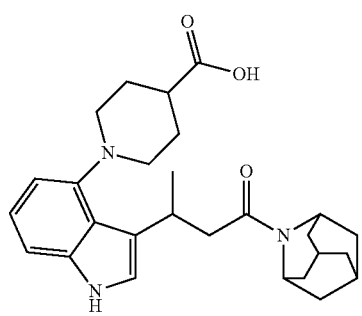

(183)

Synthesis of Compound (183)

Compound (183) was synthesized by following the procedure used to make Compound (43) (Scheme 14). The crude product was obtained by evaporating the organic layer under reduced pressure and was purified by silica gel column using DCM:MeOH as eluent to obtain Compound (183). LC-MS: (M+H)+=450.2; HPLC purity=97.82%.

Example 184

1-(5-fluoro-2-azatricyclo[3.3.1.1$^{3,7}$]dec-2-yl)-3-[4-(propan-2-yloxy)-1H-indol-3-yl]butan-1-one (Peak-1) (184)

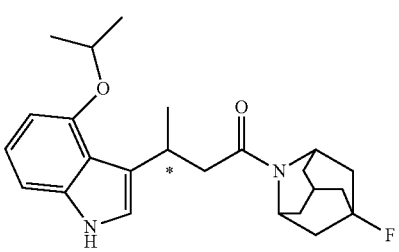

(184)

Synthesis of Compound (184)

Racemic compound (182) was purified by using chiral preparative HPLC chromatography to give Compound (184). LC-MS: (M+H)+=399.2; HPLC purity=95.51%. Chiral RT=13.60 min [column: ChiralPak IC, mobile phase: hexane:IPA:DCM (8:1:1)].

Example 185

1-(5-fluoro-2-azatricyclo[3.3.1.1$^{3,7}$]dec-2-yl)-3-[4-(propan-2-yloxy)-1H-indol-3-yl]butan-1-one (Peak-2) (185)

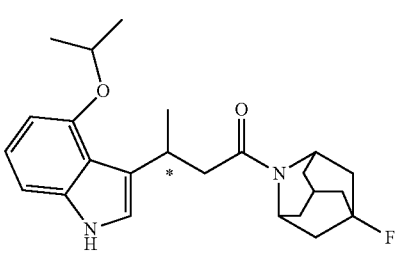

(185)

Synthesis of Compound (185)

Racemic compound 182) was purified by using chiral preparative HPLC chromatography to give Compound (185). LC-MS: (M+H)+=399.2; HPLC purity=97.38%. Chiral RT=18.54 min [column: ChiralPak IC, mobile phase: hexane:IPA:DCM (8:1:1)].

Example 186

2-{2-[3-(4-chloro-1H-indol-3-yl)butanoyl]-2-azatricyclo[3.3.1.1³,⁷]dec-5-yl}propanoic acid (186)

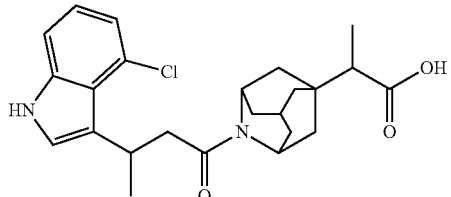
(186)

Synthesis of Compound (186)

Compound (186) was synthesized by following the procedure used to make Compound (43) (Scheme 14). The crude product was obtained by evaporating the organic layer under reduced pressure and was purified by silica gel column using DCM:MeOH as eluent to obtain Compound (186). LC-MS: (M+H)+=429.13; HPLC purity=90.92%.

Example 187

1-(5-hydroxy-2-azatricyclo[3.3.1.1³,⁷]dec-2-yl)-3-[4-(thiophen-3-yl)-1H-indol-3-yl]butan-1-one (187)

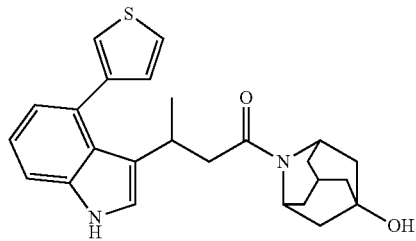
(187)

Synthesis of Compound (187)

Compound (187) was synthesized by following the procedure used to make Compound (1) (Scheme 2). The crude product was obtained by evaporating the organic layer under reduced pressure and was purified by silica gel column using DCM:MeOH as eluent to obtain Compound (187). LC-MS: (M+H)+=421.1; HPLC purity=96.22%.

Example 188

1-(6-hydroxy-2-azatricyclo[3.3.1.1³,⁷]dec-2-yl)-3-[4-(thiophen-2-yl)-1H-indol-3-yl]butan-1-one (Peak-1) (188)

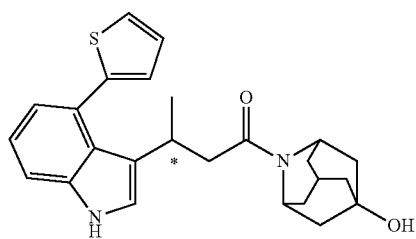
(188)

Synthesis of Compound (188)

Racemic compound (153) was purified by using chiral preparative HPLC chromatography to give Compound (188). LC-MS: (M+H)+=421.1; HPLC purity=92.0%; Chiral RT=6.57 min [column: ChiralPak IC, mobile phase: hexane:THF:EtOH (8:1:1)].

Example 189

1-(5-hydroxy-2-azatricyclo[3.3.1.1³,⁷]dec-2-yl)-3-[4-(thiophen-2-yl)-1H-indol-3-yl]butan-1-one (Peak-2) (189)

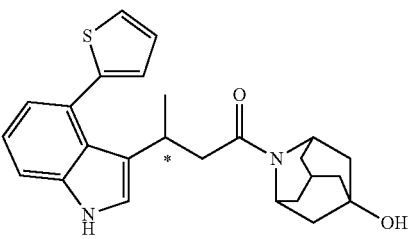
(189)

Synthesis of Compound (189)

Racemic compound (153) was purified by using chiral preparative HPLC chromatography to give Compound (189). LC-MS: (M+H)+=421.1; HPLC purity=93.52%; Chiral RT=9.17 min [column: ChiralPak IC, mobile phase: hexane:THF:EtOH (8:1:1)].

Example 190

3-(5-chloro-1,3-benzothiazol-2-yl)-1-(5-hydroxy-2-azatricyclo[3.3.1.1³,⁷]dec-2-yl)butan-1-one (190)

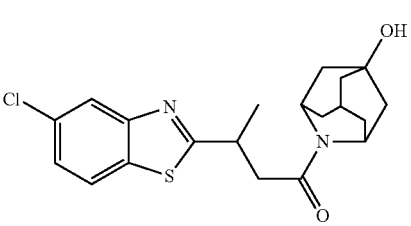
(190)

Synthesis of Compound (190)

Compound (190) was synthesized by following the procedure used to make Compound (1) (Scheme 2). The crude product was obtained by evaporating the organic layer under reduced pressure and was purified by silica gel column using DCM:MeOH as eluent to obtain Compound (190). LC-MS: (M+H)+=391.1; HPLC purity=96.40%.

Example 191

2-[3-(5-chloro-1,3-benzothiazol-2-yl)butanoyl]-2-azatricyclo[3.3.1.1³,⁷]decane-5-carbonitrile (191)

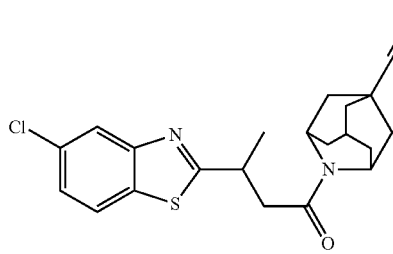
(191)

Synthesis of Compound (191)

Compound (191) was synthesized by following the procedure used to make Compound (1) (Scheme 2). The crude product was obtained by evaporating the organic layer under reduced pressure and was purified by silica gel column using DCM:MeOH as eluent to obtain Compound (191). LC-MS: (M+H)+=400.1; HPLC purity=97.71%.

Example 192

3-(6-chloro-1,3-benzothiazol-2-yl)-1-(5-hydroxy-2-azatricyclo[3.3.1.1³,⁷]dec-2-yl)butan-1-one (192)

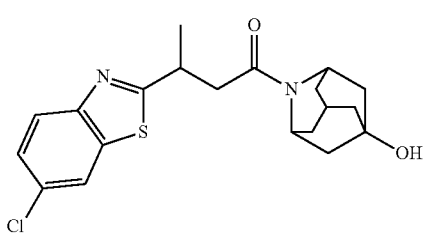
(192)

Synthesis of Compound (192)

Compound (192) was synthesized by following the procedure used to make Compound (1) (Scheme 2). The crude product was obtained by evaporating the organic layer under reduced pressure and was purified by silica gel column using DCM:MeOH as eluent to obtain Compound (192). LC-MS: (M+H)+=391.1; HPLC purity=94.40%.

Example 193

2-[3-(6-chloro-1,3-benzothiazol-2-yl)butanoyl]-2-azatricyclo[3.3.1.1³,⁷]decane-6-carbonitrile (193)

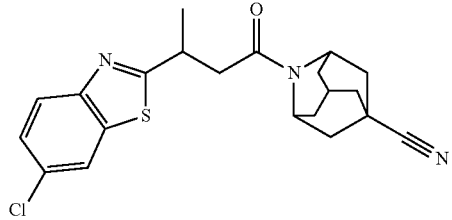
(193)

Synthesis of Compound (193)

Compound (193) was synthesized by following the procedure used to make Compound (1) (Scheme 2). The crude product was obtained by evaporating the organic layer under reduced pressure and was purified by silica gel column using DCM:MeOH as eluent to obtain Compound (193). LC-MS: (M+H)+=400.1; HPLC purity=94.39%.

Example 194

3-(6-chloro-1,3-benzothiazol-2-yl)-1-(5-hydroxy-2-azatricyclo[3.3.1.1³,⁷]dec-2-yl)butan-1-one (Peak-1) (194)

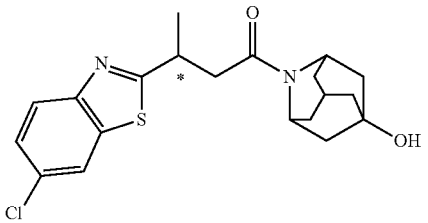
(194)

Synthesis of Compound (194)

Racemic compound (192) was purified by using chiral preparative HPLC chromatography to give Compound (194). LC-MS: (M+H)+=391.1; HPLC purity=99.6%.

Example 195

3-(6-chloro-1,3-benzothiazol-2-yl)-1-(5-hydroxy-2-azatricyclo[3.3.1.1³,⁷]dec-2-yl)butan-1-one (Peak-2) (195)

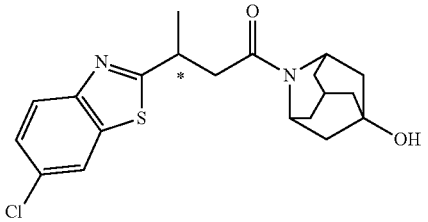
(195)

Synthesis of Compound (195)

Racemic compound (192) was purified by using chiral preparative HPLC chromatography to give Compound (195). LC-MS: (M+H)+=391.1; HPLC purity=99.56%.

Example 196

2-[3-(6-chloro-1,3-benzothiazol-2-yl)butanoyl]-2-azatricyclo[3.3.1.1$^{3,7}$]decane-5-carboxamide (196)

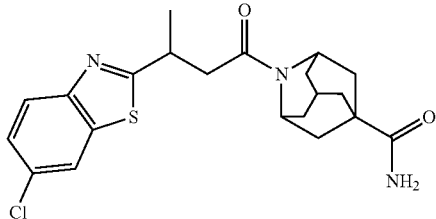

(196)

Synthesis of Compound (196)

Compound (196) was synthesized by following the procedure used to make Compound (1) (Scheme 2). The crude product was obtained by evaporating the organic layer under reduced pressure and was purified by silica gel column using DCM:MeOH as eluent to obtain Compound (196). LC-MS: (M+H)+=418.1; HPLC purity=97.62%.

Example 197

3-(4,5-dichloro-1H-pyrrolo[2,3-b]pyridin-3-yl)-1-(5-hydroxy-2-azatricyclo[3.3.1.1$^{3,7}$]dec-2-yl)butan-1-one (197)

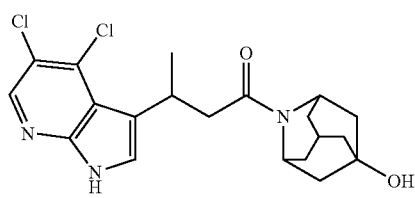

(197)

Synthesis of Compound (197)

Compound (197) was synthesized by following the procedure used to make Compound (1) (Scheme 2). The crude product was obtained by evaporating the organic layer under reduced pressure and was purified by silica gel column using DCM:MeOH as eluent to obtain Compound (197). LC-MS: (M+H)+=408.1; HPLC purity=94.42%.

Example 198

3-(5-chloro-4-cyclopropyl-1H-pyrrolo[2,3-b]pyridin-3-yl)-1-(5-hydroxy-2-azatricyclo[3.3.1.1$^{3,7}$]dec-2-yl)butan-1-one (198)

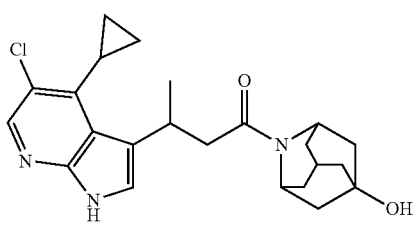

(198)

Synthesis of Compound (198)

Compound (198) was synthesized by following the procedure used to make Compound (1) (Scheme 2). The crude product was obtained by evaporating the organic layer under reduced pressure and was purified by silica gel column using DCM:MeOH as eluent to obtain Compound (198). LC-MS: (M+H)+=414.2; HPLC purity=98.68%.

Example 199

3-(5-chloro-4-cyclopropyl-1H-pyrrolo[2,3-b]pyridin-3-yl)-1-(6-hydroxy-2-azatricyclo[3.3.1.1$^{3,7}$]dec-2-yl)butan-1-one (Peak-1) (199)

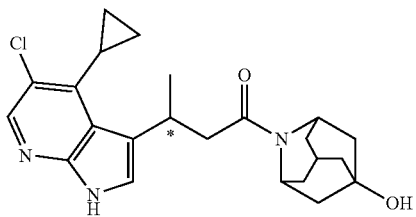

(199)

Synthesis of Compound (199)

Racemic compound (198) was purified by using chiral preparative HPLC chromatography to give Compound (199). LC-MS: (M+H)+=414.2; HPLC purity=94.06%. Chiral RT=15.94 min [column: ChiralPak IC, mobile phase: hexane: IPA:DCM (7.5:1.5:1)].

Example 200

3-(5-chloro-4-cyclopropyl-1H-pyrrolo[2,3-b]pyridin-3-yl)-1-(5-hydroxy-2-azatricyclo[3.3.1.1$^{3,7}$]dec-2-yl)butan-1-one (Peak-2) (200)

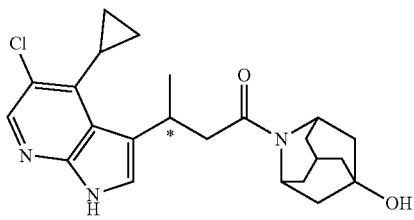

Synthesis of Compound (200)

Racemic compound (198) was purified by using chiral preparative HPLC chromatography to give Compound (200). LC-MS: (M+H)+=414.2; HPLC purity=98.40%. Chiral RT=20.09 min [column: ChiralPak IC, mobile phase: hexane: IPA:DCM (7.5:1.5:1)].

Example 201

3-(4,5-dicyclopropyl-1H-pyrrolo[2,3-b]pyridin-3-yl)-1-(5-hydroxy-2-azatricyclo[3.3.1.1$^{3,7}$]dec-2-yl)butan-1-one (201)

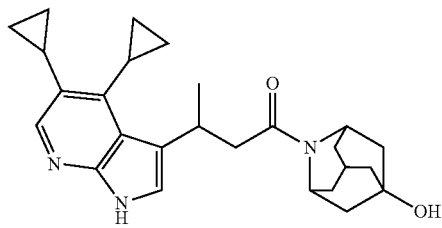

Synthesis of Compound (201)

Compound (201) was synthesized by following the procedure used to make Compound (1) (Scheme 2). The crude product was obtained by evaporating the organic layer under reduced pressure and was purified by silica gel column using DCM:MeOH as eluent to obtain Compound (201). LC-MS: (M+H)+=420.2; HPLC purity=90.88%.

Example 202

3-(6-chloro-1H-benzimidazol-2-yl)-1-(5-hydroxy-2-azatricyclo[3.3.1.1$^{3,7}$]dec-2-yl)butan-1-one (202)

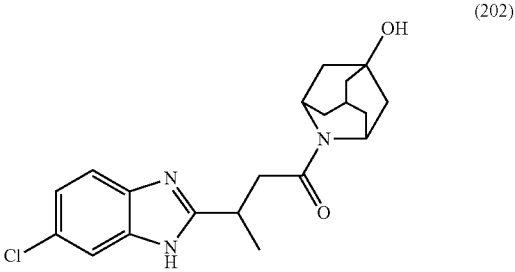 [SMILES: CC(CC(=O)N1C2CC3CC1CC(O)(C3)C2)c1nc2ccc(Cl)cc2[nH]1]

Synthesis of Compound (202)

Compound (202) was synthesized by following the procedure used to make Compound (1) (Scheme 2). The crude product was obtained by evaporating the organic layer under reduced pressure and was purified by silica gel column using DCM:MeOH as eluent to obtain Compound (202). LC-MS: (M+H)+=372.1; HPLC purity=84.69%.

Example 203

3-(6-cyclopropyl-1H-benzimidazol-2-yl)-1 (6-hydroxy-2-azatricyclo[3.3.1.1$^{3,7}$]dec-2-yl)butan-1-one (203)

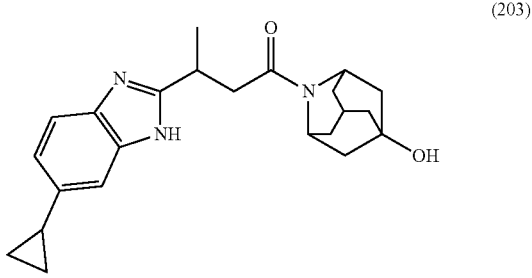 [SMILES: CC(CC(=O)N1C2CC3CC1CC(O)(C3)C2)c1nc2ccc(C3CC3)cc2[nH]1]

Synthesis of Compound (203)

Compound (203) was synthesized by following the procedure used to make Compound (1) (Scheme 2). The crude product was obtained by evaporating the organic layer under reduced pressure and was purified by silica gel column using DCM:MeOH as eluent to obtain Compound (203). LC-MS: (M+H)+=380.1; HPLC purity=98.88%.

Example 204

{2-[3-(4-cyclopropyl-1H-pyrrolo[2,3-b]pyridin-3-yl) butanoyl]-2-azatricyclo[3.3.1.1$^{3,7}$]dec-6-yl}acetic acid (204)

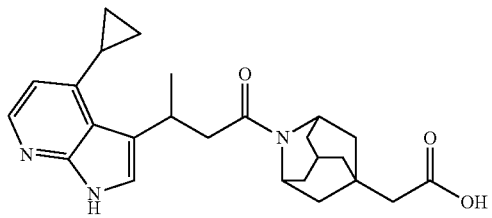

(204)

Synthesis of Compound (204)

Compound (204) was synthesized by following the procedure used to make Compound (43) (Scheme 14). The crude product was obtained by evaporating the organic layer under reduced pressure and was purified by silica gel column using DCM:MeOH as eluent to obtain Compound (204). LC-MS: (M+H)+=422.2; HPLC purity=99.63%.

Example 205

3-(1-cyclopropyl-4-methyl-1H-indol-3-yl)-1-(5-hydroxy-2-azatricyclo[3.3.1.1$^{3,7}$]dec-2-yl)butan-1-one (205)

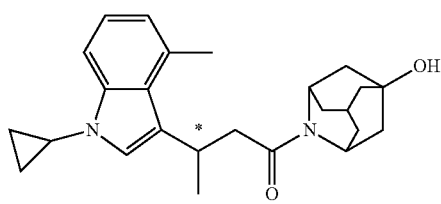

(205)

Synthesis of Compound (205)

Compound (205) was synthesized by following the procedure used to make Compound (1) (Scheme 2). The crude product was obtained by evaporating the organic layer under reduced pressure and was purified by silica gel column using DCM:MeOH as eluent to obtain Compound (205). LC-MS: (M+H)+=393.2; HPLC purity=99.04%.

Example 206

3-(1,4-dimethyl-1H-indol-3-yl)-1-(5-hydroxy-2-azatricyclo[3.3.1.1$^{3,7}$]dec-2-yl)butan-1-one (206)

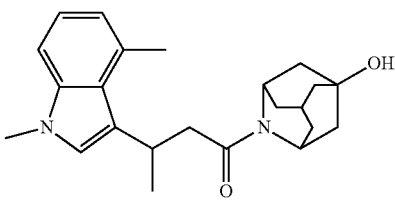

(206)

Synthesis of Compound (206)

Compound (206) was synthesized by following the procedure used to make Compound (1) (Scheme 2). The crude product was obtained by evaporating the organic layer under reduced pressure and was purified by silica gel column using DCM:MeOH as eluent to obtain Compound (206). LC-MS: (M+H)+=367.2; HPLC purity=98.36%.

Example 207

3-(4-chloro-1-methyl-1H-indol-3-yl)-1-(5-hydroxy-2-azatricyclo[3.3.1.1$^{3,7}$]dec-2-yl)butan-1-one (207)

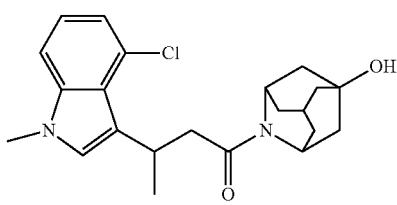

(207)

Synthesis of Compound (207)

Compound (207) was synthesized by following the procedure used to make Compound (1) (Scheme 2). The crude product was obtained by evaporating the organic layer under reduced pressure and was purified by silica gel column using DCM:MeOH as eluent to obtain Compound (207). LC-MS: (M+H)+=387.1; HPLC purity=99.49%.

Example 208

3-[4-chloro-5-(furan-2-yl)-1H-indol-3-yl]-1-(5-hydroxy-2-azatricyclo[3.3.1.1$^{3,7}$]dec-2-yl)butan-1-one (208)

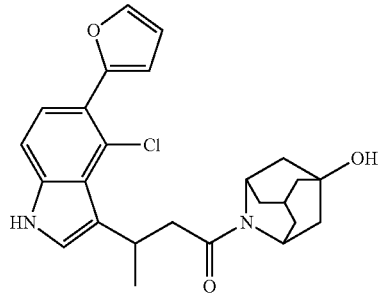

(208)

Synthesis of Compound (208)

Compound (208) was synthesized by following the procedure used to make Compound (1) (Scheme 2). The crude product was obtained by evaporating the organic layer under reduced pressure and was purified by silica gel column using DCM:MeOH as eluent to obtain Compound (208). LC-MS: (M+H)+=439.1; HPLC purity=91.39%.

Example 209

1-(5-hydroxy-2-azatricyclo[3.3.1.1$^{3,7}$]dec-2-yl)-3-(4-methoxy-5-methyl-1H-indol-3-yl)butan-1-one (209)

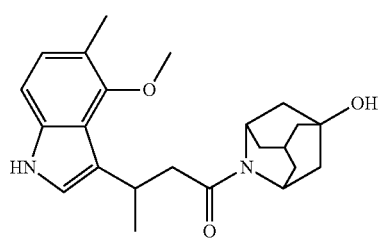

(209)

Synthesis of Compound (209)

Compound (209) was synthesized by following the procedure used to make Compound (1) (Scheme 2). The crude product was obtained by evaporating the organic layer under reduced pressure and was purified by silica gel column using DCM:MeOH as eluent to obtain Compound (209). LC-MS: (M+H)+=383.2; HPLC purity=93.48%.

Example 210

1-(6-hydroxy-2-azatricyclo[3.3.1.1$^{3,7}$]dec-2-yl)-3-[5-methyl-4-(thiophen-2-yl)-1H-indol-3-yl]butan-1-one (210)

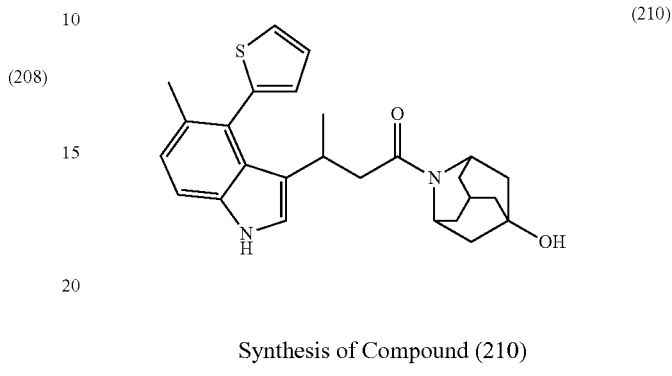

(210)

Synthesis of Compound (210)

Compound (210) was synthesized by following the procedure used to make Compound (1) (Scheme 2). The crude product was obtained by evaporating the organic layer under reduced pressure and was purified by silica gel column using DCM:MeOH as eluent to obtain Compound (210). LC-MS: (M+H)+=435.2; HPLC purity=91.98%.

Example 211

4-chloro-3-[4-(5-hydroxy-2-azatricyclo[3.3.1.1$^{3,7}$]dec-2-yl)-4-oxobutan-2-yl]-5-methyl-1,3-dihydro-2H-indol-2-one (211)

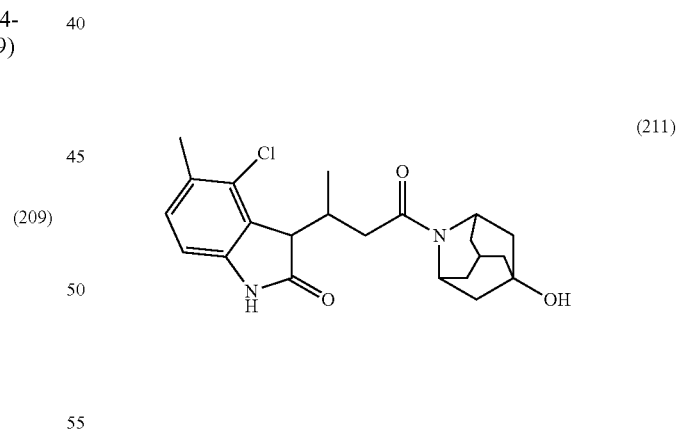

(211)

SYNTHETIC SCHEME 26

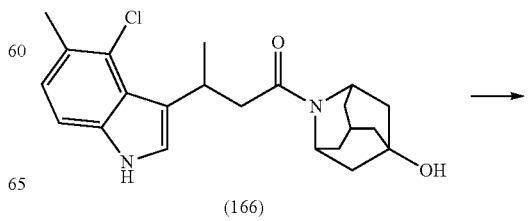

(166)

229
-continued

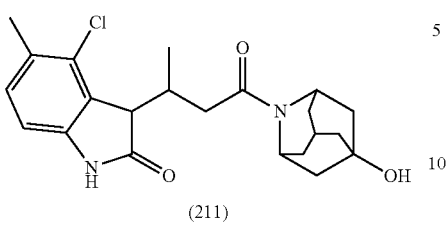

(211)

Synthesis of Compound (211)

To a stirred solution of Compound (166) (15 mg, 0.03 mmol) in DMF (2 mL) was added pyridinium tribromide (16 mg, 0.050 mmol) at 0° C. Resulted reaction mixture was stirred at room temperature for 3 hours. After reaction quenched with $H_2O$ (10 mL), extracted with ether (2×20 mL). The combined organic layers were washed with brine and concentrated. Resulted crude material was purified by preparative TLC eluting with DCM:MeOH (95:05) to give Compound (211) (5.5 mg, off white solid).

Example 212

4-cyclopropyl-3-[4-(6-hydroxy-2-azatricyclo[3.3.1.1$^{3,7}$]dec-2-yl)-4-oxobutan-2-yl]-1,3-dihydro-2H-indol-2-one (212)

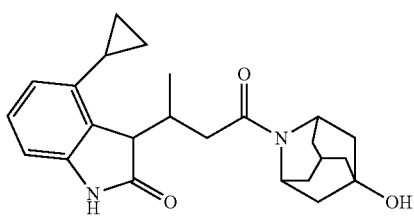

(212)

Synthesis of Compound (212)

Compound (212) was synthesized by following the procedure used to make Compound (211) (Scheme 26). The crude product was obtained by evaporating the organic layer under reduced pressure and was purified by silica gel column using DCM:MeOH as eluent to obtain Compound (212). 1H NMR (300 MHz, CDCl3): δ 7.50 (br s, 1H), 7.07-7.12 (t, 1H), 6.59-6.62 (d, 1H), 6.48-6.51 (d, 1H), 5.11 (br s, 1H), 4.54 (br s, 1H), 3.81 (br s, 1H), 3.79-3.81 (m, 1H), 2.37-2.41 (m, 2H), 2.21-2.23 (m, 1H). 1.43-1.88 (m, 11H), 1.06-1.08 (m, 2H), 0.83-0.88 (m, 2H), 0.72-0.74 (d, 3H). LC-MS: (M+H)+=395.2; HPLC purity=99.65%.

230
Example 213

3-(4-cyclopropyl-1H-indol-3-yl)-1-(5-fluoro-7-hydroxy-2-azatricyclo[3.3.1.1$^{3,7}$]dec-2-yl)butan-1-one (213)

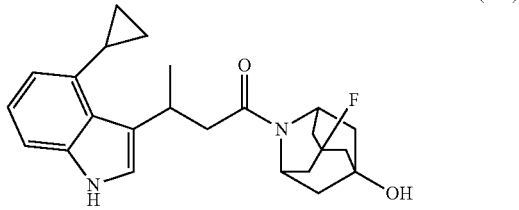

(213)

Synthesis of Compound (213)

Compound (213) was synthesized by following the procedure used to make Compound (1) (Scheme 2). The crude product was obtained by evaporating the organic layer under reduced pressure and was purified by silica gel column using DCM:MeOH as eluent to obtain Compound (213). 1H NMR (300 MHz, CDCl3): δ 8.06 (br s, 1H), 7.18-7.20 (d, 1H), 7.05-7.10 (t, 1H), 7.04 (s, 1H), 6.74-6.76 (d, 1H), 5.26 (br s, 1H), 4.40 (br s, 1H), 4.23-4.25 (m, 1H), 2.85-2.90 (m, 1H), 2.45-2.53 (m, 2H), 1.99 (br s, 2H), 1.62-1.81 (m, 8H), 1.44-1.46 (d, 3H), 0.95-0.99 (m, 2H), 0.81-0.85 (m, 2H). LC-MS: (M+H)+=397.3; HPLC purity=93.84%.

Example 214

1-(6-hydroxy-7-methyl-2-azatricyclo[3.3.1.1$^{3,7}$]dec-2-yl)-3-[4-(propan-2-yloxy)-1H-indol-3-yl]butan-1-one (214)

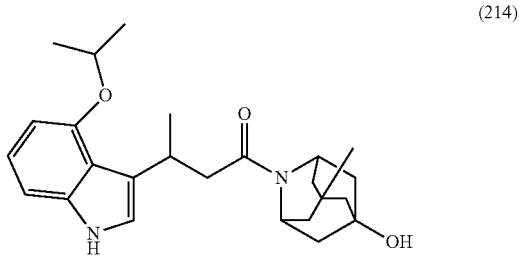 [SMILES: CC(C)Oc1cccc2[nH]cc(C(C)CC(=O)N3C4CC5(C)CC3CC(O)(C4)C5)c12]

(214)

Synthesis of Compound (214)

Compound (214) was synthesized by following the procedure used to make Compound (1) (Scheme 2). The crude product was obtained by evaporating the organic layer under reduced pressure and was purified by silica gel column using DCM:MeOH as eluent to obtain Compound (214). 1H NMR (300 MHz, CDCl3): δ 7.86 (br s, 1H), 6.96-7.01 (t, 1H), 6.84-6.86 (d, 1H), 6.83 (s, 1H), 6.39-6.42 (d, 1H), 5.00 (br s, 1H), 4.67-4.72 (m, 1H), 4.20 (br s, 1H), 3.72-3.79 (m, 1H), 2.89-3.01 (m, 1H), 2.39-2.51 (m, 1H), 1.25-1.65 (m, 19H). LC-MS: (M+H)+=411.3; HPLC purity=90.45%.

Example 215

2-(2-(3-(4-(5-fluorofuran-2-yl)-1H-indol-3-yl)butanoyl)-2-azaadamantan-5-yl)acetic acid (215)

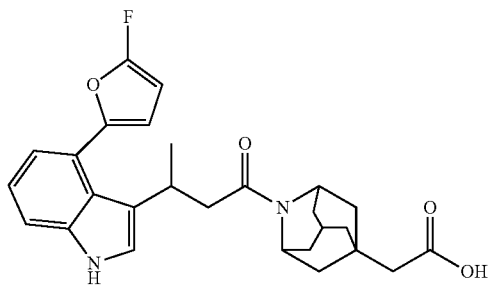
(215)

Synthesis of Compound (215)

Compound (215) was synthesized by following the procedure used to make Compound (43) (Scheme 14). The crude product was obtained by evaporating the organic layer under reduced pressure and was purified by silica gel column using DCM:MeOH as eluent to obtain Compound (215). LC-MS: (M+H)+=465.4; HPLC purity=99.37%.

Example 216

1-(5-hydroxy-2-azaadamantan-2-yl)-3-(4-methyl-1-(quinolin-8-ylsulfonyl)-1H-indol-3-yl)butan-1-one (216)

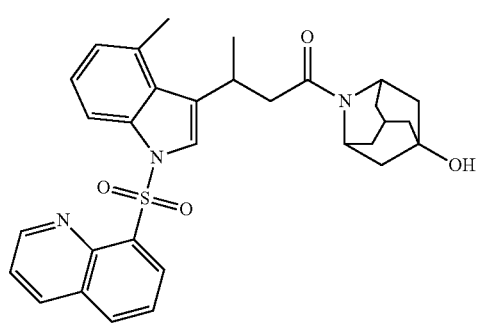
(216)

Synthesis of Compound (216)

Compound (216) was synthesized by following the procedure used to make Compound (1) (Scheme 2). LC-MS: (M+H)+=544.3; HPLC purity=98.61%.

Example 217

4-chloro-3-(4-(6-hydroxy-2-azaadamantan-2-yl)-4-oxobutan-2-yl)-5-methyl-1H-indole-2-carbonitrile (217)

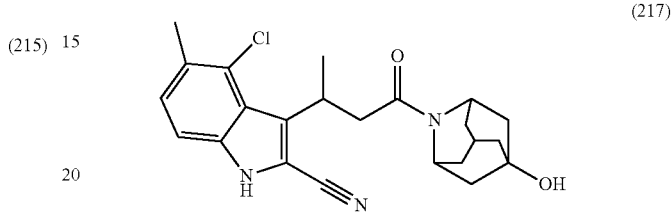
(217)

Synthesis of Compound (217)

Compound (217) was synthesized by following the procedure used to make Compound (1) (Scheme 2). LC-MS: (M+H)+=412.3.

Example 218

4-chloro-3-(4-(6-hydroxy-2-azaadamantan-2-yl)-4-oxobutan-2-yl)-1H-indole-2-carbonitrile (218)

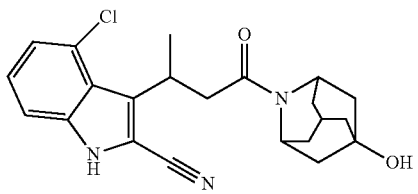
(218)

Synthesis of Compound (218)

Compound (218) was synthesized by following the procedure used to make Compound (1) (Scheme 2). LC-MS: (M+H)+=398.2; HPLC purity=98.47%.

Example 219

3-(4-chloro-5-methyl-1H-indol-3-yl)-1-(5-hydroxy-7-methyl-2-azaadamantan-2-yl)butan-1-one (219)

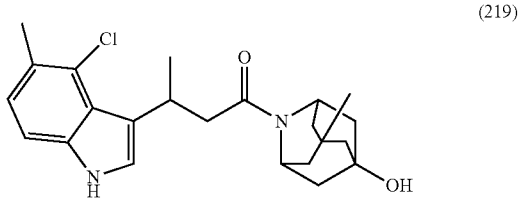 [SMILES: Cc1ccc2[nH]cc(C(C)CC(=O)N3C4CC5(C)CC3CC(O)(C4)C5)c2c1Cl]
(219)

233

Synthesis of Compound (219)

Compound (219) was synthesized by following the procedure used to make Compound (1) (Scheme 2). LC-MS: (M+H)+=401.2; HPLC purity=89.36%.

Example 220

4-cyclopropyl-3-(4-(5-hydroxy-2-azaadamantan-2-yl)-4-oxobutan-2-yl)-1H-indole-2-carbonitrile (220)

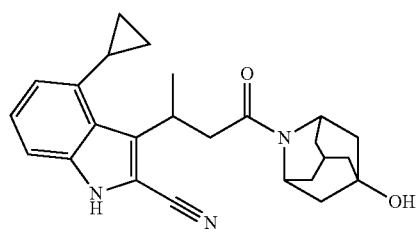

(220)

Synthesis of Compound (220)

Compound (220) was synthesized by following the procedure used to make Compound (1) (Scheme 2). LC-MS: (M+H)+=404.3; HPLC purity=98.29%.

Example 221

2-(3-(4,5-dimethyl-1H-indol-3-yl)butanoyl)-2-azaadamantane-5-carbonitrile (221)

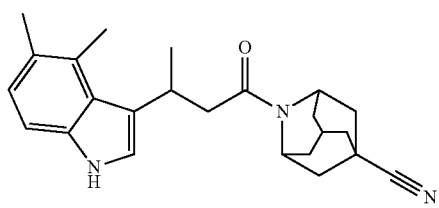

(221)

Synthesis of Compound (221)

Compound (221) was synthesized by following the procedure used to make Compound (1) (Scheme 2). LC-MS: (M+H)+=376.3; HPLC purity=85.11%.

Example 222

2-(3-(4-(furan-2-yl)-1H-indol-3-yl)butanoyl)-2-azaadamantane-5-carboxylic acid (222)

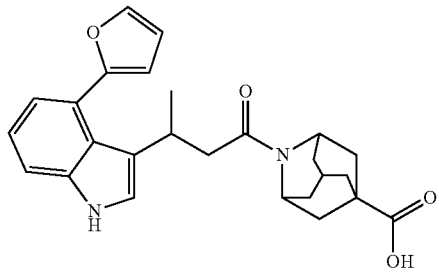

(222)

234

Synthesis of Compound (222)

Compound (222) was synthesized by following the procedure used to make Compound (43) (Scheme 14). LC-MS: (M+H)+=433.3; HPLC purity=98.85%.

Example 223

4-cyclopropyl-3-(4-(6-hydroxy-2-azaadamantan-2-yl)-4-oxobutan-2-yl)-1H-indole-2-carboxylic acid (223)

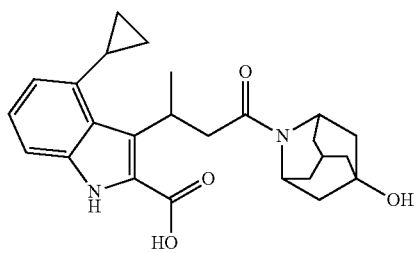

(223)

SYNTHETIC SCHEME 27

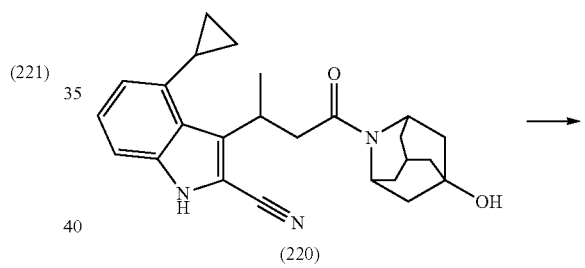

(220)

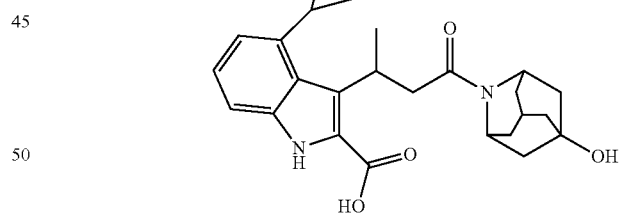

(223)

Synthesis of Compound (223)

Compound 220 (0.070 g, 0.17 mmol) was taken in a sealed tube and MeOH (3 mL) was added to it followed by addition of 50% aqueous KOH solution (2 mL). The reaction mixture was then heated at 110° C. for 24 hours and concentrated to give crude material, which was diluted with $H_2O$, acidified with 2N HCl (PH=2), extracted with EtOAc and concentrated to give crude product. The crude product was then purified by using silica gel column chromatography eluting with mixture

Example 224

1-(5-fluoro-2-azaadamantan-2-yl)-3-(5-methoxy-1H-indol-3-yl)butan-1-one (224)

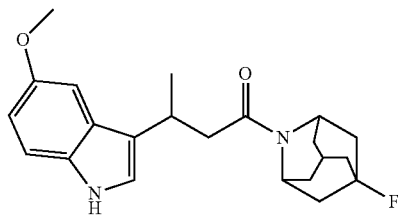
(224)

Synthesis of Compound (224)

Compound (224) was synthesized by following the procedure used to make Compound (1) (Scheme 2). LC-MS: (M+H)+=371.2; HPLC purity=92.10%.

Example 226

3-(4-(5-bromo-2-azaadamantan-2-yl)-4-oxobutan-2-yl)-1H-indol-5-yl trifluoromethanesulfonate (225)

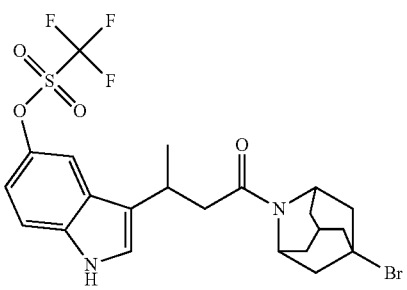
(225)

Synthesis of Compound (225)

Compound (225) was synthesized by following the procedure used to make Compound (1) (Scheme 2). LC-MS: (M+H)+=549.2; HPLC purity=92.61%.

Example 226

1-(2-azaadamantan-2-yl)-3-(5-methoxy-1H-indol-3-yl)butan-1-one (226)

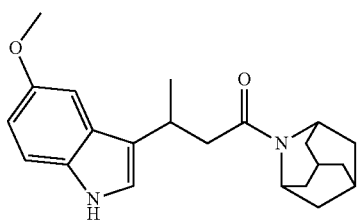
(226)

Synthesis of Compound (226)

Compound (226) was synthesized by following the procedure used to make Compound (1) (Scheme 2). LC-MS: (M+H)+=353.2; HPLC purity=90.02%.

Example 227

3-(5-methoxy-1H-indol-3-yl)-1-(5-methyl-2-azaadamantan-2-yl)butan-1-one (227)

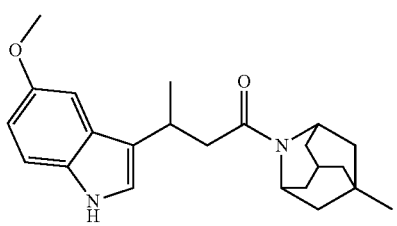
(227)

Synthesis of Compound (227)

Compound (227) was synthesized by following the procedure used to make Compound (1) (Scheme 2). LC-MS: (M+H)+=367.3; HPLC purity=92.59%.

Example 228

3-(4-(2-azaadamantan-2-yl)-4-oxobutan-2-yl)-1H-indol-6-yl trifluoromethanesulfonate (228)

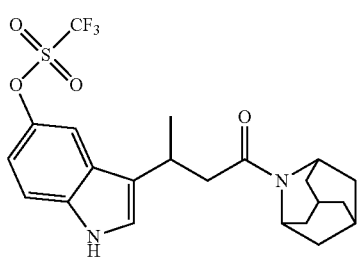
(228)

Synthesis of Compound (228)

Compound (228) was synthesized by following the procedure used to make Compound (1) (Scheme 2). 1H NMR (300 MHz, DMSO-d6): δ 11.24 (br s, 1H), 7.59 (s, 1H), 7.44-7.47 (d, 1H), 7.36 (s, 1H), 7.11-7.14 (d, 1H), 4.62 (br s, 1H), 4.01 (br s, 1H), 3.43-3.48 (m, 1H), 2.62-2.65 (m, 1H), 2.43.2.47

(m, 1H), 2.10 (s, 1H), 2.00 (s, 1H), 1.44-1.86 (m, 10H), 1.30-1.33 (d, 3H). LC-MS: (M+H)+=471.1; HPLC purity=89.84%.

Example 229

3-(4-(2-azaadamantan-2-yl)-4-oxobutan-2-yl)-1H-indol-5-yl methanesulfonate (229)

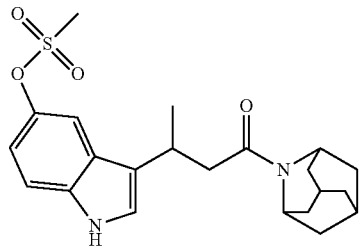
(229)

Synthesis of Compound (229)

Compound (229) was synthesized by following the procedure used to make Compound (1) (Scheme 2). 1H NMR (300 MHz, CDCl3): δ 8.37 (br s, 1H), 7.50 (s, 1H), 7.23-7.26 (d, 1H), 6.98-7.05 (m, 2H), 4.74 (br s, 1H), 3.92 (br s, 1H), 3.51-3.58 (m, 1H), 3.08 (s, 1H), 2.68-2.75 (m, 1H), 2.41-2.48 (m, 1H), 1.96 (br s, 1H), 1.84 (br s, 1H), 1.45-1.72 (m, 10H), 1.39-1.42 (d, 3H). LC-MS: (M+H)+=417.1; HPLC purity=92.90%.

Example 230

2-(3-(5-methoxy-1H-indol-3-yl)butanoyl)-2-azaadamantane-5-carbonitrile (230)

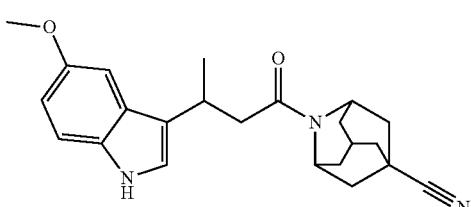
(230)

Synthesis of Compound (230)

Compound (230) was synthesized by following the procedure used to make Compound (1) (Scheme 2). 1H NMR (300 MHz, CDCl3): δ 7.95 (br s, 1H), 7.22-7.28 (m, 1H), 7.09-7.12 (m, 1H), 6.99-7.00 (d, 1H), 6.83-6.89 (m, 1H), 4.91-4.95 (d, 1H), 3.97-4.03 (d, 1H), 3.86 (s, 3H), 3.61-3.67 (m, 1H), 2.72-2.81 (m, 1H), 2.45-2.55 (m, 1H), 2.13-2.16 (m, 1H), 1.58-2.05 (m, 10H) 1.48-1.51 (d, 3H). LC-MS: (M+H)+=378.3; HPLC purity=99.49%.

Example 231

1-(5-amino-2-azaadamantan-2-yl)-3-(4-cyclopropyl-1H-indol-3-yl)butan-1-one (231)

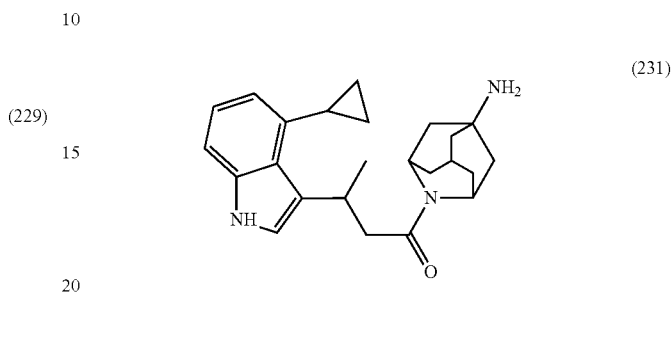
(231)

SYNTHETIC SCHEME 28

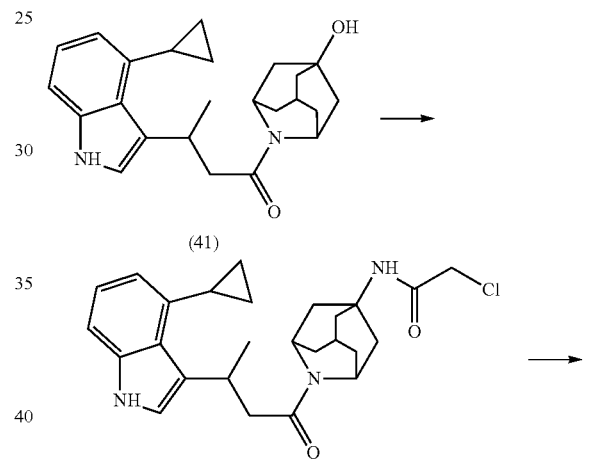

Intermediate-61

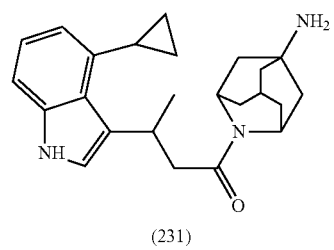
(231)

Synthesis of Intermediate-61

To a stirred solution of compound-41 (0.10 g, 0.26 mmol) in DCM (5 mL) in AcOH (2 mL), chloroaceto nitrile (117 mg, 1.56 mmol) was added at 0° C. The reaction mixture was then treated with sulfuric acid (0.75 mL). The reaction mixture was stirred at 0° C. for 1 hour and continued to stir at room temperature for 12 hours. After completion of the reaction, the reaction mixture was quenched with saturated aqueous NaHCO3 solution and extracted with EtOAc to give Intermediate-61 (90 mg). It was used for next step without any purification.

Synthesis of Compound 231

A stirred solution of Intermediate-61 (0.090 g, 0.19 mmol)) and thiourea (0.028 g, 0.38 mmol) in EtOH (5 mL) at 0° C. was treated with acetic acid (0.5 mL). The reaction mixture was heated to reflux for 12 hours. After completion of the reaction, the reaction mixture was quenched with saturated sodium bicarbonate solution, extracted with DCM and concentrated to give Compound 231 (30 mg).

Example 232

3-(4-cyclopropyl-1H-indol-3-yl)-1-(5-(methylamino)-2-azaadamantan-2-yl)butan-1-one (232)

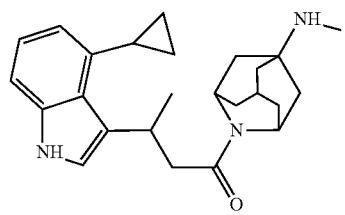

(232)

SYNTHETIC SCHEME 29

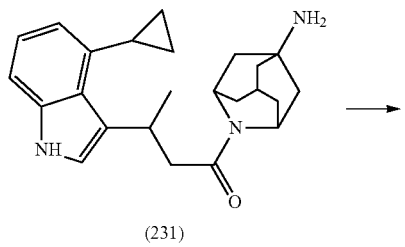

(231)

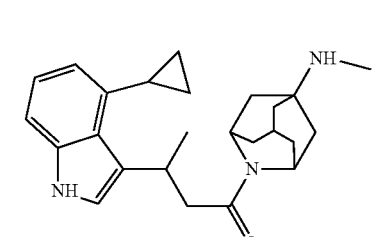

(232)

Synthesis of 232

To a stirred solution of Compound 231 (0.020 g, 0.053 mmol)) in DMF, K$_2$CO$_3$ (14.6 mg, 0.16 mmol) was added at 0° C. To this solution MeI was added and stirred at room temperature for 2 hours. After completion of the reaction, the reaction mixture was quenched with H$_2$O, extracted with EtOAc, and concentrated to give crude product, which was purified by using prep TLC to give Compound 232 (5 mg).

Example 233

3-(4-cyclopropyl-1H-indazol-3-yl)-1-(5-hydroxy-2-azatricyclo[3.3.1.1$^{3,7}$]dec-2-yl)propan-1-one (233)

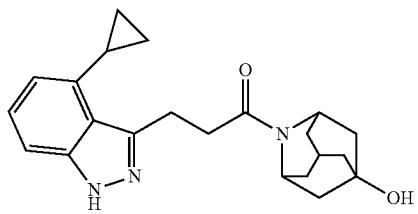

(233)

SYNTHETIC SCHEME 30

Starting Material-14 → Intermediate-62

Intermediate-63 → Intermediate-64 →

Intermediate-65

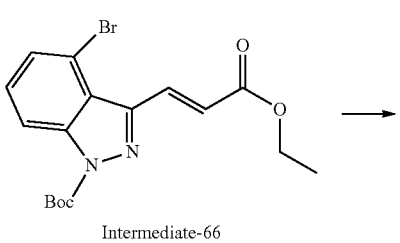

Intermediate-66

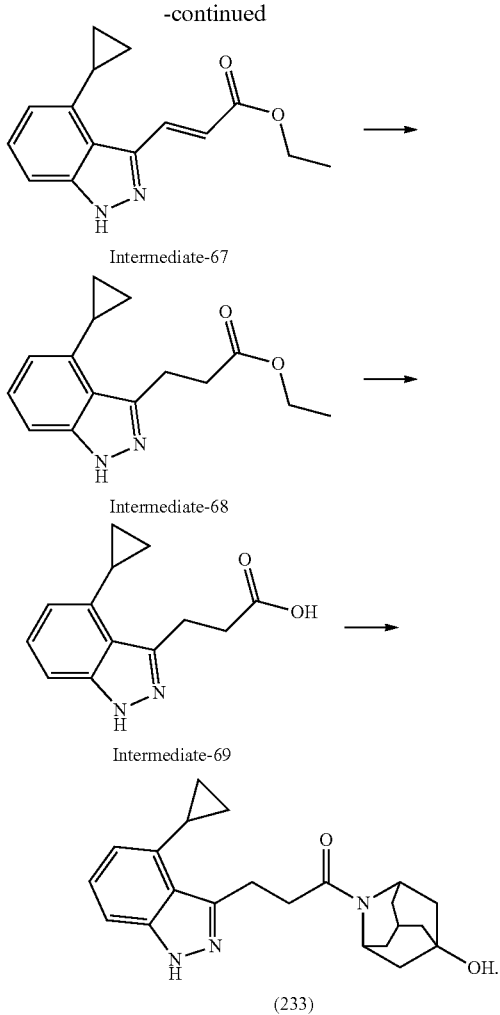

Intermediate-67

Intermediate-68

Intermediate-69

(233)

Synthesis of Intermediate-62

To a stirred solution of Starting Material-14 (2.0 g, 8.6 mmol) in THF:MeOH (40 mL, 1:1), activated Zn powder (3.71 g, 69.5 mmol) was added, followed by saturated $NH_4Cl$ solution and stirred at room temperature for 3 hours. After completion of the reaction, the reaction mixture it was concentrated and diluted with $H_2O$, extracted with EtOAc and concentrated to give Intermediate-62 (1.7 g) as pale yellow solid.

Synthesis of Intermediate-63

To a stirred solution of Intermediate-62 (1.8 g, 9.7 mmol) in chloroform (20 mL), $Ac_2O$ (2.25 mL, 22.0 mmol) was added at 0° C. The resulted reaction mixture was stirred at room temperature for 24 hours. Then KOAc (0.28 g, 2.9 mmol), followed by isoamylnitrite (2.44 g, 20 mmol) were added, and heated at 60° C. for 18 hours. After completion of the reaction, the reaction mixture quenched with $H_2O$ and concentrated, to this conc HCl (5 mL) was added and heated at 60° C. for 2 hours. The reaction mixture was then basified with 50% aqueous NaOH solution and extracted with EtOAc and concentrated to give Intermediate-63 (420 mg) as brown solid.

Synthesis of Intermediate-64

To a stirred solution of Intermediate-63 (0.50 g. 2.5 mmol) in DMF (5 mL), KOH (0.28 g, 5.0 mmol) was added and stirred at room temperature for 20 minutes. To the reaction mixture iodine (0.26 g, 5.0 mmol) in DMF was added and the reaction was continued at room temperature for 12 hours. After completion of the reaction the reaction mixture was quenched with $H_2O$, extracted with EtOAc and concentrated to give Intermediate-64 (750 mg) as brown solid, which was used in next step without any purification.

Synthesis of Intermediate-66

To a stirred solution of Intermediate-64 (0.75 g, 2.3 mmol) in MeCN (5 mL), TEA (0.696 g, 6.9 mmol), DMAP (0.024 g, 0.2 mmol) and $(Boc)_2O$ (1.00 g, 4.6 mmol) were added at 0° C. The resulted reaction mixture was stirred at room temperature for 4 hours. After completion of the reaction, the reaction mixture was quenched with $H_2O$, extracted with EtOAc and concentrated to give crude material. The crude material was purified by using silica gel column chromatography eluting with mixture of hexane:EtOAc to give Intermediate-65 (700 mg) as white solid.

Synthesis of Intermediate-66

To a stirred solution of Intermediate-65 (0.25 g, 0.7 mmol) in DMF (5 mL), TEA (0.31 mL, 2.3 mmol), ethyl crotanoate (0.11 g, 1.1 mmol) and TBAl (0.05 g, 0.14 mmol) were added, and purged with argon gas for 15 minutes. To the reaction mixture $PdCl_2(dppf)$ (0.06 g, 0.07 mmol) was added. The resulted reaction mixture was kept under micro wave conditions at 100° C. for 2 hours. After completion of the reaction, the reaction mixture was filtered through celite and concentrated, resulted crude material was purified by using silica gel column chromatography eluting with mixture of hexanes: EtrOAc to give Intermediate-66 (20 mg) as white solid.

Synthesis of Intermediate-67

To a stirred solution of Intermediate-66 (0.05 g, 0.12 mmol) in dioxane:H2O (4 mL, 3:1) cyclopropyl boronic acid (0.02 g, 0.25 mmol), $Cs_2CO_3$ (0.136 g, 0.42 mmol) were added, and purged with argon gas for 10 minutes. To the reaction mixture $PdCl_2(dppf)$ 0.009 g, 0.012 mmol) was added. The resulted reaction mixture was kept under micro wave conditions at 120° C. for 1 hour. After completion of the reaction, the reaction mixture was quenched with $H_2O$, extracted with EtOAc and concentrated. The resulted reaction mixture was purified by using silica gel column chromatography eluting with mixture of hexane:EtOAc to give Intermediate-67 (30 mg) as brown gummy material.

Synthesis of Intermediate-68

To a stirred solution of Intermediate-67 (0.030 g, 0.11 mmol) in DMF:MeOH (2 mL, 1:1), $NaBH_4$ (0.006 g, 0.17 mmol) was added, followed by cobalt chloride (0.002 g, 0.022 mmol). The resulted reaction mixture was stirred at rt for 45 min. After completion of the reaction, the reaction mixture was quenched with $H_2O$, extracted with EtOAc and concentrated to give Intermediate-68 (25 mg) as brown gummy material.

Synthesis of Intermediate-69

Intermediate-69 was synthesized by following the procedure used to make Intermediate-26 (scheme-4).

Synthesis of Compound (233)

Compound (233) was synthesized by following the procedure used to make Compound (1) (Scheme 2). 1H NMR (300

MHz, CDCl3): δ 7.22-7.33 (m, 2H), 6.75-6.78 (m, 1H), 5.09 (br s, 1H), 4.40 (br s, 1H), 3.61-3.66 (t, 2H), 2.93-2.98 (t, 2H), 2.18-2.22 (t, 1H), 1.60-2.04 (m, 11H), 1.06-1.08 (m, 2H), 0.86-0.88 (m, 2H). LC-MS: (M+H)+=366.1.

Example 234

2-(3-(4-fluoro-6-methyl-1H-indol-3-yl)butanoyl)-2-azaadamantane-5-carbonitrile (234)

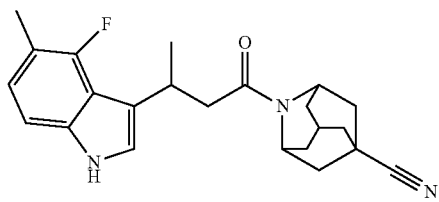

(234)

Synthesis of Compound (234)

Compound (234) was synthesized by following the procedure used to make Compound (1) (Scheme 2). 1H NMR (300 MHz, CDCl3): δ 7.97 (br s, 1H), 7.02-7.06 (m, 1H), 6.93-6.99 (m, 2H), 4.96 (br s, 1H), 4.17-4.21 (m, 1H), 3.60-3.68 (m, 1H), 2.84-2.88 (m, 1H), 2.47-2.56 (m, 1H), 2.36 (s, 3H), 2.10-2.13 (m, 1H), 1.61-2.05 (m, 10H), 1.45-1.48 (d, 3H). LC-MS: (M+H)+=380.2. HPLC purity=99.13%.

Example 235

2-(4-cyclopropyl-1H-indol-3-yl)-1-(5-hydroxy-2-azaadamantan-2-yl)propan-1-one (235)

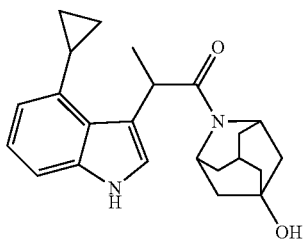

(235)

SYNTHETIC SCHEME 31

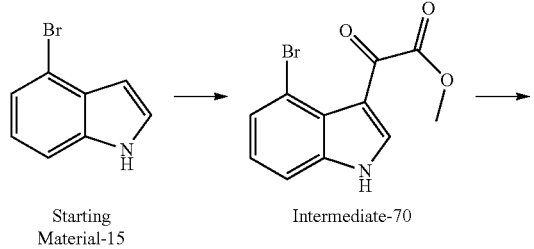

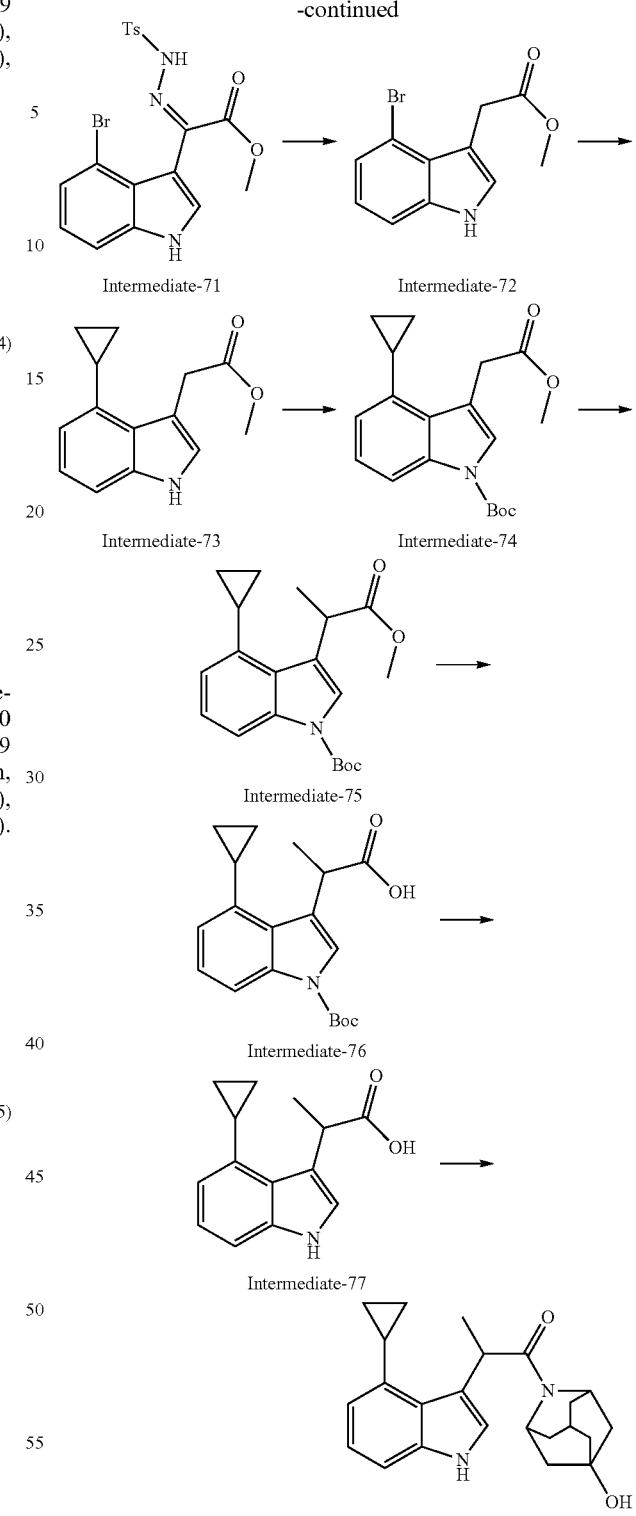

Synthesis of Intermediate-70

To a stirred solution of Starting Material-15 (40 g, 206 mmol) in ether (400 mL), oxalyl chloride (23.2 mL, 268 mmol) was added at 0° C., and stirred at room temperature for 5 hours. The reaction mixture was then filtered and washed with ether to get solid material (42 g), which was treated with MeOH (28 mL) in ether (200 mL) at 0° C. to room temperature for 5 hours. After completion of the reaction the reaction mixture was diluted with hexanes, resulted precipitate was filtered and dried to get Intermediate-70 (35 g) as yellow solid.

Synthesis of Intermediate-71

To a stirred solution of Intermediate-70 (35 g, 129 mmol) in MeOH (350 mL), tosyl hydrazine (23.1 g, 129 mmol) was added and refluxed for 4 hours. After completion of the reaction, the reaction mixture was concentrated to give crude mixture, which is diluted with $H_2O$, extracted with DCM and concentrated to give Intermediate-69 (35 g) as pale yellow solid.

Synthesis of Intermediate-72

To a stirred solution of Intermediate-71 (14 g, 31 mmol) in THF (140 mL), $NaBH_4$ (1.8 g, 46 mmol) was added at 0° C. and continued to stir at room temperature for 6 hours. After completion of the reaction, the reaction mixture was quenched with $H_2O$, extracted with DCM and concentrated. The resulted crude product was purified by using silica gel column chromatography elutive with mixture of hexanes, EtOAc to give Intermediate-72 (3 g) as pale yellow liquid.

Synthesis of Intermediate-73

Intermediate-73 was synthesized by following the procedure used to make Intermediate-67 (Scheme 30).

Synthesis of Intermediate-74

Intermediate-74 was synthesized by following the procedure used to make Intermediate-65 (Scheme 30).

Synthesis of Intermediate-75

Intermediate-75 was synthesized by following the procedure used to make intermediate-30 (Scheme 6).

Synthesis of Intermediate-76

Intermediate-76 was synthesized by following the procedure used to make Intermediate-26 (Scheme 4).

Synthesis of Intermediate-77

Intermediate-77 was synthesized by following the procedure used to make Intermediate-7 (Scheme 1).

Synthesis of Compound (233)

Compound (233) was synthesized by following the procedure used to make Compound (1) (Scheme 2). 1H NMR (300 MHz, CDCl3): δ 8.13 (br s, 1H), 7.13-7.16 (d, 1H), 6.96-7.04 (m, 2H), 6.75-6.78 (d, 1H), 5.08 (br s, 1H), 4.62-4.67 (m, 1H), 4.32 (br s), 2.25-2.30 (m, 1H), 2.05-2.08 (m, 1H), 1.53-1.79 (m, 10H), 1.46-1.49 (d, 3H), 0.93-0.98 (m, 2H), 0.83-0.88 (m, 2H). LC-MS: (M+H)+=365.2. HPLC purity=95.44%.

Example 236

3-(4-cyclopropyl-1-methyl-1H-indazol-3-yl)-1-(5-hydroxy-2-azaadamantan-2-yl)propan-1-one (236)

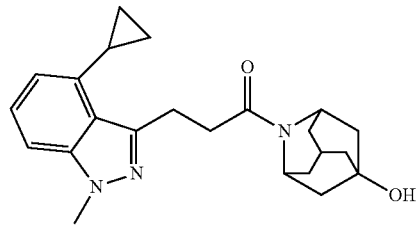

(236)

Synthesis of Compound 236

Compound (236) was synthesized by following the procedure used to make Compound (233) (Scheme 30). LC-MS: (M+H)+=380.3. HPLC purity=99.86%.

Example 237

1-(2-azaadamantan-2-yl)-3-(4-cyclopropyl-1-methyl-1H-indazol-3-yl)propan-1-one (237)

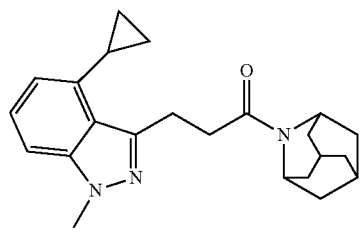

(237)

Synthesis of Compound (237)

Compound (237) was synthesized by following the procedure used to make Compound (233) (Scheme 30). LC-MS: (M+H)+=364.3. HPLC purity=91.66%.

Example 238

1-(2-azaadamantan-2-yl)-2-(4-cyclopropyl-1H-indol-3-yl)propan-1-one (238)

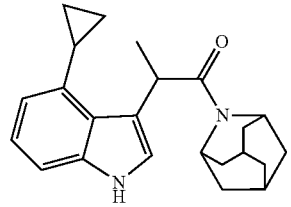

(238)

Synthesis of Compound (238)

Compound (238) was synthesized by following the procedure used to make Compound (233) (Scheme 27). LC-MS: (M+H)+=349.2.

Biological Activity

In Vitro HSD11β1 Inhibition Assay:

CHO cells were maintained in Dulbecco's modified Eagle's medium/nutrient mixture F-12 containing 5% fetal bovine serum (v/v) and 2 mM glutamine. Cells were cultured at 37° C. with 5% $CO_2$. For transient expression of human full length HSD11β1 expression vector (OriGene Technologies), cells were seeded at a density of 2×105 cells/well in a 6-well plate. Transfection was done using Turbofectin8 reagent (OriGene Technologies), according to the protocol provided with the reagent. After 24 hours post-transfection, cells were trypsinized and pooled together before they were re-seeding to 96-well plate at a density of 40000 cells/well. 24 hours after re-seeding, cells were incubated with 200 nM cortisone+500 uM NADPH (or along with small molecule inhibitors) overnight. The enzymatic activity or inhibition of enzyme activity was measured by estimating the conversion of cortisone to cortisol by LC/MS-MS method. The IC50 in nM was calculated from a 8 point log scale of concentration versus inhibition.

The results of the biological testing are shown in table 1:

| Cmpd No | 11βHSD1 (IC50) |
|---|---|
| 1 | * |
| 2 | **** |
| 3 | * |
| 4 | * |
| 5 | ** |
| 6 | * |
| 7 | * |
| 8 | * |
| 9 | * |
| 10 | * |
| 11 | * |
| 12 | * |
| 13 | * |
| 14 | **** |
| 15 | * |
| 16 | * |
| 17 | **** |
| 18 | **** |
| 19 | ** |
| 20 | * |
| 21 | * |
| 22 | * |
| 23 | * |
| 24 | * |
| 25 | * |
| 26 | ** |
| 27 | * |
| 28 | ** |
| 29 | **** |
| 30 | *** |
| 31 | ***** |
| 32 | *** |
| 33 | * |
| 34 | * |
| 35 | ***** |
| 36 | ** |
| 37 | ***** |
| 38 | * |
| 39 | **** |
| 40 | ***** |
| 41 | ***** |
| 42 | * |
| 43 | * |
| 44 | ** |
| 45 | * |
| 46 | * |
| 47 | *** |
| 48 | ***** |
| 49 | ***** |
| 50 | * |
| 51 | * |
| 52 | * |
| 53 | * |
| 54 | * |
| 55 | * |
| 56 | ***** |
| 57 | * |
| 58 | ***** |
| 59 | **** |
| 60 | * |
| 61 | * |
| 62 | * |
| 63 | * |
| 64 | **** |
| 65 | ** |
| 66 | * |
| 67 | **** |
| 68 | * |
| 69 | **** |
| 70 | *** |
| 71 | * |
| 72 | * |
| 73 | ****** |
| 74 | * |
| 75 | ** |
| 76 | * |
| 77 | * |
| 78 | * |
| 79 | **** |
| 80 | * |
| 81 | * |
| 82 | ***** |
| 83 | ***** |
| 84 | ** |
| 85 | ****** |
| 86 | * |
| 87 | *** |
| 88 | * |
| 89 | * |
| 90 | * |
| 91 | * |
| 92 | * |
| 93 | * |
| 94 | ***** |
| 95 | **** |
| 96 | **** |
| 97 | * |
| 98 | ***** |
| 99 | ***** |
| 100 | ***** |
| 101 | ** |
| 102 | ***** |
| 103 | * |
| 104 | ***** |
| 105 | ****** |
| 106 | **** |
| 107 | * |
| 108 | * |
| 109 | * |
| 110 | * |
| 111 | * |
| 112 | ** |
| 113 | * |
| 114 | * |
| 115 | ** |
| 116 | ** |
| 117 | * |
| 118 | * |
| 119 | ***** |
| 120 | * |
| 121 | * |
| 122 | * |

| Cmpd No | 11βHSD1 (IC50) |
|---|---|
| 123 | * |
| 124 | * |
| 125 | * |
| 126 | ***** |
| 127 | ***** |
| 128 | * |
| 129 | * |
| 130 | ***** |
| 131 | * |
| 132 | ***** |
| 133 | **** |
| 134 | *** |
| 135 | * |
| 136 | ***** |
| 137 | * |
| 138 | **** |
| 139 | ***** |
| 140 | * |
| 141 | **** |
| 142 | * |
| 143 | * |
| 144 | ***** |
| 145 | **** |
| 146 | * |
| 147 | **** |
| 148 | ***** |
| 149 | * |
| 150 | ***** |
| 151 | ***** |
| 152 | **** |
| 153 | ***** |
| 154 | * |
| 155 | **** |
| 156 | * |
| 157 | ***** |
| 158 | * |
| 159 | **** |
| 160 | **** |
| 161 | ***** |
| 162 | *** |
| 163 | * |
| 164 | **** |
| 165 | * |
| 166 | ***** |
| 167 | ** |
| 168 | ***** |
| 169 | ***** |
| 170 | * |
| 171 | ** |
| 172 | * |
| 173 | ***** |
| 174 | * |
| 175 | ***** |
| 176 | * |
| 177 | ***** |
| 178 | ***** |
| 179 | * |
| 180 | * |
| 181 | * |
| 182 | *** |
| 183 | * |
| 184 | ***** |
| 185 | * |
| 186 | * |
| 187 | **** |
| 188 | **** |
| 189 | * |
| 190 | *** |
| 191 | * |
| 192 | ***** |
| 193 | *** |
| 194 | ***** |
| 195 | * |
| 196 | * |
| 197 | ***** |
| 198 | ***** |
| 199 | ***** |

| Cmpd No | 11βHSD1 (IC50) |
|---|---|
| 200 | * |
| 201 | * |
| 202 | * |
| 203 | * |
| 204 | * |
| 205 | * |
| 206 | * |
| 207 | **** |
| 208 | **** |
| 209 | ** |
| 210 | **** |
| 211 | *** |
| 212 | * |
| 213 | **** |
| 214 | ***** |
| 215 | * |
| 216 | * |
| 217 | * |
| 218 | * |
| 219 | ***** |
| 220 | * |
| 221 | * |
| 222 | * |
| 223 | * |
| 224 | * |
| 225 | * |
| 226 | ***** |
| 227 | ***** |
| 228 | **** |
| 229 | * |
| 230 | * |

***** = <100 nM
**** = 100 nM< and <150 nM
*** = 150 nM< and <200 nM
** = 200 nM< and <250 nM
* = 250 nM<

The invention claimed is:

1. A compound of formula (I):

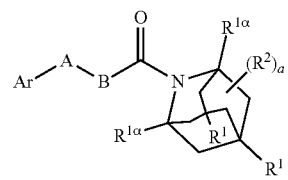

Formula (I)

wherein:

each $R^1$ is independently selected from the group consisting of H, OH, $OCF_2H$, $OCH_3$, $CH_3$, F, Br, Cl, CN, O-cyclopropyl, $CO_2H$, $CONH_2$, CONHPh, CONH(4-flouroPh), $CH_2OH$, tetrazole, $CH_2CO_2H$, $CH_2CH_2CO_2H$, $CCH_3HCO_2H$, $CH_2NH_2$, $NH_2$ and $NHCH_3$, $R^{1\alpha}$ is H;

$R^2$ is selected from the group consisting of H, OH, $CO_2H$ and tetrazole;

Ar is selected from the group consisting of:

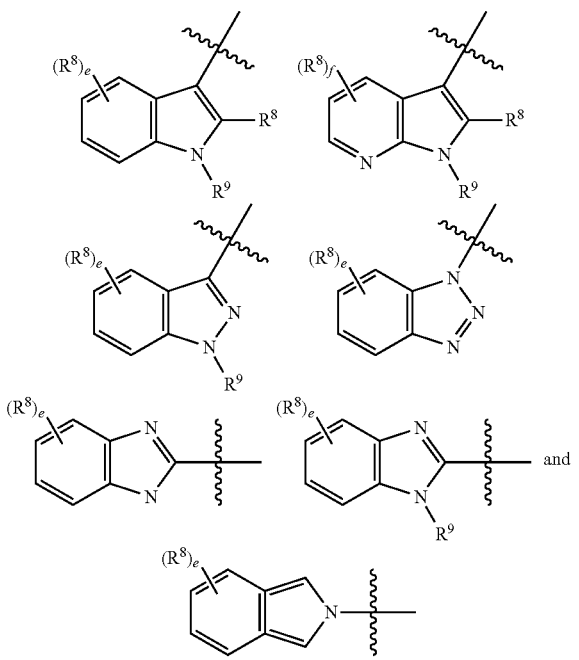

e is an integer selected from the group consisting of 0, 1, 2, 3, and 4;

f is an integer selected the group consisting of 0, 1, 2, and 3;

wherein each $R^8$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_1$heteroaryloxy, optionally substituted $C_1$-$C_{12}$alkylamino, $SR^{10}$, $SO_3H$, $SO_2NR^{10}R^{11}$, $SO_2R^{10}$, $OSO_2R^{10}$, $SONR^{10}R^{11}$, $SOR^{10}$, $COR^{10}$, COOH, $COOR^{10}$, $CONR^{10}R^{11}$, $NR^{10}COR^{11}$, $NR^{10}COOR^{11}$, $NR^{10}SO_2R^{11}$, $NR^{10}CONR^{10}R^{11}$, and $NR^{10}R^{11}$;

wherein $R^9$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, optionally substituted $C_1$-$C_{18}$heteroaryl, $SO_3H$, $SO_2NR^{10}R^{11}$, $SO_2R^{10}$, $SONR^{10}R^{11}$, $SOR^{10}$, $COR^{10}$, COOH, $COOR^{10}$, and $CONR^{10}R^{11}$;

wherein each $R^{10}$ and $R^{11}$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;

A is —$CR^aR^b$—;

B is a group of the formula —$(CR^cR^d)_n$—;

wherein each $R^a$, and $R^b$, is independently selected from the group consisting of H, halogen, OH, $NO_2$, CN, SH, $NH_2$, $CF_3$, $OCF_3$, methyl, ethyl, propyl, isopropyl, cyclopropyl, phenyl, 4-chloro-phenyl, 4-fluoro-phenyl, thiophene-2-yl, or any two $R^a$, and $R^b$, on the same carbon atom when taken together form a cyclopropyl group;

$R^c$ and $R^d$ are both H;

n is an integer selected from the group consisting of 0 and 1;

a is an integer selected from the group consisting of 0, and 1, or a pharmaceutically acceptable salt thereof.

2. A compound according to claim 1 wherein B is $CH_2$.

3. A compound according to claim 1 wherein $R^a$ and $R^b$ are different.

4. A compound according to claim 3 wherein one of $R^a$ and $R^b$ is H and the other is selected from the group consisting of methyl, ethyl, propyl, and isopropyl.

5. A compound according to claim 1 wherein the $R^8$ substituent is located in the 4 or the 5 position of the six membered ring.

6. A compound according to claim 1 wherein each $R^8$ is independently selected from the group consisting of $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$.

7. A compound according to claim 1 wherein a is 0.

8. A compound according to claim 1 wherein each $R^1$ is independently selected from the group consisting of H, OH, F, Cl, Br, $CO_2H$, $CONH_2$, $CH_2OH$, CN, $OCH_3$, and $OCHF_2$.

9. A compound according to claim 1 wherein one $R^1$ is H and the other $R^1$ is OH.

10. A compound according to claim 1 selected from the group consisting of:

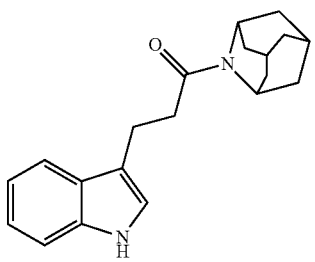

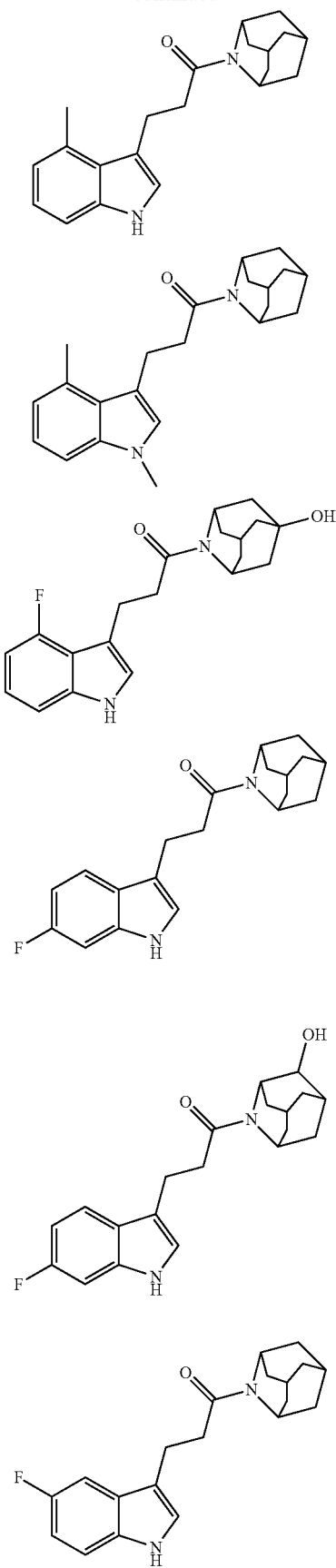
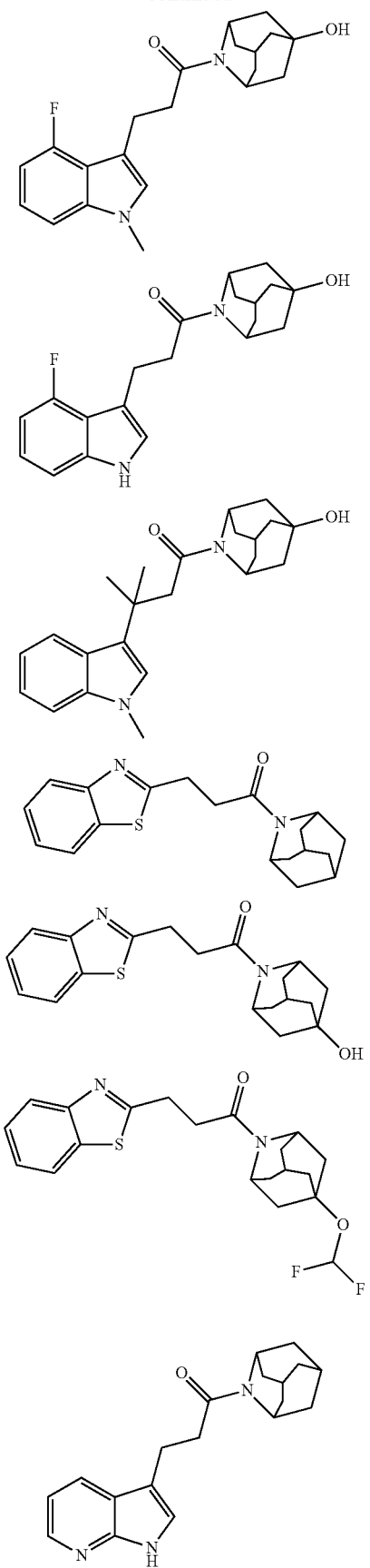

255
-continued
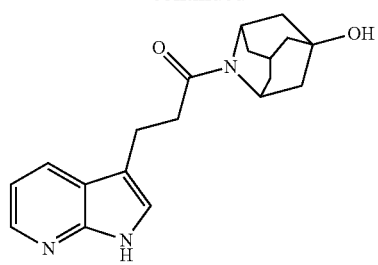
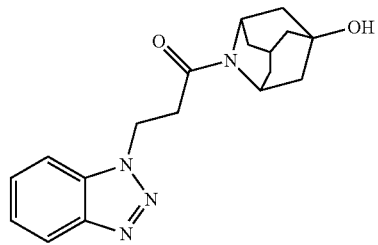
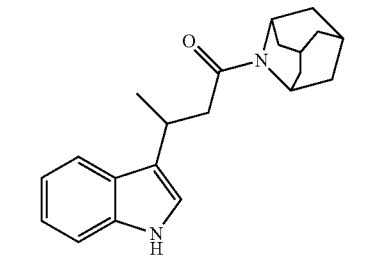
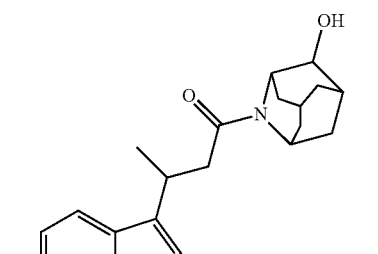
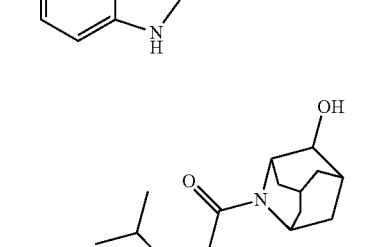
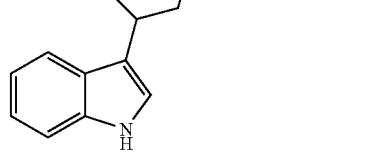
256
-continued
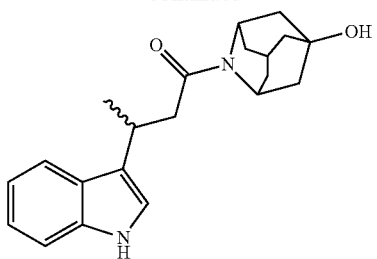
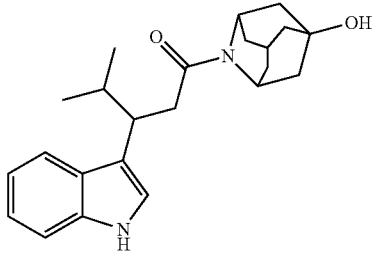
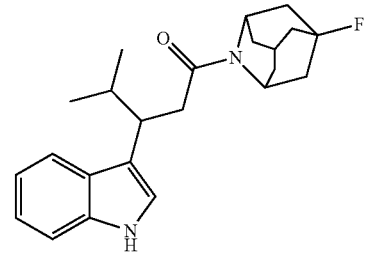
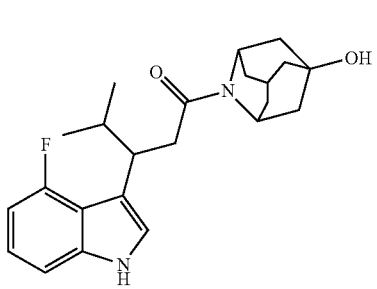
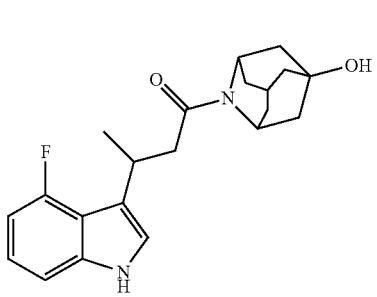
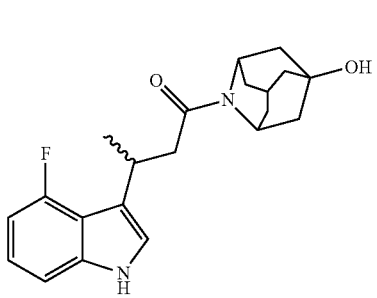

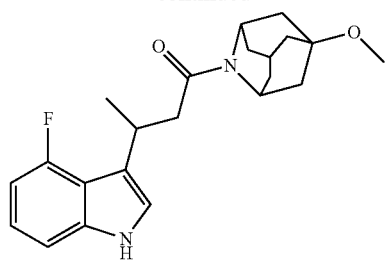
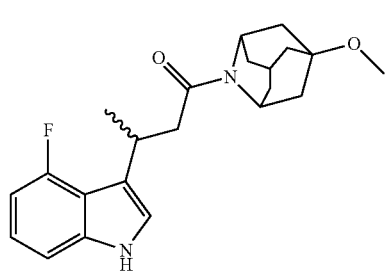
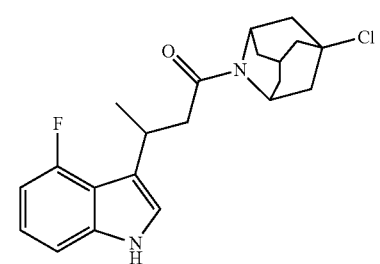
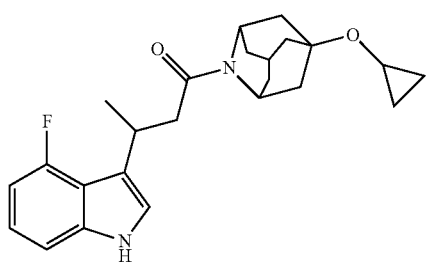
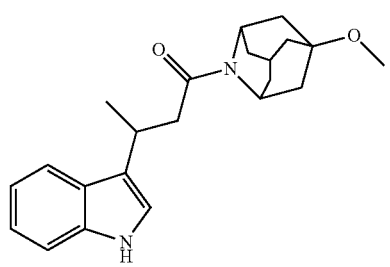
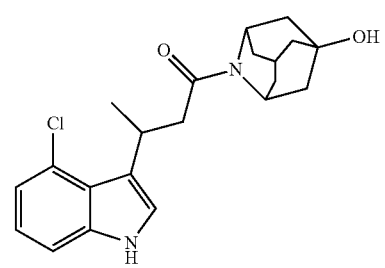
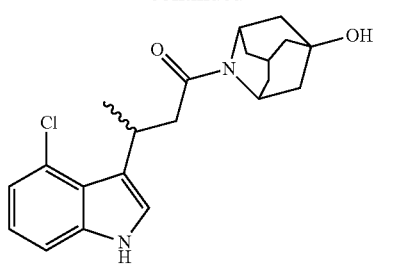
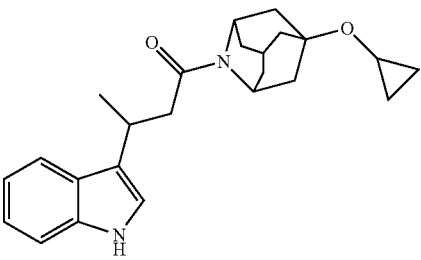
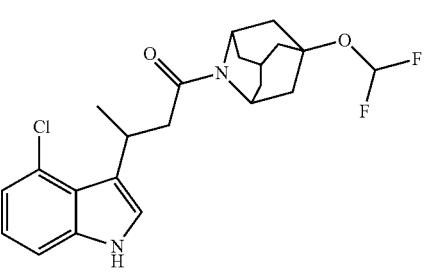
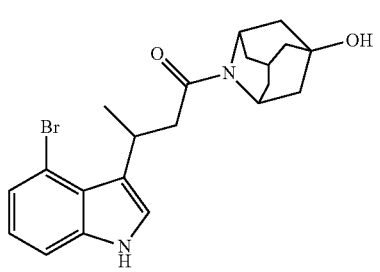
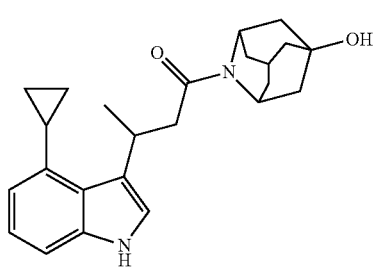
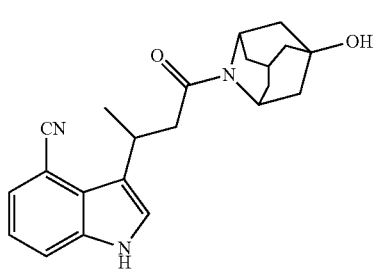

259
-continued
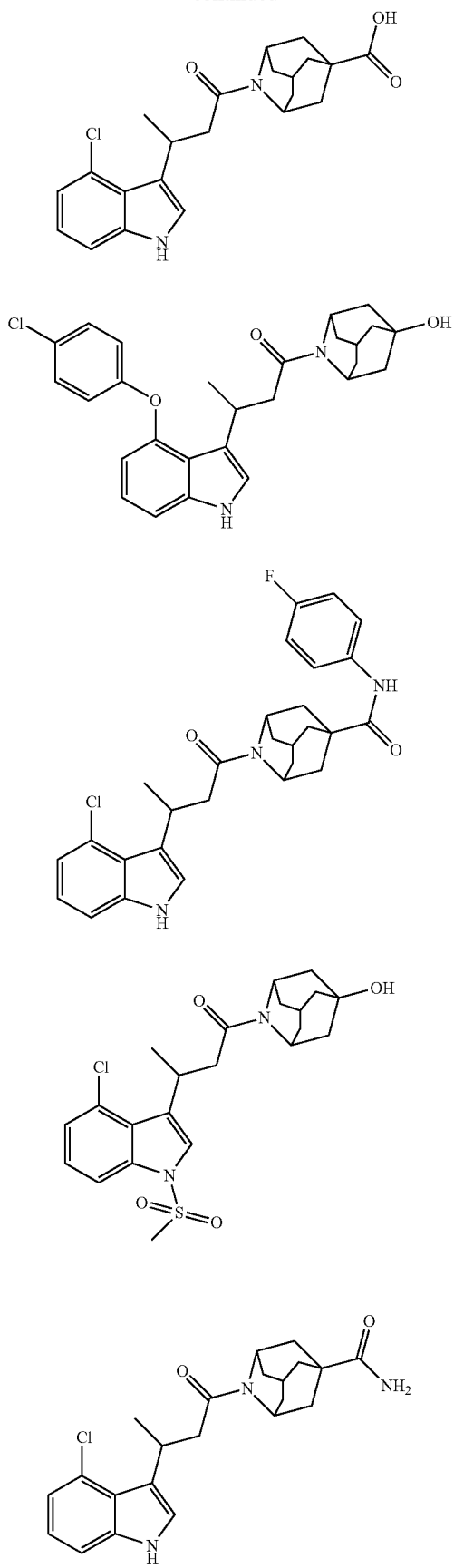
260
-continued
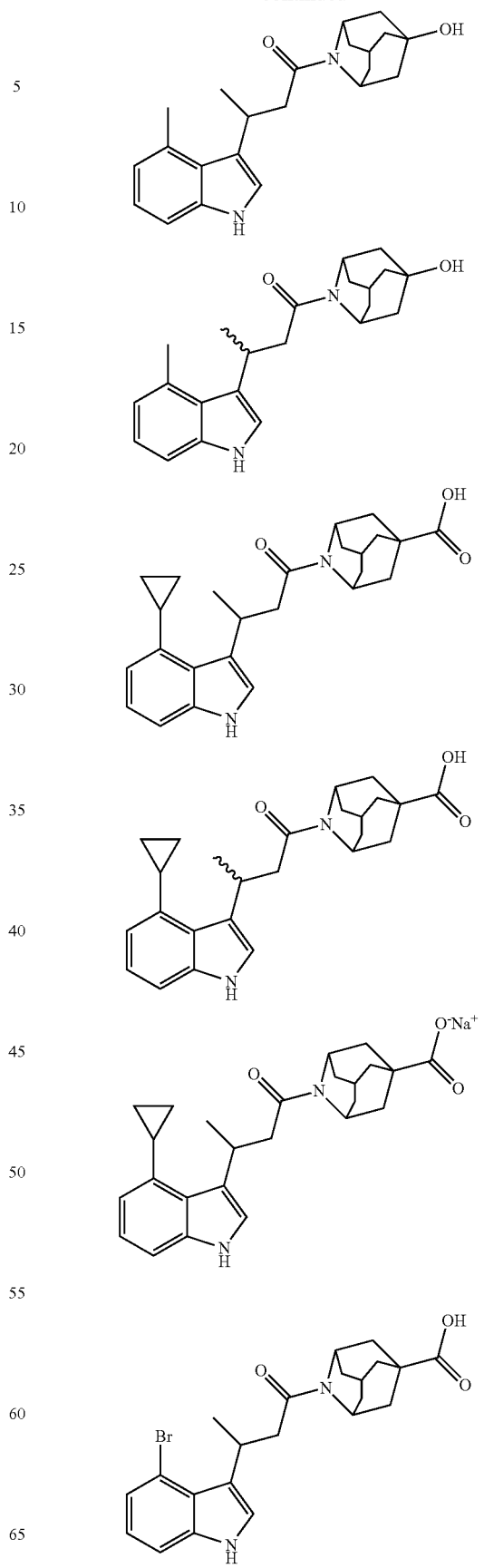

261
-continued
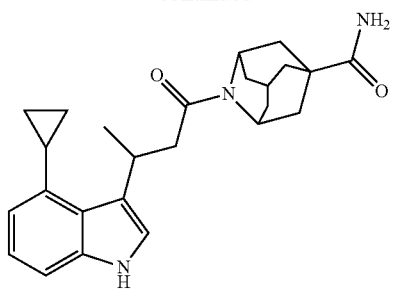
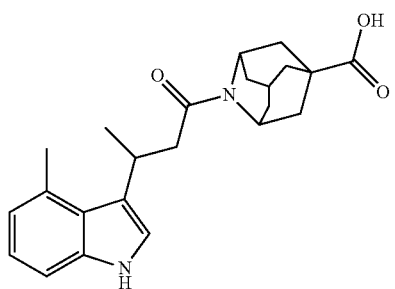
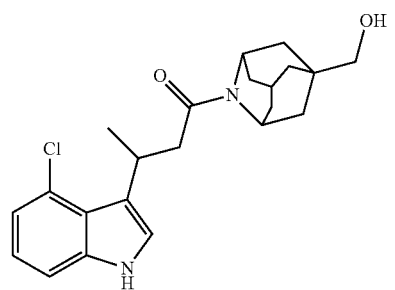
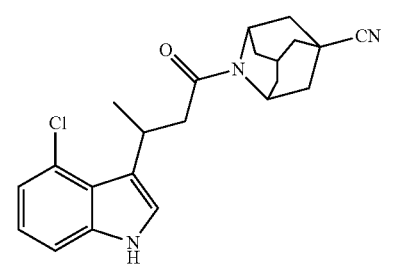
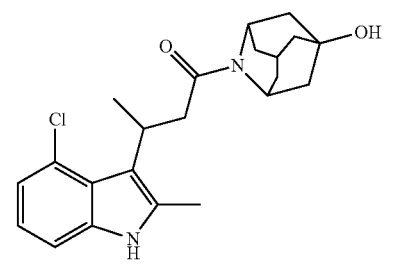
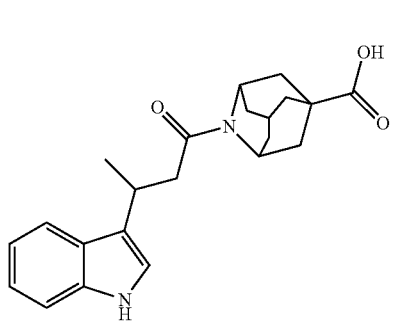
262
-continued
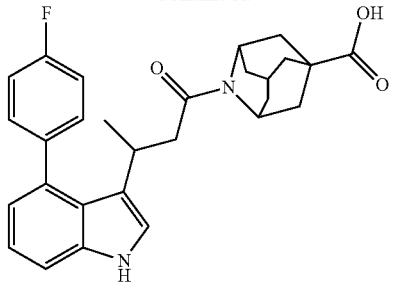
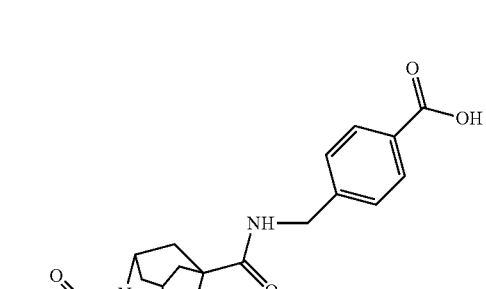
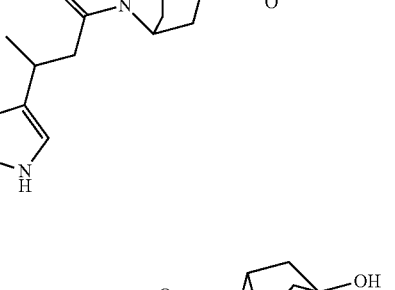
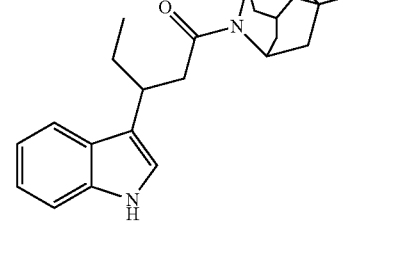
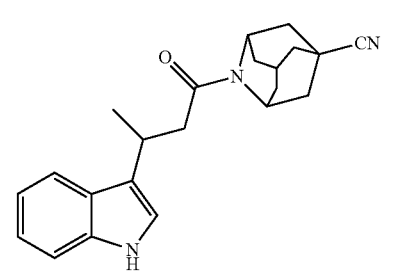
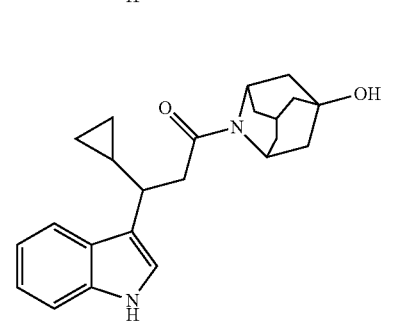

263
-continued
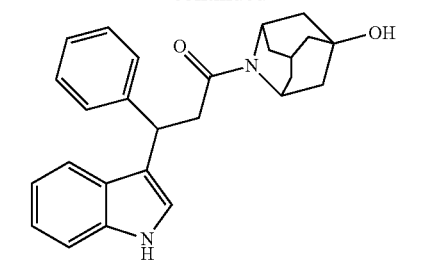
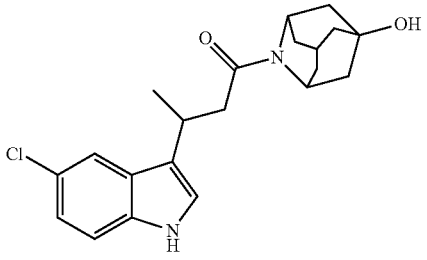
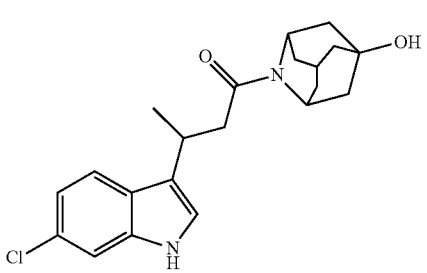
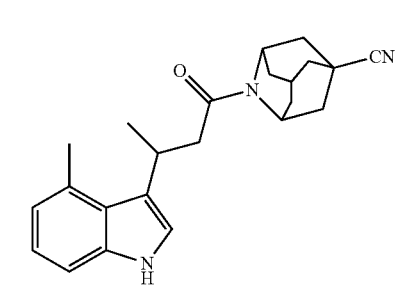
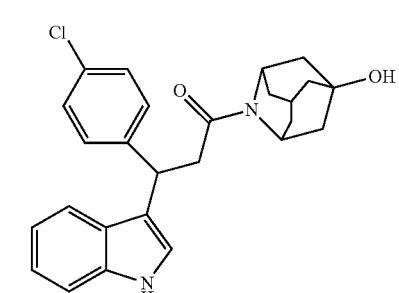
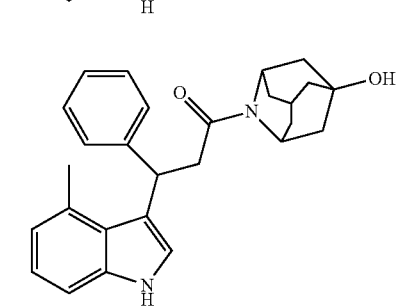
264
-continued
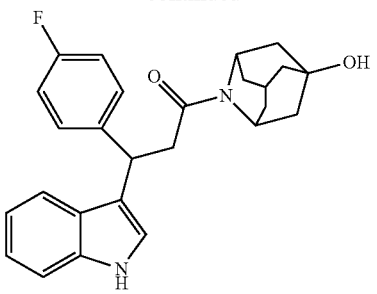
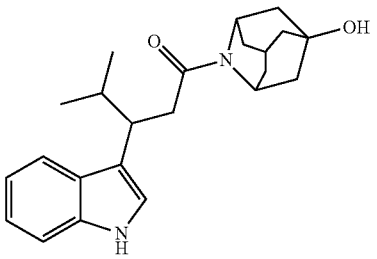
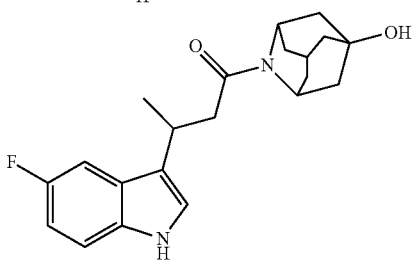
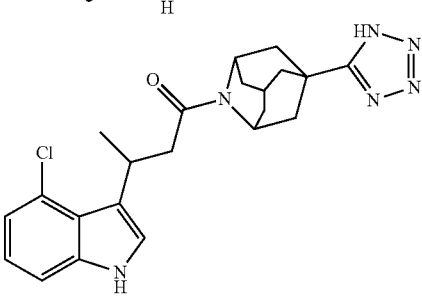
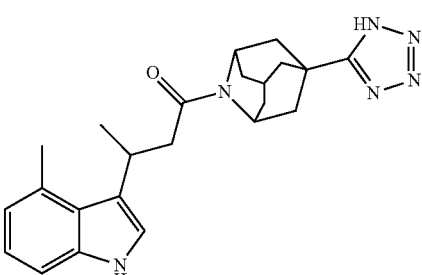
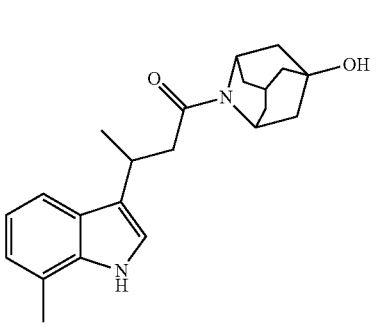

-continued
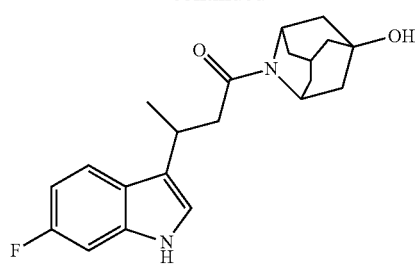
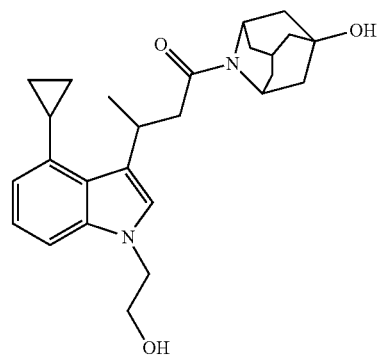
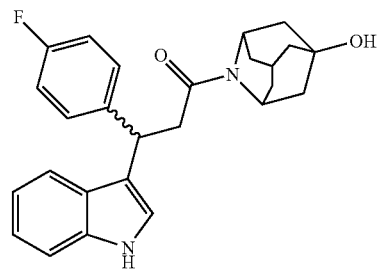
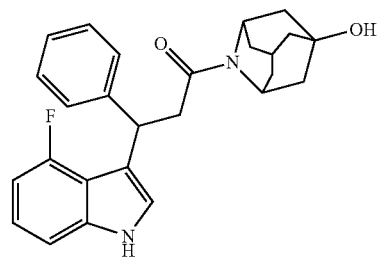
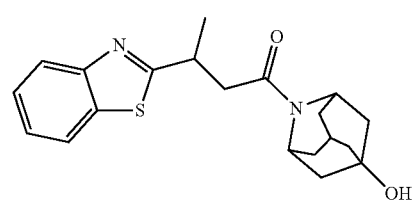
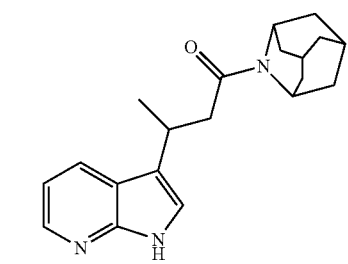
-continued
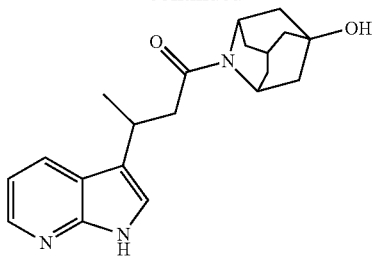
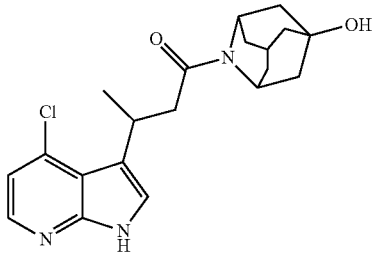
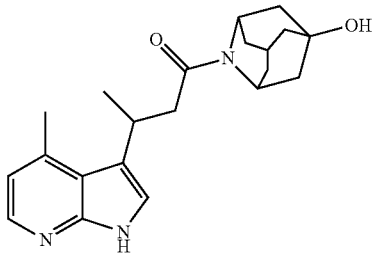
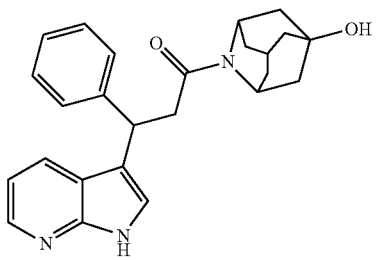
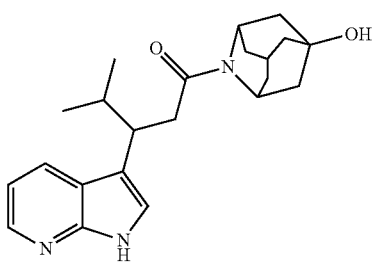
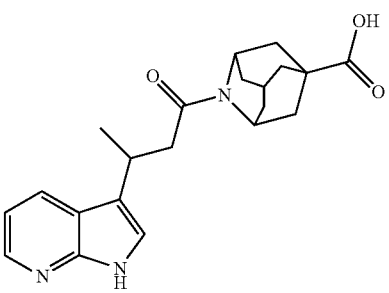

267
-continued
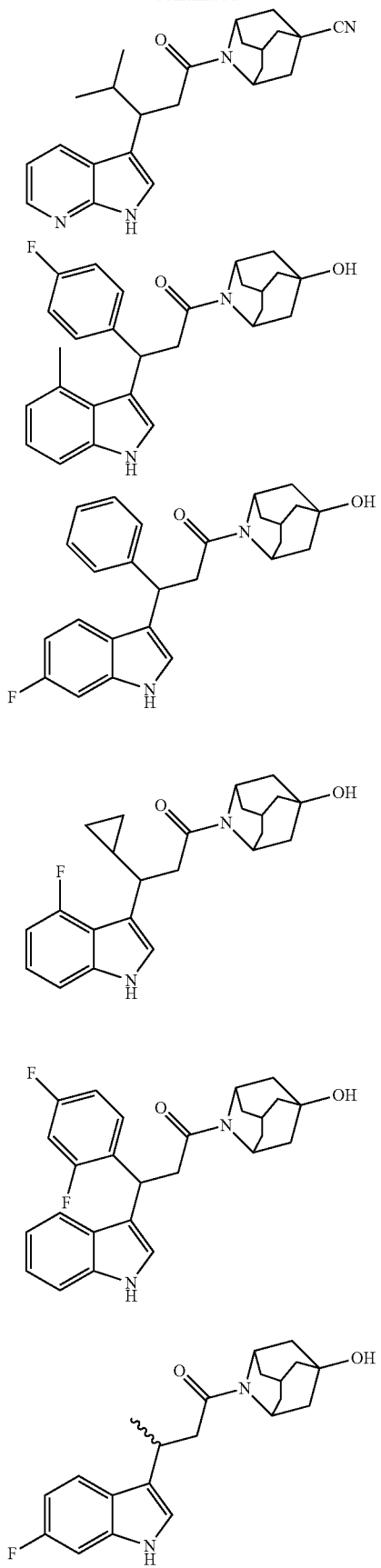
268
-continued
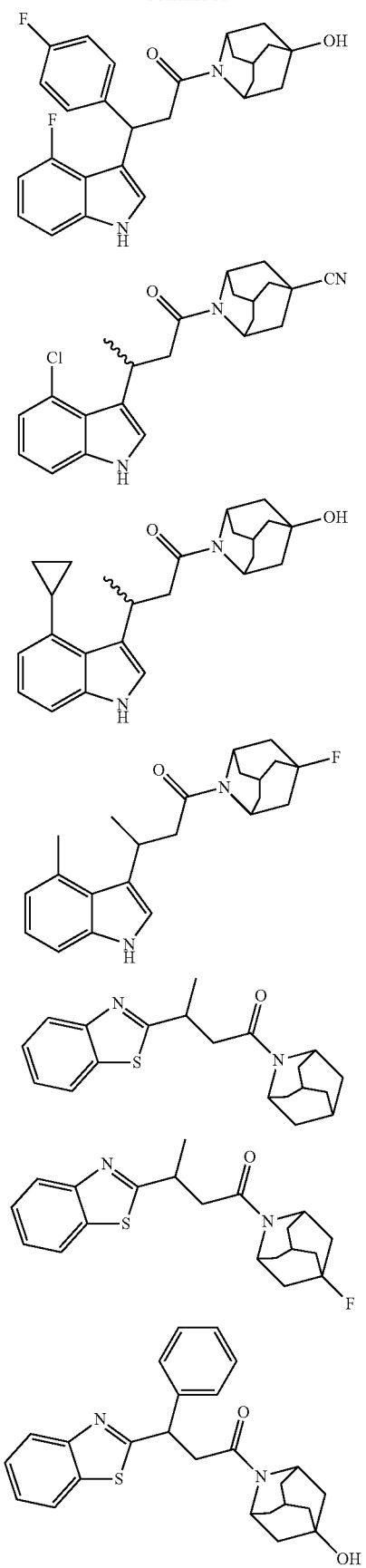

269
-continued
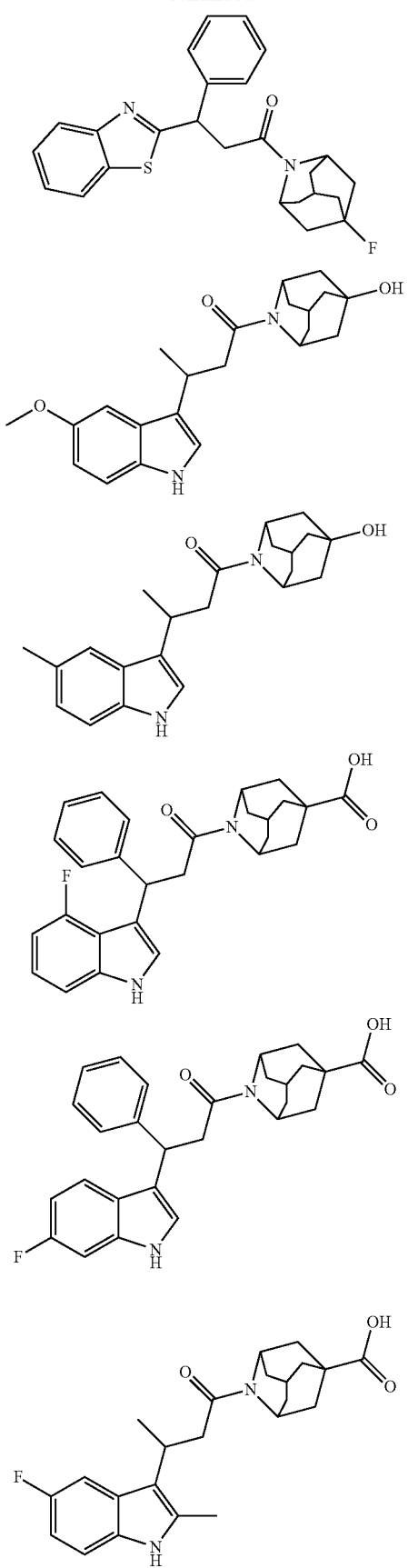
270
-continued
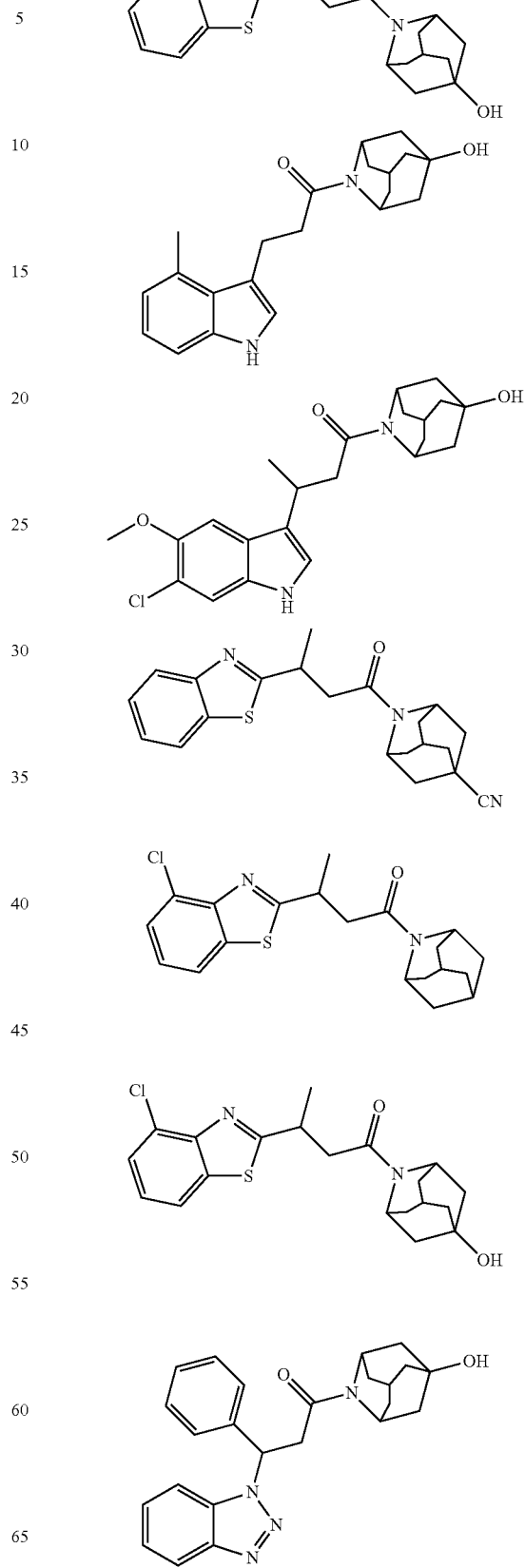

271
-continued
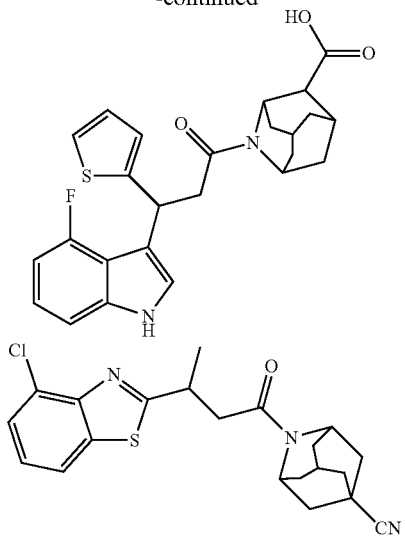
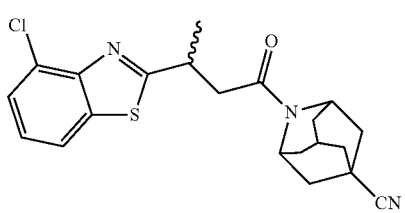
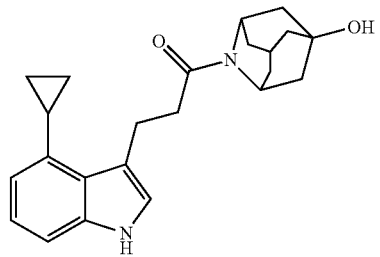
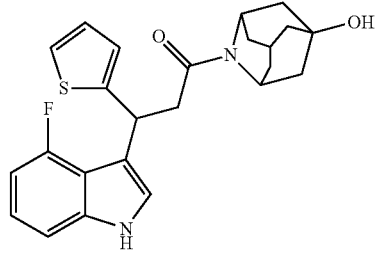
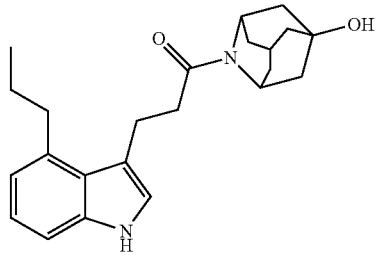
272
-continued
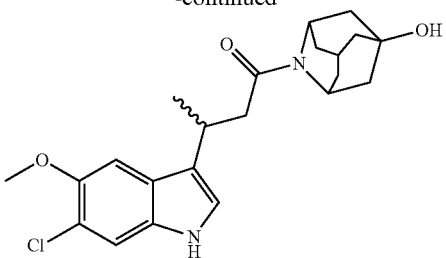
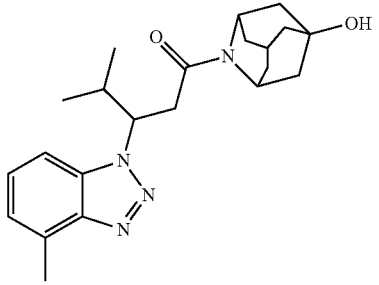
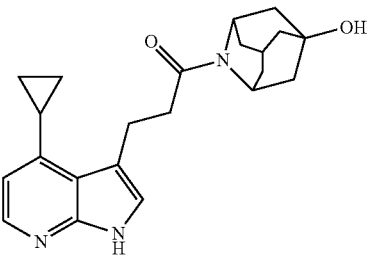
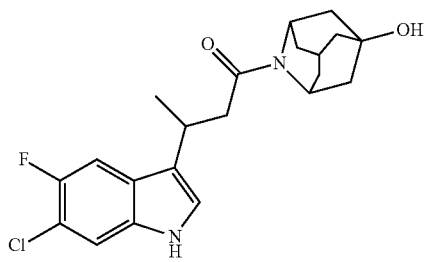
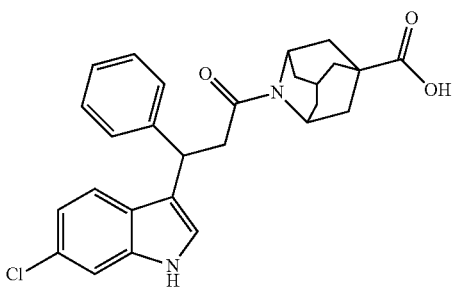
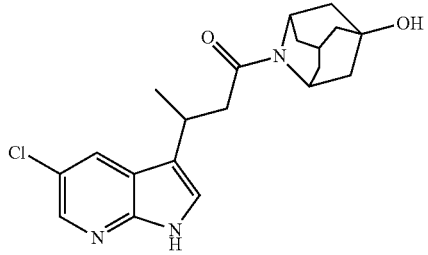

273
-continued
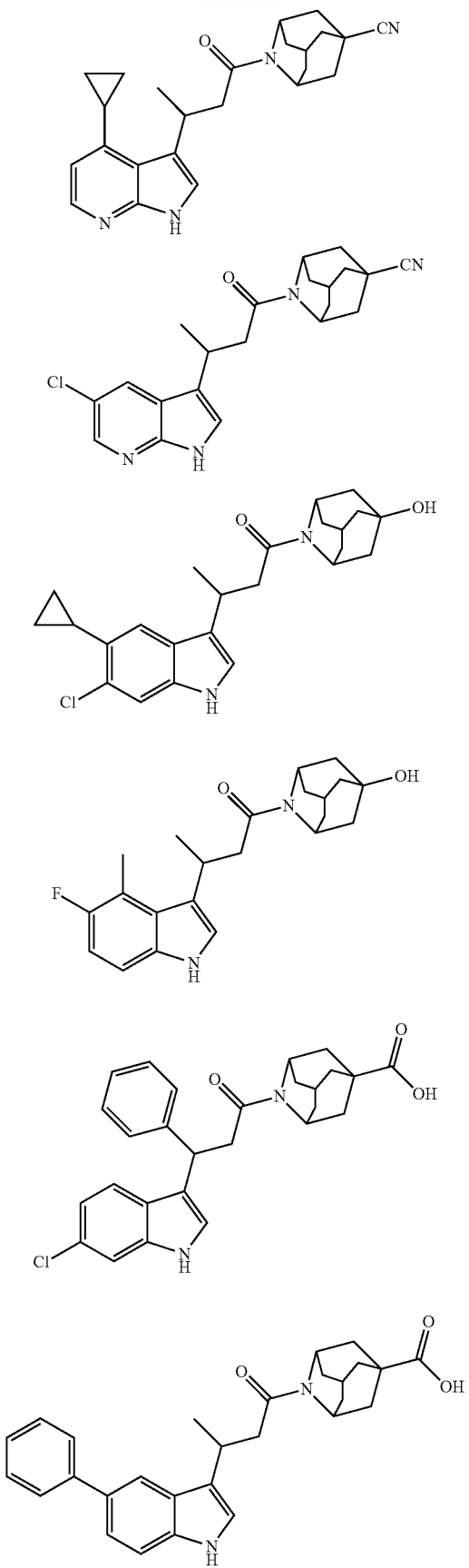
274
-continued
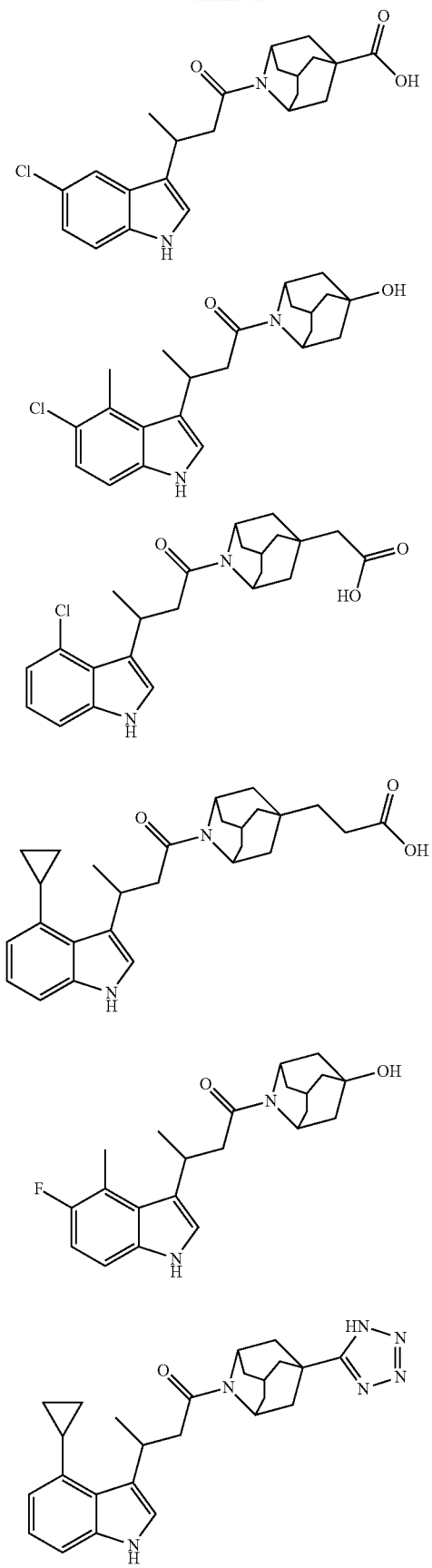

275
-continued
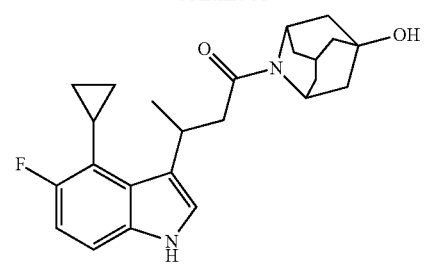
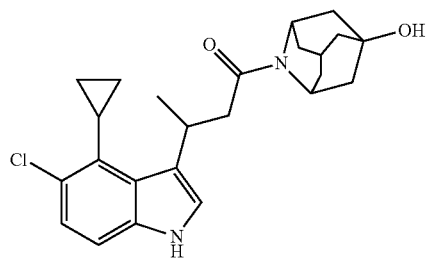
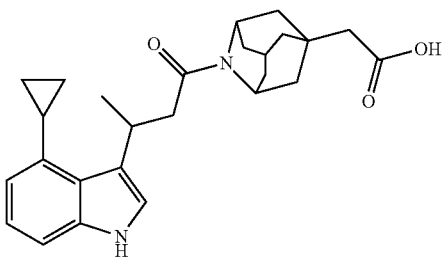
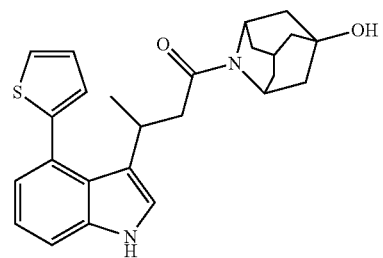
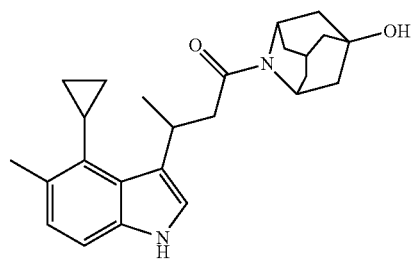
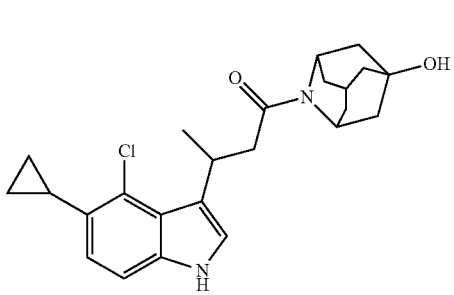
276
-continued
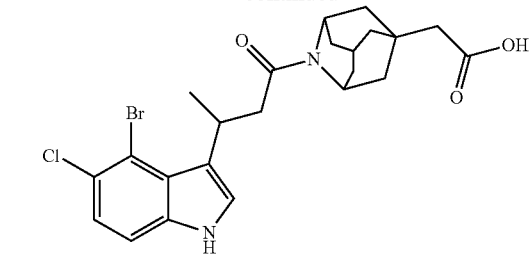
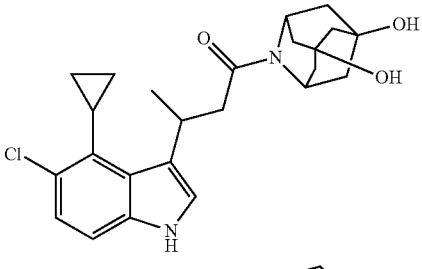
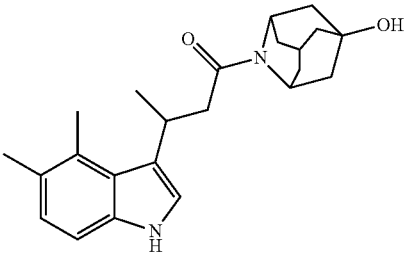
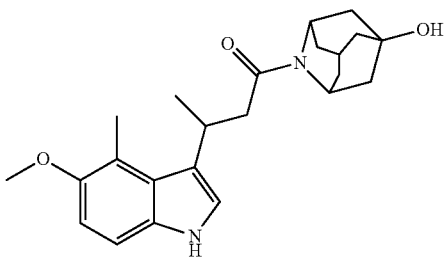
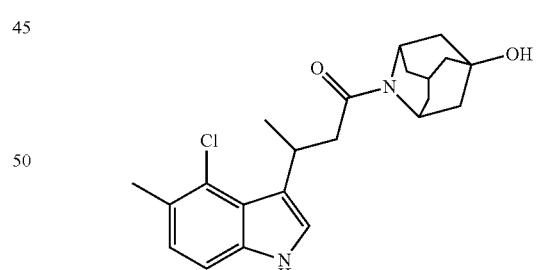
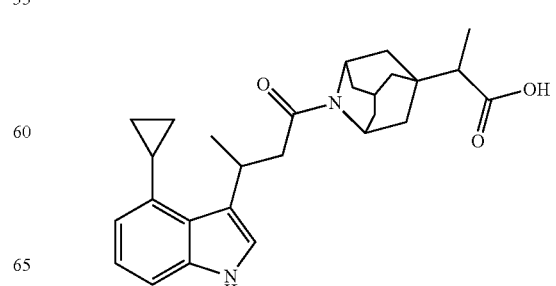

277
-continued
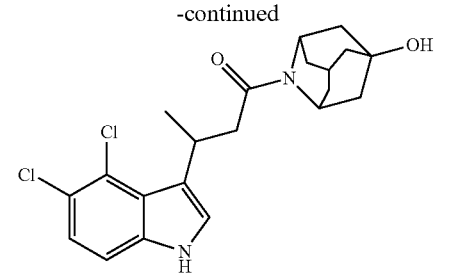
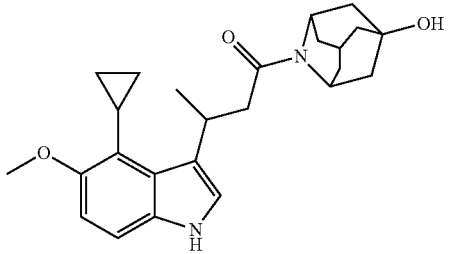
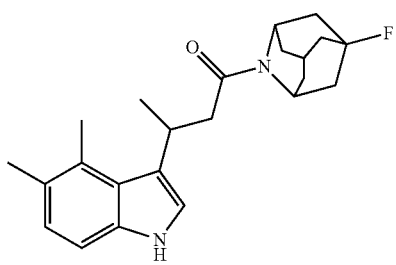
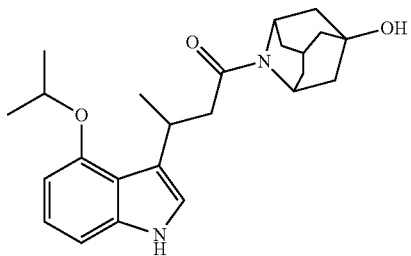
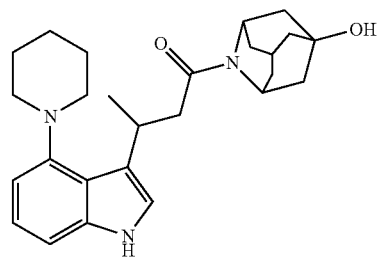
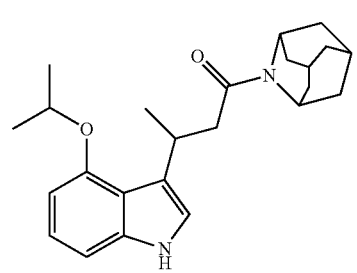
278
-continued
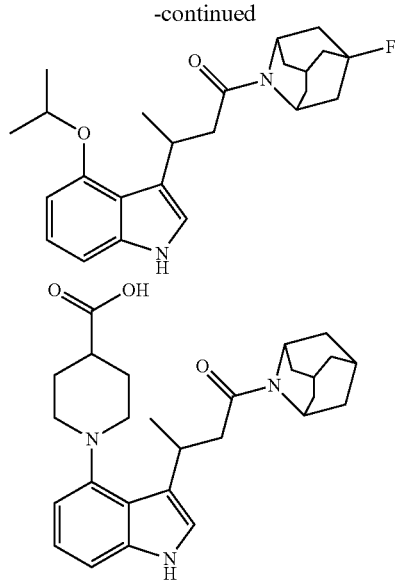
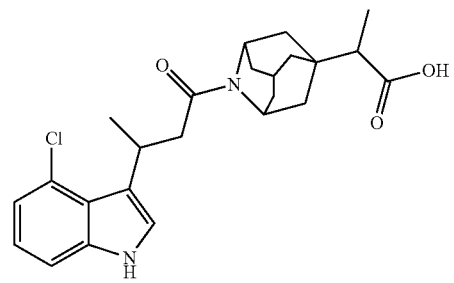
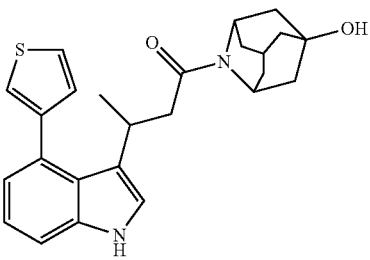
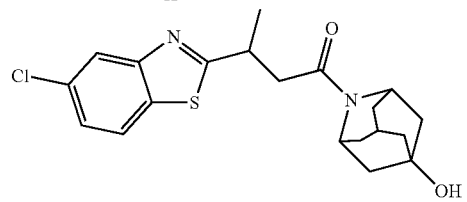
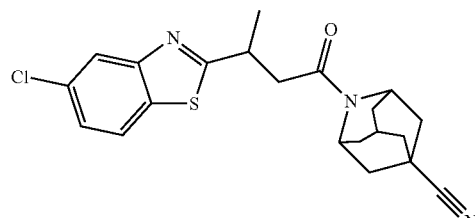
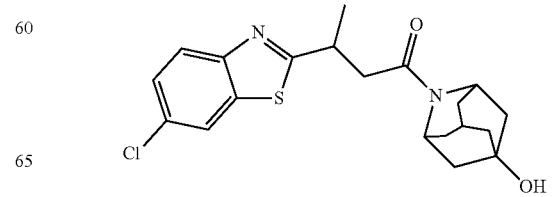

279
-continued
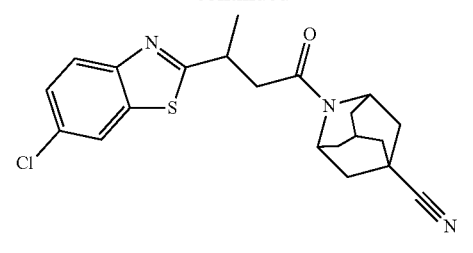
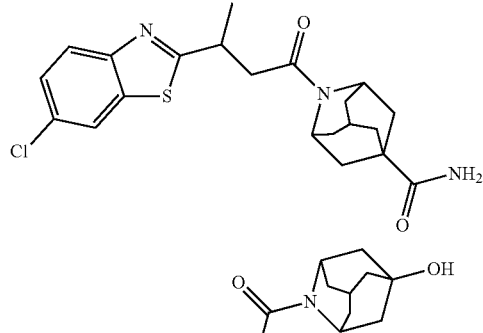
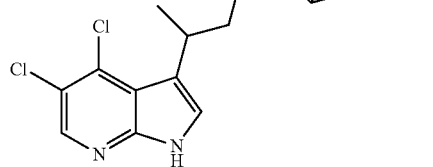
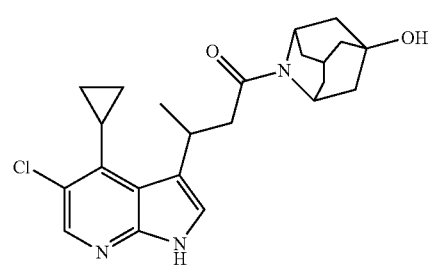
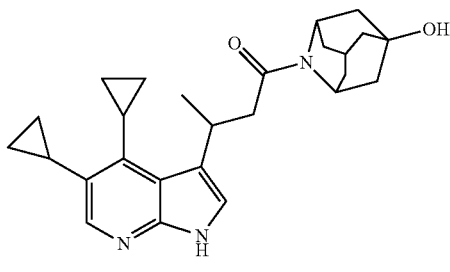
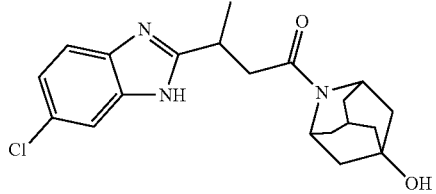
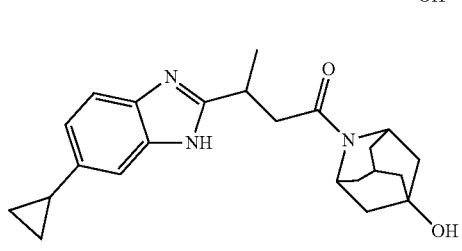
280
-continued
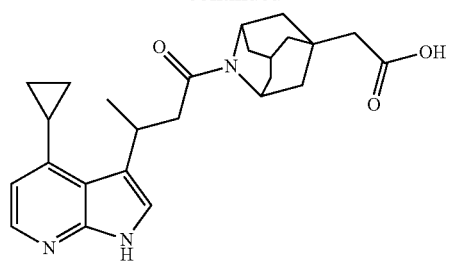
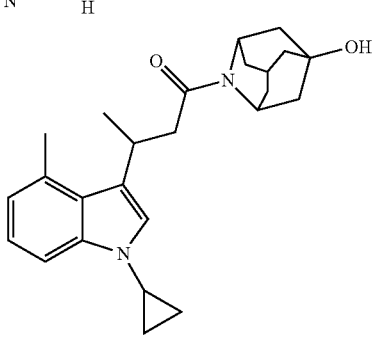
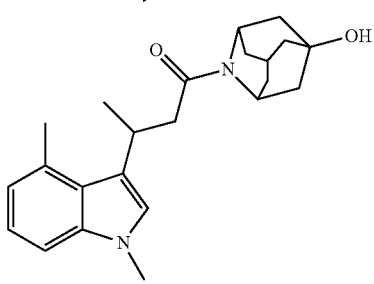
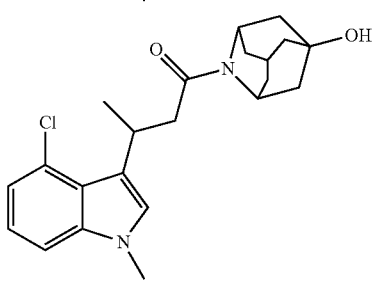
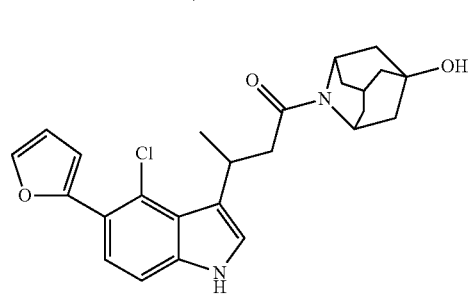
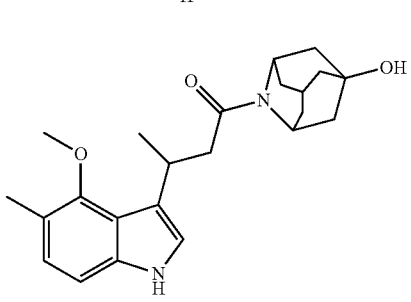

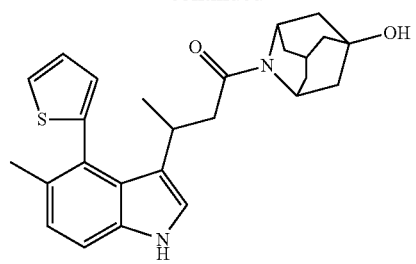
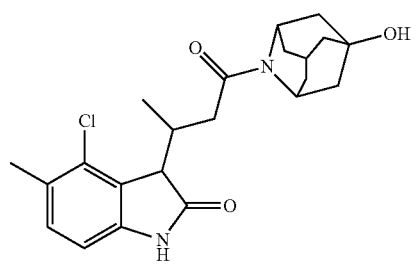
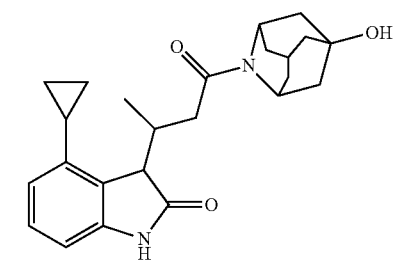
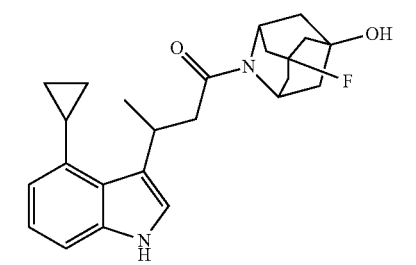
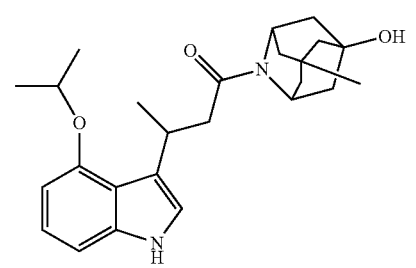
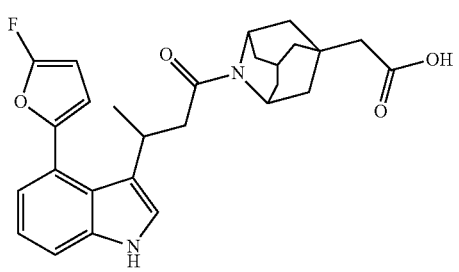
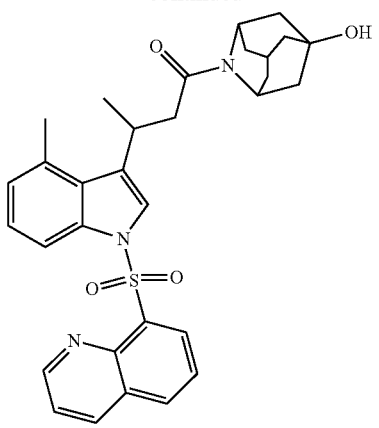
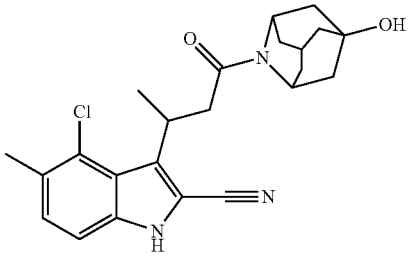
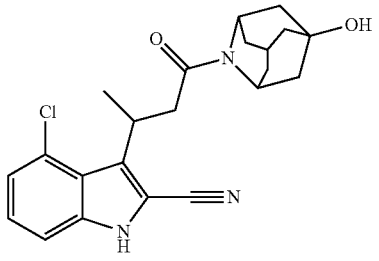
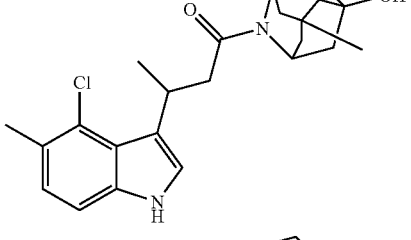
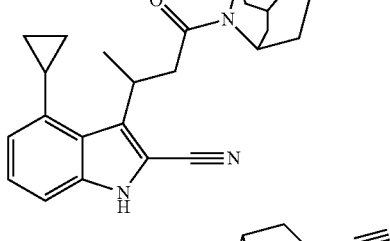
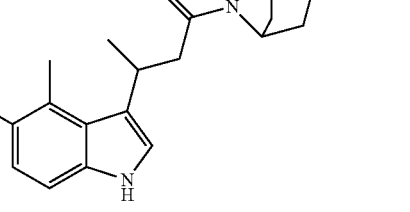

283
-continued
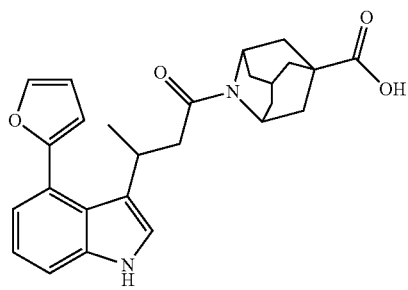
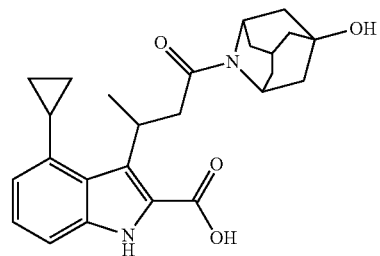
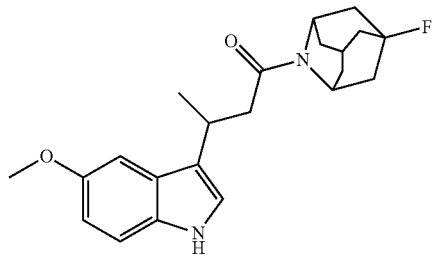
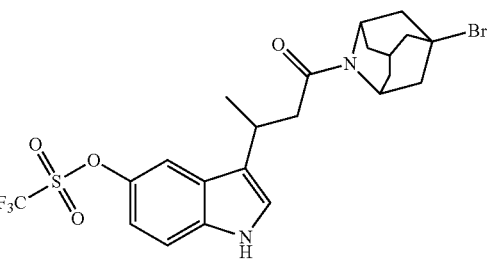
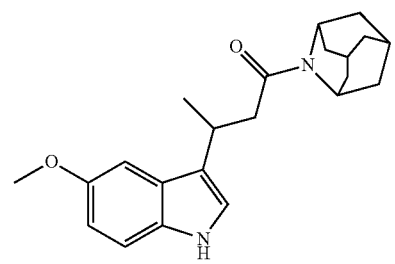
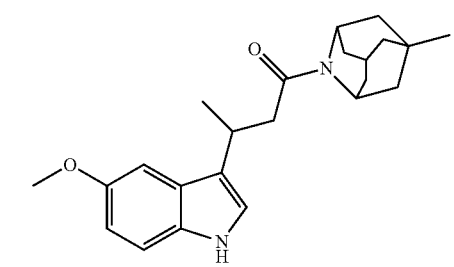
284
-continued
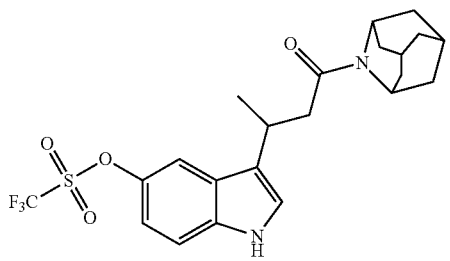
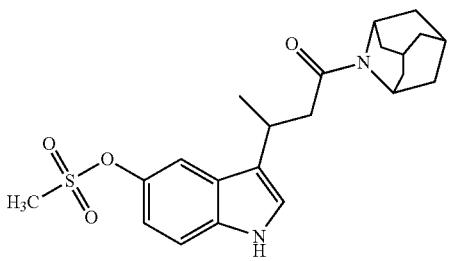
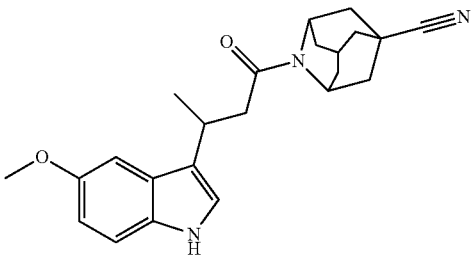
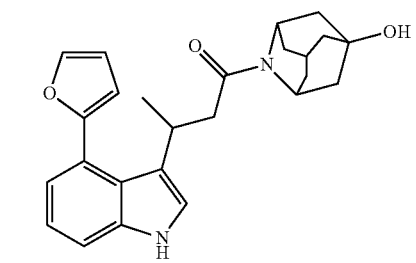
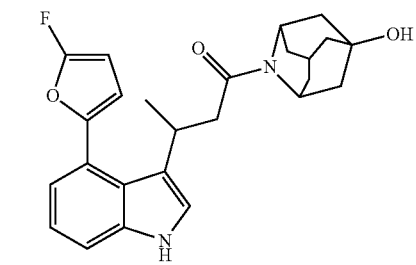
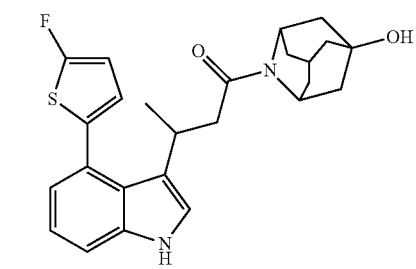

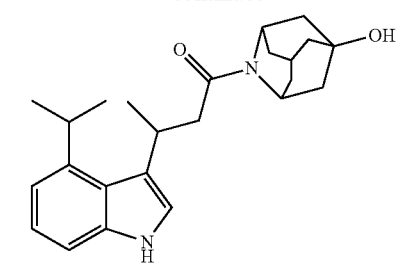
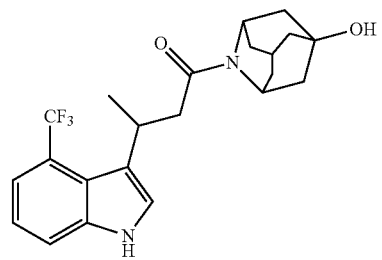
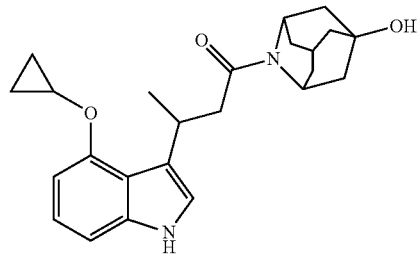
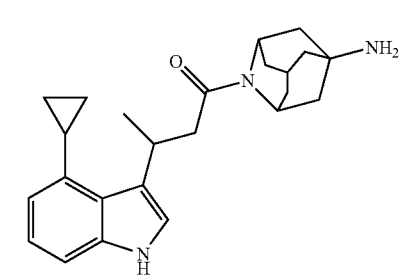
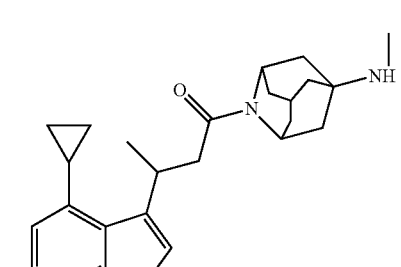
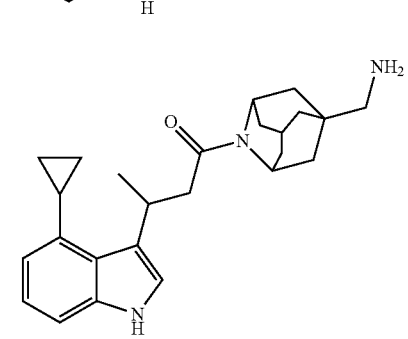
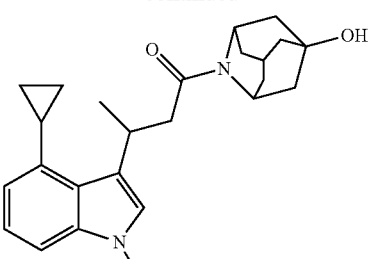
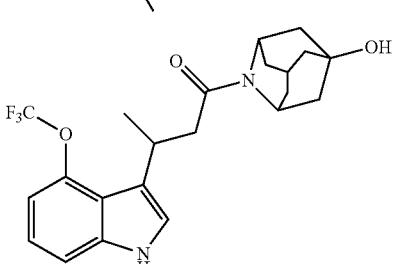
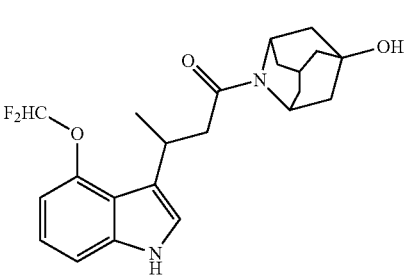
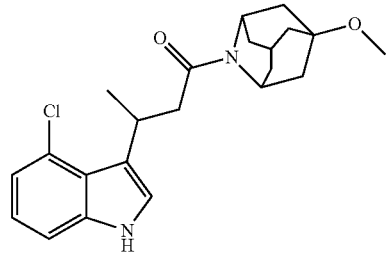
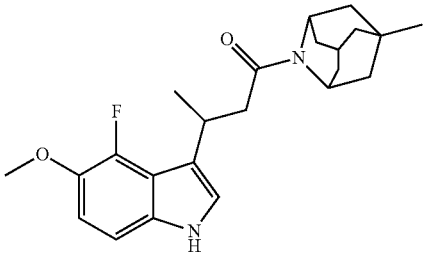
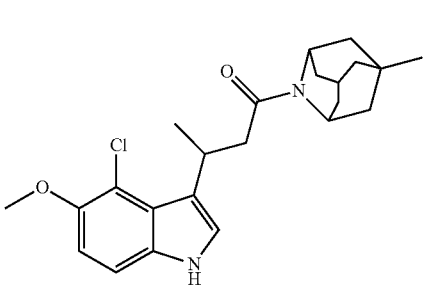

287
-continued
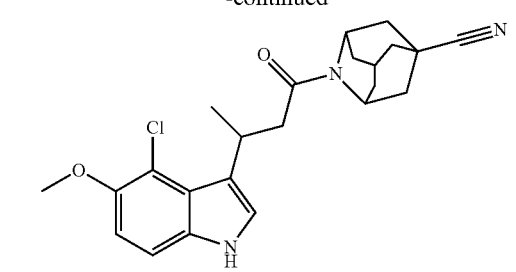
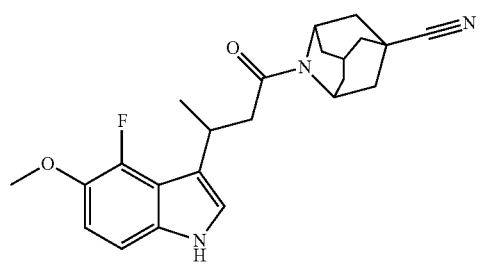
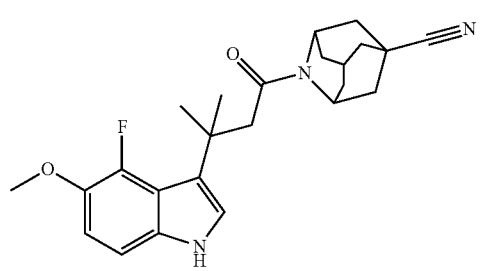
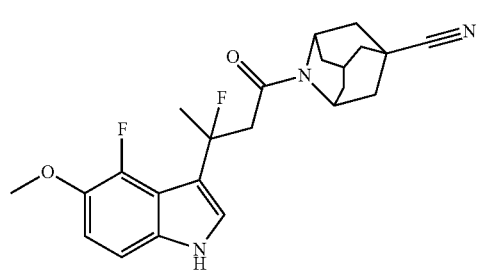
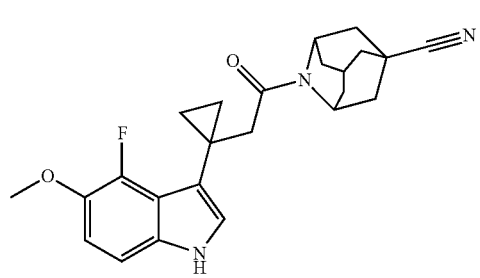
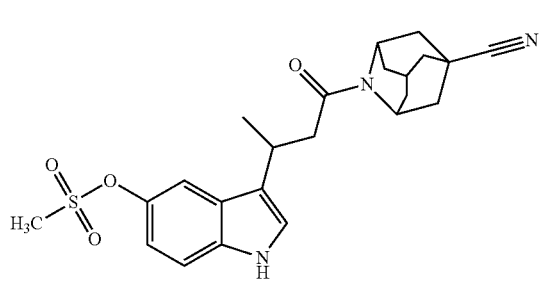
288
-continued
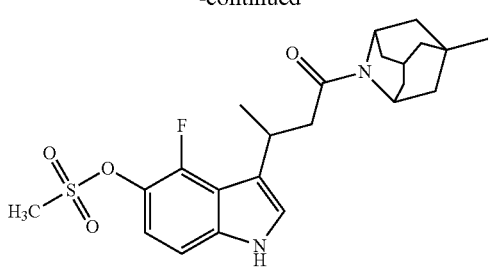
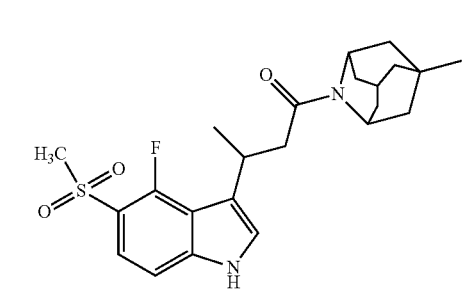
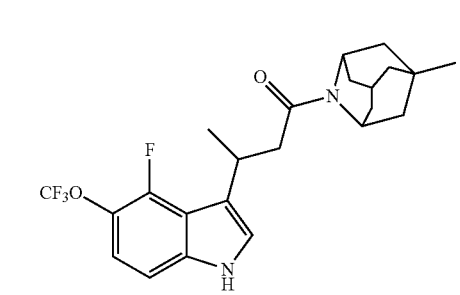
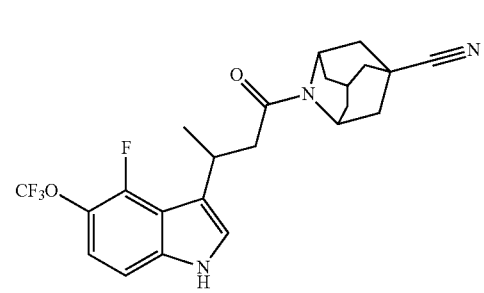
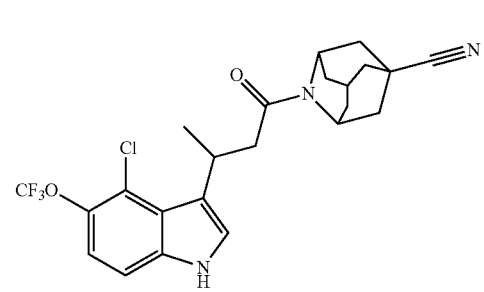
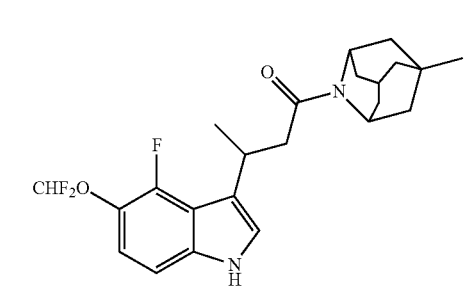

289
-continued
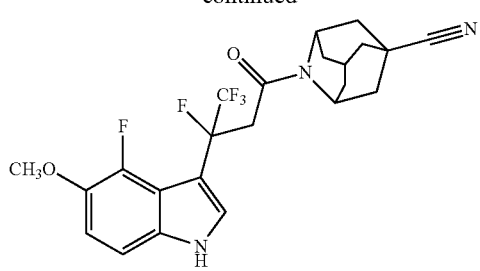
290
-continued
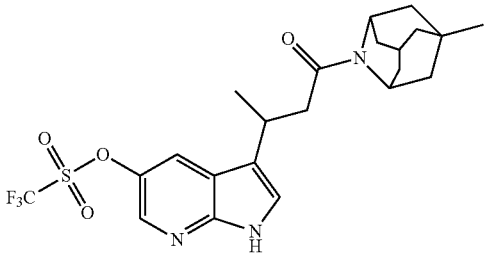
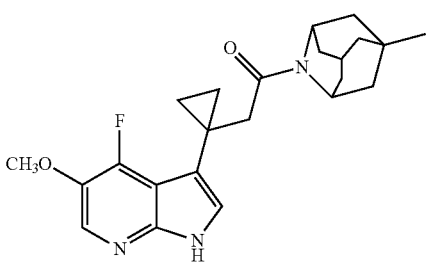
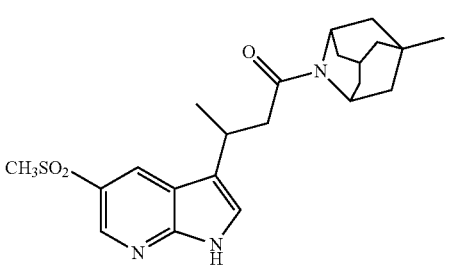
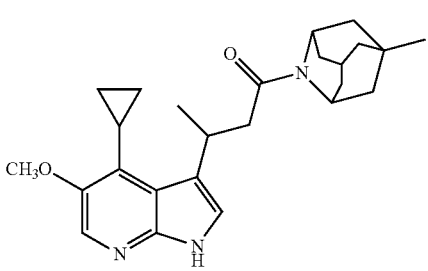
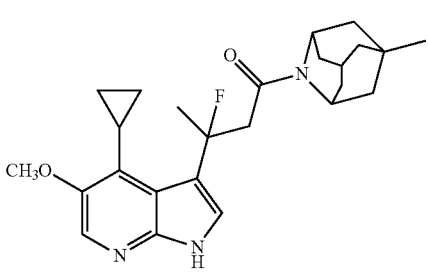
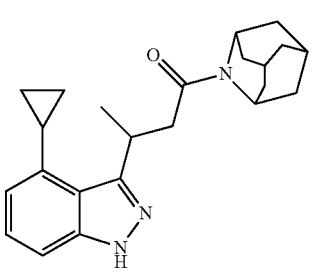

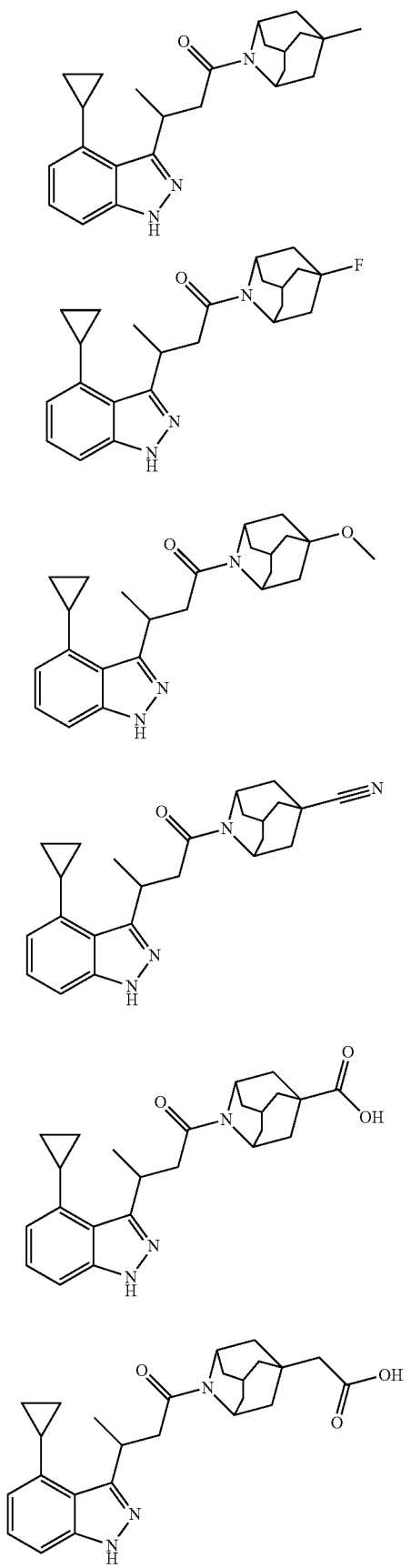
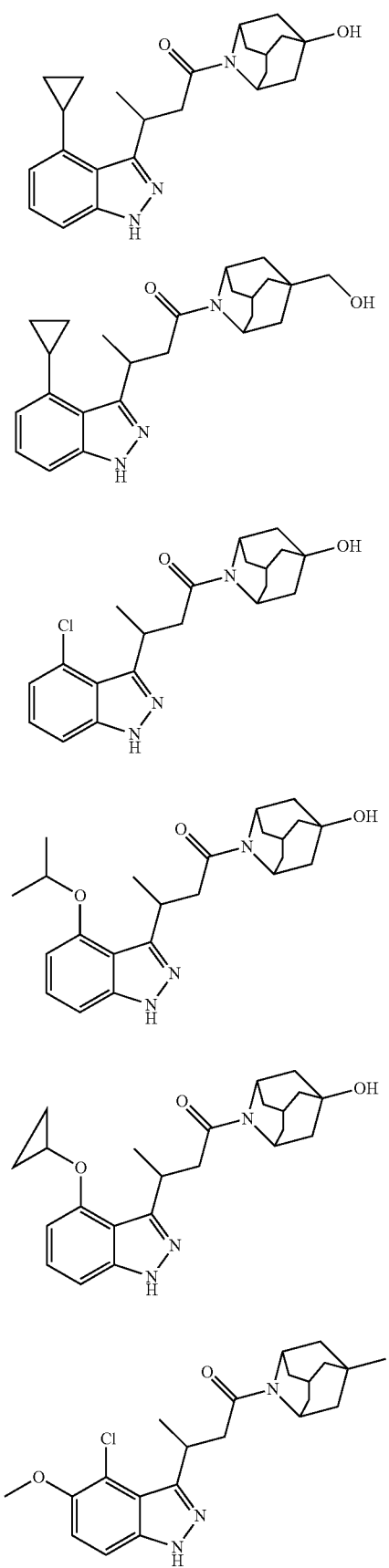

293
-continued
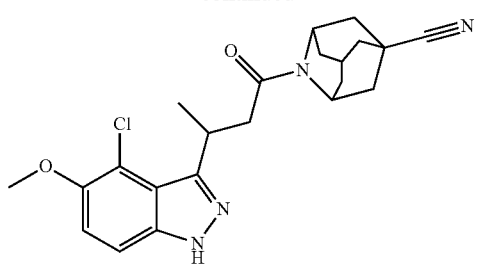
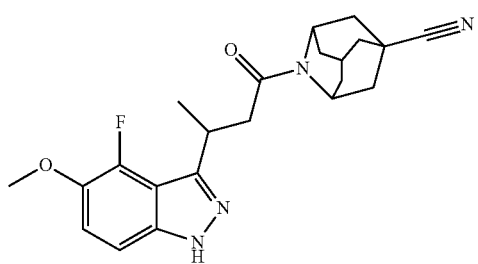
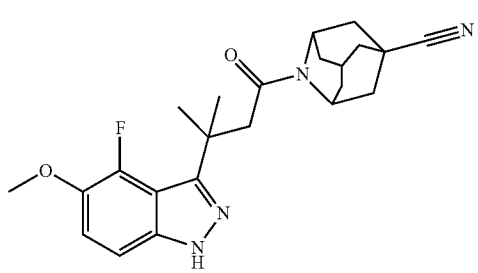
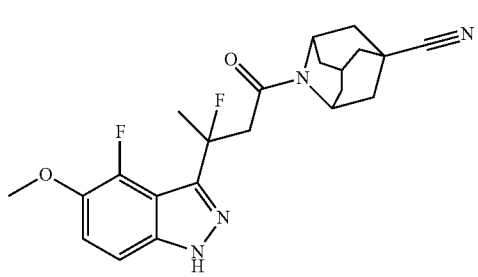
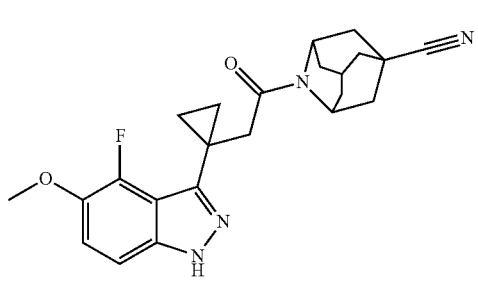
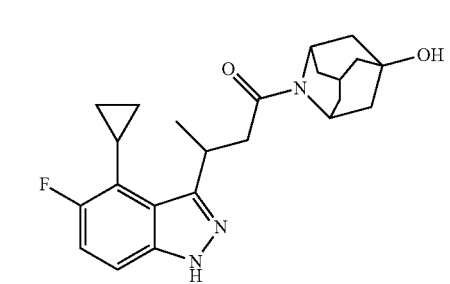
294
-continued
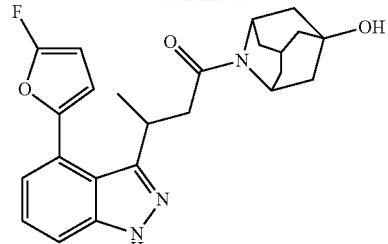
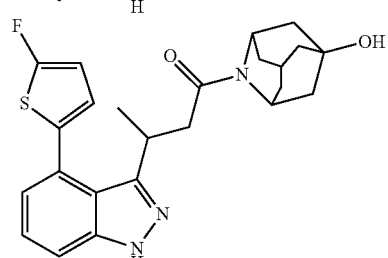
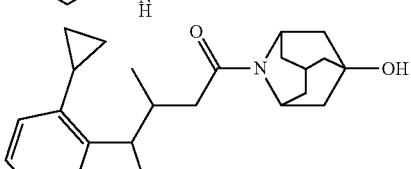
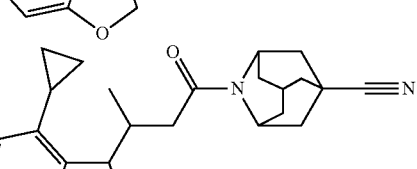
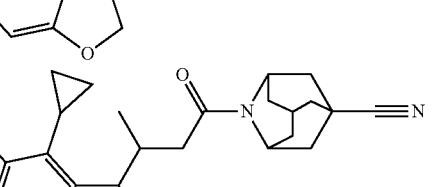
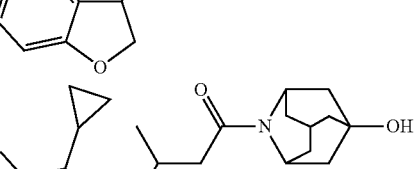
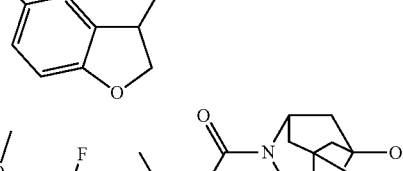
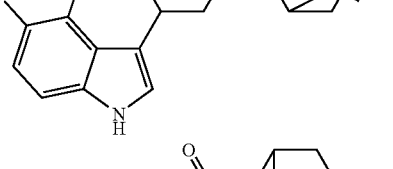
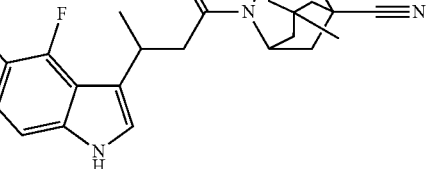

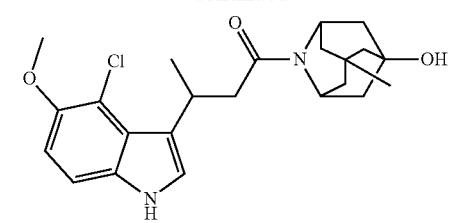
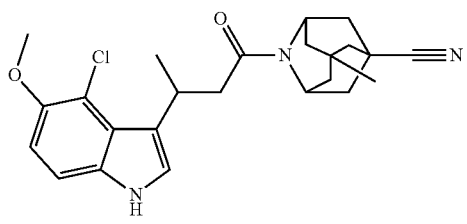
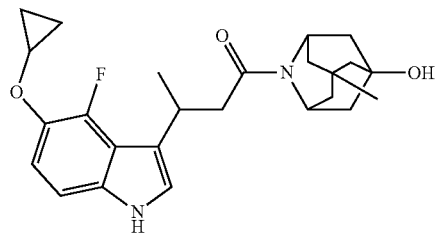
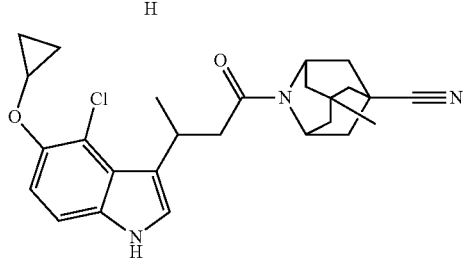
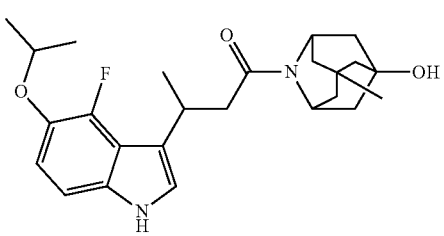
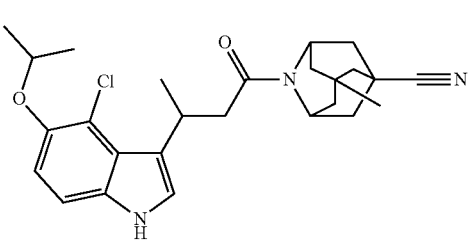
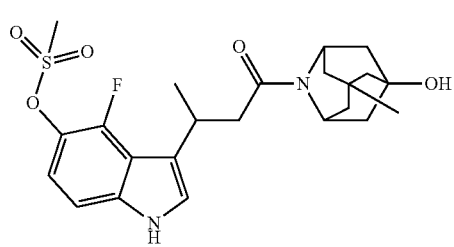
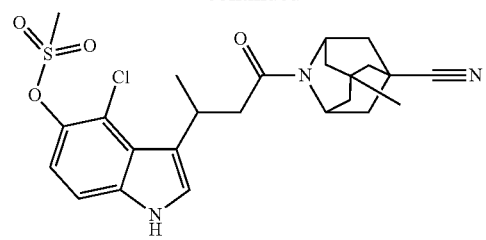
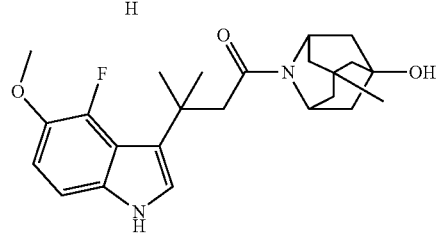
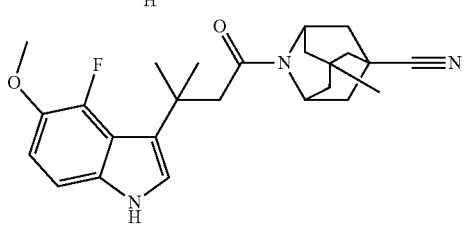
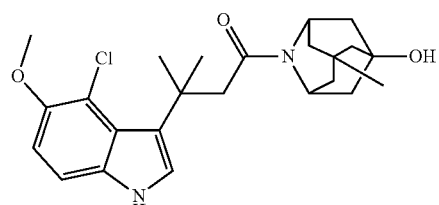
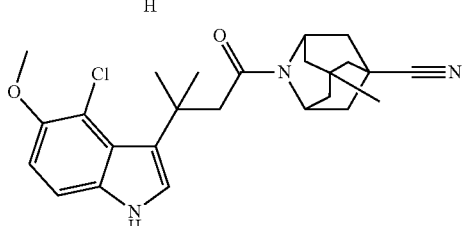
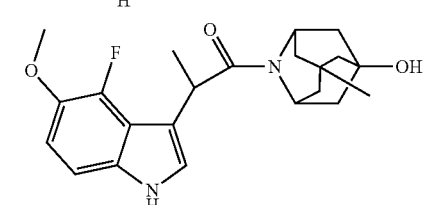
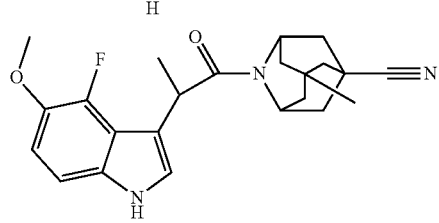
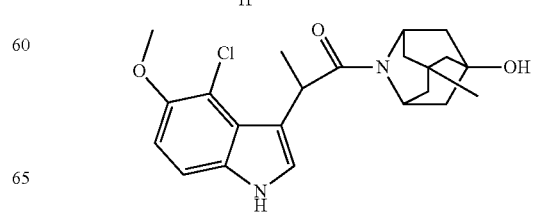

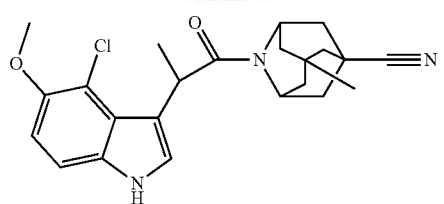
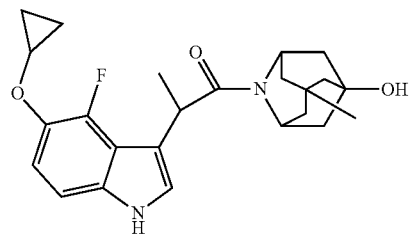
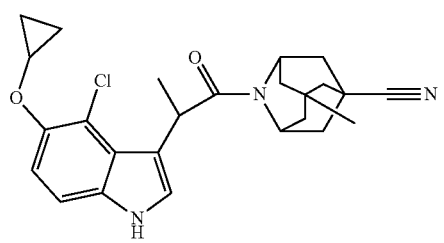
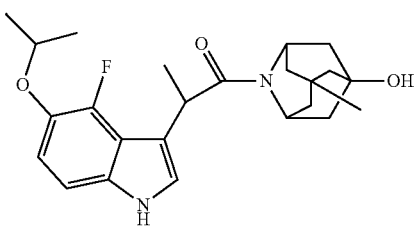
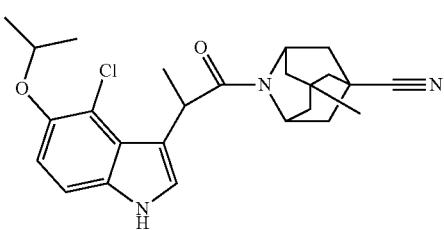
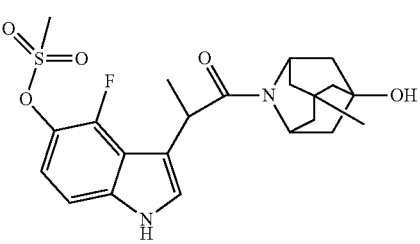
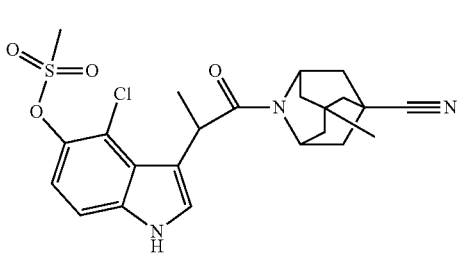
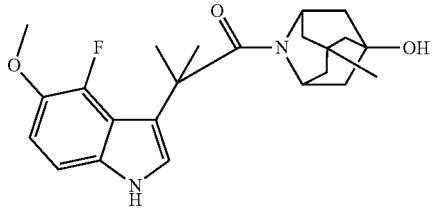
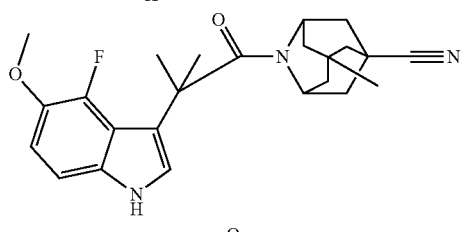
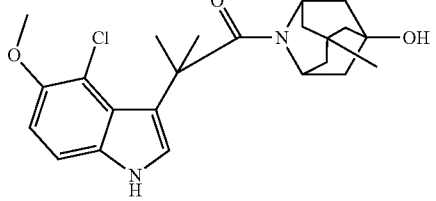
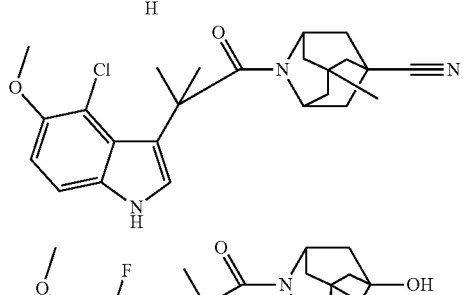
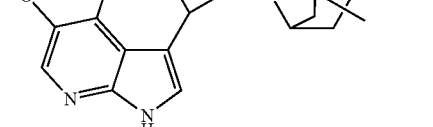
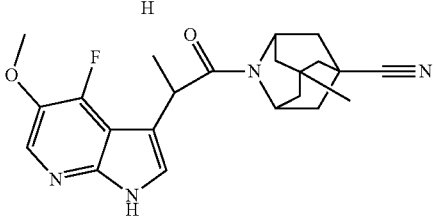
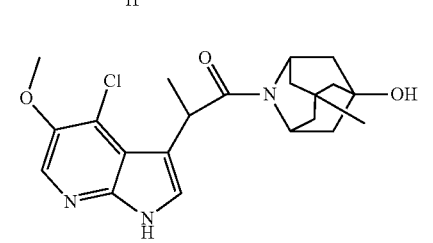

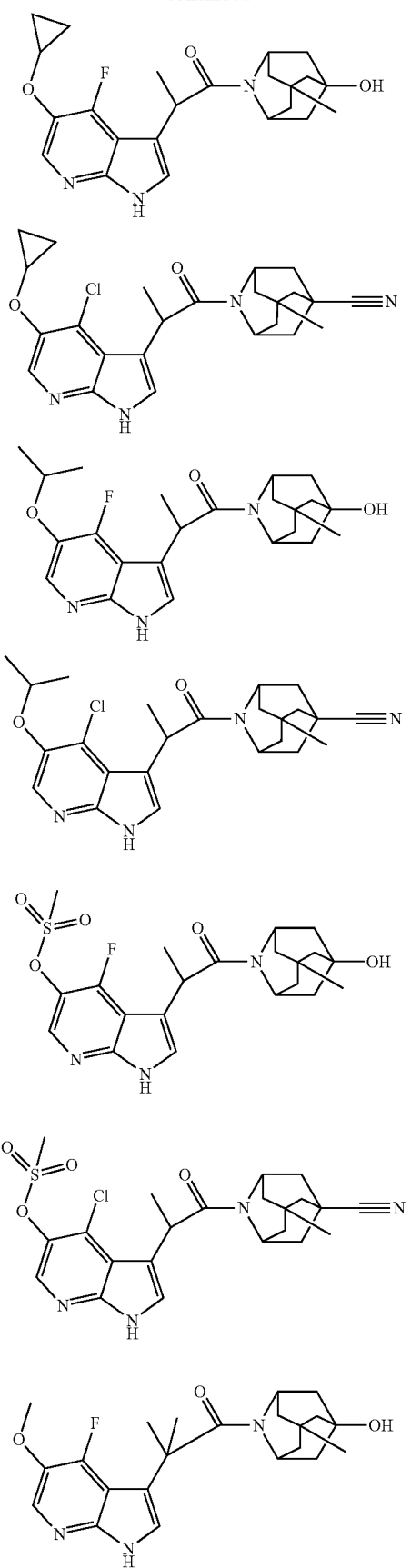
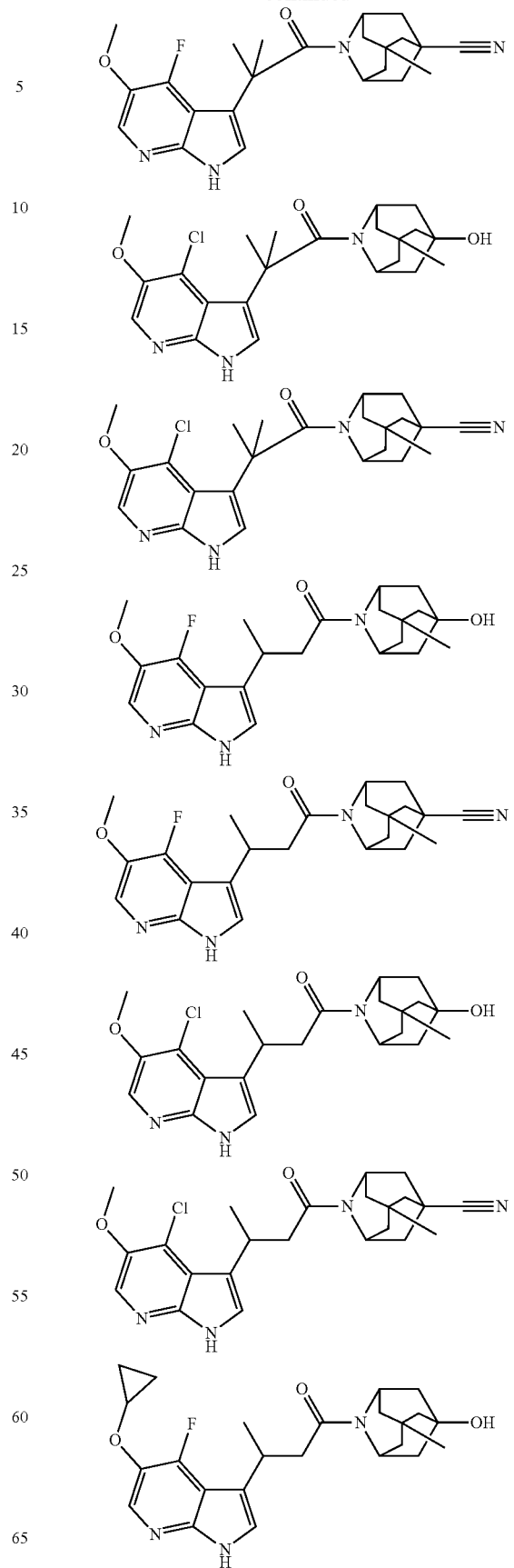

301
-continued
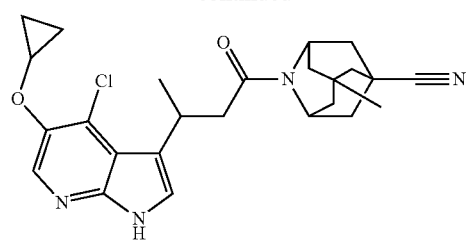
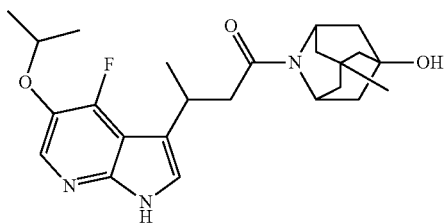
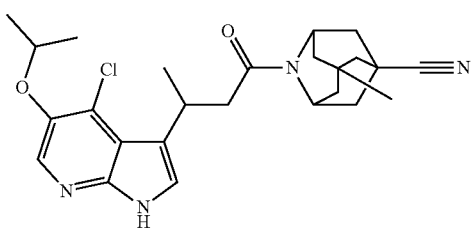
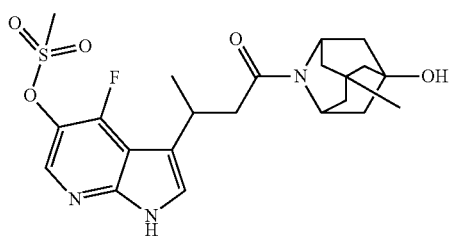
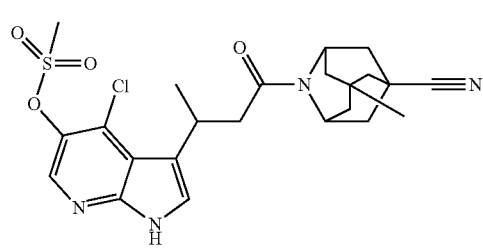
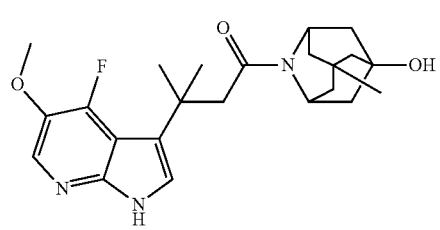
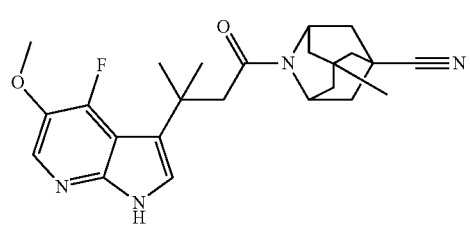
302
-continued
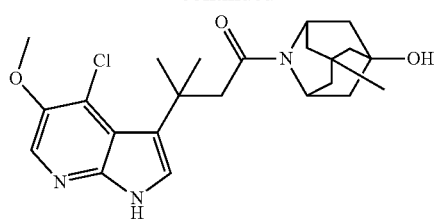
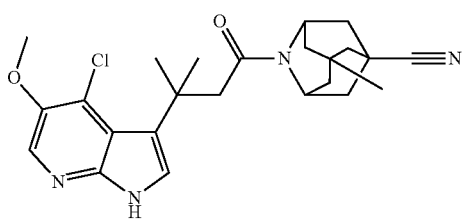
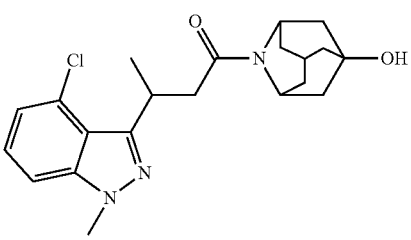
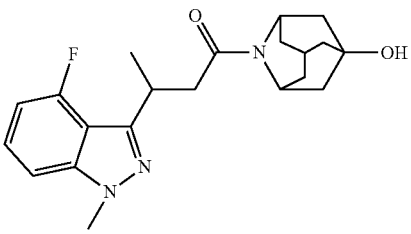
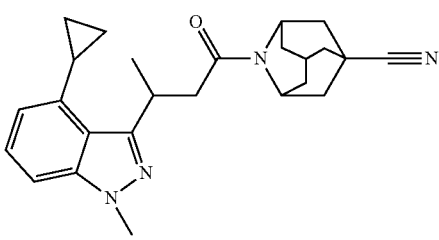
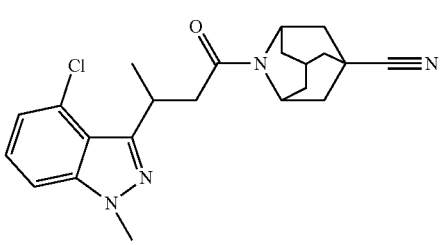
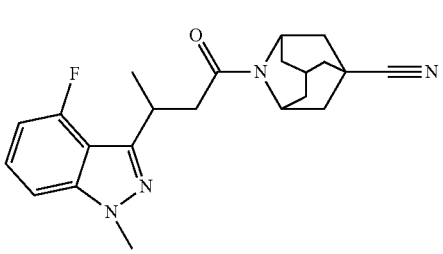

303
-continued
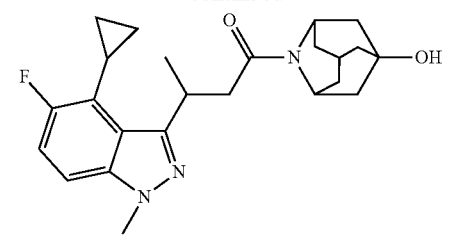
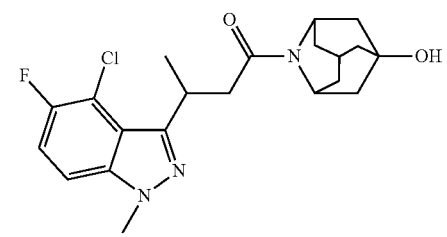
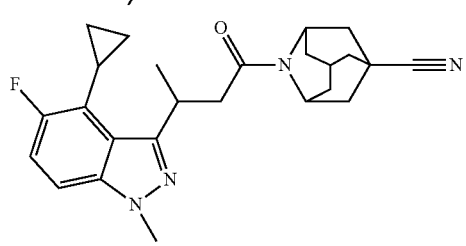
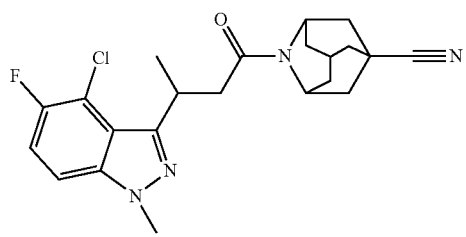
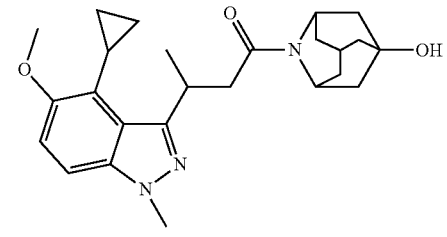
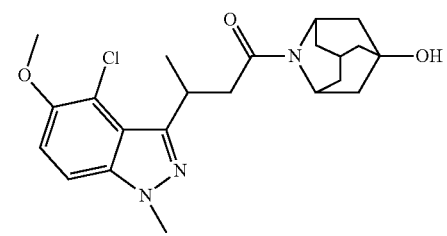
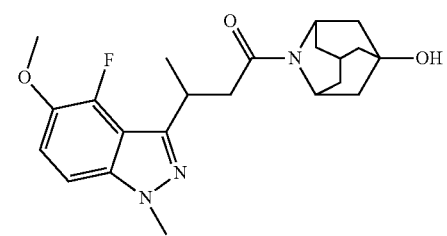
304
-continued
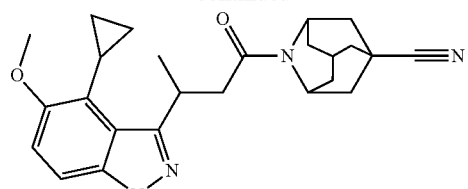
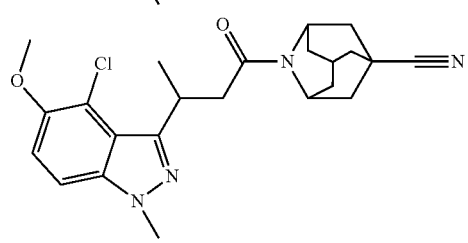
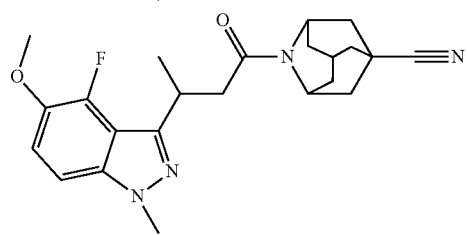
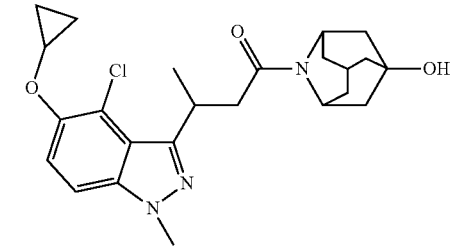
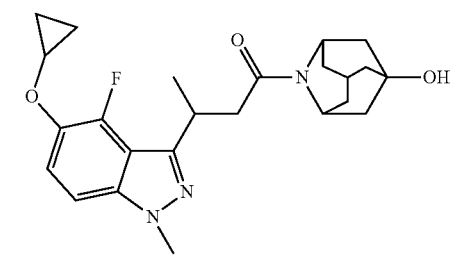
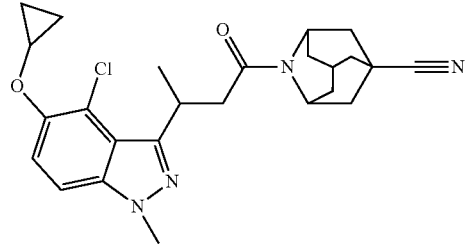
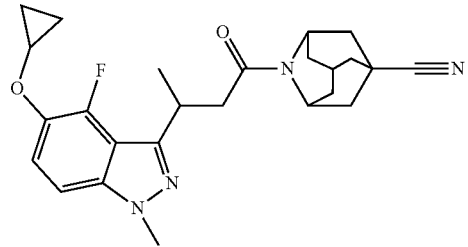

305
-continued
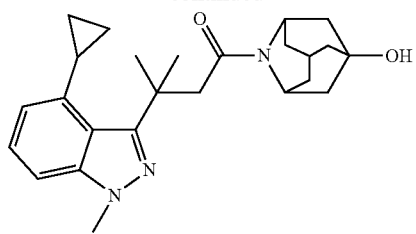
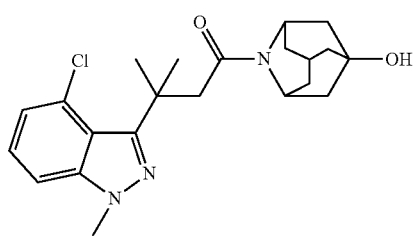
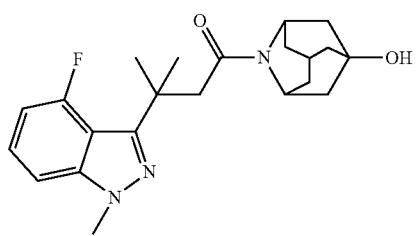
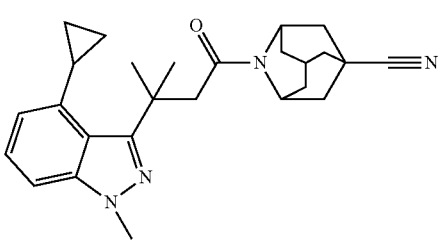
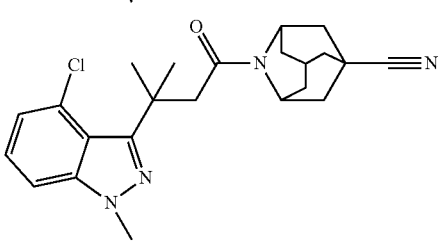
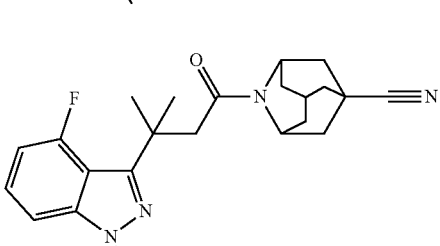
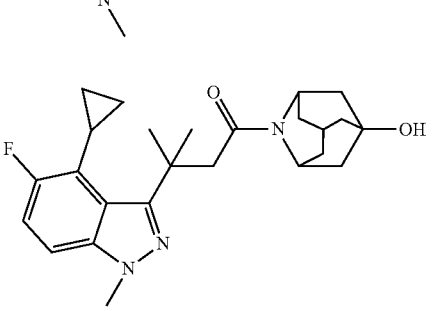
306
-continued
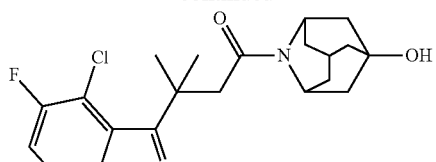
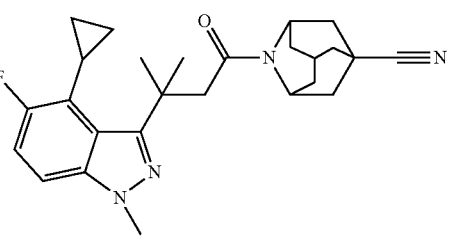
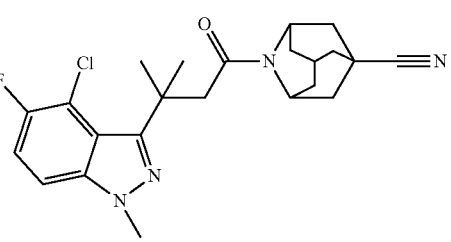
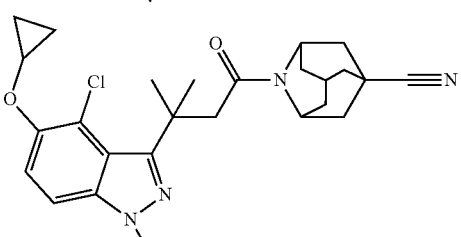
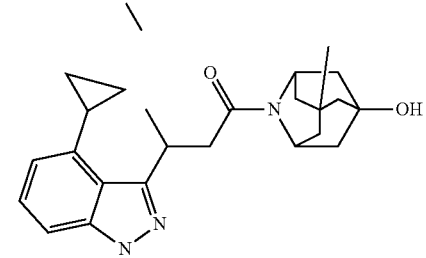
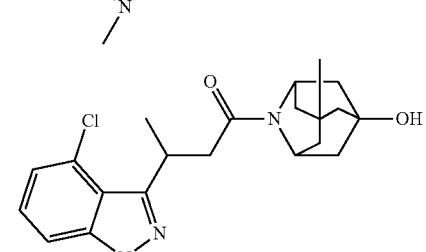
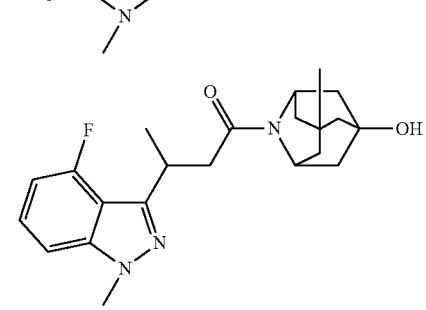

307
-continued
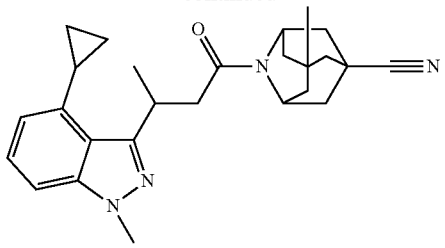
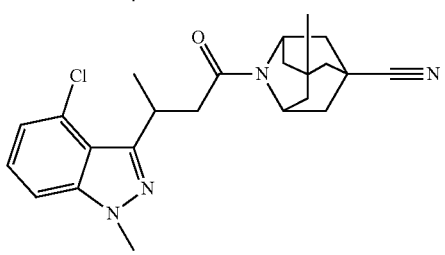
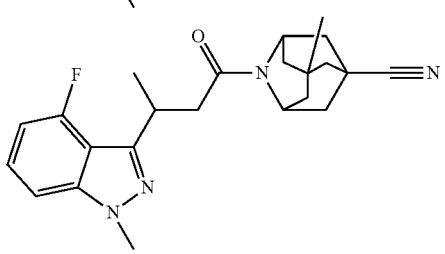
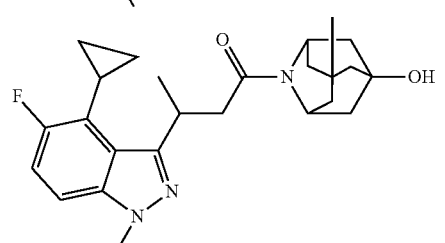
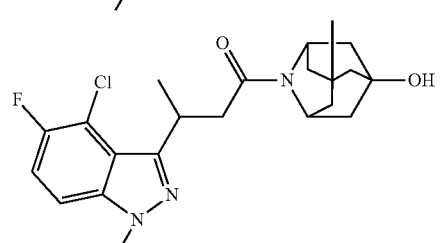
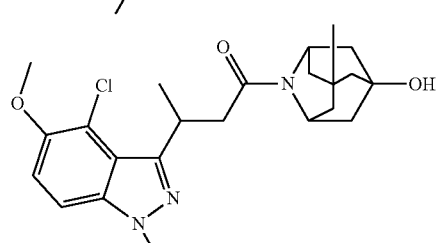
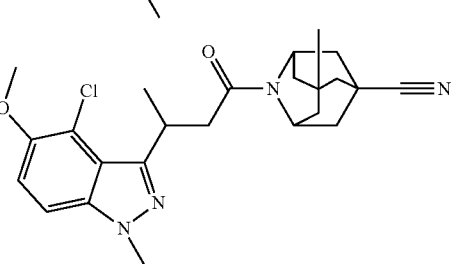
308
-continued
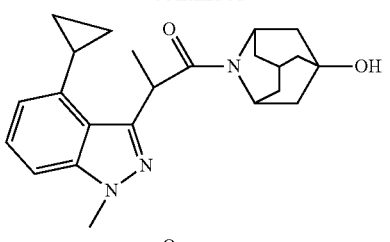
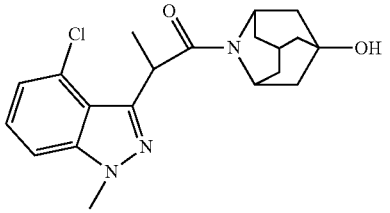
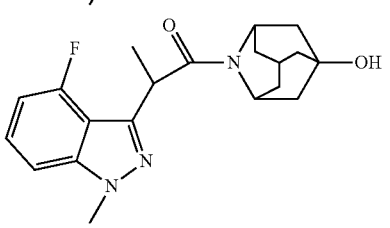
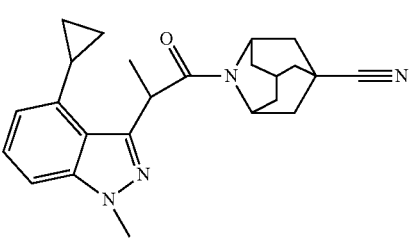
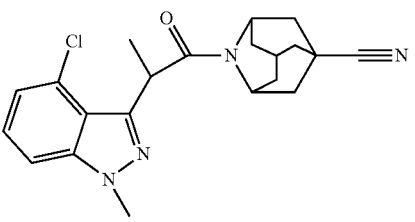
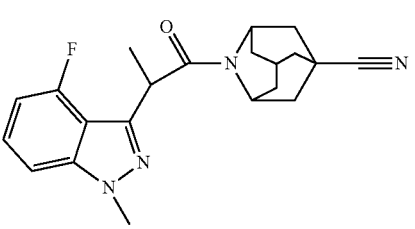
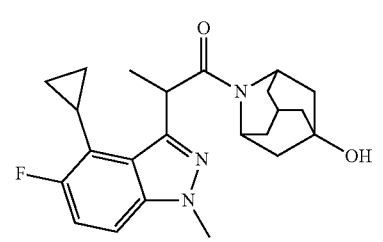

309
-continued
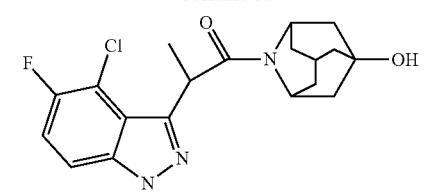
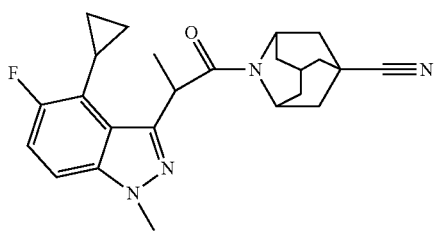
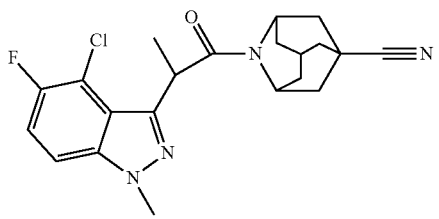
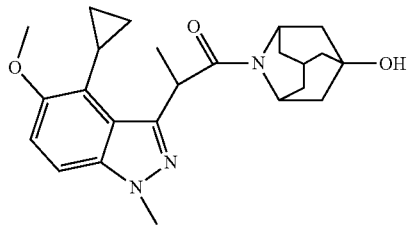
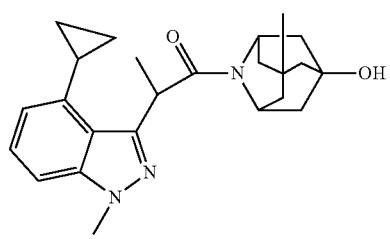
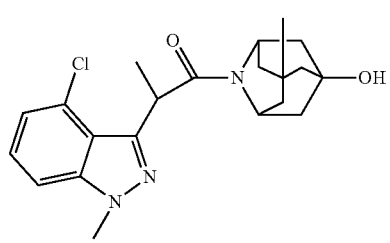
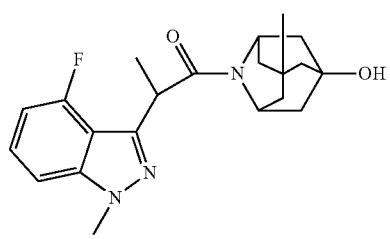
310
-continued
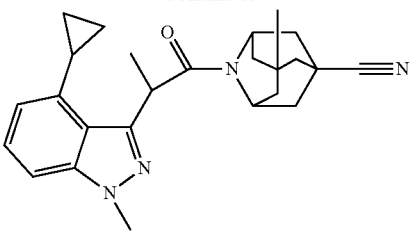
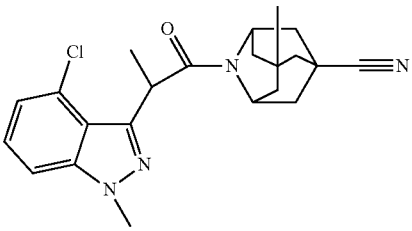
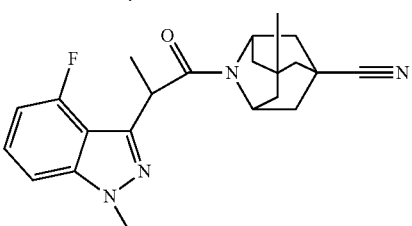
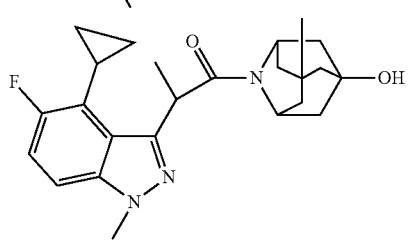
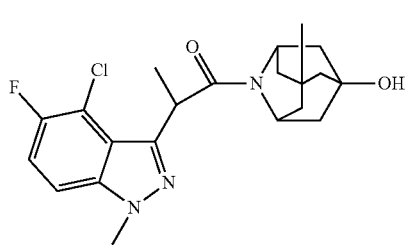
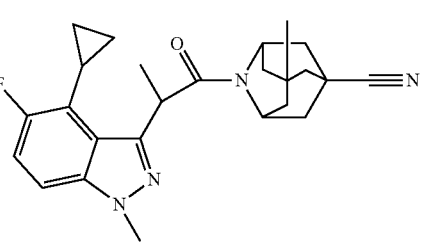
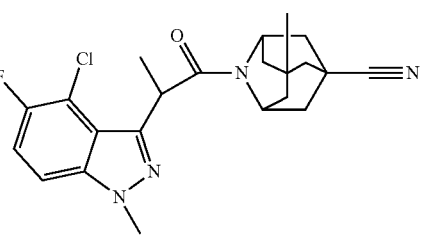

311
-continued
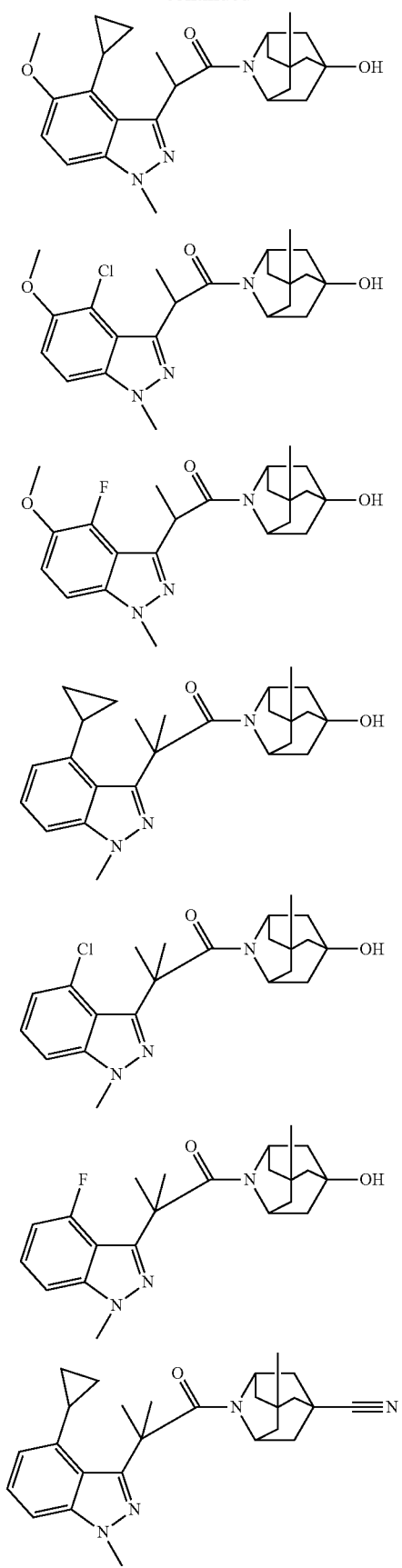
312
-continued
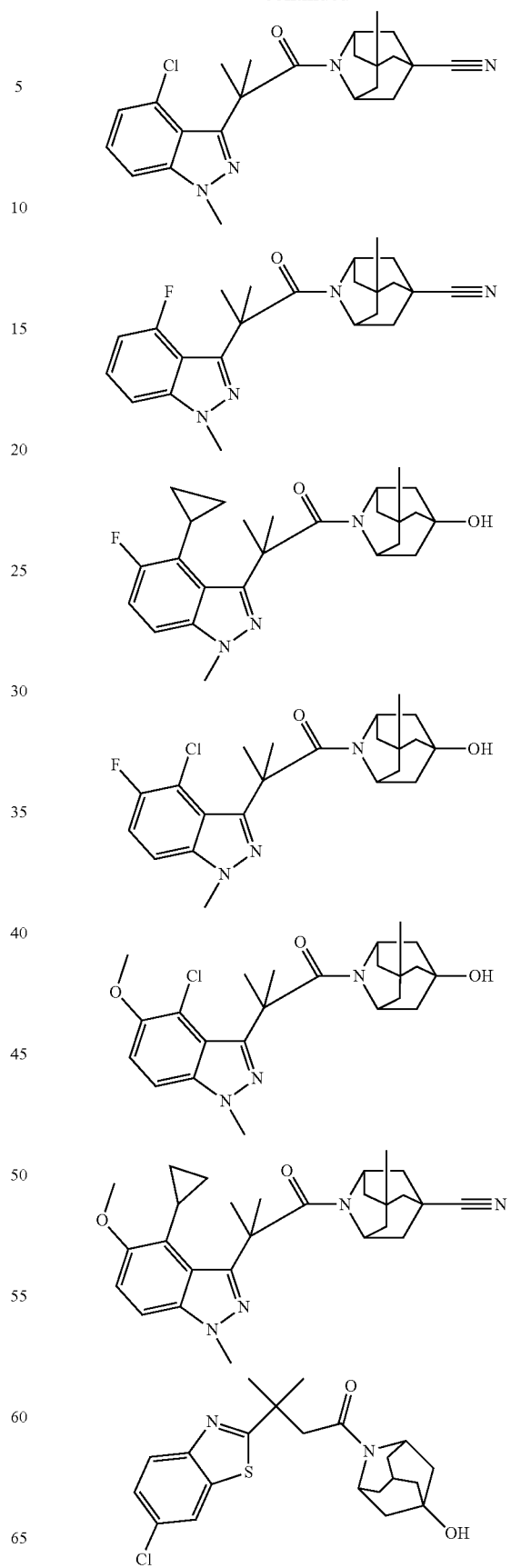

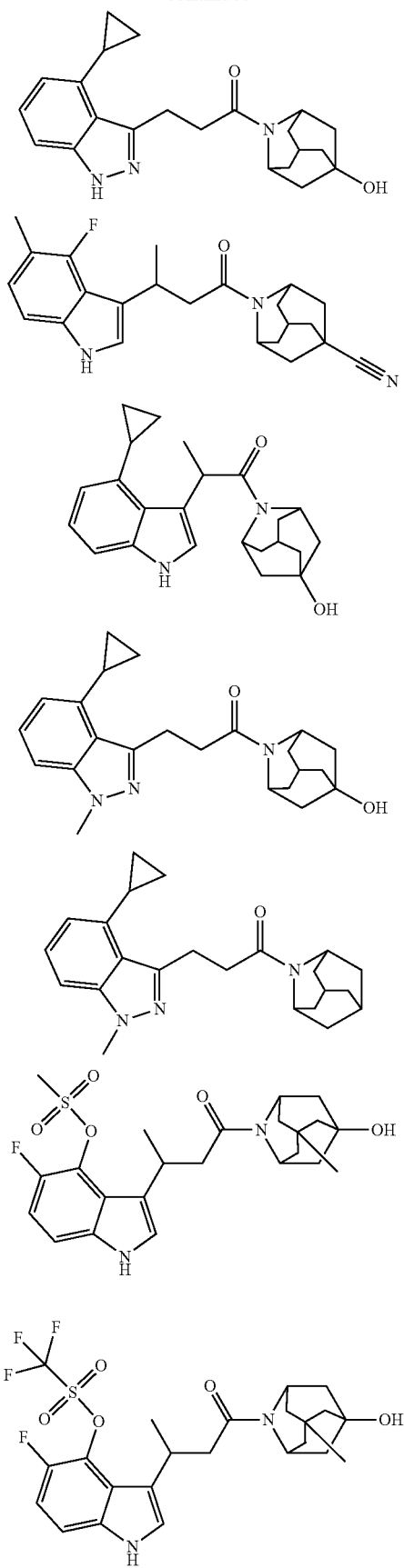
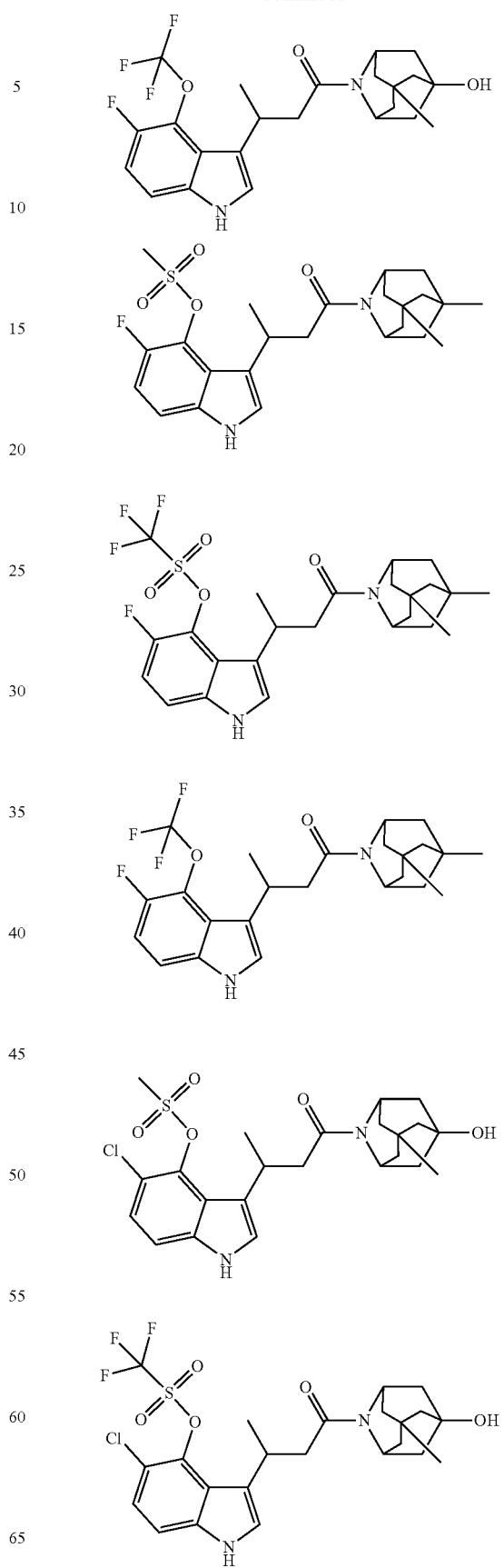

315
-continued
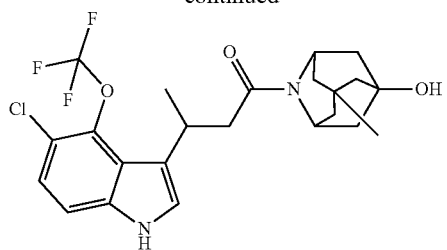
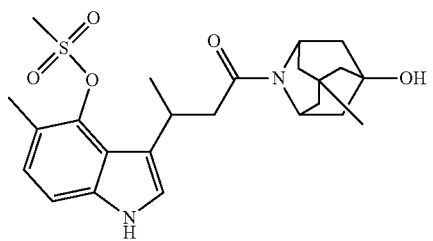
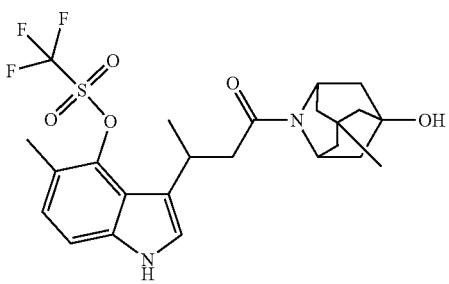
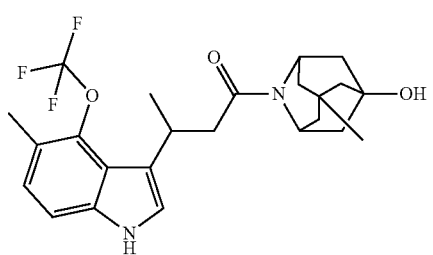
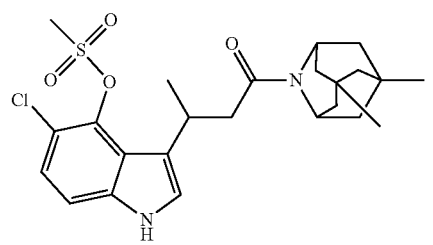
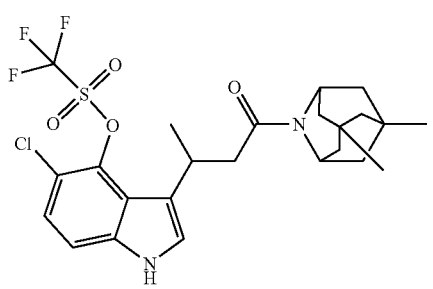
316
-continued
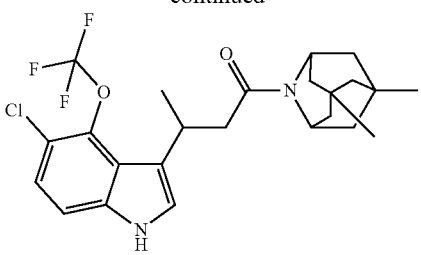
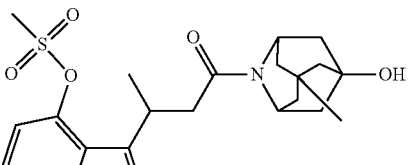
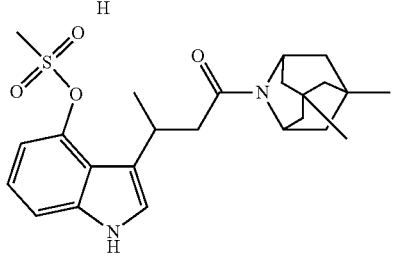
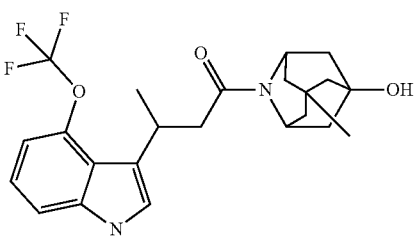
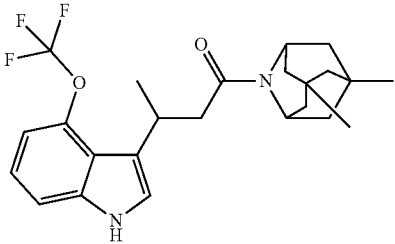
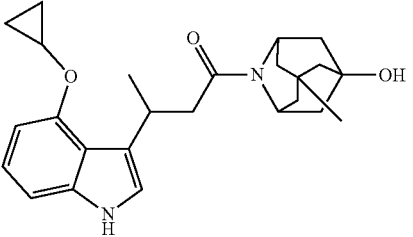
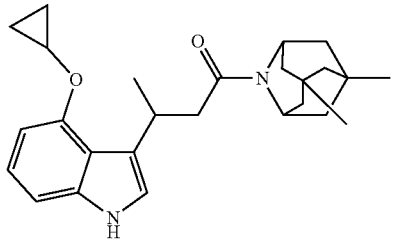

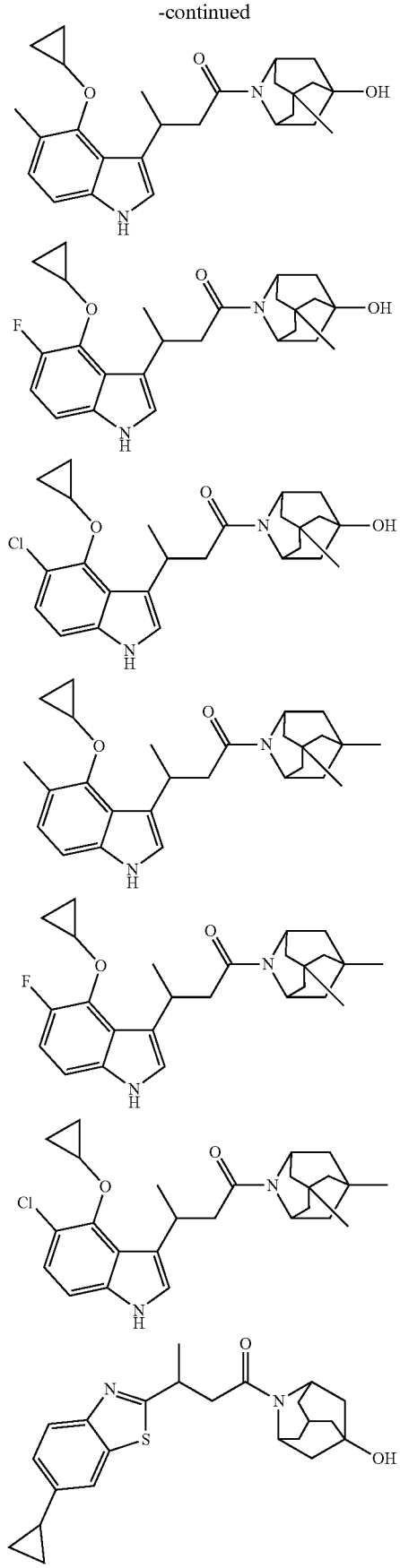
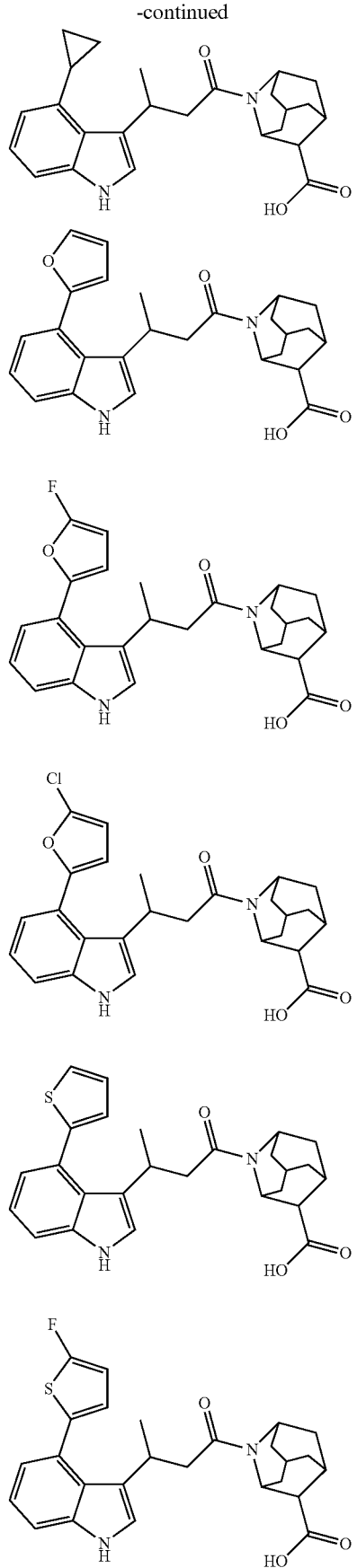

-continued

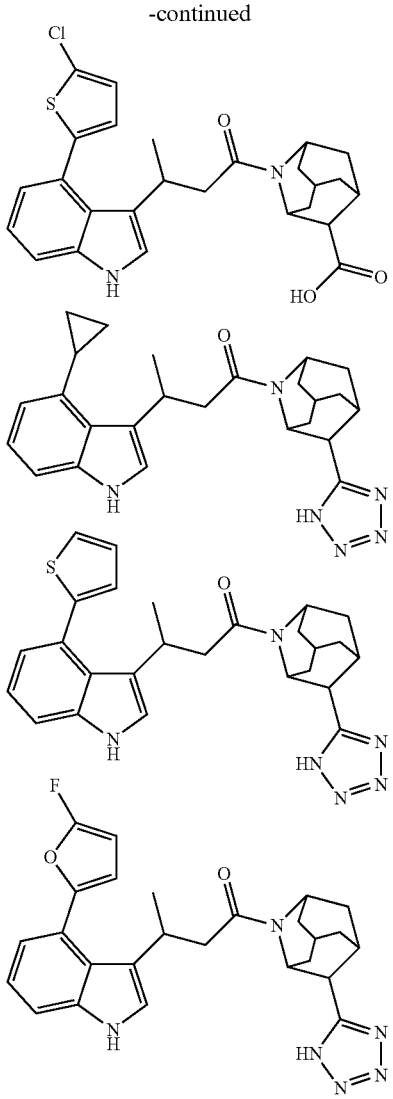

-continued

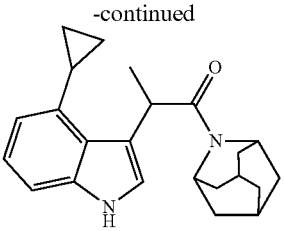

or pharmaceutically acceptable salts and isomers thereof.

11. A pharmaceutical composition including a compound according to claim 1 and a pharmaceutically acceptable diluent, excipient or carrier.

12. A method of treatment of diabetes in a mammal that is treated by inhibition of 11β HSD1, the method comprising administering an effective amount of a compound according to claim 1.

13. A method according to claim 12 wherein the diabetes is type II diabetes.

14. The method of claim 12, wherein the compound is administered in combination with an adjuvant.

15. The method of claim 14, wherein the adjuvant is selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha-glucosidase inhibitors; (f) GLP-1, GLP-1 analogs, and GLP-1 receptor agonists; and combinations thereof.

16. The method of claim 15, wherein the insulin sensitizing agents are selected from the group consisting of (i) PPAR-gamma-agonists, (ii) PPAR-alpha-agonists, (iii) PPAR-alpha/gamma-dual agonists, (iv) biguanides, and combinations thereof.

* * * * *